US009931402B2

(12) United States Patent
Hurwitz et al.

(10) Patent No.: US 9,931,402 B2
(45) Date of Patent: Apr. 3, 2018

(54) COMPOSITIONS FOR THE TREATMENT OF SOLID TUMORS

(71) Applicant: DUKE UNIVERSITY, Durham, NC (US)

(72) Inventors: Herbert I. Hurwitz, Durham, NC (US); Gordana Vlahovic, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 15/586,727

(22) Filed: May 4, 2017

(65) Prior Publication Data
US 2017/0239352 A1    Aug. 24, 2017

Related U.S. Application Data

(62) Division of application No. 14/357,039, filed as application No. PCT/US2012/064376 on Nov. 9, 2012, now Pat. No. 9,700,619.

(60) Provisional application No. 61/558,732, filed on Nov. 11, 2011.

(51) Int. Cl.
A61K 39/395 (2006.01)
A61K 31/436 (2006.01)
A61K 31/439 (2006.01)
A61K 45/06 (2006.01)
C07K 16/28 (2006.01)
A61K 39/00 (2006.01)

(52) U.S. Cl.
CPC ...... A61K 39/39558 (2013.01); A61K 31/436 (2013.01); A61K 31/439 (2013.01); A61K 39/3955 (2013.01); A61K 45/06 (2013.01); C07K 16/2863 (2013.01); A61K 2039/505 (2013.01); A61K 2039/54 (2013.01); A61K 2039/545 (2013.01); A61K 2300/00 (2013.01); C07K 2317/21 (2013.01)

(58) Field of Classification Search
None
See application file for complete search history.

(56) References Cited

U.S. PATENT DOCUMENTS

| 6,608,108 | B2 | 8/2003 | Huang et al. |
| 6,875,741 | B2 | 4/2005 | Pillutla et al. |
| 7,020,563 | B1 | 3/2006 | Bentley et al. |
| 7,037,498 | B2 | 5/2006 | Cohen et al. |
| 7,071,300 | B2 | 7/2006 | Deshayes et al. |
| 7,173,005 | B2 | 2/2007 | Pliutla et al. |
| 7,329,734 | B2 | 2/2008 | Ligensa et al. |
| 7,871,611 | B2 | 1/2011 | Calzone et al. |
| 2003/0195147 | A1 | 10/2003 | Pillutla et al. |
| 2003/0235582 | A1 | 12/2003 | Singh et al. |
| 2003/0236190 | A1 | 12/2003 | Pillutla et al. |
| 2004/0018191 | A1 | 1/2004 | Wang et al. |
| 2004/0023887 | A1 | 2/2004 | Pillutla et al. |
| 2004/0086503 | A1 | 5/2004 | Cohen et al. |
| 2004/0202655 | A1 | 10/2004 | Morton et al. |
| 2004/0228859 | A1 | 11/2004 | Graus et al. |
| 2004/0265307 | A1 | 12/2004 | Singh et al. |
| 2005/0008642 | A1 | 1/2005 | Graus et al. |
| 2005/0054638 | A1 | 3/2005 | Barlaam et al. |
| 2005/0084906 | A1 | 4/2005 | Goetsch et al. |
| 2005/0136063 | A1 | 6/2005 | Wang et al. |
| 2005/0186203 | A1 | 8/2005 | Singh et al. |
| 2005/0244408 | A1 | 11/2005 | Cohen et al. |
| 2005/0249728 | A1 | 11/2005 | Singh et al. |
| 2005/0282761 | A1 | 12/2005 | Tachas et al. |
| 2006/0040358 | A1 | 2/2006 | Ligensa et al. |
| 2007/0004634 | A1 | 1/2007 | Pillutla et al. |
| 2007/0129399 | A1 | 6/2007 | Gunzinger et al. |
| 2007/0135340 | A1 | 6/2007 | Rosenthal et al. |
| 2007/0243194 | A1 | 10/2007 | Hariharan et al. |
| 2007/0265189 | A1 | 11/2007 | Pillutla et al. |
| 2007/0299010 | A1 | 12/2007 | Nedivi |
| 2009/0274698 | A1 | 11/2009 | Bhagwat et al. |
| 2010/0316639 | A1 | 12/2010 | Lackner |

FOREIGN PATENT DOCUMENTS

| EP | 1 432 433 A2 | 8/2004 |
| EP | 1 496 935 A2 | 1/2005 |
| EP | 0 737 248 B1 | 11/2007 |
| EP | 1 732 898 131 | 1/2008 |
| WO | WO 99/28347 A1 | 10/1999 |
| WO | WO 99/60023 A1 | 11/1999 |
| WO | WO 03/027246 A2 | 4/2003 |
| WO | WO 03/059951 A2 | 7/2003 |

(Continued)

OTHER PUBLICATIONS

Battelli, Chiara and Cho, Daniel, "mTOR Inhibitors in renal cell carcinoma", disclose that these, too, differ in activity and efficacy (Therapy 8(4): 359-367 (2011).

Belani, C., "Paclitaxel/Carboplatin in the Treatment of NonSmallCell Lung Cancer", Oncology 12 (1 Suppl): pp. 74-79 (1998).

Boone, David and Lee, Adrian, "Targeting the Insulin-like Growth Factor Receptor: Developing Biomarkers from Gene Expression Profiling", Crit Rev Oncog. (2012) 17(2): pp. 161-173.

Gualberto and Pollak, "Emerging role of insulin-like growth factor receptor inhibitors in oncology: early clinical trial results and future directions", (Oncogene 28:3009-3021 (2009), Table 1. p. 3010.

Karp, "Retraction", Journal of Clinical Oncology, 30(33):4179 (2012).

(Continued)

Primary Examiner — Christine J Saoud
Assistant Examiner — Jon M Lockard
(74) Attorney, Agent, or Firm — Myers Bigel, P.A.

(57) ABSTRACT

The present invention relates to a pharmaceutical combination that comprises an IGF1R inhibitor and an mTOR inhibitor for the treatment of cancer in a subject; a pharmaceutical composition comprising such a combination; the use of such a combination for the preparation of medicament for the treatment of cancer; a kit comprising such a combination as a combined preparation for simultaneous, separate or sequential use; and a method of treating cancer in a subject, especially a human.

13 Claims, 40 Drawing Sheets

(56) References Cited

FOREIGN PATENT DOCUMENTS

| | | |
|---|---|---|
| WO | WO 03/070911 A2 | 8/2003 |
| WO | WO 2005/016970 A2 | 2/2005 |
| WO | WO 2005/037836 A2 | 4/2005 |
| WO | WO 2005/058967 A2 | 6/2005 |
| WO | WO 2005/082415 A2 | 9/2005 |
| WO | WO 2006/097800 A1 | 10/2005 |
| WO | WO 2006/009933 A2 | 1/2006 |
| WO | WO 2006/009947 A2 | 1/2006 |
| WO | WO 2006/009950 A2 | 1/2006 |
| WO | WO 2006/009962 A2 | 1/2006 |
| WO | WO 2006/012422 A1 | 2/2006 |
| WO | WO 2006/013472 A2 | 2/2006 |
| WO | WO 2006/017443 A2 | 2/2006 |
| WO | WO 2006/069202 A2 | 6/2006 |
| WO | WO 2006/074057 A2 | 7/2006 |
| WO | WO 2006/138729 A2 | 12/2006 |
| WO | WO 2007/000328 A2 | 1/2007 |
| WO | WO 2007/004060 A2 | 1/2007 |
| WO | WO 2007/012614 A2 | 2/2007 |
| WO | WO 2007/029107 A1 | 3/2007 |
| WO | WO 2007/031745 A1 | 3/2007 |
| WO | WO 20071029106 A1 | 3/2007 |
| WO | WO 2007/099166 A1 | 9/2007 |
| WO | WO 2007/099171 A2 | 9/2007 |
| WO | WO 2008/108986 A2 | 9/2008 |
| WO | WO 2010/120599 A2 | 10/2010 |

OTHER PUBLICATIONS

Stevenson et al., "NonSmall Cell Lung Cancer Treatment Protocols", *Medscape* (2016), p. 2.

Supplemental Partial European Search Report, EP 12848554, dated Apr. 23, 2015.

Alvarado Y et al. Clinical activity of mammalian target of rapamycin inhibitors in solid tumors. Targeted Oncology. May 4, 2011; 6(2): 69-94.

Kurmasheva RT et al. The insulin-like growth factor-1 receptor-targeting antibody, CP-751,871, suppresses tumor-derived VEGF and synergizes with rapamycin in models of childhood sarcoma. Cancer Research. Oct. 1, 2009; 69(19): 7662-7671.

Naing A et al. Dual inhibition of IGFR and mTOR pathways. Journal of Clinical Oncology, ASCO Annual Meeting Abstracts. vol. 28, No. 15_suppl (May 20 Supplement), 2010: 3007. Abstract.

Sathyanarayanan SH et al. Combination treatment with the antl-IGF1R antibody MK-0646 and the mTOR inhibitor deforolimus leads to more effective PI3K pathway targeting and anti-tumor activity. American Associate for Cancer Research, Proceedings of the Annual Meeting; Apr. 18-22, 2009; 50: 679. Abstract.

Baserga R. "The IGF-I Receptor in Cancer Research", Experimental Cell Research, Nov. 25, 1999; 253:1-6.

Breuhahn et al. "The Insulin-Like Growth Factor (IGF) Signaling Pathway: Strategies for Successful Therapeutic tasks in Cancer Treatment", Current Cancer Therapy Reviews May 2006, 2:157-67.

Camirand et al. "Co-targeting IGF-IR and c-kit: synergistic inhibition of proliferation and induction of apoptosis in H 209 small cell lung cancer cells", *British Journal of Cancer*, 2004, 90:1825-1829.

Camirand et al. "Inhibition of insulin-like growth factor-1 receptor signaling enhances growth-inhibitory and proapoptotic effects of gefitinib (Iressa) in human breast cancer cells", *Breast Cancer Research*, 2005 7: R570-R579.

Cohen et al. "Combination Therapy Enhances the Inhibition of Tumor Growth with the Fully Human Anti-Type 1 Insulin-Like growth Factor Receptor Monoclonal Antibody CP-751,871", *Clinical Cancer Research*, Mar. 1, 2005, 11:2063-73.

D'Ambrosio et al. "A Soluble Insulin-like Growth Factor I Receptor That Induces Apoptosis of Tumor Cells in Vivo and Inhibits Tumorigenesis", *Cancer Research*, Sep. 1, 1996, 56:4013-4020.

Garcia-Echeverria et al. "In vivo antitumor activity of NVP-AEW541-A, novel, potent, and selective inhibitor of the IGF-IR kinase", *Cancer Cell*, Mar. 2004, 5:231-239.

Ibrahim et al. "Insulin-Like Growth Factor-I and Breast Cancer Therapy", *Clinical Cancer Research*, (Suppl.) Jan. 15, 2005, 11:944s-950s.

King et al. "Insulin-like Growth Factor: Current Concepts and New Developments in Cancer Therapy", *Recent Pat Anticancer Drug Discov*, Jan. 2012, 7(1):14-30.

Larsson et al. "Role of insulin-like growth factor I receptor signaling in cancer", *Brit J. Cancer*, 2005, 92:2097-2101.

Lu et al. "Simultaneous Blockade of Both the Epidermal Growth Factor Receptor and the Insulin-like Growth Factor Receptor Signaling Pathways in Cancer Cells with a Fully Human Recombinant Bispecific Antibody", *The Journal of Biological Chemistry*, Jan. 23, 2004, 279:2856-65.

Maloney et al. "An Anti-Insulin-like Growth Factor I Receptor Antibody That Is a Potent Inhibitor of Cancer Cell Proliferation", *Cancer Research*, Aug. 15, 2003, 63:5073-83.

Mitsiades et al. "Inhibition of the insulin-like growth factor receptor-1 tyrosine kinase activity as a therapeutic strategy for multiple myeloma, other hematologic malignancies, and solid tumors", *Cancer Cell*, Mar. 2004, 5:221-230.

O'Reilly et al. "mTOR Inhibition Induces Upstream Receptor Tyrosine Kinase Signaling and Activates Akt", Cancer Res. Feb. 1, 2006; 66:1500-1508.

Sachdev et al. "Disrupting insulin-like growth factor signaling as a potential cancer therapy", *Mol Cancer Ther*. Jan. 2007; 6:1-12.

Schmelzle et al. "TOR, a Central Controller of Cell Growth", *Cell*, Oct. 13, 2000; 103:253-262.

Tabernero et al. "Dose- and Schedule-Dependent Inhibition of the Mammalian target of Rapamycin Pathway With Everolimus: A Phase I Tumor Pharmacodynamic Study in Patients With Advanced Solid Tumors", *Journal of Clinical Oncology*, vol. 26, No. 10, Apr. 1, 2008, 1603-1610.

Tolcher et al. "Phase I, Pharmacokinetic, and Pharmacodynamic Study of AMG 479, a Fully Human Monoclonal Antibody to Insulin-Like Growth Factor Receptor 1", J. Clin. Oncol., Dec. 1, 2009, 27:5800-5807.

Wan et al. "Rapamycin induces feedback activation of Akt signaling through an IGF-1R-dependent mechanlsm", *Oncogene*, 2007 26:1932-1940.

Wittman et al. "Discovery of a 1H-Benzoimidazol-2-yl)-1H-pyridin-2-one (BMS-536924) Inhibitor of Insulin-like Growth Factor I Receptor Kinase with in Vivo Antitumor Activity", *J Med Chem*. 2005, 48:5639-43.

Youngren et al. "Nordihydroguaiaretic acid (NDGA) inhibits the IGF-1 and c-erbB2/HER2/neu receptors and suppresses growth in breast cancer cells", *Breast Cancer Res Treatment*, 2005, 94:37-46.

Quek R et al. Combination mTOR and IGF-1R inhibition: Phase I trial of everolimus and figitumumab in patients with advanced sarcomas and other solid tumors. Clinical Cancer Research. Feb. 2011; 17(4): 871-879.

Beltran PJ et al. Efficacy of ganitumab (AMG 479), alone and in combination with rapamycin, in Ewing's and osteogenic sarcoma models. The Journal of Pharmacology and Experimental Therapeutics. ePub Mar. 8, 2011; 337(3): 644-54.

Haluska P et al. Safety, tolerability, and pharmacokinetics of the anti-IGF-1R monoclonal antibody figitumumab in patients with refractory adrenocortical carcinoma. Cancer Chemother Pharmacol. Mar. 2010; 65(4): 765-773.

Soria J-C et al. Efficacy of everolimus (RAD001) in patients with advanced NSCLC previously treated with chemotherapy alone or with chemotherapy and EGFR inhibitors. Annals of Oncology. 2009; 20(10): 1674-1681.

ClinicalTrials NCT01122199 Phase I study of mTOR inhibitor RAD001 in combination with IGF-1R inhibitor AMG479 for patients with advanced solid tumors and colorectal cancer. Oct. 11, 2011. [Retrieved from the Internet Mar. 30, 2013: <http://clinicaltrials.gov/archive/NCT01122199/2011_10P11>].

Gualberto A and Karp DD. Development of the monoclonal antibody figitumumab, targeting the insulin-like growth factor-1 receptor, for the treatment of patients with non-mali-cell lung cancer. Clinical Lung Cancer. Jul. 2009; 10(4): 273-280.

Pappo AS et al. Activity of R1507, a monoclonal antibody to the insulin-like growth factor-1 receptor (IGF1R) in patients (pts) with

(56) References Cited

OTHER PUBLICATIONS recurrent or refractory Ewing's sarcoma family of tumors (ESFT): results of a phase II SARC study. Journal of Clinical Oncology. May 20, 2010; 28(S15); 10000.
Vlahovic G et al. Abstract B58; Phase I study of the IGF-1R antibody ganitumab (AMG 479) in combination with everolimus in patients with advanced solid tumors, Molecular Cancer Therapeutics. Nov. 12, 2011; 10(11): Supplement 1, Abstracts: AACR-NCI-EORTC International Conference: Molecular Targets in Cancer Therapeutics Nov. 12-16, 2011 San Francisco, CA; Abstract B58.
Olmos D et al. Targeting the insulin like growth factor 1 receptor in Ewing's sarcoma: reality and expectations. Sarcoma ePub May 3, 2011, Article ID 402508, 13 pages.
Ludwig JA et al. Dual targeting of the insulin-like growth factor and collateral pathways in cancer: combating drug resistance, Cancers, Jul. 2011; 3(3): 3029-3054.
International Search Report and Written Opinion PCT/US2012/064376, dated May 13, 2013.

Fig. 1

L1 (SEQ ID NO:1)
```
      GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAGTGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCGATC ACCTTCGGCC AAGGGACACG ACTGGAGATT AAA
```

L2 (SEQ ID NO:3)
```
      GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCGATC ACCTTCGGCC AAGGGACACG ACTGGAGATT AAA
```

L3 (SEQ ID NO:5)
```
      GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCACTC ACTTTCGGCG GCGGGACCAA GGTGGAGATC AAA
```

L4 (SEQ ID NO:7)
```
       GA AATTGTGATG ACGCAGTCTC CACTCTCCCT GCCCGTCACC
CCTGGAGAGC CGGCCTCCAT CTCCTGCAGG TCTAGTCAGA GCCTCCTGCA
TAGTAATGGA TACAACTATT TGGATTGGTA CCTGCAGAAG CCAGGGCAGT
CTCCACAGCT CCTGATCTAT TTGGGTTCTA ATCGGGCCTC CGGGGTCCCT
GACAGGTTCA GTGGCAGTGG ATCAGGCACA GATTTTACAC TGAAAATCAG
CAGAGTGGAG GCTGAGGATG TTGGGGTTTA TTACTGCATG CAAGCTCTAC
AAACTCCTCA CACTTTCGGC GGAGGGACCA AGGTGGAGAT CAAA
```

L5 (SEQ ID NO:9)
```
      GAAA TTGTGCTGAC TCAGTCTCCA CTCTCCCTGC CCGTCACCCC
TGGAGAGCCG GCCTCCATCT CCTGCAGGTC TAGTCAGAGC CTCCTGCATA
GTAATGGATA CAACTATTTG GATTGGTACC TGCAGAAGCC AGGGCAGTCT
CCACAGCTCC TGATCTATTT GGGTTCTAAT CGGGCCTCCG GGGTCCCTGA
CAGGTTCAGT GGCAGTGGAT CAGGCACAGA TTTTACACTG AAAATCAGCA
GAGTGGAGGC TGAGGATGTT GGGGTTTATT ACTGCATGCA AGCTCTACAA
ACCCCTCTCA CTTTCGGCCC TGGGACCAAA GTGGATATCA AA
```

Fig. 1 (cont)

L6 (SEQ ID NO:11)
```
        GAT GTTGTGATGA CTCAGTCTCC ACTCTCCCTG GCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCGCTC ACTTTCGGCG GAGGGACCAA GGTGGAGATC AAA
```

L7 (SEQ ID NO:13)
```
        GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCTCTC ACTTTCGGCG GAGGGACCAA GGTGGAGATC AAA
```

L8 (SEQ ID NO:15)
```
  GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAG AAGCCAGGGC AGTCTCCACA
GCTCCTGATC TATTTGGGTT CTAATCGGGC TCCGGGGTC CCTGACAGGT
TCAGTGGCAG TGGATCAGGC ACAGATTTTA CACTGAAAAT CAGCAGAGTG
GAGGCTGAAG ATGTTGGGGT TTATTACTGT ATGCAAGCTC TACAAACCCC
CCTCACTTTC GGCGGAGGGA CCAAGGTGGA GATCAAA
```

L9 (SEQ ID NO:17)
```
        GATG TTGTGATGAC TCAGTCTCCA CTCTCCCTGC CCGTCACCCC
TGGAGAGCCG GCCTCCATCT CCTGCAGGTC TAGTCAGAGC CTCCTGCATA
GTAATGGATA CAACTATTTG GATTGGTACC TGCAGAAGCC AGGGCAGTCT
CCACAGCTCC TGATCTATTT GGGTTCTAAT CGGGCCTCCG GGGTCCCTGA
CAGGTTCAGT GGCAGTGGAT CAGGCACAGA TTTTACACTG AAAATCAGCA
GAGTGGAGGC TGAGGATGTT GGGGTTTATT ACTGCATGCA AGCTCTACAA
ACTCCGTTCA CCTTCGGCCA AGGGACACGA CTGGAGATTA AA
```

L10 (SEQ ID NO:19)
```
GATGTTGTGA TGACTCAGTC TCCACTCTCC CTGCCCGTCA CCCCTGGAGA
GCCGGCCTCC ATCTCCTGCA GGTCTAGTCA GAGCCTCCTG CATAGTAATG
GATACAACTA TTTGGATTGG TACCTGCAGA AGCCAGGGCA GTCTCCACAG
CTCCTGATCT ATTTGGGTTC TAATCGGGCC TCCGGGGTCC CTGACAGGTT
CAGTGGCAGT GGATCAGGCA CAGATTTTAC ACTGAAAATC AGCAGAGTGG
AGGCTGAGGA TGTTGGGGTT TATTACTGCA TGCAAGCTCT ACAAACTCCT
CTGGCGTTCG GCCAAGGGAC CAAGGTGGAA ATCAAA
```

Fig. 1 (cont)

L11 (SEQ ID NO:21)
```
   GAAATTGT GCTGACTCAG TCTCCACTCT CCCTGCCCGT CACCCCTGGA
GAGCCGGCCT CCATCTCCTG CAGGTCTAGT CAGAGCCTCC TGCATAGTAA
TGGATACAAC TATTTGAATT GGTACCTGCA GAAGCCAGGG CAGTCTCCAC
AGCTCCTGAT CTATTTGGGT TCTAATCGGG CCTCCGGGGT CCCTGACAGG
TTCAGTGCCA GTGGATCAGG CACAGATTTT ACACTGAAAA TCAGCAGAGT
GGAGGCTGAG GATGTTGGGG TTTATTACTG CATGCAAGCT CTACAAACTC
CTATCACCTT CGGCCAAGGG ACACGACTGG AGATTAAA
```

L12 (SEQ ID NO:23)
```
        AATT TTATGCTGAC TCAGCCCCAC TCTGTGTCGG AGTCTCCGGG
GAAGACGGTA ACCATCTCCT GCACCCGCAG CAGTGGCAGC ATTGCCAGCA
ACTATGTGCA GTGGTACCAG CAGCGCCCGG GCAGTTCCCC CACCACTGTG
ATCTATGAGG ATAACCAAAG ACCCTCTGGG GTCCCTGATC GGTTCTCTGG
CTCCATCGAC AGCTCCTCCA ACTCTGCCTC CCTCACCATC TCTGGACTGA
AGACTGAGGA CGAGGCTGAC TACTACTGTC AGTCTTATGA TAGCAGCAAT
CAGAGAGTGT TCGGCGGAGG GACCAAGCTG ACCGTCCTA
```

L13 (SEQ ID NO:25)
```
        GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACCCCGCTC ACTTTCGGCG GAGGGACCAA GGTGGAGATC AAA
```

L14 (SEQ ID NO:27)
```
          G ATGTTGTGAT GACTCAGTCT CCACTCTCCC TGCCCGTCAC
CCCTGGAGAG CCGGCCTCCA TCTCCTGCAG GTCTAGTCAG AGCCTCCTGC
ATAGTAATGG ATACAACTAT TTGGATTGGT ACCTGCAGAA GCCAGGGCAG
TCTCCACAGC TCCTGATCTA TTTGGGTTCT AATCGGGCCT CCGGGGTCCC
TGACAGGTTC AGTGGCAGTG GATCAGGCAC AGATTTTACA CTGAAAATCA
GCAGAGTGGA GGCTGAGGAT GTTGGGGTTT ATTACTGCAT GCAAGCTCTA
CAAACTCCTC TTACTTTCGG CGGAGGGACC AAGGTGGAGA TCAAA
```

L15 (SEQ ID NO:29)
```
  GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAA AAGCCAGGGC AGTCTCCACA
GCTCCTGATC TATTTGGGTT CTTATCGGGC CTCCGGGGTC CCTGACAGGT
TCAGTGCCAG TGGATCAGGC ACAGATTTTA CACTGAAAAT CAGCAGAGTG
GAGGCTGAGG ATGTTGGGGT TTATTACTGC ATGCAAGCTC TACAAACTCC
GATCACCTTC GGCCAAGGGA CACGACTGGA GATTAAA
```

Fig. 1 (cont)

L16 (SEQ ID NO:31)
 GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAG AAGCCAGGGC AGTCTCCACA
GCTCCTGATC TATTTGGGTT CTAATCGGGC CTCCGGGGTC CCTGACAGGT
TCAGTGGCAG TGGATCAGGC ACAGATTTTA CACTGAAAAT CAGCAGGGTG
GAGGCTGAGG ATGTTGGGGT TTATTACTGC ATGCAAGGTA CACACTGGCC
TCTGACGTTC GGCCAAGGGA CCAAGGTGGA GATCAAA

L17 (SEQ ID NO:33)
    GAAATTG TGATGACGCA GTCTCCACTC TCCCTGCCCG TCACCCCTGG
AGAGCCGGCC TCCATCTCCT GCAGGTCTAG TCAGAGCCTC CTGCATAGTA
ATGGATACAA CTATTTGGAT TGGTACCTGC AGAAGCCAGG GCAGTCTCCA
CAGCTCCTGA TCTATTTGGG TTCTAATCGG GCCTCCGGGG TCCCTGACAG
GTTCAGTGGC AGTGGATCAG GCACAGATTT TACACTGAAA ATCAGCAGAG
TGGAGGCTGA GGATGTTGGG GTTTATTACT GCATGCAAGC TCTACAAACT
CCTCTCACTT TCGGCGGAGG GACCAAGGTG GAGATCAAA

L18 (SEQ ID NO:35)
        GAC ATCCAGTTGA CCCAGTCTCC ATCTTCCGTG TCTGCGTCTG
TCGGAGACAG AGTCACCATC ACTTGTCGGG CGAGTCAGGG TATTAGCAGG
TGGTTAGCCT GGTATCAACA GAAACCAGGG AAAGCCCCTA GACTCCTGAT
CTATGCTGCG TCCGGTTTAC AAAGTGGGGT CCCATCAAGG TTCAGCGGCA
GTGGATCTGG GACAGATTTC ACTCTCACCA TCAGCAACCT GCAGCCTGAA
GATTTTGCAA CTTACTATTG TCAACAGGCT AGCAGTTTTC CAATCACCTT
CGGCCAAGGG ACACGACTGG AGACTAAA

L19 (SEQ ID NO:37)
        GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGAGTTTAT TACTGCATGC AAGCTCTACA
AACTCCGTAC ACTTTTGGCC AGGGGACCAA GCTGGAGATC AAA

L20 (SEQ ID NO:39)
 GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAG AAGCCAGGGC AGTCTCCACA
GCTCCTGATC TATTTGGGTT CTAATCGGGC CTCCGGGGTC CCTAACAGGT
TCAGTGGCAG TGGATCAGGC ACAGATTTTA CACTGAAAAT CAGCAGAGTG
GAGGCTGAGG ATGTTGGGGT TTATTACTGC ATGCAAGCTC TACAAACTCC
ATTCACTTTC GGCCCTGGGA CCAAAGTGGA TATCAAA

Fig. 1 (cont)

L21 (SEQ ID NO:41)
```
 GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTCAT
GGATACAACT ATTTGGATTG GTACCTGCAG AAGCCAGGGC AGTCTCCACA
ACTTCTGATC TATTTGGGTT CTTATCGGGC CTCCGGGGTC CCTGACAGGT
TCAGTGGCAG TGGATCAGGC ACAGATTTTA CACTGAAAAT CAGCAGAGTG
GAGGCTGAGG ATGTTGGGGT TTATTACTGC ATGCAATCTC TAGAAGTTCC
GTTCACTTTT GGCCAGGGGA CCAAGCTGGA GATCAAA
```

L22 (SEQ ID NO:43)
```
        TCT TCTGAGCTGA CTCAGGACCC TGCTGTGTCT GTGGCCTTGG
GACAGACAGT CAGGATCACA TGCCAAGGAG ACAGCCTCAG AATTTATTAT
ACAGGCTGGT ACCAACAGAA GCCAGGACAG GCCCCTGTGC TTGTCCTCTT
TGGTAAGAAC AATCGGCCCT CAGGGATCCC AGACCGATTC TCTGGCTCCC
ACTCAGGGAA CACAGCTTCC TTGACCATCA CTGGGCTCA AGCGGAAGAT
GAGGCTGACT ATTACTGTAA CTCCCGGGAC ATCACTGGTG TCCATCGATT
CGGCGGAGGG ACCAAGCTGA CCGTCCTA
```

L23 (SEQ ID NO:45)
```
        GAA ATTGTGCTGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCTCTC ACTTTCGGCG GAGGGACCAA GGTGGAGATC AAA
```

L24 (SEQ ID NO:47)
```
        GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCTAAC ACTTTCGGCG GAGGGACCAA GGTGGAGATC AAA
```

L25 (SEQ ID NO:49)
```
 GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAG AAGCCAGGGC AGTCTCCACA
GCTCCTGATC TATTTGGGTT CTAATCGGGC CTCCGGGGTC CCTGACAGGT
TCAGTGGCAG TGGATCAGGC ACAGATTTTA CACTGAAAAT CAGCAGAGTG
GAGGCTGAGG ATGTTGGGGT TTATTACTGC ATGCAAGCTC TACAAACTCC
AATCACTTTC GGCCCTGGGA CCAAAGTGGA TATCAAA
```

Fig. 1 (cont)

L26 (SEQ ID NO:51)
```
   GATGTTGT GATGACTCAG TCTCCACTCT CCCTGCCCGT CACCCCTGGA
GAGCCGGCCT CCATCTCCTG CAGGTCTAGT CAGAGCCTCC TGCATAGTAA
TGGATACACC TATTTGGATT GGTACCTGCA GAAGCCAGGG CAGTCTCCAC
AACTCCTGAT CTATTTGGGT TCTAATCGGG CCTCCGGGGT CCCTGACAGG
TTCAGCGGCA GTGGATCAGG CACAGATTTT ACACTGAAAA TCAGCAGAGT
GGAGCCTGAG GATGTTGGGG TCTATTACTG CATGCAAGCT CTAGAAATGC
CCCTCACTTT CGGCGGAGGG ACCAAGGTGG AGATCAAA
```

L27 (SEQ ID NO:53)
```
       GAC ATCCAGTTGA CCCAGTCTCC ATCCTTCCTG TCTGCATCTG
TAGGAGACAG AGTCACCATC ACTTGCCGGG CCAGTCAGGG CATTAGCAGT
TATTTAGCCT GGTATCAGCA AAAACCAGGG AAAGCCCCTA AGCTCCTGAT
CTATGCTGCA TCCACTTTGC AAAGTGGGGT CCCATCAAGG TTCAGCGGCA
GTGGATCTGG GACAGAATTC ACTCTCACAA TCAGCAGCCT GCAGCCTGAA
GATTTTGCAA CTTATTACTG TCAACAGCTT AATAGTTACC CCCTCACTTT
CGGCGGAGGG ACCAAGGTGG AGATCAAA
```

L28 (SEQ ID NO:55)
```
        TC CTATGTGCTG ACTCAGCCAC CCTCAGTGTC CGTGTCCCCA
GGACAGACAG CCAGCATCAC CTGCTCTGGA GATAAATTGG GGGATAAATA
TGTTGGCTGG TATCAGCAAA AGGCAGGCCA AGCCCCTGTT TTGGTCATCT
ATCAAGACAA CAAGCGACCC TCAGGGATCC CTGAGCGATT CTCTGGCTCC
AACTCTGGGA ACACAGCCAG TCTGACCATC AGCGGGACCC AGGCTATGGA
TGAGGCTGAC TATTACTGTC AGGCGTGGGA CAGCGGCACG GTGTTCGGCG
GAGGGACCAA GCTGACCGTC CTA
```

L29 (SEQ ID NO:57)
```
       GATG TTGTGATGAC TCAGTCTCCA CTCTCCCTGC CCGTCACCCC
TGGAGAGCCG GCCTCCATCT CCTGCAGGTC TAGTCAGAGC CTCCTGCATA
GTAATGGATA CAACTATTTG GATTGGTACC TGCAGAAGCC AGGGCAGTCT
CCACAGCTCC TGATCTATTT GGGTTCTAAT CGGGCCTCCG GGGTCCCTGA
CAGGTTCAGT GGCAGTGGAT CAGGCACAGA TTTTACACTG AAAATCAGCA
GAGTGGAGGC TGAGGATGTT GGGGTTTATT ACTGCATGCA AGCTCTACAA
ACCCCCCTCA CTTTCGGCGG AGGGACCAAG GTGGAGATCA AA
```

L30 (SEQ ID NO:59)
```
   GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAG AAGCCAGGGC AGTCTCCACA
GCTCCTGATC TATTTGGGTT CTAATCGGGC CTCCGGGGTC CCTGACAGGT
TCAGTGGCAG TGGATCAGGC ACAGATTTTA CACTGAAAAT CAGCAGAGTG
GAGGCTGAGG ATGTTGGGGT TTATTACTGC ATGGAAGCTC TACAAACTCC
ATTCACTTTC GGCCCTGGGA CCAAGGTGGA AATCAAA
```

Fig. 1 (cont)

L31 (SEQ ID NO:61)
```
     GACATC CAGTTGACCC AGTCTCCATC CTCCCTGTCT GCGTCTGTGG
GAGACAGAGT CACCATCACT TGCCGGTCAA GTCAAGGCAT TGGTTACTTC
TTAAATTGGT ATCAGCAGGA ACCAGGGAAA GCCCCAAAGA TCCTGATCTC
TGCTGCATCC ACTTTGCAAA GTGGGGTCCC ATCAAGGTTC AGTGGCAGTG
GATCTGGGAC AGATTTCACA CTCTCCATCA ACAATCTGCA ACCCGCAGAT
TTTGCGACAT ACTACTGTCA ACAGAGTCAC AGTCCCCGT ACACTTTCGG
CCAGGGGACC AAGGTGGAGA TCAAA
```

L32 (SEQ ID NO:63)
```
       GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTATT TGGGTTCTAA TCGGGCCTCC GGGGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCGCTC ACTTTCGGCG GAGGGACCAA GGTGGAGATC AAA
```

L33 (SEQ ID NO:65)
```
  GAAATTGTG CTGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAG AAGCCAGGGC AGTCTCCACA
GCTCCTGATG TATTTGGTTT CTAATCGGGC CTCCGGGGTC CCTGAGAGGT
TCAGTGGCAG TGGATCAGGC ACAGATTTTA CACTGAAAAT CAGCAGAGTG
GAGGCTGAGG ATGTTGGGGT TTATTACTGC ATGCAAACTC TACAAACTCC
TCTCAGTTTT GGCCAGGGGA CCAAGCTGGA GATCAAA
```

L34 (SEQ ID NO:67)
```
  GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAG AAGCCAGGGC AGTCTCCACA
GCTCCTGATC TATTTGGTT CTAATCGGGC CTCCGGGGTC CCTGACAGGT
TCAGTGGCAG TGGATCAGGC ACAGATTTTA CACTGAAAAT CAGCAGAGTG
GAGGCTGAGG ATGTTGGGGT TTATTACTGC ATGCAAGCTC TACAAACTCC
GCTCACTTTC GGCGGAGGGA CCAAGGTGGA GATCAAA
```

L35 (SEQ ID NO:69)
```
  AATTTTATG CTGACTCAGC CCCACTCTGT GTCGGCGTCT CCGGGGAAGA
CGGTTACCAT CTCCTGCACC CGCAGCAGTG GCGACATTGA CAACAACTAT
GTGCAGTGGT ACCAGCAGCG CCCGGGCAAT TCCCCCACCA ATGTGATTTA
TGAGGATAAC CGAAGACCCT CTGGGGTCCC GGATCGCTTC TCTGGCTCCA
TCGACAGCTC CTCCAACTCT GCCTCCCTCA CCATCTCTGG ACTGCAGCCT
GAGGACGAGG CTGACTACTA TTGTCAGTCT TATCAAAGCG ACAATTGGGT
GTTCGGCGGA GGGACCAAGG TGACCGTCCT A
```

Fig. 1 (cont)

L36 (SEQ ID NO:71)
 AATTTTATG CTGACTCAGC CCCACTCTGT GTCGGAGTCT CCGGGGAAGA
CGGTAACCAT CTCCTGCACC CGCAGCAGTG GCAGCATTGC CAGCAACTAT
GTGCAGTGGT ACCAGCAGCG CCCGGGCAGT TCCCCCACCA CTGTGATCTA
TGAGGATAAC CAAAGACCCT CTGGGGTCCC TGATCGATTC TCTGGCTCCA
TCGACAGCTC CTCCAACTCT GCCTCCCTCA CCATCTCTGG ACTGAAGACT
GAGGACGAGG CTGACTACTA CTGTCAGTCT TATGATAGCA GCAATGTGGT
GTTCGGCGGA GGGACCAAGC TGACCGTCCT A

L37 (SEQ ID NO:73)
GATGTTGTGA TGACTCAGTC TCCACTCTCC CTGCCCGTCA CCCCTGGGGA
GCCGGCCTCC ATCTCCTGCA GGTCTAGTCA GAGCCTCCTG CATAGTAATG
GATACAACTA TTTGGATTGG TACCTGCAGA AGCCAGGGCA GTCTCCACAG
CTCCTGATCT ATTTGGGTTC TAACCGGGAC TCTGGGGTCC CAGACAGATT
CAGCGGCAGT GGGTCAGGCA CTGATTTCAC ACTGAAAATC AGCAGGGTGG
AGGCTGAGGA TGTTGGGGTT TATTACTGCA TGCAAGGTAC ACACTGGCCG
TACACTTTTG GCCAGGGGAC CAGGCTGGAG ATCAAA

L38 (SEQ ID NO:75)
   GATGTTGT GATGACTCAG TCTCCACTCT CCCTGCCCGT CACCCCTGGA
GAGTCGGCCT CCATCTCCTG CAGGTCTAGT CAGAGCCTCC TGCATAGTAA
TGGATACAAC TTTTTGGATT GGTACCTGCA GAAGCCAGGG CAGTCTCCAC
AGCTCCTGAT CTATTTGGGT TCTAATCGGG CCTCCGGGGT CCCTGACAGG
TTCAGTGGCA GTGGATCAGG CACAGATTTT ACACTGAAAA TCAGCAGAGT
GGAGGCTGAG GATGTTGGGG TTTATTACTG CATGCAAGCT CTACAAACTC
CTCTCACTTT CGGCGGAGGG ACCAAGGTGG AGATCAAA

L39 (SEQ ID NO:77)
        GA TGTTGTGATG ACTCAGTCTC CACTCTCCCT GCCCGTCACC
CCTGGAGAGC CGGCCTCCAT CTCCTGCAGG TCTAGTCAGA GCCTCCTGCA
TAGTAATGGA TACAACTATT TGGATTGGTA CCTGCAGAAG CCAGGGCAGT
CTCCACAGCT CCTGATCTAT TTGGGTTCTA ATCGGGCCTC CGGGGTCCCT
GACAGGTTCA GTGGCAGTGG ATCAGGCACA GATTTTACAC TGAAAATCAG
CAGAGTGGAG GCTGAGGATG TTGGGGTTTA TTACTGCATG CAAGCTCTAC
AAACCCCCCT CACTTTCGGC GGAGGGACCA AGGTGGAGAT CAAA

L40 (SEQ ID NO:79)
   GAAACGAC ACTCACGCAG TCTCCAGCCA CCCTGTCTTT GTCTCCAGGG
CAAAGAGCCA CCCTCTCCTG CAGGGCCAGT CAGAGTGTCT ACAACTACTT
AGCCTGGTAC CAACAGAAGC CTGGCCAGGC TCCAGGCTC CTCATCTATG
ATGCATCCAG AAGGGCAACT GGCATCCCAG CCAGGTTCAG TGGCAGTGGG
TCTGGGACAG ACTTCACTCT CACCATCAGC AGCCTAGAGC TGAAGATTT
TGCAGTTTAT TACTGTCAGC AGCGTAACAA CTGGCCGCTC ACTTTCGGTG
GAGGGACCAA GGTGGAGATC AAA

Fig. 1 (cont)

L41 (SEQ ID NO:81)
```
     GACAT CCAGTTGACC CAGTCTCCAT CCTCCCTGTC TGCTTCTGTT
GGAGACAGCG TCACCATCTC TTGCCGGGCA AGTCAGAGTC CTGGCATCTT
TTTAAATTGG TATCAGCAGA TACCAGGGAA AGCCCCTAAA CTCCTGATCT
ACGCTACATC CACTCTGGAA AGTGGGGTCC CCCCCAGGTT CACCGGCAGT
GGATCTGGGA CAGATTTCAC TCTCACCATC AGCAGTCTGC AACCTGAGGA
CTTTGCAACT TACTACTGTC AACAGAGTAA CAGTGTTCCG CTCACTTTCG
GCGGCGGGAC CAAGGTGGAG ATCAAA
```

L42 (SEQ ID NO:83)
```
     GATGT TGTGATGACT CAGTCTCCAC TCTCCCTGCC CGTCACCCCT
GGAGAGCCGG CCTCCATCTC CTGCAGGTCT AGTCAGAGCC TCCTGCATAG
TAATGGATAC AACTATTTGG ATTGGTACCT GCAGAAGCCA GGGCAGTCTC
CACAGCTCCT GATCTATTTG GTTCTAATC GGGCCTCCGG GGTCCCTGAC
AGGTTCAGTG GCAGTGGATC AGGCACAGAT TTTACACTAA AAATCAGCAG
AGTGGAGGCT GAGGATGTTG GGGTTTATTA CTGCATGCAA GCTCTACAAA
CTCCTCTAAC CTTCGGCCAA GGGACACGAC TGGAGATTAA A
```

L43 (SEQ ID NO:85)
```
     GAAATT GTGATGACGC AGTCTCCAGC CACCCTGTCT GTGTCTCCAG
GGGAAAGAGC CACCTTCTCC TGTAGGGCCA GTCAGAGTGT TGGCAGCAAC
TTAGCCTGGT ACCAGCAGAA ACCTGGCCAG GCTCCCAGGC TCCTCATCTA
TGATGCATCC AACAGGGCCA CTGGCATCCC AGCCAGGTTC AGTGGCAGTG
GGTCTGGGAC AGACTTCACT CTCACCATCA GCAGACTGGA GCCTGAAGAT
TTTGCAGTGT ATTACTGTCA GCAGCGTAGC AACTGGCCCC TCACTTTCGG
CGGAGGGACC AAGGTGGAGA TCAAA
```

L44 (SEQ ID NO:87)
```
     GATGT TGTGATGACT CAGTCTCCAC TCTCCCTGCC CGTCACCCCT
GGAGAGCCGG CCTCCATCTC CTGCAGGTCT AGTCAGAGCC TCCTGCATAG
TAATGGATAC AACTATTTGG ATTGGTACCT GCAGAAGCCA GGGCAGTCTC
CACAGCTCCT GATCTATTTG GTTCTAATC GGGCCTCCGG GGTCCCTGAC
AGGTTCAGTG GCAGTGGATC AGGCACAGAT TTTACACTGA AAATCAGCAG
AGTGGAGGCT GAGGATGTTG GGGTTTATTA CTGCATGCAA GCTCTACAAA
CTCCGCTCAC TTTCGGCGGA GGGACCAAGG TGGAGATCAA A
```

L45 (SEQ ID NO:89)
```
       GAT GTTGTGATGA CTCAGTCTCC ACTCTCCCTG CCCGTCACCC
CTGGAGAGCC GGCCTCCATC TCCTGCAGGT CTAGTCAGAG CCTCCTGCAT
AGTAATGGAT ACAACTATTT GGATTGGTAC CTGCAGAAGC CAGGGCAGTC
TCCACAGCTC CTGATCTACT TGGGTTCTAC TCGGGCCTCC GGCGTCCCTG
ACAGGTTCAG TGGCAGTGGA TCAGGCACAG ATTTTACACT GAAAATCAGC
AGAGTGGAGG CTGAGGATGT TGGGGTTTAT TACTGCATGC AAGCTCTACA
AACTCCTTAC ACTTTCGGCG AGGGACCAA GGTGGAGATC AAA
```

Fig. 1 (cont)

L46 (SEQ ID NO:91)
```
     GATGT TGTGATGACT CAGTCTCCAC TCTCCCTGCC CGTCACCCCT
GGAGAGCCGG CCTCCATCTC CTGCAGGTCT AGTCAGAGCC TCCTGCATAG
TAATGGATAC AACTATTTGG ATTGGTACCT GCAGAAGCCA GGGCAGTCTC
CACAGCTCCT GATCTATTTG GGTTCTAATC GGGCCTCCGG GGTCCCTGAC
AGGTTCAGTG GCAGTGGATC AGGCACAGAT TTTACACTGA AAATCAGCAG
AGTGGAGGCT GAGGATGTTG GGGTTTATTA CTGCATGCAA GCTCTACAAA
CTCCCCTCAC TTTCGGCGGA GGGACCAAGG TGGAGATCAA A
```

L47 (SEQ ID NO:93)
```
     GATGT TGTGATGACT CAGTCTCCAC TCTCCCTGCC CGTCACCCCT
GGAGAGCCGG CCTCCATCTC CTGCAGGTCT AGTCAGAGCC TCCTGCATAC
TAATGGATAC AACTATTTGG ATTGGTACCT GCAGAAGCCA GGGCAGTCTC
CACGGCTCCT GATCTATTTG GGTTTTAATC GGGCCTCCGG GGTCCCTGAC
AGGTTCAGTG GCAGTGGATC AGGCACAGAT TTTACACTGA AAATCAGCAG
AGTGGAGGCT GAGGATGTTG GGGTTTATTA CTGTATGCAA GGTCTACAAA
CTCCCCTCAC TTTCGGCGGA GGGACCAAGG TGGAGATCAA A
```

L48 (SEQ ID NO:95)
```
  GATGTTGTG ATGACTCAGT CTCCACTCTC CCTGCCCGTC ACCCCTGGAG
AGCCGGCCTC CATCTCCTGC AGGTCTAGTC AGAGCCTCCT GCATAGTAAT
GGATACAACT ATTTGGATTG GTACCTGCAG AAGCCAGGGC AGTCTCCACA
GCTCCTGATC TATTTGGGTT CTAATCGGGC CTCCGGGGTC CCTGACAGGT
TCAGTGGCAG TGGATCAGGC ACAGATTTTA CACTGAAAAT CAGCAGGGTG
GAGGCTGAGG ATGTTGGGGT TTATTATTGC ATGCAAGCTA CACACTGGCC
GTACACTTTT GGCCAGGGGA CCAAGCTGGA GATCAAA
```

L49 (SEQ ID NO:97)
```
     AATTTTA TGCTGACTCA GCCCCACTCT GTGTCGGAGT CTCCGGGGAA
GACGGTAAGC ATCTCCTGCA CCCGCAACAG TGGCAGCATT GCCAGCAACT
TTGTGCAGTG GTACCAGCAG CGCCCGGGCA GTGCCCCCAC CATTGTAATC
TATGAGGATA ACCAAAGACC CTCTGCGGTC CCTACTCGGT TCTCTGGCTC
CATCGACAGG TCCTCCAACT CTGCCTCCCT CACCATCTCT GGACTGACGA
CTGAGGACGA GGCTGACTAC TACTGTCAGT CTTATGATAG CGCCAATGTC
ATTTTCGGCG GGGGGACCAA GCTGACCGTC CTA
```

L50 (SEQ ID NO:99)
```
     GAAACG ACACTCACGC AGTCTCCAGG CACCCTGTCT TTGTCTCCAG
GGGAGAGAGC CACCCTCTCC TGCAGGGCCA GTCAGACTAT CAGCAGCAGC
CACTTAGCCT GGTACCAGCA GAAACCTGGC CAGTCTCCCA GGCTCCTCAT
CTATGGTGCG GGCTACAGGG CCACCGGCAT TCCAGACAGG TTCAGTGGCA
GTGGGTCTGG CACAGACTTC ACTCTCACCA TCAGCAGACT GGAGCCTGAA
GATTTTGCAG TGTATTACTG TCAGCACTAT GGTAGTTCAC TCCGGACGTT
CGGCCAAGGG ACCAAGGTGG AAATCAAA
```

Fig. 1 (cont)

L51 (SEQ ID NO:101)
```
     AATTTT ATGCTGACTC AGCCCCACTC TGTGTCGGAG TCTCCGGGGA
AGACGGTAAC CATCTCCTGC ACCGGCAGCG GTGGCAACAT TGCCAGCAAT
TATGTGCAGT GGTACCAGCA GCGCCCGGGC AGGGCCCCCA CCACTGTGAT
CTATGAGGAT AATCGAACAC CCTCTGGGGT CCCTGATCGG TTCTCTGGCT
CCATCGACAG CTCCTCCAAC TCTGCCTCCC TCACCATCTC TGGACTGAAG
ACTGAAGACG AGGCTGACTA CTACTGTCAG TCTTATGATC CCTACAATCG
AGTGTTCGGC GGAGGGACCA AGCTGACCGT CCTA
```

L51 (SEQ ID NO:103)
```
       GAAA TTGTGATGAC GCAGTCTCCA CTCTCCCTGC CCGTCACCCC
TGGAGAGCCG GCCTCCATCT CCTGCAGGTC TAGTCAGAGC CTCCTGCATA
CTAATGGATA CGACTATTTG GATTGGTACC TGCAGAAGCC AGGGCAGTCT
CCACAGCTTC TGATCTATTT GGGTTCTACT CGGGCCTCCG GGTCCCTGA
CAGGTTCAGT GGCAGTGGAT CGGGCACAGA TTTTACACTG AAAATCAGCA
GAGTGGAGGC TGAGGATGTT GGGGTTTATT ACTGCATGCA AGCTTTTCAA
ACTCCGCTCA CTTTCGGCGG AGGGACCAAG ATGGAGATCA AA
```

H1 (SEQ ID NO:105)
```
GAGGTGCAGC TGGTGGAGAC CGGCCCAGGA CTGGTGAAGC CTTCGGGGAC
CCTGTCCCTC ACCTGCGCTG TCTCTGGTGG CTCCATCAGC AGTAGTAACT
GGTGGAGTTG GGTCCGCCAG CCCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCCGCGGAC ACGGCCGTGT ATTACTGTGC GAGATTTAAT
TACTATGATA GTAGTGTCTG GGGCCAGGGA ACCCTGGTCA CCGTCTCAAG
C
```

H2 (SEQ ID NO:107)
```
GAGGTGCAGC TGGTGGAGAC CGGCCCAGGA CTGGTGAAGC CTTCGGGGAC
CCTGTCCCTC ACCTGCGCTG TCTCTGGTGG CTCCATCAGC AGTAGTAACT
GGTGGAGTTG GGTCCGCCAG CCCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCCGCGGAC ACGGCCGTGT ATTACTGTGC GAGAGGGGTT
GAGCAGATTG ACTACTGGGG CCAGGGAACC CTGGTCACCG TCTCAAGC
```

H3 (SEQ ID NO:109)
```
CAGGTGCAGC TGCAGGAGTC GGGCCCAGGA CTGGTGAAGC CTTCGGGGAC
CCTGTCCCTC ACCTGCGCTG TCTCTGGTGG CTCCATCAGC AGTAGTAACT
GGTGGAGTTG GGTCCGCCAG CCCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC TGCCGCGGAC ACGGCCGTGT ATTACTGTGC GAAAAATTTA
GCAGCAGGGG CGGTTGCCTA CTGGGGCCAG GGCACCCTGG TCACCGTCTC
AAGC
```

Fig. 1 (cont)

H4 (SEQ ID NO:111)
 CAGGTGCAG CTACAGCAGT GGGGCGCAGG ACTGTTGAAG CCTTCGGAGA
CCCTGTCCCT CACCTGCGCT GTCTCTGGTG GGTCCTTCAG TGGTTACTAC
TGGAGCTGGA TCCGTCAGCC CCCAGGGAAG GGGCTGGAGT GGATTGGGGA
AATCAATCAT AGTGGAAGTA CCAACTACAA CCGGTCCCTC AAGAGTCGAG
TCACCATATC AGTAGACACG TCCAAGAACC AGTTCTCCCT GAAGCTGAGC
TCTGTGACCG CCGCGGACAC GGCTGTGTAT TACTGTGCGA GACTTTCATA
TGGTTCGGGC GTTGACTACT GGGGCCAGGG CACCCTGGTC ACCGTCTCAA
GC

H5 (SEQ ID NO:113)
         C AGCTGCAGCT GCAGGAGTCG GGCCCAGGAC TGGTGAAGCC
TTCACAGACC CTGTCCCTCA CCTGCACTGT CTCTGGTGGC TCCATCAGCA
GTAGTAACTG GTGGAGTTGG GTCCGCCAGC CCCCAGGGAA GGGGCTGGAG
TGGATTGGGG AAATCTATCA TAGTGGGAGC ACCAACTACA ACCCGTCCCT
CAAGAGTCGA GTCACCATAT CAGTAGACAA GTCCAAGAAC CAGTTCTCCC
TGAAGCTGAG CTCTGTGACC GCCGCGGACA CGGCCGTGTA TTACTGTGCG
AGGTATAGCA GCAGCCGCAA TGATGCTTTT GATATCTGGG GCCAAGGGAC
AATGGTCACC GTCTCAAGC

H6 (SEQ ID NO:115)
CAGGTGCAGC TGCAGGAGTC GGGCCCAGGA CTGGTGAAGC CTTCGGGGAC
CCTGTCCCTC ACCTGCGCTG TCTCTGGTGG CTCCATCAGC AGTAGTAACT
GGTGGAGTTG GGTCCGCCAG CCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCCGCGGAC ACGGCCGTGT ATTACTGTGC GAGAGATGGG
CAGCTGGATG CTTTTGATAT CTGGGGCCAA GGGACAATGG TCACCGTCTC
AAGC

H7 (SEQ ID NO:117)
CAGGTGCAGC TGCAGGAGTC GGGCCCAGGA CTGGTGAAGC CTTCGGGGAC
CCTGTCCCTC ACCTGCGCTG TCTCTGGTGG CTCCATCAGC AGTAGTAACT
GGTGGAGTTG GGTCCGCCAG CCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCCGCGGAC ACGGCCGTGT ATTACTGTGC GAGATTTTGG
GACTACTACG GTATGGACGT CTGGGGCCAA GGGACCACGG TCACCGTCTC
AAGC

Fig. 1 (cont)

H8 (SEQ ID NO:119)
```
     CAGGTG CAGCTACAGC AGTGGGGCCC AGGACTGGTG AAGCCTTCGG
GGACCCTGTC CCTCACCTGC GCTGTCTCTG GTGGCTCCAT CAGCAGTAGT
AACTGGTGGA GTTGGGTCCG CCAGCCCCCA GGGAAGGGGC TGGAGTGGAT
TGGGGAAATC TATCATAGTG GGAGCACCAA CTACAACCCG TCCCTCGAGA
GTCGAGTCAC CATATCAGTA GACAAGTCCA AGAACCAGTT CTCCCTGAAG
CTGAGCTCTG TGACCGCCGC AGACACGGCC GTGTATTACT GTGCGAGAGA
TCGGTACTAC GGTATGGACG TCTGGGGCCA AGGGACCACG GTCACCGTCT
CAAGC
```

H9 (SEQ ID NO:121)
```
        G AGGTGCAGCT GGTCGAGTCT GGCCCAGGAC TGGTGAAGCC
TTCGGGGACC CTGTCCCTCA CCTGCGCTGT CTCTGGTGGC TCCATCAGCA
GTAGTAACTG GTGGAGTTGG GTCCGCCAGC CCCCAGGGAA GGGGCTGGAG
TGGATTGGGT ACATCTATTA TAGTGGGAGC ACCTACTACA ACCCGTCCCT
CAAGAGTCGA GTCACCATGT CAGTAGACAC GTCCAAGAAC CAGTTCTCCC
TGAAGCTGAG CTCTGTGACC GCCGCAGACA CGGCCGTGTA TTACTGTGCG
AGATGGAGCT ACTTGGATGC TTTTGATATC TGGGGCCAAG GACAATGGT
CACCGTCTCA AGC
```

H10 (SEQ ID NO:123)
```
    GAGGTGC AGCTGGTGGA GTCTGGCCCA GGACTGGTGA AGCCTTCGGG
GACCCTGTCC CTCACCTGCG CTGTCTCTGG TGGCTCCATC AGCAGTAGTA
ACTGGTGGAG TTGGGTCCGC CAGCCCCAG GGAAGGGGCT GGAGTGGATT
GGGGAAATCT ATCATAGTGG GAGCACCAAC TACAACCCGT CCCTCAAGAG
TCGAGTCACC ATATCAGTAG ACAAGTCCAA GAACCAGTTC TCCCTGAAGC
TGAGCTCTGT GACCGCCGCG GACACGGCCG TGTATTACTG TGCGAGAGAT
TACGATATTT TCGGTATGGA CGTCTGGGGC CAAGGGACCA CGGTCACCGT
CTCAAGC
```

H11 (SEQ ID NO:125)
```
       CAGCT GCAGCTGCAG GAGTCGGGCC CAGGACTGGT GAAGCCTTCG
GGGACCCTGT CCCTCACCTG CGCTGTCTCT GGTGGCTCCA TCAGCAGTAG
TAACTGGTGG AGTTGGGTCC GCCAGCCCCC AGGGAAGGGG CTGGAGTGGA
TTGGGGAAAT CTATCATAGT GGGAGCACCA ACTACAACCC GTCCCTCAAG
AGTCGAGTCA CCATATCAGT AGACAAGTCC AAGAACCAGT CCTCCCTGAA
GCTGAGCTCT GTGACCGCCG CGGACACGGC CGTGTATTAC TGTGCGAGAG
CCAACAGAGA TGATGCTTTT GATATCTGGG GCCAAGGGAC AATGGTCACC
GTCTCAAGC
```

Fig. 1 (cont)

H12 (SEQ ID NO:127)
```
    GAGGTGC AGCTGGTGGA GTCTGGGGGA GGCTTGGTAC AGCCGGGGGG
GTCCCTGAGA CTCTCCTGTG CAGCCTCTGG ATTCACCTTT AGCAGCTATG
CCATGAGCTG GGTCCGCCAG GCTCCAGGGA AGGGGCTGGA GTGGGTCTCA
GCTATTAGTG GTAGTGGTGG TAGCACATAC TACGCAGACT CCGTGAAGGG
CCGGTTCACC ATCTCCAGAG ACAATTCCAA GAACACGCTG TATCTGCAAA
TGAACAGTCT GAGCGCCGAC GACACGGCCG TATATTTCTG TGCGTCGGGT
GGCTGGTACG GGGACTACTT TGACTACTGG GGCCAGGGAA CCCTGGTCAC
CGTCTCAAGC
```

H13 (SEQ ID NO:129)
```
CAGGTGCAGC TGCAGGAGTC CGGCCCAGGA CTGGTGAAGC CTTCGGAGAC
CCTGTCCCTC ACCTGCACTG TCTCTGGTGG CTCCATCAGC AGTAGTAACT
GGTGGAGTTG GGTCCGCCAG CCCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCCGCGGAC ACGGCCGTGT ATTACTGTGC GAGAGAAGGG
AACCGAACGG TGACTAGTGC TTTTGATATC TGGGGCCAAG GGACAATGGT
CACCGTCTCA AGC
```

H14 (SEQ ID NO:131)
```
   CAGGTGCA GCTGCAGGAG TCCGGCCCAG GACTGGTGAA GCCTTCGGGG
ACCCTGTCCC TCACCTGCGC TGTCTCTGGT GGCTCCATCA GCAGTAGTAA
CTGGTGGAGT TGGGTCCGCC AGCCCCCAGG GAAGGGGCTG GAGTGGATTG
GGGAAATCTA TCATAGTGGG AGCACCAACT ACAACCCGTC CCTCAAGAGT
CGAGTCACCA TATCAGTAGA CAAGTCCAAG AACCAGTTCT CCCTGAAGCT
GAGCTCTGTG ACCGCTGCGG ACACGGCCGT GTACTACTGT GCGAGAGGGC
TGGGGGATAG TAGTGGTTAT ATCCTTTGGG GCCAAGGGAC AATGGTCACC
GTCTCAAGC
```

H15 (SEQ ID NO:133)
```
     CAGGTG CAGCTGCAGG AGTCCGGCCC AGGACTGGTG AAGCCTTCGG
GGACCCTGTC CCTCACCTGC GCTGTCTCTG GTGGCTCCAT CAGCAGTAGT
AACTGGTGGA GTTGGGTCCG CCAGCCCCCA GGGAAGGGGC TGGAGTGGAT
TGGGGAAATC TATCATAGTG GGAGCACCAA CTACAACCCG TCCCTCAAGA
GTCGAGTCAC CATATCAGTA GACAAGTCCA AGAACCAGTT CTCCCTGAAG
CTGAGCTCTG TGACCGCTGC GGACACGGCC GTGTACTACT GTGCGAGAGG
GCTGGGGGAT AGTAGTGGTT ATATCCTTTG GGGCCAAGGG ACAATGGTCA
CCGTCTCAAG C
```

Fig. 1 (cont)

H16 (SEQ ID NO:135)
```
    CAGGTG CAGCTGCAGG AGTCGGGCCC AGGACTGGTG AAGCCTTCGG
GGACCCTGTC CCTCACCTGC GCTGTCTCTG GTGGCTCCAT CAGCAGTAGT
AACTGGTGGA GTTGGGTCCG CCAGCCCCCA GGGAAGGGGC TGGAGTGGAT
TGGGGAAATC TATCATAGTG GGAGCACCAA CTACAACCCG TCCCTCAAGA
GTCGAGTCAC CATATCAGTA GACAAGTCCA AGAACCAGTT CTCCCTGAAG
CTGAGCTCTG TGACCGCCGC GGACACGGCC GTGTATTACT GTGCGAGATG
GACCGGGCGT ACTGATGCTT TTGATATCTG GGGCCAAGGG ACAATGGTCA
CCGTCTCAAG C
```

H17 (SEQ ID NO:137)
```
      CAGG TGCAGCTGCA GGAGTCCGGC CCAGGACTGG TGAAGCCTTC
GGGGACCCTG TCCCTCACCT GCGCTGTCTC TGGTGGCTCC ATCAGCAGTA
GTAACTGGTG GAGTTGGGTC CGCCAGCCCC CAGGGAAGGG GCTGGAGTGG
ATTGGGGAAA TCTATCATAG TGGGAGCACC AACTACAACC CGTCCCTCAA
GAGTCGAGTC ACCATATCAG TAGACAAGTC CAAGAACCAG TTCTCCCTGA
AGCTGAGCTC TGTGACCGCC GCGGACACGG CCGTGTATTA CTGTGCGAGA
CAAGGGGCGT TAGATGCTTT TGATATCTGG GGCCAAGGGA CCACGGTCAC
CGTCTCAAGC
```

H18 (SEQ ID NO:139)
```
GCAGCTGGTG GAGTCCGGGG GAGGCGTGGT CCGACCTGGG GGGTCCCTGA
GACTCTCCTG TGCAGCGTCT GGATTCACCT TTAGCAGCTA TGCCATGAGC
TGGGTCCGCC AGGCTCCAGG GAAGGGGCTG GAGTGGGTCT CAACTATTAG
TGGTAGTGGT GGTAGCACAT ACTACGCAGA CTCCGTGAAG GGCCGGTTCA
CCATCTCCAG AGACAATTCC AAGAACACGC TGTATCTGCA GATGAACAGC
CTGAGAGCCG AGGACACGGC CGTATATTAC TGTGCGAAAG AGCGTGGCAG
TGGCTGGTCC TTAGACAATA TGGACGTCTG GGGCCAAGGG ACCACGGTCA
CCGTCTCAAG C
```

H19 (SEQ ID NO:141)
```
CAGGTGCAGC TGGTGGAGTC TGGCCCAGGA CTGGTGAAGC CTTCGGGGAC
CCTGTCCCTC ACCTGCGCTG TCTCTGGTGG CTCCATCAGC AGTAGTAACT
GGTGGAGTTG GGTCCGCCAG CCCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCTGCGGAC ACGGCCGTGT ATTACTGTGC GAGAGATAGC
AGTGGGTTCT ACGGTATGGA CGTCTGGGGC CAAGGGACCA CGGTCACCGT
CTCAAGC
```

Fig. 1 (cont)

H20 (SEQ ID NO:143)
```
     CAGGTG CAGCTGCAGG AGTCGGGCCC AGGACTGGTG AAGCCTTCGG
GGACCCTGTC CCTCACCTGC GCTGTCTCTG GTGGCTCCAT CAGCAGTAGT
AACTGGTGGA GTTGGGTCCG CCAGCCCCCA GGGAAGGGGC TGGAGTGGAT
TGGGGAAATC TATCATAGTG GGAGCACCAA CTACAACCCG TCCCTCAAGA
GTCGAGTCAC CATATCAGTA GACAAGTCCA AGAACCAGTT CTCCCTGAAG
CTGAGCTCTG TGACTGCCGC GGACACGGCC GTGTATTACT GTGCGAGAAG
CAGCAGCTGG TACTGGAATG CTTTTGATAT CTGGGGCCAA GGGACAATGG
TCACCGTCTC AAGC
```

H21 (SEQ ID NO:145)
```
     CAGGTG CAGCTACAGC AGTGGGGCCC AGCACTGGTG AAGCCTTCGG
GGACCCTGTC CCTCACCTGC TCTGTCTCTG GTGTCTCCAT CACCAGTAAT
ATCTGGTGGA GTTGGGTCCG CCAGTCCCCA GGGAAGGGGC TGGAGTGGAT
TGGGGAAGTC TATCATAGTG GGAGCACCAA CTACAACCCG TCCCTCAAGA
GTCGAGTCAC CATATCAGTA GACAAGTCCA AGAACCAGTT CTCCCTGAAG
CTGAGCTCTG TGACCGCCGC GGACACGGCT GTGTATTACT GTGCGGGGTA
CCGTAGCTTC GGGGAGTCCT ACTGGGGCCA GGGAACCCTG GTCACCGTCT
CAAGC
```

H22 (SEQ ID NO:147)
```
    CAGGTGCA GCTACAGCAG TGGGGCGCAG GGCTGTTGAA GCCTTCGGAG
ACCCTGTCTC TCACCTGCGT TGTCTATGGT GGGTCCTTCA GCGATTTCTA
CTGGAGCTGG ATCCGCCAGC CCCCAGGGAA GGGGCCAGAG TGGATTGGGG
AAGTCAATCC TAGAGGAAGC ACCAACTACA ACCCGTCCCT CAAGAGTCGA
GCCACCATAT CACTAGACAC GTCCAAGAAC CAGTTCTCCC TGAAGCTGAG
TTCTGTGACC GCCGCGGACA CGGCTGTGTA TTTCTGTGCG AGAGGTCCTC
GGCCCGGGAG AGATGGCTAC AATTACTTTG ACAACTGGGG CCAGGGCACC
CTGGTCACCG TCTCAAGC
```

H23 (SEQ ID NO:149)
```
CAGGTGCAGC TGCAGGAGTC GGGCCCAGGA CTGGTGAAGC CTTCGGAGAC
CCTGTCCCTC ACCTGCACTG TCTCTGGTGG CTCCATCAGC AGTAGTAACT
GGTGGAGTTG GGTCCGCCAG CCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCCGCGGAC ACGGCCGTGT ATTACTGTGC GAGAGGTATA
GCAGCAGCTG GTCAAGGTGA CTACTGGGGC CAGGGAACCC TGGTCACCGT
CTCAAGC
```

Fig. 1 (cont)

H24 (SEQ ID NO:151)
CAGGTGCAGC TGCAGGAGTC GGGCCCAGGA CTGGTGAAGC CTTCGGAGAC
CCTGTCCCTC ACCTGCACTG TCTCTGGTGG CTCCATCAGC AGTAGTAGTT
ACTACTGGGG CTGGATCCGC CAGCCCCCAG GGAAGGGGCT GGAGTGGATT
GGGAGTATCT ATTATAGTGG GAGCACCTAC TACAACCCGT CCCTCAAGAG
TCGAGTCACC ATATCCGTAG ACACGTCCAA GAACCAGTTC TCCCTGAAGC
TGAGCTCTGT GACCGCCGCG GACACGGCCG TGTATTACTG TGCGAGAGAT
GGGGGATACT ACTACTACGG TATGGACGTC TGGGGCCAAG GACCACGGT
CACCGTCTCA AGC

H25 (SEQ ID NO:153)
     CAGGTG CAGCTGCAGG AGTCGGGCCC AGGACTGGTG AAGCCTTCGG
GGACCCTGTC CCTCACCTGC GCTGTCTCTG GTGGCTCCAT CAGCAGTAGT
AACTGGTGGA GTTGGGTCCG CCAGCCCCCA GGGAAGGGGC TGGAGTGGAT
TGGGGAAATC TATCATAGTG GGAGCACCAA CTACAACCCG TCCCTCAAGA
GTCGAGTCAC CATATCAGTA GACAAGTCCA AGAACCAGTT CTCCCTGAAG
CTGAGCTCTG TGACCGCCGC GGACACGGCC GTGTATTACT GTGCGAGTAG
TGGTTATGAT GCTTTTGATA TCTGGGGCCA AGGGACCACG GTCACCGTCT
CAAGC

H26 (SEQ ID NO:155)
      CAGGT GCAGCTGCAG GAGTCGGGCC CAGGACTGGT GAAGCCTTCG
GGGACCCTGT CCCTCACCTG CGCTGTCTCT GGTGGCTCCA TCAGCAGTAG
TAATTGGTGG AGTTGGGTCC GCCAGCCCCC AGGGAAGGGG CTGGAGTGGA
TTGGGGAAAT CTATCATAGT GGGAGCACCA ACTACAACCC GTCCCTCAAG
AGTCGAGTCA CCATATCAGT AGACAAGTCC AAGAACCAGT TCTCCCTGAA
GCTGAGCTCT GTGACCGCCG CGGACACGGC CGTGTATTAC TGTGCACGAT
ACAGCTATGG AACGGTAGGA ATTGACTACT GGGGCCAGGG AACCCTGGTC
ACCGTCTCAA GC

H27 (SEQ ID NO:157)
      GAGGT GCAGCTGGTG CAGTCTGGGG GAGGCGTGGT CCAGCCTGGG
ACGTCCCTGA GACTCTCCTG TGCAGCCTCT GGATTCAGCT TCAGAAGTCA
TGGCATGCAC TGGGTCCGCC AGGCTCCAGG CAAGGGGCTG GAGTGGGTGG
CAGTTATATC ATATGATGGA AGTAATAAAT ACTATGCAGA CTCCGTGAAG
GGCCGATTCA CCATCTCCAG AGACAATTCC AAGAACACGC TGTATCTGCA
AATGAACAGC CTGAGAGCTG AGGACACGGC TGTGTATTAC TGTGCGACTA
TAGGGCCGGG GGGATTTGAC TACTGGGGCC AGGGCACCCT GGTCACCGTC
TCAAGC

Fig. 1 (cont)

H28 (SEQ ID NO:159)
```
      CAG GTGCAGCTGC AGGAGTCCGG CCCAGGACTG GTGAAGCCTT
CGGAGACCCT GTCCCTCACC TGCACTGTCT CTGGTGGCTC CATTAGAAAT
TACTACTGGA GTTGGATCCG GCAGCCCCCA GGGAAGGGAC TGGAGTGGAT
TGGGTATATT TCTGACAGTG GGAATACCAA CTACAATCCC TCCCTCAAGA
GTCGAGTCAC CATATCAGTA GACACGTCCA AGAACCAGTT CTCCCTAAAG
CTGACCTCTG TGACCGCCAC AGACACGGCT GCGTATTTCT GTGCGAGACA
TCGAAGCAGC TGGGCATGGT ACTTCGATCT CTGGGGCCGT GGCACCCTGG
TCACCGTCTC AAGC
```

H29 (SEQ ID NO:161)
```
        C AGGTGCAGCT GCAGGAGTCG GGCCCAGGAC TGGTGAAGCC
TTCGGAGACC CTGTCCCTCA CCTGCGCTGT CTCTGGTGGC TCCATCAGCA
GTAGTAACTG GTGGAGTTGG GTCCGCCAGC CCCCAGGGAA GGGGCTGGAG
TGGATTGGGG AAATCTATCA TAGTGGGAGC ACCAACTACA ACCCGTCCCT
CAAGAGTCGA GTCACCATAT CAGTAGACAA GTCCAAGAAC CAGTTCTCCC
TGAAGCTGAG CTCTGTGACC GCCGCGGACA CGGCCGTGTA TTACTGTGCG
AGAGTGGGCA GTGGCTGGTA CGTTGACTAC TGGGGCCAGG GAACCCTGGT
CACCGTCTCA AGC
```

H30 (SEQ ID NO:163)
```
    CAGGTG CAGCTGCAGG AGTCCGGCCC AGGACTGGTG AAGCCTTCGG
GGACCCTGTC CCTCACCTGC GCTGTCTCTG GTGGCTCCAT CAGCAGTAGT
AACTGGTGGA GTTGGGTCCG CCAGCCCCCA GGGAAGGGGC TGGAGTGGAT
TGGGGAAATC TATCATAGTG GGAGCACCAA CTACAACCCG TCCCTCAAGA
GTCGAGTCAC CATATCAGTA GACAAGTCCA AGAACCAGTT CTCCCTGAAG
CTGAGCTCTG TGACCGCCGC GGACACGGCC GTGTATTACT GTGCGAGAGT
TTCTGGCTAC TACTACTACG GTATGGACGT CTGGGGCCAA GGGACCACGG
TCACCGTCTC AAGC
```

H31 (SEQ ID NO:165)
```
   GAGGTCCA GCTGGTACAG TCTGGGGGAG GCGTGGTCCA GCCTGGGAGG
TCCCTGAGAC TCTCCTGTGC AGCCTCTGGA TTCACCTTCA GTAGCTATGG
CATGCACTGG GTCCGCCAGG CTCCAGGCAA GGGGCTGGAG TGGGTGGCAG
TTATATCATA TGATGGAAGT AATAAATACT ATGCAGACTC CGTGAAGGGC
CGATTCACCA TCTCCAGAGA CAATTCCAAG AACACGCTGT ATCTGCAAAT
GAACAGCCTG AGAGCTGAGG ACACGGCTGT GTATTACTGT GCGAAAGCGT
ATAGCAGTGG CTGGTACGAC TACTACGGTA TGGACGTCTG GGGCCAAGGG
ACCACGGTCA CCGTCTCAAG C
```

Fig. 1 (cont)

H32 (SEQ ID NO:167)
CAGGTGCAGC TGCAGGAGTC GGGCCCAGGA CTGGTGAAGC CTTCGGGGAC
CCTGTCCCTC ACCTGCGCTG TCTCTGGTGG CTCCATCAGC AGTAGTAACT
GGTGGAGTTG GGTCCGCCAG CCCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCCGCGGAC ACGGCCGTGT ATTACTGTGC GAGAGCCAGC
GTTGATGCTT TTGATATCTG GGGCCAAGGG ACAATGGTCA CCGTCTCAAG
C

H33 (SEQ ID NO:169)
    CAGGTG CAGCTGCAGG AGTCCGGCCC AGGACTGGTG AAGCCTTCGG
GGACCCTGTC CCTCACCTGC GCTGTCTCTG GTGGCTCCAT CAGCAGTAGT
AACTGGTGGA GTTGGGTCCG CCAGCCCCCA GGGAAGGGGC TGGAGTGGAT
TGGGGAAATC TATCATAGTG GGAGCACCAA CTACAACCCG TCCCTCAAGA
GTCGAGTCAC CATATCAGTA GACAAGTCCA AGAACCAGTT CTCCCTGAAG
CTGAGCTCTG TGACCGCTGC GGACACGGCC GTGTACTACT GTGCGAGAGG
GCTGGGGGAT AGTAGTGGTT ATATCCTTTG GGGCCAAGGG ACAATGGTCA
CCGTCTCAAG C

H34 (SEQ ID NO:171)
       CAGGTA CAGCTGCAGC AGTCAGGCCC AGGACTGGTG AAGCCTTCGG
GGACCCTGTC CCTCACCTGC GCTGTCTCTG GTGGCTCCAT CAGCAGTAGT
AACTGGTGGA GTTGGGTCCG CCAGCCCCCA GGGAAGGGGC TGGAGTGGAT
TGGGGAAATC TATCATAGTG GGAGCACCAA CTACAACCCG TCCCTCAAGA
GTCGAGTCAC CATATCAGTA GACAAGTCCA AGAACCAGTT CTCCCTGAAG
CTGAGCTCTG TGACTCCCGA GGACACGGCT GTGTATTACT GTGCAAGAGA
TCACGGCCCC TTTGACTACT GGGGCCGGGG AACCCTGGTC ACCGTCTCAA
GC

H35 (SEQ ID NO:173)
        CAGGT GCAGCTGGTG CAATCTGGGG GAGGCGTGGT CCAGCCTGGG
AGGTCCCTGA GACTCTCCTG TGCAGCCTCT GGATTCGCCT TCAGTAGCTA
TGGCATGCAC TGGGTCCGCC AGGCTCCAGG GAAGGGGCTG GAGTGGGTTT
CATACATTAG TAGTAGTAGT AGTACCATAT ACTACGCAGA CTCTGTGAAG
GGCCGATTCA CCATCTCCAG AGACAATTCC AAGAACACGC TGTATCTGCA
AATGAACAGC CTGAGAGCCG AGGACACGGC TGTGTATTAC TGTGCGAGAG
ATCGATTTGG GTCGGGCAC TTGCCCGACT ACTGGGGCCA GGGAACCCTG
GTCACCGTCT CAAGC

Fig. 1 (cont)

H36 (SEQ ID NO:175)
      CAGGT GCAGCTACAG CAGTGGGGCG CAGGACTGTT GAAGCCTTCG
GAGACCCTGT CCCTCACCTG CGCTGTCTAT GGTGGGTCCT TCAGTGGTTA
CTACTGGAGC TGGATCCGCC AGCCCCAGG GAAGGGGCTG GAGTGGATTG
GGGAAATCAA TCATAGTGGA AGCACCAACT ACAACCCGTC CCTCAAGAGT
CGAGTCACCA TATCAGTAGA CACGTCCAAG AACCAGTTCT CCCTGAAGCT
GAGCTCTGTG ACCGCCGCGG ACACGGCTGT GTATTACTGT GCGAGAGTTG
GGTATAGCAG TGGCCGTGAC GTTGACTACT GGGGCCAGGG CACCCTGGTC
ACCGTCTCAA GC

H37 (SEQ ID NO:177)
      GAGGTCC AGCTGGTGGA GTCTGGCCCA GGACTGGTGA AGCCTTCGGG
GACCCTGTCC CTCACCTGCG CTGTCTCTGG TGGCTCCATC AGCAGTAGTA
ACTGGTGGAG TTGGATCCGG CAGCCCCCAG GGAAGGGGCT GGAGTGGATT
GGGGAAATCT ATCATAGTGG GAGCACCAAC TACAACCCGT CCCTCAAGAG
TCGAGTCACC ATATCAGTAG ACAAGTCCAA GAACCAGTTC TCCCTGAAGC
TGAGCTCTGT GACCGCCGCG GACACGGCCG TGTATTACTG TGCGAGAGAT
AGCAGCAGCT GGTACTACGG TATGGACGTC TGGGGCCAAG GACCACGGT
CACCGTCTCA AGC

H38 (SEQ ID NO:179)
       GAGGT CCAGCTGGTG GAGTCCGGCC CAGGACTGGT GAAGCCTTCG
GAGACCCTGT CCCTCACCTG CGCTGTCTCT GGTGGCTCCA TCAGCAGTAG
TAACTGGTGG AGTTGGGTCC GCCAGCCCCC AGGGAAGGGG CTGGAGTGGA
TTGGGGAAAT CTATCATAGT GGGAGCACCA ACTACAACCC GTCCCTCAAG
AGTCGAGTCA CCATATCAGT AGACAAGTCC AAGAACCAGT TCTCCCTGAA
GCTGAGCTCT GTGACCGCTG CGGACACGGC CGTATATTAT TGTGCGAGAT
CGACGTGGTC CCTTGACTAC TGGGGCCAGG GCACCCTGGT CACCGTCTCA
AGC

H39 (SEQ ID NO:181)
  GAGGTCCAG CTGGTGGAGT CTGGCCCAGG ACTGGTGAAG CCTTCGGGGA
CCCTGTCCCT CACCTGCGCT GTCTCTGGTG GCTCCATCAG CAGTAGTAAC
TGGTGGAGTT GGGTCCGCCA GCCCCCAGGG AAGGGGCTGG AGTGGATTGG
GGAAATCTAT CATAGTGGGA GCACCAACTA CAACCCGTCC CTCAAGAGTC
GAGTCACCAT ATCAGTAGAC AAGTCCAAGA ACCAGTTCTC CCTGAAGCTG
AGCTCTGTGA CCGCTGCGGA CACGGCCGTA TATTACTGTG CGAGACTCTC
GTTTGCCGAT CCTTTTGATA TCTGGGGCCA AGGACAATG GTCACCGTCT
CAAGC

Fig. 1 (cont)

H40 (SEQ ID NO:183)
CAGGTCCAGC TGGTGCAGTC TGGGGCTGAG GTGAAGAAGC CTGGGTCCTC
GGTGAAGGTC TCCTGCAAGG CTTCTGGAGG CACCTTCAGC AGCTATGCTA
TCAGCTGGGT GCGACAGGCC CCTGGACAAG GGCTTGAGTG GATGGGAAGG
ATCATCCCCA TCCTTGGTAT AGCAAACTAC GCACAGAAGT TCCAGGGCAG
AGTCACGATT ACCGCGGACA AATCCACGAG CACAGCCTAC ATGGAGCTGA
GCAGCCTGAG ATCTGAGGAC ACGGCCGTGT ATTACTGTGC ATATGGTTCG
GGGAGTTATT ACGACTACTA CTACATGGAC GTCTGGGGCA AAGGGACCAC
GGTCACCGTC TCAAGC

H41 (SEQ ID NO:185)
    GAGGTCC AGCTGGTGCA GTCTGGGGGA GGCTTGGTCC AGCCTGGGGG
GTCCCTGAGA CTCTCCTGTT CAGCCTCCGG ATTCACCTTC AGTAGCTATG
CTATGCACTG GGTCCGCCAG GCTCCAGGGA AGGGACTGGA ATATGTTTCA
ACTATTAGTA GTAATGGGGA TAGCACATAC TACGCAGACT CCGTGAAGGG
CAGATTCACC ATCTCCAGAG ACAATTCCAA GAACACGCTG TATCTGCAAA
TGAACAGCCT GAGAGCTGAG GACACGGCTG TGTATTACTG TGCGAAAGAA
GAAGTATGGC TACAGGCTTT TGATATCTGG GGCCAAGGGA CAATGGTCAC
CGTCTCAAGC

H42 (SEQ ID NO:187)
        CA GCTGCAGCTG CAGGAGTCGG GCCCAGGACT GGTGAAGCCT
TCGGAGACCC TGTCCCTCAC CTGCACTGTC TCTGGTGGCT CCATCAGTAG
TAACTGGTGG AGTTGGGTCC GCCAGCCCCC AGGGAAGGGG CTGGAGTGGA
TTGGGAAAT CTATCATAGT GGGAGCACCA ACTACAACCC CTCCCTCAAG
AGTCGAGTCA CCATCTCAGT AGACACGTCC AAGAACCAGT TCTCCCTGAA
GCTGAGCTCT GTGACCGCTG CGGACACGGC CGTGTATTAC TGTGCGAGAG
ATAAGGGATA CATGGACGTC TGGGGCAAAG GGACCACGGT CACCGTCTCA
AGC

H43 (SEQ ID NO:189)
   CAGGTACA GCTGCAGCAG TCAGGGGCTG AGGTGAAGAA GCCTGGGTCC
TCGGTGAAGG TCTCCTGCAA GGCTTCTGGA GGCACCTTCA GCAGCTATGC
TATCAGCTGG GTGCGACAGG CCCCTGGACA AGGGCTTGAG TGGATGGGAA
GGATCATCCC TATCCTTGGT ATAGCAAACT ACGCACAGAA GTTCCAGGGC
AGAGTCACGA TTACCGCGGA CAAATCCACG AGCACAGCCT ACATGGAGCT
GAGCAGCCTG AGATCTGAGG ACACGGCCGT GTATTACTGT GCGAGAGATC
ATAGGTTCGA CTACGCCTGG TACTTCGATC TCTGGGGCCG TGGCACCCTG
GTCACCGTCT CAAGC

Fig. 1 (cont)

H44 (SEQ ID NO:191)
```
        CA GGTGCAGCTG CAGGAGTCGG GCCCAGGACT GCTGAAGCCT
TCGGGGACCC TGTCCCTCAC CTGCGCTGTC TCTGGTGGCT CCATCAGCAG
TAGCAACTGG TGGAGTTGGG TCCGCCAGCC CCAGGGGAG GGGCTGGAGT
GGATTGGGGA AATCTATCAT AGTGGGAGCA CCAACTACAA CCCGTCCCTC
AAGAGTCGAG TCACCATATC AGTAGACAAG TCCAAGAACC AGTTCTCCCT
GAAGCTGAGC TCTGTGACCG CCGCGGACAC GGCCGTCTAT TACTGTGCGA
GAGATCTAAC GGGGAGTCTT GACTACTGGG GCCAGGGAAC CCTGGTCACC
GTCTCAAGC
```

H45 (SEQ ID NO:193)
```
CAGGTGCAGC TGCAGGAGTC CGGCCCAGGA CTGGTGAAGC CTTCGGGGAC
CCTGTCCCTC ACCTGCGCTG TCTCTGGTGG CTCCATCAGC AGTAGTAACT
GGTGGAGTTG GGTCCGCCAG CCCCCAGGGA AGGGGCTGGA GTGGATTGGG
GAAATCTATC ATAGTGGGAG CACCAACTAC AACCCGTCCC TCAAGAGTCG
AGTCACCATA TCAGTAGACA AGTCCAAGAA CCAGTTCTCC CTGAAGCTGA
GCTCTGTGAC CGCCGCGGAC ACGGCCGTGT ATTACTGTGC GAGAATACGC
TATGATGCTT TTGATATCTG GGGCCAAGGG ACAATGGTCA CCGTCTCAAG
C
```

H46 (SEQ ID NO:195)
```
        CA GGTGCAGCTG CAGGAGTCGG GCCCAGGACT GGTGAAGCCT
TCGGAGACCC TGTCCCTCAC CTGCGCTGTC TCTGGTGGCT CCATCAGCAG
TAGTAACTGG TGGAGTTGGG TCCGCCAGCC CCAGGGAAG GGGCTGGAGT
GGATTGGGGA AATCTATCAT AGTGGGAGCA CCAACTACAA CCCGTCCCTC
AAGAGTCGAG TCACCATATC AGTAGACAAG TCCAAGAACC AGTTCTCCCT
GAAGCTGAGC TCTGTGACCG CTGCGGACAC GGCCGTGTAT TACTGTGCCG
TGACGGCAGC CCATGATGCT TTTGATATCT GGGGCCAAGG GACAATGGTC
ACCGTCTCAA GC
```

H47 (SEQ ID NO:197)
```
        CA GGTGCAGCTA CAGCAGTGGG GCCCAGGACT GGTGAAGCCT
TCGGGGACCC TGTCCCTCAC CTGCGCTGTC TCTGGTGGCT CCATCAGCAG
TAGTAACTGG TGGAGTTGGG TCCGCCAGCC CCAGGGAAG GGGCTGGAGT
GGATTGGGGA AATCTATCAT AGTGGGAGCA CCAACTACAA CCCGTCCCTC
AAGAGTCGAG TCACCATATC AGTAGACAAG TCCAAGAACC AGTTCTCCCT
GAAGCTGAGC TCTGTGACCG CCGCGGACAC GGCCGTGTAT TACTGTGCGA
GAGACAGCAG TGGCCAAGGG TACTTTGACT ACTGGGGCCA GGGCACCCTG
GTCACCGTCT CAAGC
```

Fig. 1 (cont)

H48 (SEQ ID NO:199)
```
     GAGGTG CAGCTGGTGC AGTCTGGGGC TGAGGTGAAG AAGCCTGGGG
CCTCAGTGAA GGTCTCCTGC AAGGCTTCTG GATACACCTT CACTAGCTAT
GCTATGCATT GGGTGCGCCA GGCCCCCGGA CAAAGGCTTG AGTGGATGGG
ATGGATCAAC GCTGGCAATG GTAACACAAA ATATTCACAG AAGTTCCAGG
GCAGAGTCAC CATGACCAGG GACACGTCCA CGAGCACAGT CTACATGGAG
CTGAGCAGCC TGAGATCTGA GGACACGGCC GTGTATTACT GTGCTAGACA
CTCGTACTAC TACGGTATGG ACGTCTGGGG CCAAGGCACC CTGGTCACCG
TCTCAAGC
```

H49 (SEQ ID NO:201)
```
        CAG GTGCAGCTAC AGCAGTGGGG CGCAGGACTG TTGAAGCCTT
CGGAGACCCT GTCCCTCACC TGCGCTGTCT ATGGTGGGTC CTTCAGTGGT
TACTACTGGA GCTGGATCCG CCAGCCCCCA GGGAAGGGGC TGGAGTGGAT
TGGGGAAATC AATCATAGTG GAAGCACCAA CTACAACCCG TCCCTCAAGA
GTCGAGTCAC CATATCGGTA GACACGTCCA AGAACCAGTT CTCCCTGAAG
CTGAGCTCTG TGACCGCCGC GGACACGGCT GTGTATTACT GTGCGAGAGT
CGGGTATAGC ACGGCGAAG AAGTCCTGGA CGTCTGGGGC AAAGGGACCA
CGGTCACCGT CTCAAGC
```

H50 (SEQ ID NO:203)
```
      CAGGT GCAGCTGCAG GAGTCGGGCC CAGGACTGGT GAAGCCTTCG
GAGACCCTGT CCCTCACCTG CACTGTCTCT GGTGGCTCCA TCGGCAATTA
TGACTGGAGT TGGATCCGGC AGCCCCCAGG GAAGGGACTG GAGTGGATTG
GGACTATCTA CTCTAGTGGG AGTACGTACT ACAGTCCGTC CCTCAAGAGT
CGACTCACCA TATCAGTAGA CAAGTCCAAG AACCGGTTCT CCCTGAAGCT
GAGCTCTGTG ACCGCCGCGG ACACGGCCGT GTATTACTGT GCGAGAGCAC
GAGGGTATAG CAGCCCCTTC GACCCCTGGG GCCAGGGCAC CCTGGTCACC
GTCTCAAGC
```

H51 (SEQ ID NO:205)
```
       CA GGTCCAGCTG GTACAGTCTG GGGCTGAGGT GAAGAAGCCT
GGGTCCTCGG TGAAGGTCTC CTGCAAGGCT TCTGGAGGCA CCTTCAGCAG
CTATGCTATC AGCTGGGTGC GACAGGCCCC TGGACAAGGG CTTGAGTGGA
TGGGAATAAT CAACCCTAGT GGTGGTAGCA CAAGCTACGC ACAGAAGTTC
CAGGGCAGAG TCACCATTAC CAGGGACACA TCCGCGAGCA CAGCCTACAT
GGAGCTGAGC AGCCTGAGAT CTGAAGACAC GGCTGTGTAT TACTGTGCGA
GAGATCGGTG GAGGTACGAT GCTTTTGATA TCTGGGGCCA AGGGACAATG
GTCACCGTCT CAAGC
```

Fig. 1 (cont)

H52 (SEQ ID NO:207)
```
        G AGGTGCAGCT GGTGGAGTCT GGCCCAGGAC TGGTGAAGCC
TTCGGGGACC CTGTCCCTCA CCTGCGCTGT CTCTGGTGGC TCCATCAGCA
GTAGTAACTG GTGGAGTTGG GTCCGCCAGC CCCCAGGGAA GGGGCTGGAG
TGGATTGGGG AAATCTATCA TAGTGGGAGC ACCAACTACA ACCCGTCCCT
CAAGAGTCGA GTCACCATAT CAGTAGACAA GTCCAAGAAC CAGTTCTCCC
TGAAGCTGAG CTCTGTGACC GCCGCGGACA CGGCCGTGTA TTACTGTGCG
AGAGAAAAAT CGGGTATGGA CGTCTGGGGC CAAGGGACCA CGGTCACCGT
CTCAAGC
```

Fig. 2

LIGHT CHAIN VARIABLE REGION SEQUENCES

```
          FR1                                    CDR1                          FR2                    CDR2              FR3                                              CDR3                        FR4
L1  (SEQ ID NO:2)
DVVMTQSPLSLPVTPGEPASISCRSSQSLLHSSGYNYLDWYLQKPGQSPQLLIYLGSNRASGVPDRFSGSGSGTDFTLKISRVEAEDVGVYYCMQALQTPITFGQGTRLEIK
L2  (SEQ ID NO:4)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPIFFGQGTKVEIK
L3  (SEQ ID NO:6)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGQGTKVEIK
L4  (SEQ ID NO:8)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFPHTFGGGTKVEIK
L5  (SEQ ID NO:10)
EIVLTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGPGTKVDIK
L6  (SEQ ID NO:12)
EIVLTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L7  (SEQ ID NO:14)
DVVMTQSPLSLAVTPGEPASISCRSSQSLLHSNGYNYLDWYLQKPGQSPQLLIYLGSNRASGVPDRFSGSGSGTDFTLKISRVEAEDVGVYYCMQALQTPLTFGQGTKVEIK
L8  (SEQ ID NO:16)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLFGQGTKVEIK
L9  (SEQ ID NO:18)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPFFTFGQGTKVEIK
L10 (SEQ ID NO:20)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLAFGQGTKVEIK
L11 (SEQ ID NO:22)
EIVLTQSPLSLPVTPGEPASISCRSSQSLLHSNGYNYLNWYLQKPGQSPQLLIYLGSNRASGVPDRFSGSGSGTDFTLKISRVEAEDVGVYYCMQALQTPITFGQGTRLEIK
L12 (SEQ ID NO:24)
NFMLTQPHSVSESPGKTVTISCTRSSGSIASNYVQWYQQRPGSSPTTVIYEDNQRPSGVPDRFSGSIDSSNSASLTISGLKTEDEADYCQSYDSSNQRVFGGGTKLTVL
L13 (SEQ ID NO:26)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L14 (SEQ ID NO:28)
DVVMTQSPLSLPVTPGEPASISCRSSQSLLHSNGYNYLDWYLQKPGQSPQLLIYLGSYNRASGVPDRFSGSGSGTDFTLKISRVEAEDVGVYYCMQALQTPLFGQGTKVEIK
L15 (SEQ ID NO:30)
DVVMTQSPLSLPVTPGEPASISCRSSQSLLHSNGYNYLDWYLQKPGQSPQLLIYLGSYRASGVPDRFSASGSGTDFTLKISRVEAEDVGVYYCMQALQTPIFFGQGTRLEIK
```

Fig. 2 (cont)

```
L16  (SEQ ID NO:32)
L17  (SEQ ID NO:34) DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQGTHWPLTFGQGTKVEIK
L18  (SEQ ID NO:36) EIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L19  (SEQ ID NO:38) DIQLTQSPSSVSASVGDRVTITCRASQGISRWLAWYQQKPGKAPRLLIYAASTLQSGVPSRFSGSGSGTDFTLTISNLQPEDFATYYCQQASSFFITFGGGTRLEIK
L20  (SEQ ID NO:40) DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPYTFGQGTKLEIK
L21  (SEQ ID NO:42) DVVMTQSPLSLPVTPGEPASISCRSSQSLLHSNGYNYLDWYLQKPGQSPQLLIYLGSYRASGVPNRFSGSGSGTDFTLKISRVEAEDVGVYYCMQALQTPFTFGPGTKVDIK
L22  (SEQ ID NO:44) SSELTQDPAVSVALGQTVRITCQGDSLRIYYTGWYQQKPGQAPVLVLFGKNNRPSGIPDRFSGSHSGNTASLTITGAQAEDEADYCNSRDITGVHRFGGGTKLTVL
L23  (SEQ ID NO:46) EIVLNQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L24  (SEQ ID NO:48) DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPNTFGGGTKVEIK
L25  (SEQ ID NO:50) DVVMTQSPLSLPVTPGEPASISCRSSQSLLHSNGYTYLDWYLQKPGQSPQLLIYLGSNRASGVPDRFSGSGSGTDFTLKISRVEPEDVGVYYCMQALEMPLTFGGGTKVEIK
L26  (SEQ ID NO:52) DVVMTQSPLSLPVTPGEPASISCRSSQSLLHSNGTYYLDWYLQKPGQSPQLLIYLGSNRASGVPDRFSGSGSGTDFTLKISRVEAEDVGVYYCMQALQTPITFGPGTKVDIK
L27  (SEQ ID NO:54) DVVMTQSPLSLPVTPGEPASISCRSSQSLLHSNGYNYLDWYLQKPGQSPQLLIYLGSNRASGVPDRFSGSGSGTDFTLKISRVEPEDVGVYYCMQALEMPLTFGGGTKVEIK
L28  (SEQ ID NO:56) DIQLTQSPSFLSASVGDRVTITCRASQGISSYLAWYQQKPGKAPKLLIYAASTLQSGVPSRFSGSGSGTEFTLTITSSLQPEDFATYYCQQLNSYPLTFGGGTKVEIK
L29  (SEQ ID NO:58) SYVLTQPPSVSVSPGQTASITCSGDKLGDKYVCWYQQKAGQAPVLVIYQDNKRPSGIPERFSGSNSGNTASLTISGTQAMDEADYCQAWDSGTVFGGGTKLTVL
L30  (SEQ ID NO:60) DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L31  (SEQ ID NO:62) DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMEALQTPFTFGPGTKVEIK
L32  (SEQ ID NO:64) DIQLTQSPSSLSASVGDRVTITCRASQGIGYFLMYQQKPGKAPKLLISAASTLQSGVPSRHSGSGSGTDFTLLSINNLQPADFATYYCQQSHSPPYTFGQGTKVEIK
L33  (SEQ ID NO:66) DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L33  (SEQ ID NO:68) EIVLTQSPLSLPVTPGEPASISCRSSQSLLHSNGYNYLDWYLQKPGQSPQLLMYLVSNRASGVPERFSGSGSGTDFTLKISRVEAEDVGVYYCMQTLQTPLSFGQGTKLEIK
```

Fig. 2 (cont)

L34 (SEQ ID NO:70)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L35 (SEQ ID NO:72)
NFMLTQPHSVSASPGKTVTISCTRSSGDIDNNYVQWYQQRPGNSPTNVIYEDNRRPSGSIDSSSNSASLTISGLQPEDEADYYCQSYDSDNWVFGGGTKVTVL
L36 (SEQ ID NO:74)
NFMLTQPHSVSESPGKTVTISCTRSSGSIASNYVQMYQQRPGSSPTTVIYEDNQRPSGVPDRFSGSIDSSSNSASLTISGLKTEDEADYYCQSYDSSNVFGGGTKLTVL
L37 (SEQ ID NO:76)
DVVMTQSPLSLPVTPGEPASISCRSSQSLLHSNGYNYLDWYLQKPGQSPQLLIYLGSNRDSGVPDRFSGSGSGTDFTLKISRVEAEDVGVYYCMQGTHWPYTFGGGTRLEIK
L38 (SEQ ID NO:78)
DVVMTQSPLSLPVTPGESASISCRSSQSLLHSNGYNFLDWYLQKPGQSPQLLIYLGSNRASGVPDRFSGSGSGTDFTLKISRVEAEDVGVYYCMQALQTPLTFGGGTKVEIK
L39 (SEQ ID NO:80)
DVVMTQSPLSLPVTPGEPASISCRSSQSLLHSNGYNYLDWYLQKPGQSPQLLIYDASRRATGIPARFSGSGSGTDFTLTISSLEPEDFAVYYCQQRNNWPLTFGGGTKVEIK
L40 (SEQ ID NO:82)
ETTLTQSPATLSLSPGQRATLSCRASQSVYNYLAWYQQKPGQAPRLLIYDASRRATGIPARFSGSGSGTDFTLTISSLEPEDFAVYYCQQRNNWPLTFGGGTKVEIK
L41 (SEQ ID NO:84)
DIQLTQSPSSLSASVGDSVTISCRASQSPGIFLNWYQQIPGKAPKLLIYATSTLESGVPPRFTGSGSGTDFTLHISSEQPEDFATYYCQQSNSVPLTFGGGTKVEIK
L42 (SEQ ID NO:86)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTRLEIK
L43 (SEQ ID NO:88)
EIVMTQSPATLSVSPGERATFSCRASQSVGSNLAWYQQKPGQAPRLLIYDASNRATGIPARFSGSGSGTDFTLTISRLEPEDEAVYYCQQRSNWPLTFGGGTKVEIK
L44 (SEQ ID NO:90)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L45 (SEQ ID NO:92)
DVVMTQSPLSLPVTPGEPASISCRSSQSLLHSNGYNYLDWYLQKPGQSPQLLIYLGSTRASGVPDRFSGSGSGTDFTLKISRVEAEDVGVYYCMQALQTPYTFGGGTKVEIK
L46 (SEQ ID NO:94)
DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK
L47 (SEQ ID NO:96)
DVVMTQSPLSLPVTPGEPASISCRSSQSLLHSNGYNYLDWYLQKPGQSPRLLIYLGFNRASGVPDRFSGSGSGTDFTLKISRVEAEDVGVYYCMQGLQTPLTFGGGTKVEIK
L48 (SEQ ID NO:98)
DVVMTQSPLSLPVTPGEPASISCRSSQSLLHSNGYNYLDWYLQKPGQSPQLLIYEDNQRPSGVPDRFSGSGSGTDFTLKISRVEAEDVGVYYCMQAFHWPYTFGGGTKVEIK
L49 (SEQ ID NO:100)
NFMLTQPHSVSESPGKTVSISCTRNSGSIASNFVQWYQQRPGSAPTIVIYGAGVRATGIPDRFSGSGSGTDFTLHISRLEPEDFAVYYCQHYGSSLRTFGGGTKLTVL
L50 (SEQ ID NO:102)
ETTLTQSPGTLSLSPGERATLSCRASQTISSHLAWYQQKPGQSPRLLIYGAGVRATSAVPTRFSGSIDRSSGSGSGTDFTLHISRLEPEDFAVYYCQHYGSSLRTFGGGTKLTVL
L52 (SEQ ID NO:104)
EIVMTQSPLSLPVTPGEPASISCRSSQSLLHTNGIDYLDWYLQKP

Fig. 3

HEAVY CHAIN VARIABLE REGION SEQUENCES

```
        FR1                                    CDR1            FR2                         CDR2                    FR3                                                    CDR3                    FR4

H1 (SEQ ID NO:106)
EVQLVETGPGLVKPSGTLSLTCAVSGGSISSSNWWSWVRQPPGKGLEWIGEIYHSGSTNYNPSLKSRVTISVDKSKNQFSLKLSSVTAADTAVYYCARFNYYDSSVWGQGTLVTVSS

H2 (SEQ ID NO:108)
EVQLVETGPGLVKPSGTLSLTCAVSGGSISSSNWWSWVRQPPGKGLEWIGEIYHSGSTNYNPSLKSRVTISVDKSKNQFSLKLSSVTAADTAVYYCARGVEQIDWGQGTLVTVSS

H3 (SEQ ID NO:110)
QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCAKNLAAGAVAYWGQGTLVTVSS

H4 (SEQ ID NO:112)
QVQLQQWGAGLLKPSETLSLTCAVSGGSESGIYWSWIRQPPGKGLEWIGEINHSGSTNYNRSLKSRVTISVDTSANQFSLKLSSVTAADTAVYYCARLSYGSGVDYWGQGTLVTVSS

H5 (SEQ ID NO:114)
QLQLQESGPGLVKPSQTLSLTCTVSGGSISSSNWWSWVRQPPGKGLEWIGEIYHSGSTNYNPSLKSRVTISVDKSKNQFSLKLSSVTAADTAVYYCARYSSSRNDAFDIWGQGTMVTVSS

H6 (SEQ ID NO:116)
QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARDGQLDAFDIWGQGTMVTV

H7 (SEQ ID NO:118)
QVQLQESGPGLVKPSGTLSLTCAVSGGSISSSNWWSWVRQPPGKGLEWIGEIYHSGSTNYNPSLESRVTISVDKSKNQFSLKLSSVTAADTAVYYCARFWDYYGMDYWGQGTTVTVSS

H8 (SEQ ID NO:120)
QVQLQQWGPGLVKPSGTLSLTCAVSGGSISSSNWWSWVRQPPGKGLEWIGEIYYYSGSTYINPSLKSRVIMSVDTSKNQFSLKLSSVTAADTAVYYCARDRYYGMDVWGQGTMVTVSS

H9 (SEQ ID NO:122)
EVQLVESGPGLVKPSGTLSLTCAVSGGSISSSNWWSWVRQPPGKGLEWIGEIYHSGSTNYNPSLKSRVTISVDKSKNQFSLKLSSVTAADTAVYYCARWSYLDAFDIWGQGTMVTVSS

H10 (SEQ ID NO:124)
EVQLVESGPGLVKPSGTLSLTCAVSGGSISSSNWWSWVRQPPGKGLEWIGEIYHSGSTNYNPSLKSRVTISVDKSKNQFSLKLSSVTAADTAVYYCARDYDIFGMDVWGQGTTVTVSS

H11 (SEQ ID NO:126)
QLQLQESGPGLVKPSGTLSLTCAVSGGSISSSNWWSWVRQPPGKGLEWIGEIYHSGSTNYNPSLKSRVTISVDKSKNQSSLKLSSVTAADTAVYYCARANRDDAFDIWGQGTMVTVSS
```

Fig. 3 (cont)

H12 (SEQ ID NO:128)
EVQLVESGGGLVQPGGSLRLSCAASGFTFS*SYAMS*WVRQAPGKGLEWVSA*ISGSGGSTYYADSVKG*RFTISRDNSKNTLYLQMNSLRAEDTAVYHCA*SGGWYGDYFDY*WGQGTLVTVSS

H13 (SEQ ID NO:130)
QVQLQESGPGLVKPSETLSLTCTVSGGSIS*SSNWWS*WVRQPPGKGLEWIGE*IYHSGSTNYNPSLKS*RVTISVDKSKNQFSLKLSSVTAADTAVYYCAR*EGNRIVTSAFDI*WGQGTMVTVSS

H14 (SEQ ID NO:132)
QVQLQESGPGLVKPSGTLSLTCAVSGGSIS*SSNWWS*WVRQPPGKGLEWIGE*IYHSGSTNYNPSLKS*RVTISVDKSKNQFSLKLSSVTAADTAVYYCAR*GLGDSSGYILM*WGQGTMVTVSS

H15 (SEQ ID NO:134)
QVQLQESGPGLVKPSGTLSLTCAVSGGSIS*SSNWWS*WVRQPPGKGLEWIGE*IYHSGSTNYNPSLKS*RVTISVDKSKNQFSLKLSSVTAADTAVYYCAR*GLGDSSGYILW*WGQGTMVTVSS

H16 (SEQ ID NO:136)
QVQLQESGPGLVKPSGTLSLTCAVSGGSIS*SSNWWS*WVRQPPGKGLEWIGE*IYHSGSTNYNPSLKS*RVTISVDKSKNQFSLKLSSVTAADTAVYYCAR*WTGRTDAFDI*WGQGTMVTVSS

H17 (SEQ ID NO:138)
QVQLQESGPGLVKPSGTLSLTCAVSGGSIS*SSNWWS*WVRQPPGKGLEWIGE*IYHSGSTNYNPSLKS*RVTISVDKSKNQFSLKLSSVTAADTAVYYCAR*QGALDAFDI*WGQGTTVTVSS

H18 (SEQ ID NO:140)
EVQLVESGGGVVRPGGSLRLSCAASGFTHS*SYAMS*WVRQAPGKGLEWVST*ISGSGGSTYYADSVKG*RFTISRDNSKNTLYLQMNSLRAEDTAVYYCAK*ERGSGWSLDNMDV*WGQGTTVTVSS

H19 (SEQ ID NO:142)
QVQLQESGPGLVKPSGTLSLTCAVSGGSIS*SSNWWS*WVRQPPGKGLEWIGE*IYHSGSTNYNPSLKS*RVTISVDKSKNQFSLKLSSVTAADTAVYYCAR*DSSGFYGMDV*WGQGTTVTVSS

H20 (SEQ ID NO:144)
QVQLQESGPGLVKPSGTLSLTCAVSGGSIS*SSNWWS*WVRQPPGKGLEWIGE*IYHSGSTNYNPSLKS*RVTISVDKSKNQFSLKLSSVTAADTAVYYCAR*SSWYWNAFDI*WGQGTMVTVSS

H21 (SEQ ID NO:146)
QVQLQQWGPALVKPSGTLSLRCSVSGVSITS*SNIMWS*WVRQSPGKGLEWIGE*VNPRGSTNYNPSLKS*RAHISLDTSKNQFSLKLSSVTAADTAVYYCAG*YRSFGESY*WGQGTLVTVSS

H22 (SEQ ID NO:148)
QVQLQQWGAGLLKPSETLSLTCVVYGGS*HS*DFYWS*WIRQPPGKGPEWIGE*VNPRGSTNYNPSLKS*RAHISLDTSKNQFSLKLSSVTAADTAVYFCAR*GFRPGRDGYNYFDN*WGQGTLVTVSS

H23 (SEQ ID NO:150)
QVQLQESGPGLVKPSETLSLTCTVSGGSIS*SSNWWS*WVRQPPGKGLEWIGE*IYHSGSTNYNPSLKS*RVTISVDKSKNQFSLKLSSVTAADTAVYYCAR*GIAAAGQGDY*WGQGTLVTVSS

Fig. 3 (cont)

H24 (SEQ ID NO:152)
QVQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCARDGGYYYYGMDVWGQGTTVTVSS

H25 (SEQ ID NO:154)
QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCASSGYDAFDIWGQGTTVTVSS

H26 (SEQ ID NO:156)
QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARSYGTVGIDYWGQGTLVTVSS

H27 (SEQ ID NO:158)
EVQLVQSGGGVVQPGTSLRLSCAASGFSFRSHGMHWVRQAPGKGLEWVAVLSYDGSNKYYADSVKGRFTISRDNSKNTLYLQMNSLRAEDTAVYYCATIGPGFDYWGQGTLVTVSS

H28 (SEQ ID NO:160)
EVQLVQSGPGLVKPSETLSLTCTVSGGSIRNYYWSWIRQPPGKGLEWIGYISDSGNTNYNPSLKSRVTISVDTSKNQFSLKLFSVTATDTAAVFCARHRSSWAWIFDLWGRGTLVTVSS

H29 (SEQ ID NO:162)
QVQLQESGPGLVKPSETLSLTCAVSGGSISSSNWWSWVRQPPGKGLEWIGEIYHSGSTNYNPSLKSRVTISVDKSKNQFSLKLSSVTAADTAVYYCARVGSGWYYDYWGQGTLVFVSS

H30 (SEQ ID NO:164)
QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARVSGYYYYGMDVWGQGTTVTVSS

H31 (SEQ ID NO:166)
EVQLVQSGGGVVQPGRSLRLSCAASGFTFSSYGMHWVRQAPGKGLEWVAVISYDGSNKYYADSVKGRFTISRDNSKNTLYLQMNSLRAEDTAVYYCAKAYSSGWWIDYYGMDVWGQGTTVTVSS

H32 (SEQ ID NO:168)
QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARASVDAFIWGQGTMVTVSS

H33 (SEQ ID NO:170)
QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARGLGDSSGYILWGQGTMVTVSS

H34 (SEQ ID NO:172)
QVQLQESGPGLVKPSGTLSLTCAVSGGSVSYISSSSTIYYADSVKGRFTISRNSKNQFSLKLSSVTPEDTAVYYCARDHGPFDYWGRGTLVIVSS

H35 (SEQ ID NO:174)
QVQLVQSGGGVVQPGRSLRLSCAASGFAFSSYGMHWVRQAPGKGLEWVSYISSSSTIYYADSVKGRFTISRDNSKNTLYLQMNSLRAEDTAVYYCARDRFGSGHLPDYWGQGTLVTVSS

H36 (SEQ ID NO:176)
QVQLQQWGAGLLKPSETLSLTCAVIGGSHSGSTYYWSWIRQPPGKGLEWIGEINHSGSTNYNPSLKSRVTISVDTSKNQFSLKLSSVTAADTAVYYCARVGYSSGRDVIDYWGQGTLVTVSS

Fig. 3 (cont)

H37 (SEQ ID NO:178)
EVQLVESGPGLVKPSGTLSLTCAVSGGSIS*SSNWWSW*IRQPPGKGLEWIGE*IYHSGSTNYNPSLKS*RVTISVDKSKNQFSLKLSSVTAADTAVYYCAR*DSSSWYYGMD*VWGQGTTV
TVSS

H38 (SEQ ID NO:180)
EVQLVESGPGLVKPSETLSLTCAVSGGSIS*SSNWWSW*VRQPPGKGLEWIGE*IYHSGSTNYNPSLKS*RVTISVDKSKNQFSLKLSSVTAADTAVYYCAR*STWSLDI*WGQGTLVTVSS

H39 (SEQ ID NO:182)
EVQLVESGPGLVKPSGTLSLTCAVSGGSIS*SSNWWSW*VRQPPGKGLEWIGE*IYHSGSTNYNPSLKS*RVTISVDKSKNQFSLKLSSVTAADTAVYYCAR*LSFADPFDI*WGQGTMVTV
SS

H40 (SEQ ID NO:184)
QVQLVQSGAEVKKPGSSVKVSCKASGGTFS*SYAISW*VRQAPGQGLEWMGR*IIPILGIANYAQKFQG*RVTITADKSTSTAYMELSSLRSEDTAVYYCAY*GSGSYYDYYMDV*WGKGT
TVTVSS

H41 (SEQ ID NO:186)
EVQLVQSGGGLVQPGGSLRLSCSASGFTFS*SYAMHW*VRQAPGKGLEYVS*TISSNGDSTYYADSVKG*RFTISRDNSKNTLYLQMNSLRAEDTAVYYCAK*EEVWLQAFDI*WGQGTMVT
VSS

H42 (SEQ ID NO:188)
QLQLQESGPGLVKPSETLSLTCTVSGGSIS*SNWWSW*VRQPPGKGLEWIGE*IYHSGSTNYNPSLKS*RVTISVDTSKNQFSLKLSSVTAADTAVYYCAR*DKGYMDV*WGAGTTVTVSS

H43 (SEQ ID NO:190)
QVQLQQSGAEVKKPGSSVKVSCKASGGTFS*SYAISW*VRQAPGQGLEWMGR*IIPILGIANYAQKFQG*RVTITADKSTSTAYMELSSLRSEDTAVYYCAR*DHRFDYAWYFDL*WGRGTL
VTVSS

H44 (SEQ ID NO:192)
QVQLQESGPGEGLVKPSGTLSLTCAVSGGSIS*SSNWWSW*VRQPPGEGLEWIGE*IYHSGSTNYNPSLKS*RVTISVDKSKNQFSLKLSSVTAADTAVYYCAR*DLTGSLDI*WGQGTLVTVS
S

H45 (SEQ ID NO:194)
QVQLQESGPGLVKPSGTLSLTCAVSGGSIS*SNWWSW*VRQPPGKGLEWIGE*IYHSGSTNYNPSLKS*RVTISVDKSKNQFSLKLSSVTAADTAVYYCAR*IRYDAFDI*WGQGTMVTVSS

H46 (SEQ ID NO:196)
QVQLQESGPGLVKPSETLSLTCAVSGGSIS*SSNWWSW*VRQPPGCGLEWIGE*IYHSGSTNYNPSLKS*RVTISVDKSKNQFSLKLSSVTAADTAVYYCAV*TAAHDAFTI*WGQGTMVTV
SS

H47 (SEQ ID NO:198)
QVQLQQSGPGLVKPSGTLSLTCAVSGGSIS*SSNWWSW*VRQPPGKGLEWIGE*IYHSGSTNYNPSLKS*RVTISVDKSKNQFSLKLSSVTAADTAVYYCAR*DSSGQGIFDI*WGQGTLVT
VSS

H48 (SEQ ID NO:200)
EVQLVQSGAEVKKPGASVKVSCKASGYTFT*SYAMHW*VRQAPGQRLEWMGW*INAGNGNTKYSQKFQG*RVTMTRDTSTSTVYMELSSLRSEDTAVYYCAR*HSYYYGMDV*WGQGTLVTV
SS

H49 (SEQ ID NO:202)
QVQLQQWGAGLLKPSETLSLTCAVGGSFS*GIYWSW*IRQPPGKGLEWIGE*INHSGSTNYNPSLKS*RVTISVDTSKNQFSLKLSSVTAADTAVYYCAR*VGYSHGEEVLDV*WGKGTTV
TVSS

Fig. 3 (cont)

H50 (SEQ ID NO:204)
QVQLQESGPGLVKPSETLSLTCTVSGGSIGNYIDWSWIRQPPGKGLEWIGTIYYSSGSTYYSPSIKSRLTISVDKSKNRFSLKLSSVTAADTAVYYCARARGYSSPFDPWGQGTLVTVSS

H51 (SEQ ID NO:206)
QVQLVQSGAEVKKPGSSVKVSCKASGGTFSSYAISWVRQAPGQGLEWMGIINPSGGSTSYAQKFQGRVTITRDTSASTAYMELSSLRSEDTAVYYCARDRWRYDAFDIWGQGTMVTVSS

H52 (SEQ ID NO:208)
VQLVESGPGLVKPSGTLSLTCAVSGGSISSSNWWSWVRQPPGAGLEWIGEIYHSGSTNYNPSLKSRVTISVDKSKNQFSLKLSSVTAADTAVYYCAREKSGMDVWGQGTTVTVSS

Fig.4

Light Chain        CDR1 Sequence
L2, L3, L4, L5,
L6, L7, L8, L9,
L10, L13, L14,
L15, L16, L17,
L19, L20, L23,
L24, L25, L29,
L30, L32, L33,
L34, L37, L39,
L42, L44, L45,

| | | | | | | | | | | | | | | | |
|---|---|---|---|---|---|---|---|---|---|---|---|---|---|---|---|
| L46, L48 | | R | S | S | Q | S | L | L | H | S | N | G | Y | N | Y | L | D |
| L1 | | R | S | S | Q | S | L | L | H | S | S | G | Y | N | Y | L | D |
| L11 | | R | S | S | Q | S | L | L | H | S | N | G | Y | N | Y | L | N |
| L21 | | R | S | S | Q | S | L | L | H | S | H | G | Y | N | Y | L | D |
| L26 | | R | S | S | Q | S | L | L | H | S | N | G | Y | T | Y | L | D |
| L38 | | R | S | S | Q | S | L | L | H | S | N | G | Y | N | F | L | D |
| L47 | | R | S | S | Q | S | L | L | H | T | N | G | Y | N | Y | L | D |
| L52 | | R | S | S | Q | S | L | L | H | T | N | G | Y | D | Y | L | D |
| CONSENSUS | | R | S | S | Q | S | L | L | H | S | N | G | Y | N | Y | L | D |

| | | | | | | | | | | | | | |
|---|---|---|---|---|---|---|---|---|---|---|---|---|---|
| L51 | T | G | S | G | N | I | A | S | N | Y | V | Q | | |
| L12, L36 | T | R | S | S | G | S | I | A | S | N | Y | V | Q | |
| L35 | T | R | S | S | G | D | I | D | N | N | Y | V | Q | |
| L49 | T | R | N | S | G | S | I | A | S | N | F | V | Q | W | Y | Q |

|             |   |   |   |   |   |   |   |   | H |   |   |
|---|---|---|---|---|---|---|---|---|---|---|---|
| L50 | R | A | S | Q | T | I | S | S | S^ | L | A |
| L18 | R | A | S | Q | G | I | S | R | W | L | A |
| L27 | R | A | S | Q | G | I | S | S | Y | L | A |
| L40 | R | A | S | Q | S | V | Y | N | Y | L | A |
| L43 | R | A | S | Q | S | V | G | S | N | L | A |
| L31 | R | S | S | Q | G | I | G | Y | F | L | N |
| L41 | R | A | S | Q | S | P | G | I | F | L | N |
| CONSENSUS | R | A | S | Q | G | I | G | X | Y | L | A |
|           |   |   |   |   | S | V | S |   | F |   | N |

| | | | | | | | | | |
|---|---|---|---|---|---|---|---|---|---|
| L28 | S | G | D | K | L | G | D | K | Y | V | G |
| L22 | Q | G | D | S | L | R | I | Y | Y | T | G |

| OVERALL CONSENSUS | R | S | S | Q | S | L | X | X | X | X | X | X | X | X |
|---|---|---|---|---|---|---|---|---|---|---|---|---|---|---|
| | | | | | | I | | | | | | | | |

Fig.5

| Light Chain | CDR2 Sequence |
|---|---|
| L1, L2, L3, L4, L5, L6, L7, L8, L9, L10, L11, L13, L14, L16, L17, L19, L20, L23, L24, L25, L26, L29, L30, L32, L34, L38, L39, L42, L44, L46, L48 | L G S N R A S |
| L15, L21 | L G S Y R A S |
| L33 | L V S N R A S |
| L37 | L G S N R D S |
| L45, L52 | L G S T R A S |
| L47 | L G F N R A S |
| CONSENSUS | L G S N R A S |
| | |
| L27, L31 | A A S T L Q S |
| L18 | A A S G L Q S |
| L41 | A T S T L E S |
| CONSENSUS | A A S T L Q S |
| | |
| L12, L36, L49 | E D N Q R P S |
| L35, L51 | E D N R R P S |
| L28 | Q D N K R P S |
| L22 | G K N N R P S |
| CONSENSUS | E D N X R P S |
| | |
| L40 | D A S R R A T |
| L43 | D A S N R A T |
| L50 | G A G Y R A T |

Fig.6

| Light Chain | CDR3 Sequence | | | | | | | | |
|---|---|---|---|---|---|---|---|---|---|
| L3, L5, L6, L7, L8 L13, L14, L17, L23, L29, L32, L34, L38, L39, L42, L44, L46 | M | Q | A | L | Q | T | P | L | T |
| L52 | M | Q | A | F | Q | T | P | L | T |
| L1, L2, L11, L15, L25 | M | Q | A | L | Q | T | P | I | T |
| L19, L45 | M | Q | A | L | Q | T | P | Y | T |
| L9, L20 | M | Q | A | L | Q | T | P | F | T |
| L4 | M | Q | A | L | Q | T | P | H | T |
| L24 | M | Q | A | L | Q | T | P | N | T |
| L10 | M | Q | A | L | Q | T | P | L | A |
| L47 | M | Q | G | L | Q | T | P | L | T |
| L26 | M | Q | A | L | E | M | P | L | T |
| L30 | M | E | A | L | Q | T | P | F | T |
| L33 | M | Q | T | L | Q | T | P | L | S |
| L16 | M | Q | G | T | H | W | P | L | T |
| L21 | M | Q | S | L | E | V | P | F | T |
| L48 | M | Q | A | T | H | W | P | Y | T |
| L37 | M | Q | G | T | H | W | P | Y | T |
| CONSENSUS | M | Q | A | L | Q | T | P | * | T |

"*" = nonpolar side chain amino acid

| | | | | | | | | | |
|---|---|---|---|---|---|---|---|---|---|
| L40 | Q | Q | R | N | N | W | P | L | T |
| L43 | Q | Q | R | S | N | W | P | L | T |
| L41 | Q | Q | S | N | S | V | P | L | T |
| L27 | Q | Q | L | N | S | Y | P | L | T |
| L31 | Q | Q | S | H | S | P | P | Y | T |
| L18 | Q | Q | A | S | S | F | P | I | T |
| CONSENSUS | Q | Q | R | N | * | P | L | T | |
| | | | S | S | N | | | | |

"*" = nonpolar side chain amino acid

| | | | | | | | | | |
|---|---|---|---|---|---|---|---|---|---|
| L12 | Q | S | Y | D | S | S | N | Q | R | V |
| L51 | Q | S | Y | D | P | Y | N | R | V |
| L36 | Q | S | Y | D | S | S | N | V | - | V |
| L35 | Q | S | Y | Q | S | D | N | W | - | V |
| L49 | Q | S | Y | D | S | A | N | V | I |
| | Q | S | Y | D | S | S | N | X | V |

| | | | | | | | | |
|---|---|---|---|---|---|---|---|---|
| L28 | Q | A | W | D | S | G | T | V |

| | | | | | | | | |
|---|---|---|---|---|---|---|---|---|
| L50 | Q | H | Y | G | S | S | L | R | T |

| | | | | | | | | |
|---|---|---|---|---|---|---|---|---|
| L22 | N | S | R | D | I | T | G | V | H | R |

Fig. 7

| Heavy Chain | CDR1 Sequence | | | | | | |
|---|---|---|---|---|---|---|---|
| H1, H2, H3, H5, H6, H7, H8, H9, H10, H11, H13, H14, H15, H16, H17, H19, H20, H23, H25, H26, H29, H30, H32, H33, H34, H37, H38, H39, H44, H46, H47, H52 | S | S | N | W | W | S | |
| H42, H45 | - | S | N | W | W | S | |
| H21 | S | N | I | W | W | S | |
| CONSENSUS | S | S | N | W | W | S | |
| | | | | | | | |
| H4, H36, H49 | G | Y | Y | W | S | | |
| H50 | N | Y | D | W | S | | |
| H28 | N | Y | Y | W | S | | |
| H22 | D | F | Y | W | S | | |
| CONSENSUS | X | Y | Y | W | S | | |
| | | | | | | | |
| H12, H18 | S | Y | A | M | S | | |
| H40, H43, H51 | S | Y | A | I | S | | |
| H31, H35 | S | Y | G | M | H | | |
| H41, H48 | S | Y | A | M | H | | |
| CONSENSUS | S | Y | A | M | S/H | | |
| | | | | | | | |
| H27 | S | H | G | M | H | | |
| | | | | | | | |
| H24 | S | S | S | Y | Y | W | G |

Fig.8

| Heavy Chain | | | | CDR2 Sequence | | | | | | | | | | |
|---|---|---|---|---|---|---|---|---|---|---|---|---|---|---|
| H1, H2, H3, H5, H6, H7, H10, H11, H13, H14, H15, H16, H17, H19, H20, H23, H25, H26, H29, H30, H32, H33, H34, H37, H38, H39, H42, H44, H45, H46, H47, H52 | E | I | Y | H | S | G | S | T | N | Y | N | P | S | L | K | S |
| H8 | E | I | Y | H | S | G | S | T | N | Y | N | P | S | L | E | S |
| H36, H49 | E | I | N | H | S | G | S | T | N | Y | N | P | S | L | K | S |
| H21 | E | V | Y | H | S | G | S | T | N | Y | N | P | S | L | K | S |
| H4 | E | I | N | H | S | G | S | T | N | Y | N | R | S | L | K | S |
| H9 | Y | I | Y | Y | S | G | S | T | Y | Y | N | P | S | L | K | S |
| H50 | T | I | Y | S | S | G | S | T | Y | Y | S | P | S | L | K | S |
| H24 | S | I | Y | Y | S | G | S | T | Y | Y | N | P | S | L | K | S |
| H28 | Y | I | S | D | S | G | N | T | N | Y | N | P | S | L | K | S |
| H22 | E | V | N | P | R | G | S | T | N | Y | N | P | S | L | K | S |
| CONSENSUS | E | I | Y | H | S | G | S | T | N | Y | N | P | S | L | K | S |
|  | Y | V | N | Y |  |  |  |  | Y |  |  |  |  |  |  |  |
|  |  |  |  |  |  |  |  |  |  |  |  |  |  |  |  |  |
| H18 | T | I | S | G | S | G | S | T | Y | Y | A | D | S | V | K | G |
| H12 | A | I | S | G | S | G | S | T | Y | Y | A | D | S | V | K | G |
| H41 | T | I | S | S | N | G | D | S | T | Y | Y | A | D | S | V | K | G |
| H27, H31 | V | I | S | Y | D | G | S | N | K | Y | A | D | S | V | K | G |
| H35 | Y | I | S | S | S | S | T | I | Y | Y | A | D | S | V | K | G |
| CONSENSUS | X | I | S | G | S | G | S | T | Y | Y | A | D | S | V | K | G |
|  |  |  |  | S |  | S |  |  |  |  |  |  |  |  |  |  |
|  |  |  |  |  |  |  |  |  |  |  |  |  |  |  |  |  |
| H40, H43 | R | I | I | P | I | L | G | I | A | N | Y | A | Q | K | F | Q | G |
| H48 | W | I | N | A | G | N | G | N | T | K | Y | S | Q | K | F | Q | G |
| H51 | I | I | N | P | S | G | G | S | T | S | Y | A | Q | K | F | Q | G |

Fig.9

| Heavy Chain | | | | CDR3 Sequence | | | | | | | | | | |
|---|---|---|---|---|---|---|---|---|---|---|---|---|---|---|
| H5 | - | Y | S | S | S | R | N | D | A | F | D | I | | |
| H6 | - | - | - | D | G | Q | L | D | A | F | D | I | | |
| H9 | - | - | - | W | S | Y | L | D | A | F | D | I | | |
| H11 | - | - | - | A | N | R | D | D | A | F | D | I | | |
| H13 | E | G | N | R | T | V | T | S | A | F | D | I | | |
| H16 | - | - | W | T | G | R | T | D | A | F | D | I | | |
| H17 | - | - | - | Q | G | A | L | D | A | F | D | I | | |
| H20 | - | S | S | S | W | Y | W | N | A | F | D | I | | |
| H25 | - | - | - | - | S | G | Y | D | A | F | D | I | | |
| H32 | - | - | - | - | A | S | V | D | A | F | D | I | | |
| H39 | - | - | - | L | S | F | A | D | P | F | D | I | | |
| H41 | - | - | E | E | V | W | L | Q | A | F | D | I | | |
| H45 | - | - | - | - | I | R | Y | D | A | F | D | I | | |
| H46 | - | - | - | T | A | A | H | D | A | F | D | I | | |
| H51 | | | D | R | W | R | Y | D | A | F | D | I | | |
| CONSENSUS | - | - | - | X | S | R | L | D | A | F | D | I | | |
| | | | | | | | | | | | | | | |
| H7 | | | | - | - | - | - | - | F | W | D | Y | Y | G | M | D | V |
| H52 | | | | | | | | | | E | K | S | G | M | D | V |
| H8 | | | | - | - | - | - | - | - | D | R | Y | Y | G | M | D | V |
| H10 | | | | - | - | - | - | - | D | Y | D | I | F | G | M | D | V |
| H18 | | | | - | E | R | G | S | G | W | S | L | D | N | M | D | V |
| H19 | | | | - | - | - | - | D | S | S | G | F | Y | G | M | D | V |
| H24 | | | | - | - | - | D | G | G | Y | Y | Y | Y | G | M | D | V |
| H48 | | | | | | | | | H | S | Y | Y | Y | G | M | D | V |
| H30 | | | | - | - | - | V | S | G | Y | Y | Y | Y | G | M | D | V |
| H31 | | | | A | Y | S | S | G | W | Y | D | Y | Y | G | M | D | V |
| H37 | | | | - | - | - | D | S | S | W | Y | Y | G | M | D | V |
| H40 | | | | - | G | S | G | S | Y | Y | D | Y | Y | M | D | V |
| H42 | | | | - | - | - | - | - | - | - | D | K | G | Y | M | D | V |
| CONSENSUS | | | | - | - | - | - | S | X | Y | D | Y | Y | G | M | D | V |
| | | | | | | | | | | | | | | |
| H2 | - | - | - | - | G | V | E | Q | I | D | Y | | | |
| H3 | - | - | N | L | A | A | G | A | V | A | Y | | | |
| H4 | - | - | L | S | Y | G | S | G | V | D | Y | | | |
| H12 | - | G | G | W | Y | G | D | Y | F | D | Y | | | |
| H23 | - | G | I | A | A | A | G | Q | G | D | Y | | | |
| H26 | - | Y | S | Y | G | T | V | G | I | D | Y | | | |
| H27 | - | - | - | I | G | P | G | G | F | D | Y | | | |
| H29 | - | - | V | G | S | G | W | Y | V | D | Y | | | |
| H34 | - | - | - | - | D | H | G | P | F | D | Y | | | |
| H35 | D | R | F | G | S | G | H | L | P | D | Y | | | |
| H36 | V | G | Y | S | S | G | R | D | V | D | Y | | | |
| H38 | - | - | - | - | S | T | W | S | L | D | Y | | | |
| H44 | - | - | - | D | L | T | G | S | L | D | Y | | | |
| H47 | - | D | S | S | G | Q | G | Y | F | D | Y | | | |
| CONSENSUS | - | - | X | X | G | G | G | X | * | D | Y | | | |

Fig.9 (cont)

"*" = nonpolar side chain amino acids

| | | | | | | | | | | | | | |
|---|---|---|---|---|---|---|---|---|---|---|---|---|---|
| H22 | G | P | R | P | G | R | D | G | Y | N | Y | F | D | N |
| H28 | - | - | - | H | R | S | S | W | A | W | Y | F | D | L |
| H43 | - | - | D | H | R | F | D | Y | A | W | Y | F | D | L |
| CONSENSUS | - | - | X | H | R | X | D | X | A | W | Y | F | D | L |

| | | | | | | | | | | | | | |
|---|---|---|---|---|---|---|---|---|---|---|---|---|---|
| H1 | F | N | Y | Y | D | S | S | V | | | | | |
| H14, H15, H33 | - | G | L | G | D | S | S | G | Y | I | L | | |
| H19 | - | - | - | - | D | S | S | G | F | Y | G | M | D | V |
| H37 | - | - | - | - | D | S | S | S | W | Y | Y | G | M | D | V |
| H47 | - | - | - | - | D | S | S | G | Q | G | Y | F | D | Y |
| CONSENSUS | - | - | - | - | D | S | S | G | X | X | X | - | - | - |

| | | | | | | | | | | |
|---|---|---|---|---|---|---|---|---|---|---|
| H21 | Y | R | S | F | G | E | S | Y | | |
| H49 | V | G | Y | S | H | G | E | E | V | L | D | V |
| H50 | A | R | G | Y | S | S | P | F | D | P |

Fig.10

Kappa light chain constant region
*Nucleotide Sequence*
cgaactgtggctgcaccatctgtcttcatcttcccgccatctgatgagcagttgaaatctggaactg
cctctgttgtgtgcctgctgaataacttctatcccagagaggccaaagtacagtggaaggtggataa
cgccctccaatcgggtaactcccaggagagtgtcacagagcaggacagcaaggacagcacctacagc
ctcagcagcaccctgacgctgagcaaagcagactacgagaaacacaaagtctacgcctgcgaagtca
cccatcagggcctgagctcgcccgtcacaaagagcttcaacaggggagagtgt

*Amino acid sequence*
rtvaapsvfifppsdeqlksgtasvvcllnnfypreakvqwkvdnalqsgnsqesvteqdskdstys
lsstltlskadyekhkvyacevthqglsspvtksfnrgec IgG1 heavy chain constant region
*Nucleotide Sequence*
gcctccaccaagggcccatcggtcttccccctggcaccctcctccaagagcacctctgggggcacag
cggccctgggctgcctggtcaaggactacttccccgaaccggtgacggtgtcgtggaactcaggcgc
cctgaccagcggcgtgcacaccttcccggctgtcctacagtcctcaggactctactccctcagcagc
gtggtgaccgtgccctccagcagcttgggcacccagacctacatctgcaacgtgaatcacaagccca
gcaacaccaaggtggacaagaaagttgagcccaaatcttgtgacaaaactcacacatgcccaccgtg
cccagcacctgaactcctggggggaccgtcagtcttcctcttccccccaaaacccaaggacaccctc
atgatctcccggacccctgaggtcacatgcgtggtggtggacgtgagccacgaagaccctgaggtca
agttcaactggtacgtggacggcgtggaggtgcataatgccaagacaaagccgcgggaggagcagta
caacagcacgtaccgtgtggtcagcgtcctcaccgtcctgcaccaggactggctgaatggcaaggag
tacaagtgcaaggtctccaacaaagccctcccagcccccatcgagaaaaccatctccaaagccaaag
ggcagccccgagaaccacaggtgtacaccctgcccccatcccgggatgagctgaccaagaaccaggt
cagcctgacctgcctggtcaaaggcttctatcccagcgacatcgccgtggagtgggagagcaatggg
cagccggagaacaactacaagaccacgcctcccgtgctggactccgacggctccttcttcctctata
gcaagctcaccgtggacaagagcaggtggcagcaggggaacgtcttctcatgctccgtgatgcatga
ggctctgcacaaccactacacgcagaagagcctctccctgtctccgggtaaa

*Amino acid sequence*
astkgpsvfplapsskstsggtaalgclvkdyfpepvtvswnsgaltsgvhtfpavlqssglyslss
vvtvpssslgtqtyicnvnhkpsntkvdkkvepkscdkthtcppcpapellggpsvflfppkpkdtl
misrtpevtcvvvdvshedpevkfnwyvdgvevhnaktkpreeqynstyrvvsvltvlhqdwlngke
ykckvsnkalpapiektiskakgqprepqvytlppsrdeltknqvsltclvkgfypsdiavewesng
qpennykttppvldsdgsfflyskltvdksrwqqgnvfscsvmhealhnhytqkslslspgk

SEQUENCE LISTING

<160> NUMBER OF SEQ ID NOS: 380

<210> SEQ ID NO 1
<211> LENGTH: 336

-continued

```
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 1 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt     96
Glu Pro Ala Ser Ile Ser Cys Arg Ser Ser Gln Ser Leu Leu His Ser
            20                  25                  30 agt gga tac aac tat ttg gat tgg tac ctg cag aag cca ggg cag tct    144
Ser Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct    192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc    240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct    288
Ser Arg Val Glu Ala Glu Asp Val Gly Val Tyr Tyr Cys Met Gln Ala
                85                  90                  95 cta caa act ccg atc acc ttc ggc caa ggg aca cga ctg gag att aaa    336
Leu Gln Thr Pro Ile Thr Phe Gly Gln Gly Thr Arg Leu Glu Ile Lys
            100                 105                 110

<210> SEQ ID NO 2
<211> LENGTH: 112
<212> TYPE: PRT
<213> ORGANISM: Artificial
<220> FEATURE:
<223> OTHER INFORMATION: Synthetic Construct

<400> SEQUENCE: 2

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Ser Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 3
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
```

```
<221> NAME/KEY: CDS
<222> LOCATION: (1)..(336)

<400> SEQUENCE: 3 gat gtt gtg atg act cag tct cca ctc tcc ctg ccc gtc acc cct gga         48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt         96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct        144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct        192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc        240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct        288
Ser Arg Val Glu Ala Glu Asp Val Gly Val Tyr Tyr Cys Met Gln Ala
                85                  90                  95 cta caa act ccg atc acc ttc ggc caa ggg aca cga ctg gag att aaa        336
Leu Gln Thr Pro Ile Thr Phe Gly Gln Gly Thr Arg Leu Glu Ile Lys
            100                 105                 110

<210> SEQ ID NO 4
<211> LENGTH: 112
<212> TYPE: PRT
<213> ORGANISM: Artificial
<220> FEATURE:
<223> OTHER INFORMATION: Synthetic Construct

<400> SEQUENCE: 4

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 5
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 5 gat gtt gtg atg act cag tct cca ctc tcc ctg ccc gtc acc cct gga         48
```

```
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt    96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct   144
Asn Gly Tyr Asn Tyr Leu Asp Trp Tyr Leu Gln Lys Pro Gly Gln Ser
                35                  40                  45 cca cag ctc ctg atc tat ttg ggt tct aat cgg gcc tcc ggg gtc cct   192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca ctg aaa atc   240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct   288
Ser Arg Val Glu Ala Glu Asp Val Gly Val Tyr Tyr Cys Met Gln Ala
                85                  90                  95 cta caa act cca ctc act ttc ggc ggc ggg acc aag gtg gag atc aaa   336
Leu Gln Thr Pro Leu Thr Phe Gly Gly Gly Thr Lys Val Glu Ile Lys
            100                 105                 110
```

<210> SEQ ID NO 6
<211> LENGTH: 112
<212> TYPE: PRT
<213> ORGANISM: Artificial
<220> FEATURE:
<223> OTHER INFORMATION: Synthetic Construct

<400> SEQUENCE: 6

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 7
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 7

```
gaa att gtg atg acg cag tct cca ctc tcc ctg ccc gtc acc cct gga    48
Glu Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt    96
Glu Pro Ala Ser Ile Ser Cys Arg Ser Ser Gln Ser Leu Leu His Ser
            20                  25                  30
```

```
aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
             35                  40                  45 cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
 50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct      288
Ser Arg Val Glu Ala Glu Asp Val Gly Val Tyr Tyr Cys Met Gln Ala
                 85                  90                  95 cta caa act cct cac act ttc ggc gga ggg acc aag gtg gag atc aaa      336
Leu Gln Thr Pro His Thr Phe Gly Gly Gly Thr Lys Val Glu Ile Lys
            100                 105                 110

<210> SEQ ID NO 8
<211> LENGTH: 112
<212> TYPE: PRT
<213> ORGANISM: Artificial
<220> FEATURE:
<223> OTHER INFORMATION: Synthetic Construct

<400> SEQUENCE: 8

Glu Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro His Thr Phe Gly Gly Gly Thr Lys Val Glu Ile Lys
            100                 105                 110

<210> SEQ ID NO 9
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 9 gaa att gtg ctg act cag tct cca ctc tcc ctg ccc gtc acc cct gga       48
Glu Ile Val Leu Thr Gln Ser Pro Leu Ser Leu Pro Val Thr Pro Gly
  1               5                  10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
             20                  25                  30 aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
         35                  40                  45 cca cag ctc ctg atc tat ttg ggt tct aat cgg gcc tcc ggg gtc cct      192
```

```
Pro Gln Leu Leu Ile Tyr Leu Gly Ser Asn Arg Ala Ser Gly Val Pro
     50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                 85                  90                  95 cta caa acc cct ctc act ttc ggc cct ggg acc aaa gtg gat atc aaa       336
Leu Gln Thr Pro Leu Thr Phe Gly Pro Gly Thr Lys Val Asp Ile Lys
            100                 105                 110

<210> SEQ ID NO 10
<211> LENGTH: 112
<212> TYPE: PRT
<213> ORGANISM: Artificial
<220> FEATURE:
<223> OTHER INFORMATION: Synthetic Construct

<400> SEQUENCE: 10

Glu Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Pro Gly Thr Lys Val Asp Ile Lys
            100                 105                 110

<210> SEQ ID NO 11
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 11 gat gtt gtg atg act cag tct cca ctc tcc ctg gcc gtc acc cct gga        48
Asp Val Val Met Thr Gln Ser Pro Leu Ser Leu Ala Val Thr Pro Gly
 1               5                  10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
             20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
         35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
     50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
 65                  70                  75                  80
```

```
agc aga gtg gag gct gag gat gtt ggg gtt tat tac tgc atg caa gct      288
Ser Arg Val Glu Ala Glu Asp Val Gly Val Tyr Tyr Cys Met Gln Ala
                85                  90                  95 cta caa act ccg ctc act ttc ggc gga ggg acc aag gtg gag atc aaa      336
Leu Gln Thr Pro Leu Thr Phe Gly Gly Gly Thr Lys Val Glu Ile Lys
            100                 105                 110
```

<210> SEQ ID NO 12
<211> LENGTH: 112
<212> TYPE: PRT
<213> ORGANISM: Artificial
<220> FEATURE:
<223> OTHER INFORMATION: Synthetic Construct

<400> SEQUENCE: 12

```
Asp Val Val Met Thr Gln Ser Pro Leu Ser Leu Ala Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 13
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 13

```
gat gtt gtg atg act cag tct cca ctc tcc ctg ccc gtc acc cct gga       48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct      288
Ser Arg Val Glu Ala Glu Asp Val Gly Val Tyr Tyr Cys Met Gln Ala
                85                  90                  95 cta caa act cct ctc act ttc ggc gga ggg acc aag gtg gag atc aaa      336
Leu Gln Thr Pro Leu Thr Phe Gly Gly Gly Thr Lys Val Glu Ile Lys
            100                 105                 110
```

```
Leu Gln Thr Pro Leu Thr Phe Gly Gly Gly Thr Lys Val Glu Ile Lys
            100                 105                 110
```

<210> SEQ ID NO 14
<211> LENGTH: 112
<212> TYPE: PRT
<213> ORGANISM: Artificial
<220> FEATURE:
<223> OTHER INFORMATION: Synthetic Construct

<400> SEQUENCE: 14

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 15
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 15

```
gat gtt gtg atg act cag tct cca ctc tcc ctg ccc gtc acc cct gga        48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gaa gat gtt ggg gtt tat tac tgt atg caa gct       288
Ser Arg Val Glu Ala Glu Asp Val Gly Val Tyr Tyr Cys Met Gln Ala
                85                  90                  95 cta caa acc ccc ctc act ttc ggc gga ggg acc aag gtg gag atc aaa       336
Leu Gln Thr Pro Leu Thr Phe Gly Gly Gly Thr Lys Val Glu Ile Lys
            100                 105                 110
```

<210> SEQ ID NO 16
<211> LENGTH: 112

```
<212> TYPE: PRT
<213> ORGANISM: Artificial
<220> FEATURE:
<223> OTHER INFORMATION: Synthetic Construct

<400> SEQUENCE: 16

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 17
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 17 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccg ttc acc ttc ggc caa ggg aca cga ctg gag att aaa     336
Leu Gln Thr Pro Phe Thr Phe Gly Gln Gly Thr Arg Leu Glu Ile Lys
            100                 105                 110

<210> SEQ ID NO 18
<211> LENGTH: 112
<212> TYPE: PRT
<213> ORGANISM: Artificial
<220> FEATURE:
<223> OTHER INFORMATION: Synthetic Construct

<400> SEQUENCE: 18
```

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Gln Gly Thr Arg Leu Glu Ile Lys
            100                 105                 110
```

<210> SEQ ID NO 19
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 19

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct ctg gcg ttc ggc caa ggg acc aag gtg gaa atc aaa     336
Leu Gln Thr Pro Leu Ala Phe Gly Gln Gly Thr Lys Val Glu Ile Lys
            100                 105                 110
```

<210> SEQ ID NO 20
<211> LENGTH: 112
<212> TYPE: PRT
<213> ORGANISM: Artificial
<220> FEATURE:
<223> OTHER INFORMATION: Synthetic Construct

<400> SEQUENCE: 20

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ala Phe Gly Gln Gly Thr Lys Val Glu Ile Lys
            100                 105                 110

<210> SEQ ID NO 21
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 21 gaa att gtg ctg act cag tct cca ctc tcc ctg ccc gtc acc cct gga       48
Glu Ile Val Leu Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg aat tgg tac ctg cag aag cca ggg cag tct     144
Asn Gly Tyr Asn Tyr Leu Asn Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt gcc agt gga tca ggc aca gat ttt aca ctg aaa atc     240
Asp Arg Phe Ser Ala Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct atc acc ttc ggc caa ggg aca cga ctg gag att aaa     336
Leu Gln Thr Pro Ile Thr Phe Gly Gln Gly Thr Arg Leu Glu Ile Lys
            100                 105                 110

<210> SEQ ID NO 22
<211> LENGTH: 112
<212> TYPE: PRT
<213> ORGANISM: Artificial
<220> FEATURE:
<223> OTHER INFORMATION: Synthetic Construct

<400> SEQUENCE: 22

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Ala Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Ile Thr Phe Gly Gln Gly Thr Arg Leu Glu Ile Lys
            100                 105                 110

<210> SEQ ID NO 23
<211> LENGTH: 333
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(333)

<400> SEQUENCE: 23 aat ttt atg ctg act cag ccc cac tct gtg tcg gag tct ccg ggg aag        48
Asn Phe Met Leu Thr Gln Pro His Ser Val Ser Glu Ser Pro Gly Lys
1               5                   10                  15 acg gta acc atc tcc tgc acc cgc agc agt ggc agc att gcc agc aac        96
Thr Val Thr Ile Ser Cys Thr Arg Ser Ser Gly Ser Ile Ala Ser Asn
            20                  25                  30 tat gtg cag tgg tac cag cag cgc ccg ggc agt tcc ccc acc act gtg       144
Tyr Val Gln Trp Tyr Gln Gln Arg Pro Gly Ser Ser Pro Thr Thr Val
        35                  40                  45 atc tat gag gat aac caa aga ccc tct ggg gtc cct gat cgg ttc tct       192
Ile Tyr Glu Asp Asn Gln Arg Pro Ser Gly Val Pro Asp Arg Phe Ser
    50                  55                  60 ggc tcc atc gac agc tcc tcc aac tct gcc tcc ctc acc atc tct gga       240
Gly Ser Ile Asp Ser Ser Ser Asn Ser Ala Ser Leu Thr Ile Ser Gly
65                  70                  75                  80 ctg aag act gag gac gag gct gac tac tac tgt cag tct tat gat agc       288
Leu Lys Thr Glu Asp Glu Ala Asp Tyr Tyr Cys Gln Ser Tyr Asp Ser
                85                  90                  95 agc aat cag aga gtg ttc ggc gga ggg acc aag ctg acc gtc cta            333
Ser Asn Gln Arg Val Phe Gly Gly Gly Thr Lys Leu Thr Val Leu
            100                 105                 110

<210> SEQ ID NO 24
<211> LENGTH: 111
<212> TYPE: PRT
<213> ORGANISM: Artificial
<220> FEATURE:
<223> OTHER INFORMATION: Synthetic Construct

<400> SEQUENCE: 24

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95
```

```
Ser Asn Gln Arg Val Phe Gly Gly Gly Thr Lys Leu Thr Val Leu
            100                 105                 110
```

<210> SEQ ID NO 25
<211> LENGTH: 336
<212> TYPE: DNA
<213> ORGANISM: Artificial
<220> FEATURE:
<223> OTHER INFORMATION: Anti-IGF1R antibody light chain variable domain sequence
<220> FEATURE:
<221> NAME/KEY: CDS
<222> LOCATION: (1)..(336)

<400> SEQUENCE: 25

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa acc ccg ctc act ttc ggc gga ggg acc aag gtg gag atc aaa     336
Leu Gln Thr Pro Leu Thr Phe Gly Gly Gly Thr Lys Val Glu Ile Lys
            100                 105                 110
```

<210> SEQ ID NO 26
<211> LENGTH: 112
<212> TYPE: PRT
<213> ORGANISM: Artificial
<220> FEATURE:
<223> OTHER INFORMATION: Synthetic Construct

<400> SEQUENCE: 26

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 27

<211> LENGTH: 336
<212> TYPE: DNA
<213> ORGANISM: Artificial
<220> FEATURE:
<223> OTHER INFORMATION: Anti-IGF1R antibody light chain variable domain sequence
<220> FEATURE:
<221> NAME/KEY: CDS
<222> LOCATION: (1)..(336)

<400> SEQUENCE: 27

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct ctt act ttc ggc gga ggg acc aag gtg gag atc aaa     336
Leu Gln Thr Pro Leu Thr Phe Gly Gly Gly Thr Lys Val Glu Ile Lys
                100                 105                 110
```

<210> SEQ ID NO 28
<211> LENGTH: 112
<212> TYPE: PRT
<213> ORGANISM: Artificial
<220> FEATURE:
<223> OTHER INFORMATION: Synthetic Construct

<400> SEQUENCE: 28

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
                100                 105                 110
```

<210> SEQ ID NO 29
<211> LENGTH: 336
<212> TYPE: DNA
<213> ORGANISM: Artificial
<220> FEATURE:
<223> OTHER INFORMATION: Anti-IGF1R antibody light chain variable domain sequence

```
<220> FEATURE:
<221> NAME/KEY: CDS
<222> LOCATION: (1)..(336)

<400> SEQUENCE: 29 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                  10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
             20                  25                  30 aat gga tac aac tat ttg gat tgg tac ctg caa aag cca ggg cag tct     144
Asn Gly Tyr Asn Tyr Leu Asp Trp Tyr Leu Gln Lys Pro Gly Gln Ser
         35                  40                  45 cca cag ctc ctg atc tat ttg ggt tct tat cgg gcc tcc ggg gtc cct     192
Pro Gln Leu Leu Ile Tyr Leu Gly Ser Tyr Arg Ala Ser Gly Val Pro
     50                  55                  60 gac agg ttc agt gcc agt gga tca ggc aca gat ttt aca ctg aaa atc     240
Asp Arg Phe Ser Ala Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                 85                  90                  95 cta caa act ccg atc acc ttc ggc caa ggg aca cga ctg gag att aaa     336
Leu Gln Thr Pro Ile Thr Phe Gly Gln Gly Thr Arg Leu Glu Ile Lys
            100                 105                 110

<210> SEQ ID NO 30
<211> LENGTH: 112
<212> TYPE: PRT
<213> ORGANISM: Artificial
<220> FEATURE:
<223> OTHER INFORMATION: Synthetic Construct

<400> SEQUENCE: 30

Asp Val Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Tyr Arg Ala Ser Gly Val Pro
     50                  55                  60

Asp Arg Phe Ser Ala Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                 85                  90                  95

Leu Gln Thr Pro Ile Thr Phe Gly Gln Gly Thr Arg Leu Glu Ile Lys
            100                 105                 110

<210> SEQ ID NO 31
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 31
```

```
gat gtt gtg atg act cag tct cca ctc tcc ctg ccc gtc acc cct gga    48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt    96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct   144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct   192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc   240
Asp Arg Phe Ser Gly Ser Gly Ser Gly Thr Asp Phe Thr Leu Lys Ile
65              70                  75                  80 agc agg gtg gag gct gag gat gtt ggg gtt tat tac tgc atg caa ggt   288
Ser Arg Val Glu Ala Glu Asp Val Gly Val Tyr Tyr Cys Met Gln Gly
                85                  90                  95 aca cac tgg cct ctg acg ttc ggc caa ggg acc aag gtg gag atc aaa   336
Thr His Trp Pro Leu Thr Phe Gly Gln Gly Thr Lys Val Glu Ile Lys
            100                 105                 110

<210> SEQ ID NO 32
<211> LENGTH: 112
<212> TYPE: PRT
<213> ORGANISM: Artificial
<220> FEATURE:
<223> OTHER INFORMATION: Synthetic Construct

<400> SEQUENCE: 32

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

<210> SEQ ID NO 33
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 33 gaa att gtg atg acg cag tct cca ctc tcc ctg ccc gtc acc cct gga    48
Glu Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt    96
Glu Pro Ala Ser Ile Ser Cys Arg Ser Ser Gln Ser Leu Leu His Ser
```

```
aat gga tac aac tat ttg gat tgg tac ctg cag aag cca ggg cag tct    144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct    192
Pro Gln Leu Leu Ile Tyr Leu Gly Ser Asn Arg Ala Ser Gly Val Pro
 50                  55                  60 gac agg ttc agt ggc agt gga tca ggc aca gat ttt aca ctg aaa atc    240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct    288
Ser Arg Val Glu Ala Glu Asp Val Gly Val Tyr Tyr Cys Met Gln Ala
                 85                  90                  95 cta caa act cct ctc act ttc ggc gga ggg acc aag gtg gag atc aaa    336
Leu Gln Thr Pro Leu Thr Phe Gly Gly Gly Thr Lys Val Glu Ile Lys
            100                 105                 110
```

<210> SEQ ID NO 34
<211> LENGTH: 112
<212> TYPE: PRT
<213> ORGANISM: Artificial
<220> FEATURE:
<223> OTHER INFORMATION: Synthetic Construct

<400> SEQUENCE: 34

```
Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                 85                 90                   95

Leu Gln Thr Pro Leu Thr Phe Gly Gly Gly Thr Lys Val Glu Ile Lys
            100                 105                 110
```

<210> SEQ ID NO 35
<211> LENGTH: 321
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(321)

<400> SEQUENCE: 35

```
gac atc cag ttg acc cag tct cca tct tcc gtg tct gcg tct gtc gga    48
Asp Ile Gln Leu Thr Gln Ser Pro Ser Ser Val Ser Ala Ser Val Gly
1               5                   10                  15 gac aga gtc acc atc act tgt cgg gcg agt cag ggt att agc agg tgg    96
Asp Arg Val Thr Ile Thr Cys Arg Ala Ser Gln Gly Ile Ser Arg Trp
            20                  25                  30 tta gcc tgg tat caa cag aaa cca ggg aaa gcc cct aga ctc ctg atc    144
Leu Ala Trp Tyr Gln Gln Lys Pro Gly Lys Ala Pro Arg Leu Leu Ile
        35                  40                  45
```

```
tat gct gcg tcc ggt tta caa agt ggg gtc cca tca agg ttc agc ggc      192
Tyr Ala Ala Ser Gly Leu Gln Ser Gly Val Pro Ser Arg Phe Ser Gly
         50                  55                  60 agt gga tct ggg aca gat ttc act ctc acc atc agc aac ctg cag cct      240
Ser Gly Ser Gly Thr Asp Phe Thr Leu Thr Ile Ser Asn Leu Gln Pro
 65                  70                  75                  80 gaa gat ttt gca act tac tat tgt caa cag gct agc agt ttt cca atc      288
Glu Asp Phe Ala Thr Tyr Tyr Cys Gln Gln Ala Ser Ser Phe Pro Ile
                 85                  90                  95 acc ttc ggc caa ggg aca cga ctg gag act aaa                          321
Thr Phe Gly Gln Gly Thr Arg Leu Glu Thr Lys
                100                 105
```

<210> SEQ ID NO 36
<211> LENGTH: 107
<212> TYPE: PRT
<213> ORGANISM: Artificial
<220> FEATURE:
<223> OTHER INFORMATION: Synthetic Construct

<400> SEQUENCE: 36

```
Asp Ile Gln Leu Thr Gln Ser Pro Ser Ser Val Ser Ala Ser Val Gly
 1               5                  10                  15

Asp Arg Val Thr Ile Thr Cys Arg Ala Ser Gln Gly Ile Ser Arg Trp
             20                  25                  30

Leu Ala Trp Tyr Gln Gln Lys Pro Gly Lys Ala Pro Arg Leu Leu Ile
         35                  40                  45

Tyr Ala Ala Ser Gly Leu Gln Ser Gly Val Pro Ser Arg Phe Ser Gly
     50                  55                  60

Ser Gly Ser Gly Thr Asp Phe Thr Leu Thr Ile Ser Asn Leu Gln Pro
 65                  70                  75                  80

Glu Asp Phe Ala Thr Tyr Tyr Cys Gln Gln Ala Ser Ser Phe Pro Ile
                 85                  90                  95

Thr Phe Gly Gln Gly Thr Arg Leu Glu Thr Lys
                100                 105
```

<210> SEQ ID NO 37
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 37

```
gat gtt gtg atg act cag tct cca ctc tcc ctg ccc gtc acc cct gga       48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
             20                  25                  30 aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
         35                  40                  45 cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
     50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
```

```
              65                  70                  75                  80
agc aga gtg gag gct gag gat gtt gga gtt tat tac tgc atg caa gct        288
Ser Arg Val Glu Ala Glu Asp Val Gly Val Tyr Tyr Cys Met Gln Ala
                    85                  90                  95 cta caa act ccg tac act ttt ggc cag ggg acc aag ctg gag atc aaa        336
Leu Gln Thr Pro Tyr Thr Phe Gly Gln Gly Thr Lys Leu Glu Ile Lys
            100                 105                 110

<210> SEQ ID NO 38
<211> LENGTH: 112
<212> TYPE: PRT
<213> ORGANISM: Artificial
<220> FEATURE:
<223> OTHER INFORMATION: Synthetic Construct

<400> SEQUENCE: 38

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 39
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 39 gat gtt gtg atg act cag tct cca ctc tcc ctg ccc gtc acc cct gga        48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 aac agg ttc agt ggc agt gga tca ggc aca gat ttt aca ctg aaa atc       240
Asn Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                85                  90                  95
```

```
cta caa act cca ttc act ttc ggc cct ggg acc aaa gtg gat atc aaa       336
Leu Gln Thr Pro Phe Thr Phe Gly Pro Gly Thr Lys Val Asp Ile Lys
            100                 105                 110
```

<210> SEQ ID NO 40
<211> LENGTH: 112
<212> TYPE: PRT
<213> ORGANISM: Artificial
<220> FEATURE:
<223> OTHER INFORMATION: Synthetic Construct

<400> SEQUENCE: 40

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110
```

<210> SEQ ID NO 41
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 41

```
gat gtt gtg atg act cag tct cca ctc tcc ctg ccc gtc acc cct gga       48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
            20                  25                  30 cat gga tac aac tat ttg gat tgg tac ctg cag aag cca ggg cag tct       144
His Gly Tyr Asn Tyr Leu Asp Trp Tyr Leu Gln Lys Pro Gly Gln Ser
        35                  40                  45 cca caa ctt ctg atc tat ttg ggt tct tat cgg gcc tcc ggg gtc cct       192
Pro Gln Leu Leu Ile Tyr Leu Gly Ser Tyr Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa tct       288
Ser Arg Val Glu Ala Glu Asp Val Gly Val Tyr Tyr Cys Met Gln Ser
                85                  90                  95 cta gaa gtt ccg ttc act ttt ggc cag ggg acc aag ctg gag atc aaa       336
Leu Glu Val Pro Phe Thr Phe Gly Gln Gly Thr Lys Leu Glu Ile Lys
            100                 105                 110
```

<210> SEQ ID NO 42

```
<211> LENGTH: 112
<212> TYPE: PRT
<213> ORGANISM: Artificial
<220> FEATURE:
<223> OTHER INFORMATION: Synthetic Construct

<400> SEQUENCE: 42

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Val Pro Phe Thr Phe Gly Gln Gly Thr Lys Leu Glu Ile Lys
            100                 105                 110

<210> SEQ ID NO 43
<211> LENGTH: 321
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(321)

<400> SEQUENCE: 43 tct tct gag ctg act cag gac cct gct gtg tct gtg gcc ttg gga cag      48
Ser Ser Glu Leu Thr Gln Asp Pro Ala Val Ser Val Ala Leu Gly Gln
1               5                   10                  15 aca gtc agg atc aca tgc caa gga gac agc ctc aga att tat tat aca      96
Thr Val Arg Ile Thr Cys Gln Gly Asp Ser Leu Arg Ile Tyr Tyr Thr
            20                  25                  30 ggc tgg tac caa cag aag cca gga cag gcc cct gtg ctt gtc ctc ttt     144
Gly Trp Tyr Gln Gln Lys Pro Gly Gln Ala Pro Val Leu Val Leu Phe
        35                  40                  45 ggt aag aac aat cgg ccc tca ggg atc cca gac cga ttc tct ggc tcc     192
Gly Lys Asn Asn Arg Pro Ser Gly Ile Pro Asp Arg Phe Ser Gly Ser
    50                  55                  60 cac tca ggg aac aca gct tcc ttg acc atc act ggg gct caa gcg gaa     240
His Ser Gly Asn Thr Ala Ser Leu Thr Ile Thr Gly Ala Gln Ala Glu
65                  70                  75                  80 gat gag gct gac tat tac tgt aac tcc cgg gac atc act ggt gtc cat     288
Asp Glu Ala Asp Tyr Tyr Cys Asn Ser Arg Asp Ile Thr Gly Val His
                85                  90                  95 cga ttc ggc gga ggg acc aag ctg acc gtc cta                         321
Arg Phe Gly Gly Gly Thr Lys Leu Thr Val Leu
            100                 105

<210> SEQ ID NO 44
<211> LENGTH: 107
<212> TYPE: PRT
<213> ORGANISM: Artificial
<220> FEATURE:
<223> OTHER INFORMATION: Synthetic Construct
```

```
<400> SEQUENCE: 44

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ile Tyr Tyr Thr
            20                  25                  30

Gly Trp Tyr Gln Gln Lys Pro Gly Gln Ala Pro Val Leu Val Leu Phe
        35                  40                  45

Gly Lys Asn Asn Arg Pro Ser Gly Ile Pro Asp Arg Phe Ser Gly Ser
50                  55                  60

His Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Thr Gly Val His
                85                  90                  95

Arg Phe Gly Gly Gly Thr Lys Leu Thr Val Leu
            100                 105

<210> SEQ ID NO 45
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 45 gaa att gtg ctg act cag tct cca ctc tcc ctg ccc gtc acc cct gga        48
Glu Ile Val Leu Thr Gln Ser Pro Leu Ser Leu Pro Val Thr Pro Gly
1               5                   10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct      288
Ser Arg Val Glu Ala Glu Asp Val Gly Val Tyr Tyr Cys Met Gln Ala
                85                  90                  95 cta caa act cct ctc act ttc ggc gga ggg acc aag gtg gag atc aaa      336
Leu Gln Thr Pro Leu Thr Phe Gly Gly Gly Thr Lys Val Glu Ile Lys
            100                 105                 110

<210> SEQ ID NO 46
<211> LENGTH: 112
<212> TYPE: PRT
<213> ORGANISM: Artificial
<220> FEATURE:
<223> OTHER INFORMATION: Synthetic Construct

<400> SEQUENCE: 46

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
```

20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
                100                 105                 110

<210> SEQ ID NO 47
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 47 gat gtt gtg atg act cag tct cca ctc tcc ctg ccc gtc acc cct gga        48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                85                  90                  95 cta caa act cct aac act ttc ggc gga ggg acc aag gtg gag atc aaa       336
Leu Gln Thr Pro Asn Thr Phe Gly Gly Gly Thr Lys Val Glu Ile Lys
                100                 105                 110

<210> SEQ ID NO 48
<211> LENGTH: 112
<212> TYPE: PRT
<213> ORGANISM: Artificial
<220> FEATURE:
<223> OTHER INFORMATION: Synthetic Construct

<400> SEQUENCE: 48

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro

```
              50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Asn Thr Phe Gly Gly Gly Thr Lys Val Glu Ile Lys
            100                 105                 110

<210> SEQ ID NO 49
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 49 gat gtt gtg atg act cag tct cca ctc tcc ctg ccc gtc acc cct gga        48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
             20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
         35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
     50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                 85                  90                  95 cta caa act cca atc act ttc ggc cct ggg acc aaa gtg gat atc aaa       336
Leu Gln Thr Pro Ile Thr Phe Gly Pro Gly Thr Lys Val Asp Ile Lys
            100                 105                 110

<210> SEQ ID NO 50
<211> LENGTH: 112
<212> TYPE: PRT
<213> ORGANISM: Artificial
<220> FEATURE:
<223> OTHER INFORMATION: Synthetic Construct

<400> SEQUENCE: 50

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
```

```
                     85                  90                  95
Leu Gln Thr Pro Ile Thr Phe Gly Pro Gly Thr Lys Val Asp Ile Lys
            100                 105                 110
```

<210> SEQ ID NO 51
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 51

```
gat gtt gtg atg act cag tct cca ctc tcc ctg ccc gtc acc cct gga    48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt    96
Glu Pro Ala Ser Ile Ser Cys Arg Ser Ser Gln Ser Leu Leu His Ser
            20                  25                  30 aat gga tac acc tat ttg gat tgg tac ctg cag aag cca ggg cag tct   144
Asn Gly Tyr Thr Tyr Leu Asp Trp Tyr Leu Gln Lys Pro Gly Gln Ser
        35                  40                  45 cca caa ctc ctg atc tat ttg ggt tct aat cgg gcc tcc ggg gtc cct   192
Pro Gln Leu Leu Ile Tyr Leu Gly Ser Asn Arg Ala Ser Gly Val Pro
    50                  55                  60 gac agg ttc agc ggc agt gga tca ggc aca gat ttt aca ctg aaa atc   240
Asp Arg Phe Ser Gly Ser Gly Ser Gly Thr Asp Phe Thr Leu Lys Ile
65                  70                  75                  80 agc aga gtg gag cct gag gat gtt ggg gtc tat tac tgc atg caa gct   288
Ser Arg Val Glu Pro Glu Asp Val Gly Val Tyr Tyr Cys Met Gln Ala
                85                  90                  95 cta gaa atg ccc ctc act ttc ggc gga ggg acc aag gtg gag atc aaa   336
Leu Glu Met Pro Leu Thr Phe Gly Gly Gly Thr Lys Val Glu Ile Lys
            100                 105                 110
```

<210> SEQ ID NO 52
<211> LENGTH: 112
<212> TYPE: PRT
<213> ORGANISM: Artificial
<220> FEATURE:
<223> OTHER INFORMATION: Synthetic Construct

<400> SEQUENCE: 52

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Val Gly Val Tyr Tyr Cys Met Gln Ala
                85                  90                  95

Leu Glu Met Pro Leu Thr Phe Gly Gly Gly Thr Lys Val Glu Ile Lys
            100                 105                 110
```

```
<210> SEQ ID NO 53
<211> LENGTH: 321
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(321)

<400> SEQUENCE: 53 gac atc cag ttg acc cag tct cca tcc ttc ctg tct gca tct gta gga        48
Asp Ile Gln Leu Thr Gln Ser Pro Ser Phe Leu Ser Ala Ser Val Gly
1               5                   10                  15 gac aga gtc acc atc act tgc cgg gcc agt cag ggc att agc agt tat        96
Asp Arg Val Thr Ile Thr Cys Arg Ala Ser Gln Gly Ile Ser Ser Tyr
            20                  25                  30 tta gcc tgg tat cag caa aaa cca ggg aaa gcc cct aag ctc ctg atc       144
Leu Ala Trp Tyr Gln Gln Lys Pro Gly Lys Ala Pro Lys Leu Leu Ile
        35                  40                  45 tat gct gca tcc act ttg caa agt ggg gtc cca tca agg ttc agc ggc       192
Tyr Ala Ala Ser Thr Leu Gln Ser Gly Val Pro Ser Arg Phe Ser Gly
    50                  55                  60 agt gga tct ggg aca gaa ttc act ctc aca atc agc agc ctg cag cct       240
Ser Gly Ser Gly Thr Glu Phe Thr Leu Thr Ile Ser Ser Leu Gln Pro
65                  70                  75                  80 gaa gat ttt gca act tat tac tgt caa cag ctt aat agt tac ccc ctc       288
Glu Asp Phe Ala Thr Tyr Tyr Cys Gln Gln Leu Asn Ser Tyr Pro Leu
                85                  90                  95 act ttc ggc gga ggg acc aag gtg gag atc aaa                           321
Thr Phe Gly Gly Gly Thr Lys Val Glu Ile Lys
            100                 105

<210> SEQ ID NO 54
<211> LENGTH: 107
<212> TYPE: PRT
<213> ORGANISM: Artificial
<220> FEATURE:
<223> OTHER INFORMATION: Synthetic Construct

<400> SEQUENCE: 54

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 55
<211> LENGTH: 315
<212> TYPE: DNA
<213> ORGANISM: Artificial
<220> FEATURE:
<223> OTHER INFORMATION: Anti-IGF1R antibody light chain variable domain
```

```
                                              sequence
<220> FEATURE:
<221> NAME/KEY: CDS
<222> LOCATION: (1)..(315)

<400> SEQUENCE: 55 tcc tat gtg ctg act cag cca ccc tca gtg tcc gtg tcc cca gga cag        48
Ser Tyr Val Leu Thr Gln Pro Pro Ser Val Ser Val Ser Pro Gly Gln
1               5                   10                  15 aca gcc agc atc acc tgc tct gga gat aaa ttg ggg gat aaa tat gtt        96
Thr Ala Ser Ile Thr Cys Ser Gly Asp Lys Leu Gly Asp Lys Tyr Val
            20                  25                  30 ggc tgg tat cag caa aag gca ggc caa gcc cct gtt ttg gtc atc tat       144
Gly Trp Tyr Gln Gln Lys Ala Gly Gln Ala Pro Val Leu Val Ile Tyr
        35                  40                  45 caa gac aac aag cga ccc tca ggg atc cct gag cga ttc tct ggc tcc       192
Gln Asp Asn Lys Arg Pro Ser Gly Ile Pro Glu Arg Phe Ser Gly Ser
    50                  55                  60 aac tct ggg aac aca gcc agt ctg acc atc agc ggg acc cag gct atg       240
Asn Ser Gly Asn Thr Ala Ser Leu Thr Ile Ser Gly Thr Gln Ala Met
65                  70                  75                  80 gat gag gct gac tat tac tgt cag gcg tgg gac agc ggc acg gtg ttc       288
Asp Glu Ala Asp Tyr Tyr Cys Gln Ala Trp Asp Ser Gly Thr Val Phe
                85                  90                  95 ggc gga ggg acc aag ctg acc gtc cta                                   315
Gly Gly Gly Thr Lys Leu Thr Val Leu
            100                 105

<210> SEQ ID NO 56
<211> LENGTH: 105
<212> TYPE: PRT
<213> ORGANISM: Artificial
<220> FEATURE:
<223> OTHER INFORMATION: Synthetic Construct

<400> SEQUENCE: 56

Ser Tyr Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Gly Trp Tyr Gln Gln Lys Ala Gly Gln Ala Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Ser Leu Thr Ile Ser Gly Thr Gln Ala Met
65                  70                  75                  80

Asp Glu Ala Asp Tyr Tyr Cys Gln Ala Trp Asp Ser Gly Thr Val Phe
                85                  90                  95

Gly Gly Gly Thr Lys Leu Thr Val Leu
            100                 105

<210> SEQ ID NO 57
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 57
```

```
gat gtt gtg atg act cag tct cca ctc tcc ctg ccc gtc acc cct gga        48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                85                  90                  95 cta caa acc ccc ctc act ttc ggc gga ggg acc aag gtg gag atc aaa       336
Leu Gln Thr Pro Leu Thr Phe Gly Gly Gly Thr Lys Val Glu Ile Lys
            100                 105                 110

<210> SEQ ID NO 58
<211> LENGTH: 112
<212> TYPE: PRT
<213> ORGANISM: Artificial
<220> FEATURE:
<223> OTHER INFORMATION: Synthetic Construct

<400> SEQUENCE: 58

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 59
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 59 gat gtt gtg atg act cag tct cca ctc tcc ctg ccc gtc acc cct gga        48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
```

```
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct    144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct    192
Pro Gln Leu Leu Ile Tyr Leu Gly Ser Asn Arg Ala Ser Gly Val Pro
 50                  55                  60 gac agg ttc agt ggc agt gga tca ggc aca gat ttt aca ctg aaa atc    240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg gaa gct    288
Ser Arg Val Glu Ala Glu Asp Val Gly Val Tyr Tyr Cys Met Glu Ala
                 85                  90                  95 cta caa act cca ttc act ttc ggc cct ggg acc aag gtg gaa atc aaa    336
Leu Gln Thr Pro Phe Thr Phe Gly Pro Gly Thr Lys Val Glu Ile Lys
            100                 105                 110

<210> SEQ ID NO 60
<211> LENGTH: 112
<212> TYPE: PRT
<213> ORGANISM: Artificial
<220> FEATURE:
<223> OTHER INFORMATION: Synthetic Construct

<400> SEQUENCE: 60

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Glu Ala
                 85                  90                  95

Leu Gln Thr Pro Phe Thr Phe Gly Pro Gly Thr Lys Val Glu Ile Lys
            100                 105                 110

<210> SEQ ID NO 61
<211> LENGTH: 321
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(321)

<400> SEQUENCE: 61 gac atc cag ttg acc cag tct cca tcc tcc ctg tct gcg tct gtg gga     48
Asp Ile Gln Leu Thr Gln Ser Pro Ser Ser Leu Ser Ala Ser Val Gly
1               5                   10                  15 gac aga gtc acc atc act tgc cgg tca agt caa ggc att ggt tac ttc     96
Asp Arg Val Thr Ile Thr Cys Arg Ser Ser Gln Gly Ile Gly Tyr Phe
                20                  25                  30 tta aat tgg tat cag cag gaa cca ggg aaa gcc cca aag atc ctg atc    144
Leu Asn Trp Tyr Gln Gln Glu Pro Gly Lys Ala Pro Lys Ile Leu Ile
            35                  40                  45
```

```
tct gct gca tcc act ttg caa agt ggg gtc cca tca agg ttc agt ggc       192
Ser Ala Ala Ser Thr Leu Gln Ser Gly Val Pro Ser Arg Phe Ser Gly
    50                  55                  60 agt gga tct ggg aca gat ttc aca ctc tcc atc aac aat ctg caa ccc       240
Ser Gly Ser Gly Thr Asp Phe Thr Leu Ser Ile Asn Asn Leu Gln Pro
65                  70                  75                  80 gca gat ttt gcg aca tac tac tgt caa cag agt cac agt ccc ccg tac       288
Ala Asp Phe Ala Thr Tyr Tyr Cys Gln Gln Ser His Ser Pro Pro Tyr
                85                  90                  95 act ttc ggc cag ggg acc aag gtg gag atc aaa                           321
Thr Phe Gly Gln Gly Thr Lys Val Glu Ile Lys
            100                 105

<210> SEQ ID NO 62
<211> LENGTH: 107
<212> TYPE: PRT
<213> ORGANISM: Artificial
<220> FEATURE:
<223> OTHER INFORMATION: Synthetic Construct

<400> SEQUENCE: 62

Asp Ile Gln Leu Thr Gln Ser Pro Ser Ser Leu Ser Ala Ser Val Gly
1               5                   10                  15

Asp Arg Val Thr Ile Thr Cys Arg Ser Ser Gln Gly Ile Gly Tyr Phe
            20                  25                  30

Leu Asn Trp Tyr Gln Gln Glu Pro Gly Lys Ala Pro Lys Ile Leu Ile
        35                  40                  45

Ser Ala Ala Ser Thr Leu Gln Ser Gly Val Pro Ser Arg Phe Ser Gly
    50                  55                  60

Ser Gly Ser Gly Thr Asp Phe Thr Leu Ser Ile Asn Asn Leu Gln Pro
65                  70                  75                  80

Ala Asp Phe Ala Thr Tyr Tyr Cys Gln Gln Ser His Ser Pro Pro Tyr
                85                  90                  95

Thr Phe Gly Gln Gly Thr Lys Val Glu Ile Lys
            100                 105

<210> SEQ ID NO 63
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 63 gat gtt gtg atg act cag tct cca ctc tcc ctg ccc gtc acc cct gga       48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc       240
```

```
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct      288
Ser Arg Val Glu Ala Glu Asp Val Gly Val Tyr Tyr Cys Met Gln Ala
                 85                  90                  95 cta caa act ccg ctc act ttc ggc gga ggg acc aag gtg gag atc aaa      336
Leu Gln Thr Pro Leu Thr Phe Gly Gly Gly Thr Lys Val Glu Ile Lys
            100                 105                 110

<210> SEQ ID NO 64
<211> LENGTH: 112
<212> TYPE: PRT
<213> ORGANISM: Artificial
<220> FEATURE:
<223> OTHER INFORMATION: Synthetic Construct

<400> SEQUENCE: 64

Asp Val Val Met Thr Gln Ser Pro Leu Ser Leu Pro Val Thr Pro Gly
 1                5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110

<210> SEQ ID NO 65
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 65 gaa att gtg ctg act cag tct cca ctc tcc ctg ccc gtc acc cct gga       48
Glu Ile Val Leu Thr Gln Ser Pro Leu Ser Leu Pro Val Thr Pro Gly
 1                5                  10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
                 20                  25                  30 aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
            35                  40                  45 cca cag ctc ctg atg tat ttg gtt tct aat cgg gcc tcc ggg gtc cct      192
Pro Gln Leu Leu Met Tyr Leu Val Ser Asn Arg Ala Ser Gly Val Pro
    50                  55                  60 gag agg ttc agt ggc agt gga tca ggc aca gat ttt aca ctg aaa atc      240
Glu Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa act      288
Ser Arg Val Glu Ala Glu Asp Val Gly Val Tyr Tyr Cys Met Gln Thr
                 85                  90                  95
```

```
cta caa act cct ctc agt ttt ggc cag ggg acc aag ctg gag atc aaa    336
Leu Gln Thr Pro Leu Ser Phe Gly Gln Gly Thr Lys Leu Glu Ile Lys
            100                 105                 110
```

<210> SEQ ID NO 66
<211> LENGTH: 112
<212> TYPE: PRT
<213> ORGANISM: Artificial
<220> FEATURE:
<223> OTHER INFORMATION: Synthetic Construct

<400> SEQUENCE: 66

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Met Tyr Leu Val Ser Asn Arg Ala Ser Gly Val Pro
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Ser Phe Gly Gln Gly Thr Lys Leu Glu Ile Lys
            100                 105                 110
```

<210> SEQ ID NO 67
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 67

```
gat gtt gtg atg act cag tct cca ctc tcc ctg ccc gtc acc cct gga    48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt    96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct    144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct    192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc    240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct    288
Ser Arg Val Glu Ala Glu Asp Val Gly Val Tyr Tyr Cys Met Gln Ala
                85                  90                  95 cta caa act ccg ctc act ttc ggc gga ggg acc aag gtg gag atc aaa    336
Leu Gln Thr Pro Leu Thr Phe Gly Gly Gly Thr Lys Val Glu Ile Lys
            100                 105                 110
```

<210> SEQ ID NO 68
<211> LENGTH: 112
<212> TYPE: PRT
<213> ORGANISM: Artificial
<220> FEATURE:
<223> OTHER INFORMATION: Synthetic Construct

<400> SEQUENCE: 68

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 69
<211> LENGTH: 330
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(330)

<400> SEQUENCE: 69

```
aat ttt atg ctg act cag ccc cac tct gtg tcg gcg tct ccg ggg aag      48
Asn Phe Met Leu Thr Gln Pro His Ser Val Ser Ala Ser Pro Gly Lys
1               5                   10                  15 acg gtt acc atc tcc tgc acc cgc agc agt ggc gac att gac aac aac      96
Thr Val Thr Ile Ser Cys Thr Arg Ser Ser Gly Asp Ile Asp Asn Asn
            20                  25                  30 tat gtg cag tgg tac cag cag cgc ccg ggc aat tcc ccc acc aat gtg     144
Tyr Val Gln Trp Tyr Gln Gln Arg Pro Gly Asn Ser Pro Thr Asn Val
        35                  40                  45 att tat gag gat aac cga aga ccc tct ggg gtc ccg gat cgc ttc tct     192
Ile Tyr Glu Asp Asn Arg Arg Pro Ser Gly Val Pro Asp Arg Phe Ser
    50                  55                  60 ggc tcc atc gac agc tcc tcc aac tct gcc tcc ctc acc atc tct gga     240
Gly Ser Ile Asp Ser Ser Ser Asn Ser Ala Ser Leu Thr Ile Ser Gly
65                  70                  75                  80 ctg cag cct gag gac gag gct gac tac tat tgt cag tct tat caa agc     288
Leu Gln Pro Glu Asp Glu Ala Asp Tyr Tyr Cys Gln Ser Tyr Gln Ser
                85                  90                  95 gac aat tgg gtg ttc ggc gga ggg acc aag gtg acc gtc cta             330
Asp Asn Trp Val Phe Gly Gly Gly Thr Lys Val Thr Val Leu
            100                 105                 110
```

<210> SEQ ID NO 70
<211> LENGTH: 110
<212> TYPE: PRT
<213> ORGANISM: Artificial
<220> FEATURE:
<223> OTHER INFORMATION: Synthetic Construct

<400> SEQUENCE: 70

| Asn | Phe | Met | Leu | Thr | Gln | Pro | His | Ser | Val | Ser | Ala | Ser | Pro | Gly | Lys |
|---|---|---|---|---|---|---|---|---|---|---|---|---|---|---|---|
| 1 | | | | 5 | | | | | 10 | | | | | 15 | |

| Thr | Val | Thr | Ile | Ser | Cys | Thr | Arg | Ser | Ser | Gly | Asp | Ile | Asp | Asn | Asn |
|---|---|---|---|---|---|---|---|---|---|---|---|---|---|---|---|
| | | | 20 | | | | | 25 | | | | | 30 | | |

| Tyr | Val | Gln | Trp | Tyr | Gln | Gln | Arg | Pro | Gly | Asn | Ser | Pro | Thr | Asn | Val |
|---|---|---|---|---|---|---|---|---|---|---|---|---|---|---|---|
| | | | 35 | | | | | 40 | | | | | 45 | | |

| Ile | Tyr | Glu | Asp | Asn | Arg | Arg | Pro | Ser | Gly | Val | Pro | Asp | Arg | Phe | Ser |
|---|---|---|---|---|---|---|---|---|---|---|---|---|---|---|---|
| | 50 | | | | | 55 | | | | | 60 | | | | |

| Gly | Ser | Ile | Asp | Ser | Ser | Ser | Asn | Ser | Ala | Ser | Leu | Thr | Ile | Ser | Gly |
|---|---|---|---|---|---|---|---|---|---|---|---|---|---|---|---|
| 65 | | | | | 70 | | | | | 75 | | | | | 80 |

| Leu | Gln | Pro | Glu | Asp | Glu | Ala | Asp | Tyr | Tyr | Cys | Gln | Ser | Tyr | Gln | Ser |
|---|---|---|---|---|---|---|---|---|---|---|---|---|---|---|---|
| | | | | 85 | | | | | 90 | | | | | 95 | |

| Asp | Asn | Trp | Val | Phe | Gly | Gly | Gly | Thr | Lys | Val | Thr | Val | Leu |
|---|---|---|---|---|---|---|---|---|---|---|---|---|---|
| | | | 100 | | | | | 105 | | | | | 110 |

<210> SEQ ID NO 71
<211> LENGTH: 330
<212> TYPE: DNA
<213> ORGANISM: Artificial
<220> FEATURE:
<223> OTHER INFORMATION: Anti-IGF1R antibody light chain variable domain sequence
<220> FEATURE:
<221> NAME/KEY: CDS
<222> LOCATION: (1)..(330)

<400> SEQUENCE: 71

| aat | ttt | atg | ctg | act | cag | ccc | cac | tct | gtg | tcg | gag | tct | ccg | ggg | aag | 48 |
|---|---|---|---|---|---|---|---|---|---|---|---|---|---|---|---|---|
| Asn | Phe | Met | Leu | Thr | Gln | Pro | His | Ser | Val | Ser | Glu | Ser | Pro | Gly | Lys | |
| 1 | | | | 5 | | | | | 10 | | | | | 15 | | |

| acg | gta | acc | atc | tcc | tgc | acc | cgc | agc | agt | ggc | agc | att | gcc | agc | aac | 96 |
|---|---|---|---|---|---|---|---|---|---|---|---|---|---|---|---|---|
| Thr | Val | Thr | Ile | Ser | Cys | Thr | Arg | Ser | Ser | Gly | Ser | Ile | Ala | Ser | Asn | |
| | | | 20 | | | | | 25 | | | | | 30 | | | |

| tat | gtg | cag | tgg | tac | cag | cag | cgc | ccg | ggc | agt | tcc | ccc | acc | act | gtg | 144 |
|---|---|---|---|---|---|---|---|---|---|---|---|---|---|---|---|---|
| Tyr | Val | Gln | Trp | Tyr | Gln | Gln | Arg | Pro | Gly | Ser | Ser | Pro | Thr | Thr | Val | |
| | | | 35 | | | | | 40 | | | | | 45 | | | |

| atc | tat | gag | gat | aac | caa | aga | ccc | tct | ggg | gtc | cct | gat | cga | ttc | tct | 192 |
|---|---|---|---|---|---|---|---|---|---|---|---|---|---|---|---|---|
| Ile | Tyr | Glu | Asp | Asn | Gln | Arg | Pro | Ser | Gly | Val | Pro | Asp | Arg | Phe | Ser | |
| | 50 | | | | | 55 | | | | | 60 | | | | | |

| ggc | tcc | atc | gac | agc | tcc | tcc | aac | tct | gcc | tcc | ctc | acc | atc | tct | gga | 240 |
|---|---|---|---|---|---|---|---|---|---|---|---|---|---|---|---|---|
| Gly | Ser | Ile | Asp | Ser | Ser | Ser | Asn | Ser | Ala | Ser | Leu | Thr | Ile | Ser | Gly | |
| 65 | | | | | 70 | | | | | 75 | | | | | 80 | |

| ctg | aag | act | gag | gac | gag | gct | gac | tac | tac | tgt | cag | tct | tat | gat | agc | 288 |
|---|---|---|---|---|---|---|---|---|---|---|---|---|---|---|---|---|
| Leu | Lys | Thr | Glu | Asp | Glu | Ala | Asp | Tyr | Tyr | Cys | Gln | Ser | Tyr | Asp | Ser | |
| | | | | 85 | | | | | 90 | | | | | 95 | | |

| agc | aat | gtg | gtg | ttc | ggc | gga | ggg | acc | aag | ctg | acc | gtc | cta | | | 330 |
|---|---|---|---|---|---|---|---|---|---|---|---|---|---|---|---|---|
| Ser | Asn | Val | Val | Phe | Gly | Gly | Gly | Thr | Lys | Leu | Thr | Val | Leu | | | |
| | | | 100 | | | | | 105 | | | | | 110 | | | |

<210> SEQ ID NO 72
<211> LENGTH: 110
<212> TYPE: PRT
<213> ORGANISM: Artificial
<220> FEATURE:
<223> OTHER INFORMATION: Synthetic Construct

<400> SEQUENCE: 72

| Asn | Phe | Met | Leu | Thr | Gln | Pro | His | Ser | Val | Ser | Glu | Ser | Pro | Gly | Lys |
|---|---|---|---|---|---|---|---|---|---|---|---|---|---|---|---|
| 1 | | | | 5 | | | | | 10 | | | | | 15 | |

```
Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Val Phe Gly Gly Gly Thr Lys Leu Thr Val Leu
            100                 105                 110

<210> SEQ ID NO 73
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 73 gat gtt gtg atg act cag tct cca ctc tcc ctg ccc gtc acc cct ggg      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aac cgg gac tct ggg gtc cca     192
Pro Gln Leu Leu Ile Tyr Leu Gly Ser Asn Arg Asp Ser Gly Val Pro
    50                  55                  60 gac aga ttc agc ggc agt ggg tca ggc act gat ttc aca ctg aaa atc     240
Asp Arg Phe Ser Gly Ser Gly Ser Gly Thr Asp Phe Thr Leu Lys Ile
65                  70                  75                  80 agc agg gtg gag gct gag gat gtt ggg gtt tat tac tgc atg caa ggt     288
Ser Arg Val Glu Ala Glu Asp Val Gly Val Tyr Tyr Cys Met Gln Gly
                85                  90                  95 aca cac tgg ccg tac act ttt ggc cag ggg acc agg ctg gag atc aaa     336
Thr His Trp Pro Tyr Thr Phe Gly Gln Gly Thr Arg Leu Glu Ile Lys
            100                 105                 110

<210> SEQ ID NO 74
<211> LENGTH: 112
<212> TYPE: PRT
<213> ORGANISM: Artificial
<220> FEATURE:
<223> OTHER INFORMATION: Synthetic Construct

<400> SEQUENCE: 74

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

```
Pro Gln Leu Leu Ile Tyr Leu Gly Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Pro Tyr Thr Phe Gly Gln Gly Thr Arg Leu Glu Ile Lys
            100                 105                 110
```

<210> SEQ ID NO 75
<211> LENGTH: 336
<212> TYPE: DNA
<213> ORGANISM: Artificial
<220> FEATURE:
<223> OTHER INFORMATION: Anti-IGF1R antibody light chain variable domain sequence
<220> FEATURE:
<221> NAME/KEY: CDS
<222> LOCATION: (1)..(336)

<400> SEQUENCE: 75

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                  10                  15 gag tcg gcc tcc atc tcc tgc agg tct agt cag agc ctc ctg cat agt      96
Glu Ser Ala Ser Ile Ser Cys Arg Ser Ser Gln Ser Leu Leu His Ser
            20                  25                  30 aat gga tac aac ttt ttg gat tgg tac ctg cag aag cca ggg cag tct     144
Asn Gly Tyr Asn Phe Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct ctc act ttc ggc gga ggg acc aag gtg gag atc aaa     336
Leu Gln Thr Pro Leu Thr Phe Gly Gly Gly Thr Lys Val Glu Ile Lys
            100                 105                 110
```

<210> SEQ ID NO 76
<211> LENGTH: 112
<212> TYPE: PRT
<213> ORGANISM: Artificial
<220> FEATURE:
<223> OTHER INFORMATION: Synthetic Construct

<400> SEQUENCE: 76

```
Asp Val Val Met Thr Gln Ser Pro Leu Ser Leu Pro Val Thr Pro Gly
1               5                  10                  15

Glu Ser Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 77
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 77 gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct    144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct    192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc    240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct    288
Ser Arg Val Glu Ala Glu Asp Val Gly Val Tyr Tyr Cys Met Gln Ala
                85                  90                  95 cta caa acc ccc ctc act ttc ggc gga ggg acc aag gtg gag atc aaa    336
Leu Gln Thr Pro Leu Thr Phe Gly Gly Gly Thr Lys Val Glu Ile Lys
            100                 105                 110

<210> SEQ ID NO 78
<211> LENGTH: 112
<212> TYPE: PRT
<213> ORGANISM: Artificial
<220> FEATURE:
<223> OTHER INFORMATION: Synthetic Construct

<400> SEQUENCE: 78

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 79
<211> LENGTH: 321
<212> TYPE: DNA
<213> ORGANISM: Artificial
<220> FEATURE:
<223> OTHER INFORMATION: Anti-IGF1R antibody light chain variable domain sequence
<220> FEATURE:
<221> NAME/KEY: CDS
<222> LOCATION: (1)..(321)

<400> SEQUENCE: 79

```
gaa acg aca ctc acg cag tct cca gcc acc ctg tct ttg tct cca ggg        48
Glu Thr Thr Leu Thr Gln Ser Pro Ala Thr Leu Ser Leu Ser Pro Gly
1               5                   10                  15 caa aga gcc acc ctc tcc tgc agg gcc agt cag agt gtc tac aac tac        96
Gln Arg Ala Thr Leu Ser Cys Arg Ala Ser Gln Ser Val Tyr Asn Tyr
            20                  25                  30 tta gcc tgg tac caa cag aag cct ggc cag gct ccc agg ctc ctc atc       144
Leu Ala Trp Tyr Gln Gln Lys Pro Gly Gln Ala Pro Arg Leu Leu Ile
        35                  40                  45 tat gat gca tcc aga agg gca act ggc atc cca gcc agg ttc agt ggc       192
Tyr Asp Ala Ser Arg Arg Ala Thr Gly Ile Pro Ala Arg Phe Ser Gly
    50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
65                  70                  75                  80 gaa gat ttt gca gtt tat tac tgt cag cag cgt aac aac tgg ccg ctc       288
Glu Asp Phe Ala Val Tyr Tyr Cys Gln Gln Arg Asn Asn Trp Pro Leu
                85                  90                  95 act ttc ggt gga ggg acc aag gtg gag atc aaa                           321
Thr Phe Gly Gly Gly Thr Lys Val Glu Ile Lys
            100                 105
```

<210> SEQ ID NO 80
<211> LENGTH: 107
<212> TYPE: PRT
<213> ORGANISM: Artificial
<220> FEATURE:
<223> OTHER INFORMATION: Synthetic Construct

<400> SEQUENCE: 80

```
Glu Thr Thr Leu Thr Gln Ser Pro Ala Thr Leu Ser Leu Ser Pro Gly
1               5                   10                  15

Gln Arg Ala Thr Leu Ser Cys Arg Ala Ser Gln Ser Val Tyr Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Arg Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Leu
                85                  90                  95

Thr Phe Gly Gly Gly Thr Lys Val Glu Ile Lys
            100                 105
```

<210> SEQ ID NO 81
<211> LENGTH: 321
<212> TYPE: DNA
<213> ORGANISM: Artificial
<220> FEATURE:

<223> OTHER INFORMATION: Anti-IGF1R antibody light chain variable domain
      sequence
<220> FEATURE:
<221> NAME/KEY: CDS
<222> LOCATION: (1)..(321)

<400> SEQUENCE: 81

```
gac atc cag ttg acc cag tct cca tcc tcc ctg tct gct tct gtt gga      48
Asp Ile Gln Leu Thr Gln Ser Pro Ser Ser Leu Ser Ala Ser Val Gly
1               5                   10                  15 gac agc gtc acc atc tct tgc cgg gca agt cag agt cct ggc atc ttt      96
Asp Ser Val Thr Ile Ser Cys Arg Ala Ser Gln Ser Pro Gly Ile Phe
            20                  25                  30 tta aat tgg tat cag cag ata cca ggg aaa gcc cct aaa ctc ctg atc     144
Leu Asn Trp Tyr Gln Gln Ile Pro Gly Lys Ala Pro Lys Leu Leu Ile
        35                  40                  45 tac gct aca tcc act ctg gaa agt ggg gtc ccc ccc agg ttc acc ggc     192
Tyr Ala Thr Ser Thr Leu Glu Ser Gly Val Pro Pro Arg Phe Thr Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gag gac ttt gca act tac tac tgt caa cag agt aac agt gtt ccg ctc     288
Glu Asp Phe Ala Thr Tyr Tyr Cys Gln Gln Ser Asn Ser Val Pro Leu
                85                  90                  95 act ttc ggc ggc ggg acc aag gtg gag atc aaa                         321
Thr Phe Gly Gly Gly Thr Lys Val Glu Ile Lys
            100                 105
```

<210> SEQ ID NO 82
<211> LENGTH: 107
<212> TYPE: PRT
<213> ORGANISM: Artificial
<220> FEATURE:
<223> OTHER INFORMATION: Synthetic Construct

<400> SEQUENCE: 82

```
Asp Ile Gln Leu Thr Gln Ser Pro Ser Ser Leu Ser Ala Ser Val Gly
1               5                   10                  15

Asp Ser Val Thr Ile Ser Cys Arg Ala Ser Gln Ser Pro Gly Ile Phe
            20                  25                  30

Leu Asn Trp Tyr Gln Gln Ile Pro Gly Lys Ala Pro Lys Leu Leu Ile
        35                  40                  45

Tyr Ala Thr Ser Thr Leu Glu Ser Gly Val Pro Pro Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Val Pro Leu
                85                  90                  95

Thr Phe Gly Gly Gly Thr Lys Val Glu Ile Lys
            100                 105
```

<210> SEQ ID NO 83
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 83

```
gat gtt gtg atg act cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca cta aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cct cta acc ttc ggc caa ggg aca cga ctg gag att aaa     336
Leu Gln Thr Pro Leu Thr Phe Gly Gln Gly Thr Arg Leu Glu Ile Lys
            100                 105                 110
```

<210> SEQ ID NO 84
<211> LENGTH: 112
<212> TYPE: PRT
<213> ORGANISM: Artificial
<220> FEATURE:
<223> OTHER INFORMATION: Synthetic Construct

<400> SEQUENCE: 84

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gln Gly Thr Arg Leu Glu Ile Lys
            100                 105                 110
```

<210> SEQ ID NO 85
<211> LENGTH: 321
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(321)

<400> SEQUENCE: 85

```
gaa att gtg atg acg cag tct cca gcc acc ctg tct gtg tct cca ggg      48
Glu Ile Val Met Thr Gln Ser Pro Ala Thr Leu Ser Val Ser Pro Gly
1               5                   10                  15
```

| | |
|---|---|
| gaa aga gcc acc ttc tcc tgt agg gcc agt cag agt gtt ggc agc aac<br>Glu Arg Ala Thr Phe Ser Cys Arg Ala Ser Gln Ser Val Gly Ser Asn<br>20 25 30 | 96 |
| tta gcc tgg tac cag cag aaa cct ggc cag gct ccc agg ctc ctc atc<br>Leu Ala Trp Tyr Gln Gln Lys Pro Gly Gln Ala Pro Arg Leu Leu Ile<br>35 40 45 | 144 |
| tat gat gca tcc aac agg gcc act ggc atc cca gcc agg ttc agt ggc<br>Tyr Asp Ala Ser Asn Arg Ala Thr Gly Ile Pro Ala Arg Phe Ser Gly<br>50 55 60 | 192 |
| agt ggg tct ggg aca gac ttc act ctc acc atc agc aga ctg gag cct<br>Ser Gly Ser Gly Thr Asp Phe Thr Leu Thr Ile Ser Arg Leu Glu Pro<br>65 70 75 80 | 240 |
| gaa gat ttt gca gtg tat tac tgt cag cag cgt agc aac tgg ccc ctc<br>Glu Asp Phe Ala Val Tyr Tyr Cys Gln Gln Arg Ser Asn Trp Pro Leu<br>85 90 95 | 288 |
| act ttc ggc gga ggg acc aag gtg gag atc aaa<br>Thr Phe Gly Gly Gly Thr Lys Val Glu Ile Lys<br>100 105 | 321 |

<210> SEQ ID NO 86
<211> LENGTH: 107
<212> TYPE: PRT
<213> ORGANISM: Artificial
<220> FEATURE:
<223> OTHER INFORMATION: Synthetic Construct

<400> SEQUENCE: 86

Glu Ile Val Met Thr Gln Ser Pro Ala Thr Leu Ser Val Ser Pro Gly
1               5                   10                  15

Glu Arg Ala Thr Phe Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 87
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 87

| | |
|---|---|
| gat gtt gtg atg act cag tct cca ctc tcc ctg ccc gtc acc cct gga<br>Asp Val Val Met Thr Gln Ser Pro Leu Ser Leu Pro Val Thr Pro Gly<br>1               5                   10                  15 | 48 |
| gag ccg gcc tcc atc tcc tgc agg tct agt cag agc ctc ctg cat agt<br>Glu Pro Ala Ser Ile Ser Cys Arg Ser Ser Gln Ser Leu Leu His Ser<br>            20                  25                  30 | 96 |
| aat gga tac aac tat ttg gat tgg tac ctg cag aag cca ggg cag tct<br>Asn Gly Tyr Asn Tyr Leu Asp Trp Tyr Leu Gln Lys Pro Gly Gln Ser | 144 |

```
                 35                  40                  45
cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
         50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc atg caa gct      288
Ser Arg Val Glu Ala Glu Asp Val Gly Val Tyr Tyr Cys Met Gln Ala
                 85                  90                  95 cta caa act ccg ctc act ttc ggc gga ggg acc aag gtg gag atc aaa      336
Leu Gln Thr Pro Leu Thr Phe Gly Gly Gly Thr Lys Val Glu Ile Lys
             100                 105                 110
```

<210> SEQ ID NO 88
<211> LENGTH: 112
<212> TYPE: PRT
<213> ORGANISM: Artificial
<220> FEATURE:
<223> OTHER INFORMATION: Synthetic Construct

<400> SEQUENCE: 88

```
Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
             100                 105                 110
```

<210> SEQ ID NO 89
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 89

```
gat gtt gtg atg act cag tct cca ctc tcc ctg ccc gtc acc cct gga       48
Asp Val Val Met Thr Gln Ser Pro Leu Ser Leu Pro Val Thr Pro Gly
  1               5                  10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
             20                  25                  30 aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
         35                  40                  45 cca cag ctc ctg atc tac ttg ggt tct act cgg gcc tcc ggc gtc cct      192
Pro Gln Leu Leu Ile Tyr Leu Gly Ser Thr Arg Ala Ser Gly Val Pro
     50                  55                  60
```

| | | | | | | | | | | | | | | | |
|---|---|---|---|---|---|---|---|---|---|---|---|---|---|---|---|
| gac | agg | ttc | agt | ggc | agt | gga | tca | ggc | aca | gat | ttt | aca | ctg | aaa | atc | 240 |
| Asp | Arg | Phe | Ser | Gly | Ser | Gly | Ser | Gly | Thr | Asp | Phe | Thr | Leu | Lys | Ile |
| 65 | | | | 70 | | | | | 75 | | | | | 80 | |

| | | | | | | | | | | | | | | | |
|---|---|---|---|---|---|---|---|---|---|---|---|---|---|---|---|
| agc | aga | gtg | gag | gct | gag | gat | gtt | ggg | gtt | tat | tac | tgc | atg | caa | gct | 288 |
| Ser | Arg | Val | Glu | Ala | Glu | Asp | Val | Gly | Val | Tyr | Tyr | Cys | Met | Gln | Ala |
| | | | | 85 | | | | | 90 | | | | | 95 | |

| | | | | | | | | | | | | | | | |
|---|---|---|---|---|---|---|---|---|---|---|---|---|---|---|---|
| cta | caa | act | cct | tac | act | ttc | ggc | gga | ggg | acc | aag | gtg | gag | atc | aaa | 336 |
| Leu | Gln | Thr | Pro | Tyr | Thr | Phe | Gly | Gly | Gly | Thr | Lys | Val | Glu | Ile | Lys |
| | | | 100 | | | | | 105 | | | | | 110 | | |

<210> SEQ ID NO 90
<211> LENGTH: 112
<212> TYPE: PRT
<213> ORGANISM: Artificial
<220> FEATURE:
<223> OTHER INFORMATION: Synthetic Construct

<400> SEQUENCE: 90

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gly Gly Thr Lys Val Glu Ile Lys
            100                 105                 110

<210> SEQ ID NO 91
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 91

| | | | | | | | | | | | | | | | |
|---|---|---|---|---|---|---|---|---|---|---|---|---|---|---|---|
| gat | gtt | gtg | atg | act | cag | tct | cca | ctc | tcc | ctg | ccc | gtc | acc | cct | gga | 48 |
| Asp | Val | Val | Met | Thr | Gln | Ser | Pro | Leu | Ser | Leu | Pro | Val | Thr | Pro | Gly |
| 1 | | | | 5 | | | | | 10 | | | | | 15 | |

| | | | | | | | | | | | | | | | |
|---|---|---|---|---|---|---|---|---|---|---|---|---|---|---|---|
| gag | ccg | gcc | tcc | atc | tcc | tgc | agg | tct | agt | cag | agc | ctc | ctg | cat | agt | 96 |
| Glu | Pro | Ala | Ser | Ile | Ser | Cys | Arg | Ser | Ser | Gln | Ser | Leu | Leu | His | Ser |
| | | | 20 | | | | | 25 | | | | | 30 | | |

| | | | | | | | | | | | | | | | |
|---|---|---|---|---|---|---|---|---|---|---|---|---|---|---|---|
| aat | gga | tac | aac | tat | ttg | gat | tgg | tac | ctg | cag | aag | cca | ggc | cag | tct | 144 |
| Asn | Gly | Tyr | Asn | Tyr | Leu | Asp | Trp | Tyr | Leu | Gln | Lys | Pro | Gly | Gln | Ser |
| | | 35 | | | | | 40 | | | | | 45 | | | |

| | | | | | | | | | | | | | | | |
|---|---|---|---|---|---|---|---|---|---|---|---|---|---|---|---|
| cca | cag | ctc | ctg | atc | tat | ttg | ggt | tct | aat | cgg | gcc | tcc | ggg | gtc | cct | 192 |
| Pro | Gln | Leu | Leu | Ile | Tyr | Leu | Gly | Ser | Asn | Arg | Ala | Ser | Gly | Val | Pro |
| | 50 | | | | | 55 | | | | | 60 | | | | |

| | | | | | | | | | | | | | | | |
|---|---|---|---|---|---|---|---|---|---|---|---|---|---|---|---|
| gac | agg | ttc | agt | ggc | agt | gga | tca | ggc | aca | gat | ttt | aca | ctg | aaa | atc | 240 |
| Asp | Arg | Phe | Ser | Gly | Ser | Gly | Ser | Gly | Thr | Asp | Phe | Thr | Leu | Lys | Ile |
| 65 | | | | 70 | | | | | 75 | | | | | 80 | |

| | | | | | | | | | | | | | | | |
|---|---|---|---|---|---|---|---|---|---|---|---|---|---|---|---|
| agc | aga | gtg | gag | gct | gag | gat | gtt | ggg | gtt | tat | tac | tgc | atg | caa | gct | 288 |
| Ser | Arg | Val | Glu | Ala | Glu | Asp | Val | Gly | Val | Tyr | Tyr | Cys | Met | Gln | Ala |

```
                85                  90                  95
cta caa act ccc ctc act ttc ggc gga ggg acc aag gtg gag atc aaa    336
Leu Gln Thr Pro Leu Thr Phe Gly Gly Gly Thr Lys Val Glu Ile Lys
            100                 105                 110

<210> SEQ ID NO 92
<211> LENGTH: 112
<212> TYPE: PRT
<213> ORGANISM: Artificial
<220> FEATURE:
<223> OTHER INFORMATION: Synthetic Construct

<400> SEQUENCE: 92

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 93
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 93 gat gtt gtg atg act cag tct cca ctc tcc ctg ccc gtc acc cct gga    48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat act    96
Glu Pro Ala Ser Ile Ser Cys Arg Ser Ser Gln Ser Leu Leu His Thr
            20                  25                  30 aat gga tac aac tat ttg gat tgg tac ctg cag aag cca ggg cag tct   144
Asn Gly Tyr Asn Tyr Leu Asp Trp Tyr Leu Gln Lys Pro Gly Gln Ser
        35                  40                  45 cca cgg ctc ctg atc tat ttg ggt ttt aat cgg gcc tcc ggg gtc cct   192
Pro Arg Leu Leu Ile Tyr Leu Gly Phe Asn Arg Ala Ser Gly Val Pro
    50                  55                  60 gac agg ttc agt ggc agt gga tca ggc aca gat ttt aca ctg aaa atc   240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgt atg caa ggt   288
Ser Arg Val Glu Ala Glu Asp Val Gly Val Tyr Tyr Cys Met Gln Gly
                85                  90                  95 cta caa act ccc ctc act ttc ggc gga ggg acc aag gtg gag atc aaa   336
Leu Gln Thr Pro Leu Thr Phe Gly Gly Gly Thr Lys Val Glu Ile Lys
            100                 105                 110
```

<210> SEQ ID NO 94
<211> LENGTH: 112
<212> TYPE: PRT
<213> ORGANISM: Artificial
<220> FEATURE:
<223> OTHER INFORMATION: Synthetic Construct

<400> SEQUENCE: 94

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Leu Gln Lys Pro Gly Gln Ser
        35                  40                  45

Pro Arg Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Leu Thr Phe Gly Gly Gly Thr Lys Val Glu Ile Lys
            100                 105                 110
```

<210> SEQ ID NO 95
<211> LENGTH: 336
<212> TYPE: DNA
<213> ORGANISM: Artificial
<220> FEATURE:
<223> OTHER INFORMATION: Anti-IGF1R antibody light chain variable domain sequence
<220> FEATURE:
<221> NAME/KEY: CDS
<222> LOCATION: (1)..(336)

<400> SEQUENCE: 95

```
gat gtt gtg atg act cag tct cca ctc tcc ctg ccc gtc acc cct gga        48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc agg gtg gag gct gag gat gtt ggg gtt tat tat tgc atg caa gct       288
Ser Arg Val Glu Ala Glu Asp Val Gly Val Tyr Tyr Cys Met Gln Ala
                85                  90                  95 aca cac tgg ccg tac act ttt ggc cag ggg acc aag ctg gag atc aaa       336
Thr His Trp Pro Tyr Thr Phe Gly Gln Gly Thr Lys Leu Glu Ile Lys
            100                 105                 110
```

<210> SEQ ID NO 96
<211> LENGTH: 112
<212> TYPE: PRT
<213> ORGANISM: Artificial
<220> FEATURE:

<223> OTHER INFORMATION: Synthetic Construct

<400> SEQUENCE: 96

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Tyr Thr Phe Gly Gln Gly Thr Lys Leu Glu Ile Lys
            100                 105                 110

<210> SEQ ID NO 97
<211> LENGTH: 330
<212> TYPE: DNA
<213> ORGANISM: Artificial
<220> FEATURE:
<223> OTHER INFORMATION: Anti-IGF1R antibody light chain variable domain
    sequence
<220> FEATURE:
<221> NAME/KEY: CDS
<222> LOCATION: (1)..(330)

<400> SEQUENCE: 97 aat ttt atg ctg act cag ccc cac tct gtg tcg gag tct ccg ggg aag      48
Asn Phe Met Leu Thr Gln Pro His Ser Val Ser Glu Ser Pro Gly Lys
1               5                   10                  15 acg gta agc atc tcc tgc acc cgc aac agt ggc agc att gcc agc aac      96
Thr Val Ser Ile Ser Cys Thr Arg Asn Ser Gly Ser Ile Ala Ser Asn
            20                  25                  30 ttt gtg cag tgg tac cag cag cgc ccg ggc agt gcc ccc acc att gta     144
Phe Val Gln Trp Tyr Gln Gln Arg Pro Gly Ser Ala Pro Thr Ile Val
        35                  40                  45 atc tat gag gat aac caa aga ccc tct gcg gtc cct act cgg ttc tct     192
Ile Tyr Glu Asp Asn Gln Arg Pro Ser Ala Val Pro Thr Arg Phe Ser
    50                  55                  60 ggc tcc atc gac agg tcc tcc aac tct gcc tcc ctc acc atc tct gga     240
Gly Ser Ile Asp Arg Ser Ser Asn Ser Ala Ser Leu Thr Ile Ser Gly
65                  70                  75                  80 ctg acg act gag gac gag gct gac tac tac tgt cag tct tat gat agc     288
Leu Thr Thr Glu Asp Glu Ala Asp Tyr Tyr Cys Gln Ser Tyr Asp Ser
                85                  90                  95 gcc aat gtc att ttc ggc ggg ggg acc aag ctg acc gtc cta             330
Ala Asn Val Ile Phe Gly Gly Gly Thr Lys Leu Thr Val Leu
            100                 105                 110

<210> SEQ ID NO 98
<211> LENGTH: 110
<212> TYPE: PRT
<213> ORGANISM: Artificial
<220> FEATURE:
<223> OTHER INFORMATION: Synthetic Construct

<400> SEQUENCE: 98

Asn Phe Met Leu Thr Gln Pro His Ser Val Ser Glu Ser Pro Gly Lys
1               5                   10                  15

```
Thr Val Ser Ile Ser Cys Thr Arg Asn Ser Gly Ser Ile Ala Ser Asn
            20                  25                  30

Phe Val Gln Trp Tyr Gln Gln Arg Pro Gly Ser Ala Pro Thr Ile Val
        35                  40                  45

Ile Tyr Glu Asp Asn Gln Arg Pro Ser Ala Val Pro Thr Arg Phe Ser
 50                  55                  60

Gly Ser Ile Asp Arg Ser Ser Asn Ser Ala Ser Leu Thr Ile Ser Gly
 65                  70                  75                  80

Leu Thr Thr Glu Asp Glu Ala Asp Tyr Tyr Cys Gln Ser Tyr Asp Ser
                85                  90                  95

Ala Asn Val Ile Phe Gly Gly Gly Thr Lys Leu Thr Val Leu
            100                 105                 110

<210> SEQ ID NO 99
<211> LENGTH: 324
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(324)

<400> SEQUENCE: 99 gaa acg aca ctc acg cag tct cca ggc acc ctg tct ttg tct cca ggg      48
Glu Thr Thr Leu Thr Gln Ser Pro Gly Thr Leu Ser Leu Ser Pro Gly
 1               5                  10                  15 gag aga gcc acc ctc tcc tgc agg gcc agt cag act atc agc agc agc      96
Glu Arg Ala Thr Leu Ser Cys Arg Ala Ser Gln Thr Ile Ser Ser Ser
            20                  25                  30 cac tta gcc tgg tac cag cag aaa cct ggc cag tct ccc agg ctc ctc     144
His Leu Ala Trp Tyr Gln Gln Lys Pro Gly Gln Ser Pro Arg Leu Leu
        35                  40                  45 atc tat ggt gcg ggc tac agg gcc acc ggc att cca gac agg ttc agt     192
Ile Tyr Gly Ala Gly Tyr Arg Ala Thr Gly Ile Pro Asp Arg Phe Ser
 50                  55                  60 ggc agt ggg tct ggc aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cac tat ggt agt tca ctc     288
Pro Glu Asp Phe Ala Val Tyr Tyr Cys Gln His Tyr Gly Ser Ser Leu
                85                  90                  95 cgg acg ttc ggc caa ggg acc aag gtg gaa atc aaa                     324
Arg Thr Phe Gly Gln Gly Thr Lys Val Glu Ile Lys
            100                 105

<210> SEQ ID NO 100
<211> LENGTH: 108
<212> TYPE: PRT
<213> ORGANISM: Artificial
<220> FEATURE:
<223> OTHER INFORMATION: Synthetic Construct

<400> SEQUENCE: 100

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Thr Ile Ser Ser Ser
            20                  25                  30

His Leu Ala Trp Tyr Gln Gln Lys Pro Gly Gln Ser Pro Arg Leu Leu
        35                  40                  45
```

Ile Tyr Gly Ala Gly Tyr Arg Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Ser Ser Leu
                 85                  90                  95

Arg Thr Phe Gly Gln Gly Thr Lys Val Glu Ile Lys
            100                 105

<210> SEQ ID NO 101
<211> LENGTH: 330
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(330)

<400> SEQUENCE: 101 aat ttt atg ctg act cag ccc cac tct gtg tcg gag tct ccg ggg aag      48
Asn Phe Met Leu Thr Gln Pro His Ser Val Ser Glu Ser Pro Gly Lys
 1               5                  10                  15 acg gta acc atc tcc tgc acc ggc agc ggt ggc aac att gcc agc aat      96
Thr Val Thr Ile Ser Cys Thr Gly Ser Gly Gly Asn Ile Ala Ser Asn
             20                  25                  30 tat gtg cag tgg tac cag cag cgc ccg ggc agg gcc ccc acc act gtg     144
Tyr Val Gln Trp Tyr Gln Gln Arg Pro Gly Arg Ala Pro Thr Thr Val
         35                  40                  45 atc tat gag gat aat cga aga ccc tct ggg gtc cct gat cgg ttc tct     192
Ile Tyr Glu Asp Asn Arg Arg Pro Ser Gly Val Pro Asp Arg Phe Ser
     50                  55                  60 ggc tcc atc gac agc tcc tcc aac tct gcc tcc ctc acc atc tct gga     240
Gly Ser Ile Asp Ser Ser Ser Asn Ser Ala Ser Leu Thr Ile Ser Gly
 65                  70                  75                  80 ctg aag act gaa gac gag gct gac tac tac tgt cag tct tat gat ccc     288
Leu Lys Thr Glu Asp Glu Ala Asp Tyr Tyr Cys Gln Ser Tyr Asp Pro
                 85                  90                  95 tac aat cga gtg ttc ggc gga ggg acc aag ctg acc gtc cta             330
Tyr Asn Arg Val Phe Gly Gly Gly Thr Lys Leu Thr Val Leu
            100                 105                 110

<210> SEQ ID NO 102
<211> LENGTH: 110
<212> TYPE: PRT
<213> ORGANISM: Artificial
<220> FEATURE:
<223> OTHER INFORMATION: Synthetic Construct

<400> SEQUENCE: 102

Asn Phe Met Leu Thr Gln Pro His Ser Val Ser Glu Ser Pro Gly Lys
 1               5                  10                  15

Thr Val Thr Ile Ser Cys Thr Gly Ser Gly Gly Asn Ile Ala Ser Asn
             20                  25                  30

Tyr Val Gln Trp Tyr Gln Gln Arg Pro Gly Arg Ala Pro Thr Thr Val
         35                  40                  45

Ile Tyr Glu Asp Asn Arg Arg Pro Ser Gly Val Pro Asp Arg Phe Ser
     50                  55                  60

Gly Ser Ile Asp Ser Ser Ser Asn Ser Ala Ser Leu Thr Ile Ser Gly
 65                  70                  75                  80

```
Leu Lys Thr Glu Asp Glu Ala Asp Tyr Tyr Cys Gln Ser Tyr Asp Pro
                85                  90                  95

Tyr Asn Arg Val Phe Gly Gly Gly Thr Lys Leu Thr Val Leu
            100                 105                 110

<210> SEQ ID NO 103
<211> LENGTH: 336
<212> TYPE: DNA
<213> ORGANISM: Artificial
<220> FEATURE:
<223> OTHER INFORMATION: Anti-IGF1R antibody light chain variable domain
      sequence
<220> FEATURE:
<221> NAME/KEY: CDS
<222> LOCATION: (1)..(336)

<400> SEQUENCE: 103 gaa att gtg atg acg cag tct cca ctc tcc ctg ccc gtc acc cct gga      48
Glu Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat act      96
Glu Pro Ala Ser Ile Ser Cys Arg Ser Ser Gln Ser Leu Leu His Thr
            20                  25                  30 aat gga tac gac tat ttg gat tgg tac ctg cag aag cca ggg cag tct     144
Asn Gly Tyr Asp Tyr Leu Asp Trp Tyr Leu Gln Lys Pro Gly Gln Ser
        35                  40                  45 cca cag ctt ctg atc tat ttg ggt tct act cgg gcc tcc ggg gtc cct     192
Pro Gln Leu Leu Ile Tyr Leu Gly Ser Thr Arg Ala Ser Gly Val Pro
    50                  55                  60 gac agg ttc agt ggc agt gga tcg ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 ttt caa act ccg ctc act ttc ggc gga ggg acc aag atg gag atc aaa     336
Phe Gln Thr Pro Leu Thr Phe Gly Gly Gly Thr Lys Met Glu Ile Lys
            100                 105                 110

<210> SEQ ID NO 104
<211> LENGTH: 112
<212> TYPE: PRT
<213> ORGANISM: Artificial
<220> FEATURE:
<223> OTHER INFORMATION: Synthetic Construct

<400> SEQUENCE: 104

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asp Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Phe Gln Thr Pro Leu Thr Phe Gly Gly Gly Thr Lys Met Glu Ile Lys
            100                 105                 110
```

<210> SEQ ID NO 105
<211> LENGTH: 351
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(351)

<400> SEQUENCE: 105

```
gag gtg cag ctg gtg gag acc ggc cca gga ctg gtg aag cct tcg ggg      48
Glu Val Gln Leu Val Glu Thr Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga ttt aat tac tat gat agt agt gtc tgg ggc cag gga acc ctg     336
Ala Arg Phe Asn Tyr Tyr Asp Ser Ser Val Trp Gly Gln Gly Thr Leu
            100                 105                 110 gtc acc gtc tca agc                                                  351
Val Thr Val Ser Ser
        115
```

<210> SEQ ID NO 106
<211> LENGTH: 117
<212> TYPE: PRT
<213> ORGANISM: Artificial
<220> FEATURE:
<223> OTHER INFORMATION: Synthetic Construct

<400> SEQUENCE: 106

```
Glu Val Gln Leu Val Glu Thr Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Asn Tyr Tyr Asp Ser Ser Val Trp Gly Gln Gly Thr Leu
            100                 105                 110

Val Thr Val Ser Ser
```

-continued

```
<210> SEQ ID NO 107
<211> LENGTH: 348
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(348)

<400> SEQUENCE: 107 gag gtg cag ctg gtg gag acc ggc cca gga ctg gtg aag cct tcg ggg      48
Glu Val Gln Leu Val Glu Thr Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga ggg gtt gag cag att gac tac tgg ggc cag gga acc ctg gtc     336
Ala Arg Gly Val Glu Gln Ile Asp Tyr Trp Gly Gln Gly Thr Leu Val
            100                 105                 110 acc gtc tca agc                                                     348
Thr Val Ser Ser
        115

<210> SEQ ID NO 108
<211> LENGTH: 116
<212> TYPE: PRT
<213> ORGANISM: Artificial
<220> FEATURE:
<223> OTHER INFORMATION: Synthetic Construct

<400> SEQUENCE: 108

Glu Val Gln Leu Val Glu Thr Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Val Glu Gln Ile Asp Tyr Trp Gly Gln Gly Thr Leu Val
            100                 105                 110
```

Thr Val Ser Ser
        115

<210> SEQ ID NO 109
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 109

```
cag gtg cag ctg cag gag tcg ggc cca gga ctg gtg aag cct tcg ggg      48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg act gcc gcg gac acg gcc gtg tat tac tgt     288
Leu Lys Leu Ser Ser Val Thr Ala Ala Asp Thr Ala Val Tyr Tyr Cys
                85                  90                  95 gcg aaa aat tta gca gca ggg gcg gtt gcc tac tgg ggc cag ggc acc     336
Ala Lys Asn Leu Ala Ala Gly Ala Val Ala Tyr Trp Gly Gln Gly Thr
            100                 105                 110 ctg gtc acc gtc tca agc                                             354
Leu Val Thr Val Ser Ser
        115
```

<210> SEQ ID NO 110
<211> LENGTH: 118
<212> TYPE: PRT
<213> ORGANISM: Artificial
<220> FEATURE:
<223> OTHER INFORMATION: Synthetic Construct

<400> SEQUENCE: 110

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Lys Asn Leu Ala Ala Gly Ala Val Ala Tyr Trp Gly Gln Gly Thr
            100                 105                 110
```

```
Leu Val Thr Val Ser Ser
        115

<210> SEQ ID NO 111
<211> LENGTH: 351
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(351)

<400> SEQUENCE: 111 cag gtg cag cta cag cag tgg ggc gca gga ctg ttg aag cct tcg gag      48
Gln Val Gln Leu Gln Gln Trp Gly Ala Gly Leu Leu Lys Pro Ser Glu
1               5                   10                  15 acc ctg tcc ctc acc tgc gct gtc tct ggt ggg tcc ttc agt ggt tac      96
Thr Leu Ser Leu Thr Cys Ala Val Ser Gly Gly Ser Phe Ser Gly Tyr
            20                  25                  30 tac tgg agc tgg atc cgt cag ccc cca ggg aag ggg ctg gag tgg att     144
Tyr Trp Ser Trp Ile Arg Gln Pro Pro Gly Lys Gly Leu Glu Trp Ile
        35                  40                  45 ggg gaa atc aat cat agt gga agt acc aac tac aac cgg tcc ctc aag     192
Gly Glu Ile Asn His Ser Gly Ser Thr Asn Tyr Asn Arg Ser Leu Lys
    50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
65                  70                  75                  80 aag ctg agc tct gtg acc gcc gcg gac acg gct gtg tat tac tgt gcg     288
Lys Leu Ser Ser Val Thr Ala Ala Asp Thr Ala Val Tyr Tyr Cys Ala
                85                  90                  95 aga ctt tca tat ggt tcg ggc gtt gac tac tgg ggc cag ggc acc ctg     336
Arg Leu Ser Tyr Gly Ser Gly Val Asp Tyr Trp Gly Gln Gly Thr Leu
            100                 105                 110 gtc acc gtc tca agc                                                 351
Val Thr Val Ser Ser
        115

<210> SEQ ID NO 112
<211> LENGTH: 117
<212> TYPE: PRT
<213> ORGANISM: Artificial
<220> FEATURE:
<223> OTHER INFORMATION: Synthetic Construct

<400> SEQUENCE: 112

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Arg Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Ser Tyr Gly Ser Gly Val Asp Tyr Trp Gly Gln Gly Thr Leu
```

Val Thr Val Ser Ser
        115

<210> SEQ ID NO 113
<211> LENGTH: 360
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(360)

<400> SEQUENCE: 113

```
cag ctg cag ctg cag gag tcg ggc cca gga ctg gtg aag cct tca cag      48
Gln Leu Gln Leu Gln Glu Ser Gly Pro Gly Leu Val Lys Pro Ser Gln
1               5                   10                  15 acc ctg tcc ctc acc tgc act gtc tct ggt ggc tcc atc agc agt agt      96
Thr Leu Ser Leu Thr Cys Thr Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg agg tat agc agc agc cgc aat gat gct ttt gat atc tgg ggc caa     336
Ala Arg Tyr Ser Ser Ser Arg Asn Asp Ala Phe Asp Ile Trp Gly Gln
            100                 105                 110 ggg aca atg gtc acc gtc tca agc                                     360
Gly Thr Met Val Thr Val Ser Ser
        115                 120
```

<210> SEQ ID NO 114
<211> LENGTH: 120
<212> TYPE: PRT
<213> ORGANISM: Artificial
<220> FEATURE:
<223> OTHER INFORMATION: Synthetic Construct

<400> SEQUENCE: 114

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

```
Ala Arg Tyr Ser Ser Arg Asn Asp Ala Phe Asp Ile Trp Gly Gln
            100                 105                 110
Gly Thr Met Val Thr Val Ser Ser
        115                 120

<210> SEQ ID NO 115
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 115 cag gtg cag ctg cag gag tcg ggc cca gga ctg gtg aag cct tcg ggg     48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt     96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt    288
Leu Lys Leu Ser Ser Val Thr Ala Ala Asp Thr Ala Val Tyr Tyr Cys
                85                  90                  95 gcg aga gat ggg cag ctg gat gct ttt gat atc tgg ggc caa ggg aca    336
Ala Arg Asp Gly Gln Leu Asp Ala Phe Asp Ile Trp Gly Gln Gly Thr
            100                 105                 110 atg gtc acc gtc tca agc                                            354
Met Val Thr Val Ser Ser
        115

<210> SEQ ID NO 116
<211> LENGTH: 118
<212> TYPE: PRT
<213> ORGANISM: Artificial
<220> FEATURE:
<223> OTHER INFORMATION: Synthetic Construct

<400> SEQUENCE: 116

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

```
Ala Arg Asp Gly Gln Leu Asp Ala Phe Asp Ile Trp Gly Gln Gly Thr
            100                 105                 110

Met Val Thr Val Ser Ser
        115

<210> SEQ ID NO 117
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 117 cag gtg cag ctg cag gag tcg ggc cca gga ctg gtg aag cct tcg ggg       48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
Leu Lys Leu Ser Ser Val Thr Ala Ala Asp Thr Ala Val Tyr Tyr Cys
                85                  90                  95 gcg aga ttt tgg gac tac tac ggt atg gac gtc tgg ggc caa ggg acc      336
Ala Arg Phe Trp Asp Tyr Tyr Gly Met Asp Val Trp Gly Gln Gly Thr
            100                 105                 110 acg gtc acc gtc tca agc                                              354
Thr Val Thr Val Ser Ser
        115

<210> SEQ ID NO 118
<211> LENGTH: 118
<212> TYPE: PRT
<213> ORGANISM: Artificial
<220> FEATURE:
<223> OTHER INFORMATION: Synthetic Construct

<400> SEQUENCE: 118

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
```

```
                    85                  90                  95
Ala Arg Phe Trp Asp Tyr Tyr Gly Met Asp Val Trp Gly Gln Gly Thr
                100                 105                 110

Thr Val Thr Val Ser Ser
        115

<210> SEQ ID NO 119
<211> LENGTH: 351
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(351)

<400> SEQUENCE: 119 cag gtg cag cta cag cag tgg ggc cca gga ctg gtg aag cct tcg ggg       48
Gln Val Gln Leu Gln Gln Trp Gly Pro Gly Leu Val Lys Pro Ser Gly
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
                20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
        50                  55                  60 gag agt cga gtc acc ata tca gta gac aag tcc aag aac cag ttc tcc      240
Glu Ser Arg Val Thr Ile Ser Val Asp Lys Ser Lys Asn Gln Phe Ser
65                  70                  75                  80 ctg aag ctg agc tct gtg acc gcc gca gac acg gcc gtg tat tac tgt      288
Leu Lys Leu Ser Ser Val Thr Ala Ala Asp Thr Ala Val Tyr Tyr Cys
                85                  90                  95 gcg aga gat cgg tac tac ggt atg gac gtc tgg ggc caa ggg acc acg      336
Ala Arg Asp Arg Tyr Tyr Gly Met Asp Val Trp Gly Gln Gly Thr Thr
                100                 105                 110 gtc acc gtc tca agc                                                  351
Val Thr Val Ser Ser
        115

<210> SEQ ID NO 120
<211> LENGTH: 117
<212> TYPE: PRT
<213> ORGANISM: Artificial
<220> FEATURE:
<223> OTHER INFORMATION: Synthetic Construct

<400> SEQUENCE: 120

Gln Val Gln Leu Gln Gln Trp Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Glu Ser Arg Val Thr Ile Ser Val Asp Lys Ser Lys Asn Gln Phe Ser
65                  70                  75                  80
```

```
Leu Lys Leu Ser Ser Val Thr Ala Ala Asp Thr Ala Val Tyr Tyr Cys
            85                  90                  95

Ala Arg Asp Arg Tyr Tyr Gly Met Asp Val Trp Gly Gln Gly Thr Thr
            100                 105                 110

Val Thr Val Ser Ser
        115

<210> SEQ ID NO 121
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 121 gag gtg cag ctg gtc gag tct ggc cca gga ctg gtg aag cct tcg ggg     48
Glu Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt     96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
        35                  40                  45 att ggg tac atc tat tat agt ggg agc acc tac tac aac ccg tcc ctc    192
Ile Gly Tyr Ile Tyr Tyr Ser Gly Ser Thr Tyr Tyr Asn Pro Ser Leu
    50                  55                  60 aag agt cga gtc acc atg tca gta gac acg tcc aag aac cag ttc tcc    240
Lys Ser Arg Val Thr Met Ser Val Asp Thr Ser Lys Asn Gln Phe Ser
65                  70                  75                  80 ctg aag ctg agc tct gtg acc gcc gca gac acg gcc gtg tat tac tgt    288
Leu Lys Leu Ser Ser Val Thr Ala Ala Asp Thr Ala Val Tyr Tyr Cys
                85                  90                  95 gcg aga tgg agc tac ttg gat gct ttt gat atc tgg ggc caa ggg aca    336
Ala Arg Trp Ser Tyr Leu Asp Ala Phe Asp Ile Trp Gly Gln Gly Thr
            100                 105                 110 atg gtc acc gtc tca agc                                            354
Met Val Thr Val Ser Ser
        115

<210> SEQ ID NO 122
<211> LENGTH: 118
<212> TYPE: PRT
<213> ORGANISM: Artificial
<220> FEATURE:
<223> OTHER INFORMATION: Synthetic Construct

<400> SEQUENCE: 122

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Ala Arg Trp Ser Tyr Leu Asp Ala Phe Asp Ile Trp Gly Gln Gly Thr
            100                 105                 110

Met Val Thr Val Ser Ser
        115

<210> SEQ ID NO 123
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 123 gag gtg cag ctg gtg gag tct ggc cca gga ctg gtg aag cct tcg ggg      48
Glu Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga gat tac gat att ttc ggt atg gac gtc tgg ggc caa ggg acc     336
Ala Arg Asp Tyr Asp Ile Phe Gly Met Asp Val Trp Gly Gln Gly Thr
            100                 105                 110 acg gtc acc gtc tca agc                                             354
Thr Val Thr Val Ser Ser
        115

<210> SEQ ID NO 124
<211> LENGTH: 118
<212> TYPE: PRT
<213> ORGANISM: Artificial
<220> FEATURE:
<223> OTHER INFORMATION: Synthetic Construct

<400> SEQUENCE: 124

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
```

```
                     65                  70                  75                  80
Leu Lys Leu Ser Ser Val Thr Ala Ala Asp Thr Ala Val Tyr Tyr Cys
                85                  90                  95

Ala Arg Asp Tyr Asp Ile Phe Gly Met Asp Val Trp Gly Gln Gly Thr
            100                 105                 110

Thr Val Thr Val Ser Ser
        115

<210> SEQ ID NO 125
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 125 cag ctg cag ctg cag gag tcg ggc cca gga ctg gtg aag cct tcg ggg        48
Gln Leu Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt        96
Thr Leu Ser Leu Thr Cys Ala Val Ser Gly Gly Ser Ile Ser Ser Ser
                20                  25                  30 aac tgg tgg agt tgg gtc cgc cag ccc cca ggg aag ggg ctg gag tgg       144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc       192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag tcc tcc       240
Lys Ser Arg Val Thr Ile Ser Val Asp Lys Ser Lys Asn Gln Ser Ser
65                  70                  75                  80 ctg aag ctg agc tct gtg acc gcc gcg gac acg gcc gtg tat tac tgt       288
Leu Lys Leu Ser Ser Val Thr Ala Ala Asp Thr Ala Val Tyr Tyr Cys
                85                  90                  95 gcg aga gcc aac aga gat gat gct ttt gat atc tgg ggc caa ggg aca       336
Ala Arg Ala Asn Arg Asp Asp Ala Phe Asp Ile Trp Gly Gln Gly Thr
            100                 105                 110 atg gtc acc gtc tca agc                                               354
Met Val Thr Val Ser Ser
        115

<210> SEQ ID NO 126
<211> LENGTH: 118
<212> TYPE: PRT
<213> ORGANISM: Artificial
<220> FEATURE:
<223> OTHER INFORMATION: Synthetic Construct

<400> SEQUENCE: 126

Gln Leu Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60
```

```
Lys Ser Arg Val Thr Ile Ser Val Asp Lys Ser Lys Asn Gln Ser Ser
 65                  70                  75                  80

Leu Lys Leu Ser Ser Val Thr Ala Ala Asp Thr Ala Val Tyr Tyr Cys
                 85                  90                  95

Ala Arg Ala Asn Arg Asp Asp Ala Phe Asp Ile Trp Gly Gln Gly Thr
            100                 105                 110

Met Val Thr Val Ser Ser
        115

<210> SEQ ID NO 127
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 127 gag gtg cag ctg gtg gag tct ggg gga ggc ttg gta cag ccg ggg ggg        48
Glu Val Gln Leu Val Glu Ser Gly Gly Gly Leu Val Gln Pro Gly Gly
  1               5                  10                  15 tcc ctg aga ctc tcc tgt gca gcc tct gga ttc acc ttt agc agc tat        96
Ser Leu Arg Leu Ser Cys Ala Ala Ser Gly Phe Thr Phe Ser Ser Tyr
             20                  25                  30 gcc atg agc tgg gtc cgc cag gct cca ggg aag ggg ctg gag tgg gtc       144
Ala Met Ser Trp Val Arg Gln Ala Pro Gly Lys Gly Leu Glu Trp Val
         35                  40                  45 tca gct att agt ggt agt ggt ggt agc aca tac tac gca gac tcc gtg       192
Ser Ala Ile Ser Gly Ser Gly Gly Ser Thr Tyr Tyr Ala Asp Ser Val
     50                  55                  60 aag ggc cgg ttc acc atc tcc aga gac aat tcc aag aac acg ctg tat       240
Lys Gly Arg Phe Thr Ile Ser Arg Asp Asn Ser Lys Asn Thr Leu Tyr
 65                  70                  75                  80 ctg caa atg aac agt ctg agc gcc gac gac acg gcc gta tat ttc tgt       288
Leu Gln Met Asn Ser Leu Ser Ala Asp Asp Thr Ala Val Tyr Phe Cys
                 85                  90                  95 gcg tcg ggt ggc tgg tac ggg gac tac ttt gac tac tgg ggc cag gga       336
Ala Ser Gly Gly Trp Tyr Gly Asp Tyr Phe Asp Tyr Trp Gly Gln Gly
            100                 105                 110 acc ctg gtc acc gtc tca agc                                           357
Thr Leu Val Thr Val Ser Ser
        115

<210> SEQ ID NO 128
<211> LENGTH: 119
<212> TYPE: PRT
<213> ORGANISM: Artificial
<220> FEATURE:
<223> OTHER INFORMATION: Synthetic Construct

<400> SEQUENCE: 128

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Ser Ala Asp Asp Thr Ala Val Tyr Phe Cys
                 85                  90                  95

Ala Ser Gly Gly Trp Tyr Gly Asp Tyr Phe Asp Tyr Trp Gly Gln Gly
            100                 105                 110

Thr Leu Val Thr Val Ser Ser
        115

<210> SEQ ID NO 129
<211> LENGTH: 363
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(363)

<400> SEQUENCE: 129 cag gtg cag ctg cag gag tcc ggc cca gga ctg gtg aag cct tcg gag      48
Gln Val Gln Leu Gln Glu Ser Gly Pro Gly Leu Val Lys Pro Ser Glu
 1               5                  10                  15 acc ctg tcc ctc acc tgc act gtc tct ggt ggc tcc atc agc agt agt      96
Thr Leu Ser Leu Thr Cys Thr Val Ser Gly Gly Ser Ile Ser Ser Ser
             20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
         35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
     50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
 65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                 85                  90                  95 gcg aga gaa ggg aac cga acg gtg act agt gct ttt gat atc tgg ggc     336
Ala Arg Glu Gly Asn Arg Thr Val Thr Ser Ala Phe Asp Ile Trp Gly
            100                 105                 110 caa ggg aca atg gtc acc gtc tca agc                                 363
Gln Gly Thr Met Val Thr Val Ser Ser
        115                 120

<210> SEQ ID NO 130
<211> LENGTH: 121
<212> TYPE: PRT
<213> ORGANISM: Artificial
<220> FEATURE:
<223> OTHER INFORMATION: Synthetic Construct

<400> SEQUENCE: 130

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
             20                  25                  30

Asn Trp Trp Ser Trp Val Arg Gln Pro Pro Gly Lys Gly Leu Glu Trp
         35                  40                  45

Ile Gly Glu Ile Tyr His Ser Gly Ser Thr Asn Tyr Asn Pro Ser Leu
```

```
                50                  55                  60
Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Gly Asn Arg Thr Val Thr Ser Ala Phe Asp Ile Trp Gly
                100                 105                 110

Gln Gly Thr Met Val Thr Val Ser Ser
            115                 120

<210> SEQ ID NO 131
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 131 cag gtg cag ctg cag gag tcc ggc cca gga ctg gtg aag cct tcg ggg      48
Gln Val Gln Leu Gln Glu Ser Gly Pro Gly Leu Val Lys Pro Ser Gly
 1               5                  10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
                 20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
             35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
     50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
 65                  70                  75                  80 ctg aag ctg agc tct gtg acc gct gcg gac acg gcc gtg tac tac tgt     288
Leu Lys Leu Ser Ser Val Thr Ala Ala Asp Thr Ala Val Tyr Tyr Cys
                 85                  90                  95 gcg aga ggg ctg ggg gat agt agt ggt tat atc ctt tgg ggc caa ggg     336
Ala Arg Gly Leu Gly Asp Ser Ser Gly Tyr Ile Leu Trp Gly Gln Gly
                100                 105                 110 aca atg gtc acc gtc tca agc                                         357
Thr Met Val Thr Val Ser Ser
            115

<210> SEQ ID NO 132
<211> LENGTH: 119
<212> TYPE: PRT
<213> ORGANISM: Artificial
<220> FEATURE:
<223> OTHER INFORMATION: Synthetic Construct

<400> SEQUENCE: 132

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                 20                  25                  30

Asn Trp Trp Ser Trp Val Arg Gln Pro Pro Gly Lys Gly Leu Glu Trp
             35                  40                  45
```

```
Ile Gly Glu Ile Tyr His Ser Gly Ser Thr Asn Tyr Asn Pro Ser Leu
         50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Leu Gly Asp Ser Ser Gly Tyr Ile Leu Trp Gly Gln Gly
             100                 105                 110

Thr Met Val Thr Val Ser Ser
             115

<210> SEQ ID NO 133
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 133 cag gtg cag ctg cag gag tcc ggc cca gga ctg gtg aag cct tcg ggg      48
Gln Val Gln Leu Gln Glu Ser Gly Pro Gly Leu Val Lys Pro Ser Gly
 1               5                  10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
             20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
         35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
     50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
 65                  70                  75                  80 ctg aag ctg agc tct gtg acc gct gcg gac acg gcc gtg tac tac tgt     288
Leu Lys Leu Ser Ser Val Thr Ala Ala Asp Thr Ala Val Tyr Tyr Cys
                 85                  90                  95 gcg aga ggg ctg ggg gat agt agt ggt tat atc ctt tgg ggc caa ggg     336
Ala Arg Gly Leu Gly Asp Ser Ser Gly Tyr Ile Leu Trp Gly Gln Gly
             100                 105                 110 aca atg gtc acc gtc tca agc                                         357
Thr Met Val Thr Val Ser Ser
             115

<210> SEQ ID NO 134
<211> LENGTH: 119
<212> TYPE: PRT
<213> ORGANISM: Artificial
<220> FEATURE:
<223> OTHER INFORMATION: Synthetic Construct

<400> SEQUENCE: 134

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
             20                  25                  30

Asn Trp Trp Ser Trp Val Arg Gln Pro Pro Gly Lys Gly Leu Glu Trp
         35                  40                  45
```

```
Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Gly Leu Gly Asp Ser Ser Gly Tyr Ile Leu Trp Gly Gln Gly
            100                 105                 110

Thr Met Val Thr Val Ser Ser
            115
```

<210> SEQ ID NO 135
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 135

```
cag gtg cag ctg cag gag tcg ggc cca gga ctg gtg aag cct tcg ggg       48
Gln Val Gln Leu Gln Glu Ser Gly Pro Gly Leu Val Lys Pro Ser Gly
 1               5                  10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
                20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
 65                  70                  75                  80 ctg aag ctg agc tct gtg acc gcc gcg gac acg gcc gtg tat tac tgt      288
Leu Lys Leu Ser Ser Val Thr Ala Ala Asp Thr Ala Val Tyr Tyr Cys
                85                  90                  95 gcg aga tgg acc ggg cgt act gat gct ttt gat atc tgg ggc caa ggg      336
Ala Arg Trp Thr Gly Arg Thr Asp Ala Phe Asp Ile Trp Gly Gln Gly
            100                 105                 110 aca atg gtc acc gtc tca agc                                          357
Thr Met Val Thr Val Ser Ser
            115
```

<210> SEQ ID NO 136
<211> LENGTH: 119
<212> TYPE: PRT
<213> ORGANISM: Artificial
<220> FEATURE:
<223> OTHER INFORMATION: Synthetic Construct

<400> SEQUENCE: 136

```
Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
```

```
                35                  40                  45
Ile Gly Glu Ile Tyr His Ser Gly Ser Thr Asn Tyr Asn Pro Ser Leu
         50                  55                  60
Lys Ser Arg Val Thr Ile Ser Val Asp Lys Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Ala Arg Trp Thr Gly Arg Thr Asp Ala Phe Asp Ile Trp Gly Gln Gly
                100                 105                 110
Thr Met Val Thr Val Ser Ser
        115

<210> SEQ ID NO 137
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 137 cag gtg cag ctg cag gag tcc ggc cca gga ctg gtg aag cct tcg ggg    48
Gln Val Gln Leu Gln Glu Ser Gly Pro Gly Leu Val Lys Pro Ser Gly
 1               5                  10                  15 acc ctg tcc ctc acc tgc gct gtc tct ggt ggc tcc atc agc agt agt    96
Thr Leu Ser Leu Thr Cys Ala Val Ser Gly Gly Ser Ile Ser Ser Ser
             20                  25                  30 aac tgg tgg agt tgg gtc cgc cag ccc cca ggg aag ggg ctg gag tgg   144
Asn Trp Trp Ser Trp Val Arg Gln Pro Pro Gly Lys Gly Leu Glu Trp
         35                  40                  45 att ggg gaa atc tat cat agt ggg agc acc aac tac aac ccg tcc ctc   192
Ile Gly Glu Ile Tyr His Ser Gly Ser Thr Asn Tyr Asn Pro Ser Leu
     50                  55                  60 aag agt cga gtc acc ata tca gta gac aag tcc aag aac cag ttc tcc   240
Lys Ser Arg Val Thr Ile Ser Val Asp Lys Ser Lys Asn Gln Phe Ser
 65                  70                  75                  80 ctg aag ctg agc tct gtg acc gcc gcg gac acg gcc gtg tat tac tgt   288
Leu Lys Leu Ser Ser Val Thr Ala Ala Asp Thr Ala Val Tyr Tyr Cys
                 85                  90                  95 gcg aga caa ggg gcg tta gat gct ttt gat atc tgg ggc caa ggg acc   336
Ala Arg Gln Gly Ala Leu Asp Ala Phe Asp Ile Trp Gly Gln Gly Thr
                100                 105                 110 acg gtc acc gtc tca agc                                           354
Thr Val Thr Val Ser Ser
        115

<210> SEQ ID NO 138
<211> LENGTH: 118
<212> TYPE: PRT
<213> ORGANISM: Artificial
<220> FEATURE:
<223> OTHER INFORMATION: Synthetic Construct

<400> SEQUENCE: 138

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
             20                  25                  30
```

```
Asn Trp Trp Ser Trp Val Arg Gln Pro Pro Gly Lys Gly Leu Glu Trp
             35                  40                  45

Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gln Gly Ala Leu Asp Ala Phe Asp Ile Trp Gly Gln Gly Thr
                100                 105                 110

Thr Val Thr Val Ser Ser
            115
```

<210> SEQ ID NO 139
<211> LENGTH: 361
<212> TYPE: DNA
<213> ORGANISM: Artificial
<220> FEATURE:
<223> OTHER INFORMATION: Anti-IGF1R antibody heavy chain variable domain
      sequence

<400> SEQUENCE: 139

```
gcagctggtg gagtccgggg gaggcgtggt ccgacctggg gggtccctga gactctcctg      60
tgcagcgtct ggattcacct ttagcagcta tgccatgagc tgggtccgcc aggctccagg     120
gaaggggctg gagtgggtct caactattag tggtagtggt ggtagcacat actacgcaga     180
ctccgtgaag ggccggttca ccatctccag agacaattcc aagaacacgc tgtatctgca     240
gatgaacagc ctgagagccg aggacacggc cgtatattac tgtgcgaaag agcgtggcag     300
tggctggtcc ttagacaata tggacgtctg gggccaaggg accacggtca ccgtctcaag     360
c                                                                     361
```

<210> SEQ ID NO 140
<211> LENGTH: 122
<212> TYPE: PRT
<213> ORGANISM: Artificial
<220> FEATURE:
<223> OTHER INFORMATION: Synthetic construct

<400> SEQUENCE: 140

```
Glu Val Gln Leu Val Glu Ser Gly Gly Gly Val Val Arg Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
             35                  40                  45

Ser Thr Ile Ser Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Arg Gly Ser Gly Trp Ser Leu Asp Asn Met Asp Val Trp
                100                 105                 110

Gly Gln Gly Thr Thr Val Thr Val Ser Ser
            115                 120
```

<210> SEQ ID NO 141

```
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 141 cag gtg cag ctg gtg gag tct ggc cca gga ctg gtg aag cct tcg ggg       48
Gln Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gct gcg gac acg gcc gtg tat tac tgt      288
Leu Lys Leu Ser Ser Val Thr Ala Ala Asp Thr Ala Val Tyr Tyr Cys
                85                  90                  95 gcg aga gat agc agt ggg ttc tac ggt atg gac gtc tgg ggc caa ggg      336
Ala Arg Asp Ser Ser Gly Phe Tyr Gly Met Asp Val Trp Gly Gln Gly
            100                 105                 110 acc acg gtc acc gtc tca agc                                          357
Thr Thr Val Thr Val Ser Ser
        115

<210> SEQ ID NO 142
<211> LENGTH: 119
<212> TYPE: PRT
<213> ORGANISM: Artificial
<220> FEATURE:
<223> OTHER INFORMATION: Synthetic Construct

<400> SEQUENCE: 142

Gln Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ser Ser Gly Phe Tyr Gly Met Asp Val Trp Gly Gln Gly
            100                 105                 110

Thr Thr Val Thr Val Ser Ser
        115
```

<210> SEQ ID NO 143
<211> LENGTH: 360
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(360)

<400> SEQUENCE: 143

```
cag gtg cag ctg cag gag tcg ggc cca gga ctg gtg aag cct tcg ggg        48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt        96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg       144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc       192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc       240
Lys Ser Arg Val Thr Ile Ser Val Asp Lys Ser Lys Asn Gln Phe Ser
65                  70                  75                  80 ctg aag ctg agc tct gtg act gcc gcg gac acg gcc gtg tat tac tgt       288
Leu Lys Leu Ser Ser Val Thr Ala Ala Asp Thr Ala Val Tyr Tyr Cys
                85                  90                  95 gcg aga agc agc agc tgg tac tgg aat gct ttt gat atc tgg ggc caa       336
Ala Arg Ser Ser Ser Trp Tyr Trp Asn Ala Phe Asp Ile Trp Gly Gln
            100                 105                 110 ggg aca atg gtc acc gtc tca agc                                       360
Gly Thr Met Val Thr Val Ser Ser
        115                 120
```

<210> SEQ ID NO 144
<211> LENGTH: 120
<212> TYPE: PRT
<213> ORGANISM: Artificial
<220> FEATURE:
<223> OTHER INFORMATION: Synthetic Construct

<400> SEQUENCE: 144

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Ser Ser Trp Tyr Trp Asn Ala Phe Asp Ile Trp Gly Gln
            100                 105                 110

Gly Thr Met Val Thr Val Ser Ser
        115                 120
```

<210> SEQ ID NO 145
<211> LENGTH: 351
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(351)

<400> SEQUENCE: 145

```
cag gtg cag cta cag cag tgg ggc cca gca ctg gtg aag cct tcg ggg      48
Gln Val Gln Leu Gln Gln Trp Gly Pro Ala Leu Val Lys Pro Ser Gly
1               5                   10                  15 acc ctg tcc ctc acc tgc tct gtc tct ggt gtc tcc atc acc agt aat      96
Thr Leu Ser Leu Thr Cys Ser Val Ser Gly Val Ser Ile Thr Ser Asn
            20                  25                  30 atc tgg tgg agt tgg gtc cgc cag tcc cca ggg aag ggg ctg gag tgg     144
Ile Trp Trp Ser Trp Val Arg Gln Ser Pro Gly Lys Gly Leu Glu Trp
        35                  40                  45 att ggg gaa gtc tat cat agt ggg agc acc aac tac aac ccg tcc ctc     192
Ile Gly Glu Val Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gct gtg tat tac tgt     288
Leu Lys Leu Ser Ser Val Thr Ala Ala Asp Thr Ala Val Tyr Tyr Cys
                85                  90                  95 gcg ggg tac cgt agc ttc ggg gag tcc tac tgg ggc cag gga acc ctg     336
Ala Gly Tyr Arg Ser Phe Gly Glu Ser Tyr Trp Gly Gln Gly Thr Leu
            100                 105                 110 gtc acc gtc tca agc                                                  351
Val Thr Val Ser Ser
        115
```

<210> SEQ ID NO 146
<211> LENGTH: 117
<212> TYPE: PRT
<213> ORGANISM: Artificial
<220> FEATURE:
<223> OTHER INFORMATION: Synthetic Construct

<400> SEQUENCE: 146

```
Gln Val Gln Leu Gln Gln Trp Gly Pro Ala Leu Val Lys Pro Ser Gly
1               5                   10                  15

Thr Leu Ser Leu Thr Cys Ser Val Ser Gly Val Ser Ile Thr Ser Asn
            20                  25                  30

Ile Trp Trp Ser Trp Val Arg Gln Ser Pro Gly Lys Gly Leu Glu Trp
        35                  40                  45

Ile Gly Glu Val Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Gly Tyr Arg Ser Phe Gly Glu Ser Tyr Trp Gly Gln Gly Thr Leu
            100                 105                 110

Val Thr Val Ser Ser
        115
```

<210> SEQ ID NO 147
<211> LENGTH: 366
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(366)

<400> SEQUENCE: 147

```
cag gtg cag cta cag cag tgg ggc gca ggg ctg ttg aag cct tcg gag       48
Gln Val Gln Leu Gln Gln Trp Gly Ala Gly Leu Leu Lys Pro Ser Glu
1               5                   10                  15 acc ctg tct ctc acc tgc gtt gtc tat ggt ggg tcc ttc agc gat ttc       96
Thr Leu Ser Leu Thr Cys Val Val Tyr Gly Gly Ser Phe Ser Asp Phe
            20                  25                  30 tac tgg agc tgg atc cgc cag ccc cca ggg aag ggg cca gag tgg att      144
Tyr Trp Ser Trp Ile Arg Gln Pro Pro Gly Lys Gly Pro Glu Trp Ile
        35                  40                  45 ggg gaa gtc aat cct aga gga agc acc aac tac aac ccg tcc ctc aag      192
Gly Glu Val Asn Pro Arg Gly Ser Thr Asn Tyr Asn Pro Ser Leu Lys
    50                  55                  60 agt cga gcc acc ata tca cta gac acg tcc aag aac cag ttc tcc ctg      240
Ser Arg Ala Thr Ile Ser Leu Asp Thr Ser Lys Asn Gln Phe Ser Leu
65                  70                  75                  80 aag ctg agt tct gtg acc gcc gcg gac acg gct gtg tat ttc tgt gcg      288
Lys Leu Ser Ser Val Thr Ala Ala Asp Thr Ala Val Tyr Phe Cys Ala
                85                  90                  95 aga ggt cct cgg ccc ggg aga gat ggc tac aat tac ttt gac aac tgg      336
Arg Gly Pro Arg Pro Gly Arg Asp Gly Tyr Asn Tyr Phe Asp Asn Trp
            100                 105                 110 ggc cag ggc acc ctg gtc acc gtc tca agc                              366
Gly Gln Gly Thr Leu Val Thr Val Ser Ser
        115                 120
```

<210> SEQ ID NO 148
<211> LENGTH: 122
<212> TYPE: PRT
<213> ORGANISM: Artificial
<220> FEATURE:
<223> OTHER INFORMATION: Synthetic Construct

<400> SEQUENCE: 148

Gln Val Gln Leu Gln Gln Trp Gly Ala Gly Leu Leu Lys Pro Ser Glu
1               5                   10                  15

Thr Leu Ser Leu Thr Cys Val Val Tyr Gly Gly Ser Phe Ser Asp Phe
            20                  25                  30

Tyr Trp Ser Trp Ile Arg Gln Pro Pro Gly Lys Gly Pro Glu Trp Ile
        35                  40                  45

Gly Glu Val Asn Pro Arg Gly Ser Thr Asn Tyr Asn Pro Ser Leu Lys
    50                  55                  60

Ser Arg Ala Thr Ile Ser Leu Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Gly Pro Arg Pro Gly Arg Asp Gly Tyr Asn Tyr Phe Asp Asn Trp
            100                 105                 110

Gly Gln Gly Thr Leu Val Thr Val Ser Ser
        115                 120

<210> SEQ ID NO 149
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 149

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agc agt agt      96
Thr Leu Ser Leu Thr Cys Thr Val Ser Gly Gly Ser Ile Ser Ser Ser
                20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga ggt ata gca gca gct ggt caa ggt gac tac tgg ggc cag gga     336
Ala Arg Gly Ile Ala Ala Ala Gly Gln Gly Asp Tyr Trp Gly Gln Gly
            100                 105                 110 acc ctg gtc acc gtc tca agc                                         357
Thr Leu Val Thr Val Ser Ser
        115
```

<210> SEQ ID NO 150
<211> LENGTH: 119
<212> TYPE: PRT
<213> ORGANISM: Artificial
<220> FEATURE:
<223> OTHER INFORMATION: Synthetic Construct

<400> SEQUENCE: 150

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ile Ala Ala Ala Gly Gln Gly Asp Tyr Trp Gly Gln Gly
            100                 105                 110
```

```
Thr Leu Val Thr Val Ser Ser
        115

<210> SEQ ID NO 151
<211> LENGTH: 363
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(363)

<400> SEQUENCE: 151 cag gtg cag ctg cag gag tcg ggc cca gga ctg gtg aag cct tcg gag         48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agc agt agt         96
Thr Leu Ser Leu Thr Cys Thr Val Ser Gly Gly Ser Ile Ser Ser Ser
                20                  25                  30 agt tac tac tgg ggc tgg atc cgc cag ccc cca ggg aag ggg ctg gag        144
Ser Tyr Tyr Trp Gly Trp Ile Arg Gln Pro Pro Gly Lys Gly Leu Glu
            35                  40                  45 tgg att ggg agt atc tat tat agt ggg agc acc tac tac aac ccg tcc        192
Trp Ile Gly Ser Ile Tyr Tyr Ser Gly Ser Thr Tyr Tyr Asn Pro Ser
        50                  55                  60 ctc aag agt cga gtc acc ata tcc gta gac acg tcc aag aac cag ttc        240
Leu Lys Ser Arg Val Thr Ile Ser Val Asp Thr Ser Lys Asn Gln Phe
65                  70                  75                  80 tcc ctg aag ctg agc tct gtg acc gcc gcg gac acg gcc gtg tat tac        288
Ser Leu Lys Leu Ser Ser Val Thr Ala Ala Asp Thr Ala Val Tyr Tyr
                85                  90                  95 tgt gcg aga gat ggg gga tac tac tac tac ggt atg gac gtc tgg ggc        336
Cys Ala Arg Asp Gly Gly Tyr Tyr Tyr Tyr Gly Met Asp Val Trp Gly
            100                 105                 110 caa ggg acc acg gtc acc gtc tca agc                                    363
Gln Gly Thr Thr Val Thr Val Ser Ser
        115                 120

<210> SEQ ID NO 152
<211> LENGTH: 121
<212> TYPE: PRT
<213> ORGANISM: Artificial
<220> FEATURE:
<223> OTHER INFORMATION: Synthetic Construct

<400> SEQUENCE: 152

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Gly Tyr Tyr Tyr Tyr Gly Met Asp Val Trp Gly
            100                 105                 110
```

```
Gln Gly Thr Thr Val Thr Val Ser Ser
        115                 120

<210> SEQ ID NO 153
<211> LENGTH: 351
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(351)

<400> SEQUENCE: 153 cag gtg cag ctg cag gag tcg ggc cca gga ctg gtg aag cct tcg ggg      48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg agt agt ggt tat gat gct ttt gat atc tgg ggc caa ggg acc acg     336
Ala Ser Ser Gly Tyr Asp Ala Phe Asp Ile Trp Gly Gln Gly Thr Thr
            100                 105                 110 gtc acc gtc tca agc                                                 351
Val Thr Val Ser Ser
        115

<210> SEQ ID NO 154
<211> LENGTH: 117
<212> TYPE: PRT
<213> ORGANISM: Artificial
<220> FEATURE:
<223> OTHER INFORMATION: Synthetic Construct

<400> SEQUENCE: 154

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Ser Gly Tyr Asp Ala Phe Asp Ile Trp Gly Gln Gly Thr Thr
```

Val Thr Val Ser Ser
        115

<210> SEQ ID NO 155
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 155 cag gtg cag ctg cag gag tcg ggc cca gga ctg gtg aag cct tcg ggg     48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt     96
Thr Leu Ser Leu Thr Cys Ala Val Ser Gly Gly Ser Ile Ser Ser Ser
            20                  25                  30 aat tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt    288
Leu Lys Leu Ser Ser Val Thr Ala Ala Asp Thr Ala Val Tyr Tyr Cys
                85                  90                  95 gca cga tac agc tat gga acg gta gga att gac tac tgg ggc cag gga    336
Ala Arg Tyr Ser Tyr Gly Thr Val Gly Ile Asp Tyr Trp Gly Gln Gly
            100                 105                 110 acc ctg gtc acc gtc tca agc                                        357
Thr Leu Val Thr Val Ser Ser
            115

<210> SEQ ID NO 156
<211> LENGTH: 119
<212> TYPE: PRT
<213> ORGANISM: Artificial
<220> FEATURE:
<223> OTHER INFORMATION: Synthetic Construct

<400> SEQUENCE: 156

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

```
Ala Arg Tyr Ser Tyr Gly Thr Val Gly Ile Asp Tyr Trp Gly Gln Gly
            100                 105                 110

Thr Leu Val Thr Val Ser Ser
        115

<210> SEQ ID NO 157
<211> LENGTH: 351
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(351)

<400> SEQUENCE: 157 gag gtg cag ctg gtg cag tct ggg gga ggc gtg gtc cag cct ggg acg      48
Glu Val Gln Leu Val Gln Ser Gly Gly Gly Val Val Gln Pro Gly Thr
1               5                   10                  15 tcc ctg aga ctc tcc tgt gca gcc tct gga ttc agc ttc aga agt cat      96
Ser Leu Arg Leu Ser Cys Ala Ala Ser Gly Phe Ser Phe Arg Ser His
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg     192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg act ata ggg ccg ggg gga ttt gac tac tgg ggc cag ggc acc ctg     336
Ala Thr Ile Gly Pro Gly Gly Phe Asp Tyr Trp Gly Gln Gly Thr Leu
            100                 105                 110 gtc acc gtc tca agc                                                  351
Val Thr Val Ser Ser
        115

<210> SEQ ID NO 158
<211> LENGTH: 117
<212> TYPE: PRT
<213> ORGANISM: Artificial
<220> FEATURE:
<223> OTHER INFORMATION: Synthetic Construct

<400> SEQUENCE: 158

Glu Val Gln Leu Val Gln Ser Gly Gly Gly Val Val Gln Pro Gly Thr
1               5                   10                  15

Ser Leu Arg Leu Ser Cys Ala Ala Ser Gly Phe Ser Phe Arg Ser His
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Thr Ile Gly Pro Gly Gly Phe Asp Tyr Trp Gly Gln Gly Thr Leu
            100                 105                 110

Val Thr Val Ser Ser
        115

<210> SEQ ID NO 159
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 159 cag gtg cag ctg cag gag tcc ggc cca gga ctg gtg aag cct tcg gag     48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc att aga aat tac     96
Thr Leu Ser Leu Thr Cys Thr Val Ser Gly Gly Ser Ile Arg Asn Tyr
            20                  25                  30 tac tgg agt tgg atc cgg cag ccc cca ggg aag gga ctg gag tgg att    144
Tyr Trp Ser Trp Ile Arg Gln Pro Pro Gly Lys Gly Leu Glu Trp Ile
        35                  40                  45 ggg tat att tct gac agt ggg aat acc aac tac aat ccc tcc ctc aag    192
Gly Tyr Ile Ser Asp Ser Gly Asn Thr Asn Tyr Asn Pro Ser Leu Lys
    50                  55                  60 agt cga gtc acc ata tca gta gac acg tcc aag aac cag ttc tcc cta    240
Ser Arg Val Thr Ile Ser Val Asp Thr Ser Lys Asn Gln Phe Ser Leu
65                  70                  75                  80 aag ctg acc tct gtg acc gcc aca gac acg gct gcg tat ttc tgt gcg    288
Lys Leu Thr Ser Val Thr Ala Thr Asp Thr Ala Ala Tyr Phe Cys Ala
                85                  90                  95 aga cat cga agc agc tgg gca tgg tac ttc gat ctc tgg ggc cgt ggc    336
Arg His Arg Ser Ser Trp Ala Trp Tyr Phe Asp Leu Trp Gly Arg Gly
            100                 105                 110 acc ctg gtc acc gtc tca agc                                        357
Thr Leu Val Thr Val Ser Ser
        115

<210> SEQ ID NO 160
<211> LENGTH: 119
<212> TYPE: PRT
<213> ORGANISM: Artificial
<220> FEATURE:
<223> OTHER INFORMATION: Synthetic Construct

<400> SEQUENCE: 160

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Asn Tyr
            20                  25                  30

Tyr Trp Ser Trp Ile Arg Gln Pro Pro Gly Lys Gly Leu Glu Trp Ile
        35                  40                  45

Gly Tyr Ile Ser Asp Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Thr Asp Thr Ala Ala Tyr Phe Cys Ala

-continued

```
                    85                  90                  95
Arg His Arg Ser Ser Trp Ala Trp Tyr Phe Asp Leu Trp Gly Arg Gly
                100                 105                 110

Thr Leu Val Thr Val Ser Ser
        115
```

<210> SEQ ID NO 161
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 161

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
                20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga gtg ggc agt ggc tgg tac gtt gac tac tgg ggc cag gga acc     336
Ala Arg Val Gly Ser Gly Trp Tyr Val Asp Tyr Trp Gly Gln Gly Thr
                100                 105                 110 ctg gtc acc gtc tca agc                                             354
Leu Val Thr Val Ser Ser
        115
```

<210> SEQ ID NO 162
<211> LENGTH: 118
<212> TYPE: PRT
<213> ORGANISM: Artificial
<220> FEATURE:
<223> OTHER INFORMATION: Synthetic Construct

<400> SEQUENCE: 162

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80
```

```
Leu Lys Leu Ser Ser Val Thr Ala Ala Asp Thr Ala Val Tyr Tyr Cys
            85                  90                  95

Ala Arg Val Gly Ser Gly Trp Tyr Val Asp Tyr Trp Gly Gln Gly Thr
        100                 105                 110

Leu Val Thr Val Ser Ser
        115

<210> SEQ ID NO 163
<211> LENGTH: 360
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(360)

<400> SEQUENCE: 163 cag gtg cag ctg cag gag tcc ggc cca gga ctg gtg aag cct tcg ggg       48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt       96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg      144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc      192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc      240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt      288
Leu Lys Leu Ser Ser Val Thr Ala Ala Asp Thr Ala Val Tyr Tyr Cys
                85                  90                  95 gcg aga gtt tct ggc tac tac tac tac ggt atg gac gtc tgg ggc caa      336
Ala Arg Val Ser Gly Tyr Tyr Tyr Tyr Gly Met Asp Val Trp Gly Gln
            100                 105                 110 ggg acc acg gtc acc gtc tca agc                                      360
Gly Thr Thr Val Thr Val Ser Ser
        115                 120

<210> SEQ ID NO 164
<211> LENGTH: 120
<212> TYPE: PRT
<213> ORGANISM: Artificial
<220> FEATURE:
<223> OTHER INFORMATION: Synthetic Construct

<400> SEQUENCE: 164

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80
```

```
Leu Lys Leu Ser Ser Val Thr Ala Ala Asp Thr Ala Val Tyr Tyr Cys
            85                  90                  95

Ala Arg Val Ser Gly Tyr Tyr Tyr Gly Met Asp Val Trp Gly Gln
            100                 105                 110

Gly Thr Thr Val Thr Val Ser Ser
        115                 120

<210> SEQ ID NO 165
<211> LENGTH: 369
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(369)

<400> SEQUENCE: 165 gag gtc cag ctg gta cag tct ggg gga ggc gtg gtc cag cct ggg agg      48
Glu Val Gln Leu Val Gln Ser Gly Gly Gly Val Val Gln Pro Gly Arg
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg     192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg aaa gcg tat agc agt ggc tgg tac gac tac tac ggt atg gac gtc     336
Ala Lys Ala Tyr Ser Ser Gly Trp Tyr Asp Tyr Tyr Gly Met Asp Val
            100                 105                 110 tgg ggc caa ggg acc acg gtc acc gtc tca agc                         369
Trp Gly Gln Gly Thr Thr Val Thr Val Ser Ser
        115                 120

<210> SEQ ID NO 166
<211> LENGTH: 123
<212> TYPE: PRT
<213> ORGANISM: Artificial
<220> FEATURE:
<223> OTHER INFORMATION: Synthetic Construct

<400> SEQUENCE: 166

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys Ala Tyr Ser Ser Gly Trp Tyr Asp Tyr Tyr Gly Met Asp Val
                100                 105                 110

Trp Gly Gln Gly Thr Thr Val Thr Val Ser Ser
        115                 120

<210> SEQ ID NO 167
<211> LENGTH: 351
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(351)

<400> SEQUENCE: 167 cag gtg cag ctg cag gag tcg ggc cca gga ctg gtg aag cct tcg ggg      48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
                20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga gcc agc gtt gat gct ttt gat atc tgg ggc caa ggg aca atg     336
Ala Arg Ala Ser Val Asp Ala Phe Asp Ile Trp Gly Gln Gly Thr Met
                100                 105                 110 gtc acc gtc tca agc                                                  351
Val Thr Val Ser Ser
        115

<210> SEQ ID NO 168
<211> LENGTH: 117
<212> TYPE: PRT
<213> ORGANISM: Artificial
<220> FEATURE:
<223> OTHER INFORMATION: Synthetic Construct

<400> SEQUENCE: 168

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60
```

```
Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Ala Ser Val Asp Ala Phe Asp Ile Trp Gly Gln Gly Thr Met
            100                 105                 110

Val Thr Val Ser Ser
        115

<210> SEQ ID NO 169
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 169 cag gtg cag ctg cag gag tcc ggc cca gga ctg gtg aag cct tcg ggg      48
Gln Val Gln Leu Gln Glu Ser Gly Pro Gly Leu Val Lys Pro Ser Gly
  1               5                  10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
             20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
         35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
     50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
 65                  70                  75                  80 ctg aag ctg agc tct gtg acc gct gcg gac acg gcc gtg tac tac tgt     288
Leu Lys Leu Ser Ser Val Thr Ala Ala Asp Thr Ala Val Tyr Tyr Cys
                 85                  90                  95 gcg aga ggg ctg ggg gat agt agt ggt tat atc ctt tgg ggc caa ggg     336
Ala Arg Gly Leu Gly Asp Ser Ser Gly Tyr Ile Leu Trp Gly Gln Gly
            100                 105                 110 aca atg gtc acc gtc tca agc                                         357
Thr Met Val Thr Val Ser Ser
        115

<210> SEQ ID NO 170
<211> LENGTH: 119
<212> TYPE: PRT
<213> ORGANISM: Artificial
<220> FEATURE:
<223> OTHER INFORMATION: Synthetic Construct

<400> SEQUENCE: 170

Gln Val Gln Leu Gln Glu Ser Gly Pro Gly Leu Val Lys Pro Ser Gly
  1               5                  10                  15

Thr Leu Ser Leu Thr Cys Ala Val Ser Gly Gly Ser Ile Ser Ser Ser
             20                  25                  30

Asn Trp Trp Ser Trp Val Arg Gln Pro Pro Gly Lys Gly Leu Glu Trp
         35                  40                  45

Ile Gly Glu Ile Tyr His Ser Gly Ser Thr Asn Tyr Asn Pro Ser Leu
     50                  55                  60
```

```
Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Leu Gly Asp Ser Gly Tyr Ile Leu Trp Gly Gln Gly
            100                 105                 110

Thr Met Val Thr Val Ser Ser
        115
```

<210> SEQ ID NO 171
<211> LENGTH: 348
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(348)

<400> SEQUENCE: 171

```
cag gta cag ctg cag cag tca ggc cca gga ctg gtg aag cct tcg ggg     48
Gln Val Gln Leu Gln Gln Ser Gly Pro Gly Leu Val Lys Pro Ser Gly
 1               5                  10                  15 acc ctg tcc ctc acc tgc gct gtc tct ggt ggc tcc atc agc agt agt     96
Thr Leu Ser Leu Thr Cys Ala Val Ser Gly Gly Ser Ile Ser Ser Ser
                 20                  25                  30 aac tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
             35                  40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
         50                  55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
 65                  70                  75                  80 ctg aag ctg agc tct gtg act ccc gag gac acg gct gtg tat tac tgt    288
Leu Lys Leu Ser Ser Val Thr Pro Glu Asp Thr Ala Val Tyr Tyr Cys
                 85                  90                  95 gca aga gat cac ggc ccc ttt gac tac tgg ggc cgg gga acc ctg gtc    336
Ala Arg Asp His Gly Pro Phe Asp Tyr Trp Gly Arg Gly Thr Leu Val
            100                 105                 110 acc gtc tca agc                                                    348
Thr Val Ser Ser
        115
```

<210> SEQ ID NO 172
<211> LENGTH: 116
<212> TYPE: PRT
<213> ORGANISM: Artificial
<220> FEATURE:
<223> OTHER INFORMATION: Synthetic Construct

<400> SEQUENCE: 172

```
Gln Val Gln Leu Gln Gln Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                 20                  25                  30

Asn Trp Trp Ser Trp Val Arg Gln Pro Pro Gly Lys Gly Leu Glu Trp
             35                  40                  45

Ile Gly Glu Ile Tyr His Ser Gly Ser Thr Asn Tyr Asn Pro Ser Leu
```

```
                    50                  55                  60
Lys Ser Arg Val Thr Ile Ser Val Asp Lys Ser Lys Asn Gln Phe Ser
 65                  70                  75                  80

Leu Lys Leu Ser Ser Val Thr Pro Glu Asp Thr Ala Val Tyr Tyr Cys
                 85                  90                  95

Ala Arg Asp His Gly Pro Phe Asp Tyr Trp Gly Arg Gly Thr Leu Val
            100                 105                 110

Thr Val Ser Ser
        115
```

<210> SEQ ID NO 173
<211> LENGTH: 360
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(360)

<400> SEQUENCE: 173

```
cag gtg cag ctg gtg caa tct ggg gga ggc gtg gtc cag cct ggg agg      48
Gln Val Gln Leu Val Gln Ser Gly Gly Gly Val Val Gln Pro Gly Arg
  1               5                  10                  15 tcc ctg aga ctc tcc tgt gca gcc tct gga ttc gcc ttc agt agc tat      96
Ser Leu Arg Leu Ser Cys Ala Ala Ser Gly Phe Ala Phe Ser Ser Tyr
                 20                  25                  30 ggc atg cac tgg gtc cgc cag gct cca ggg aag ggg ctg gag tgg gtt     144
Gly Met His Trp Val Arg Gln Ala Pro Gly Lys Gly Leu Glu Trp Val
             35                  40                  45 tca tac att agt agt agt agt acc ata tac tac gca gac tct gtg         192
Ser Tyr Ile Ser Ser Ser Ser Thr Ile Tyr Tyr Ala Asp Ser Val
         50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                 85                  90                  95 gcg aga gat cga ttt ggg tcg ggg cac ttg ccc gac tac tgg ggc cag     336
Ala Arg Asp Arg Phe Gly Ser Gly His Leu Pro Asp Tyr Trp Gly Gln
            100                 105                 110 gga acc ctg gtc acc gtc tca agc                                     360
Gly Thr Leu Val Thr Val Ser Ser
            115                 120
```

<210> SEQ ID NO 174
<211> LENGTH: 120
<212> TYPE: PRT
<213> ORGANISM: Artificial
<220> FEATURE:
<223> OTHER INFORMATION: Synthetic Construct

<400> SEQUENCE: 174

```
Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Ala Phe Ser Ser Tyr
                 20                  25                  30

Gly Met His Trp Val Arg Gln Ala Pro Gly Lys Gly Leu Glu Trp Val
             35                  40                  45
```

```
Ser Tyr Ile Ser Ser Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Phe Gly Ser Gly His Leu Pro Asp Tyr Trp Gly Gln
            100                 105                 110

Gly Thr Leu Val Thr Val Ser Ser
        115                 120

<210> SEQ ID NO 175
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 175 cag gtg cag cta cag cag tgg ggc gca gga ctg ttg aag cct tcg gag      48
Gln Val Gln Leu Gln Gln Trp Gly Ala Gly Leu Leu Lys Pro Ser Glu
 1               5                  10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
             20                  25                  30 tac tgg agc tgg atc cgc cag ccc cca ggg aag ggg ctg gag tgg att     144
Tyr Trp Ser Trp Ile Arg Gln Pro Pro Gly Lys Gly Leu Glu Trp Ile
         35                  40                  45 ggg gaa atc aat cat agt gga agc acc aac tac aac ccg tcc ctc aag     192
Gly Glu Ile Asn His Ser Gly Ser Thr Asn Tyr Asn Pro Ser Leu Lys
     50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
 65                  70                  75                  80 aag ctg agc tct gtg acc gcc gcg gac acg gct gtg tat tac tgt gcg     288
Lys Leu Ser Ser Val Thr Ala Ala Asp Thr Ala Val Tyr Tyr Cys Ala
                 85                  90                  95 aga gtt ggg tat agc agt ggc cgt gac gtt gac tac tgg ggc cag ggc     336
Arg Val Gly Tyr Ser Ser Gly Arg Asp Val Asp Tyr Trp Gly Gln Gly
            100                 105                 110 acc ctg gtc acc gtc tca agc                                         357
Thr Leu Val Thr Val Ser Ser
        115

<210> SEQ ID NO 176
<211> LENGTH: 119
<212> TYPE: PRT
<213> ORGANISM: Artificial
<220> FEATURE:
<223> OTHER INFORMATION: Synthetic Construct

<400> SEQUENCE: 176

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45
```

```
Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Val Gly Tyr Ser Ser Gly Arg Asp Val Asp Tyr Trp Gly Gln Gly
            100                 105                 110

Thr Leu Val Thr Val Ser Ser
            115
```

<210> SEQ ID NO 177
<211> LENGTH: 360
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(360)

<400> SEQUENCE: 177

```
gag gtc cag ctg gtg gag tct ggc cca gga ctg gtg aag cct tcg ggg        48
Glu Val Gln Leu Val Glu Ser Gly Pro Gly Leu Val Lys Pro Ser Gly
 1               5                  10                  15 acc ctg tcc ctc acc tgc gct gtc tct ggt ggc tcc atc agc agt agt        96
Thr Leu Ser Leu Thr Cys Ala Val Ser Gly Gly Ser Ile Ser Ser Ser
                20                  25                  30 aac tgg tgg agt tgg atc cgg cag ccc cca ggg aag ggg ctg gag tgg       144
Asn Trp Trp Ser Trp Ile Arg Gln Pro Pro Gly Lys Gly Leu Glu Trp
            35                  40                  45 att ggg gaa atc tat cat agt ggg agc acc aac tac aac ccg tcc ctc       192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc       240
Lys Ser Arg Val Thr Ile Ser Val Asp Lys Ser Lys Asn Gln Phe Ser
 65                  70                  75                  80 ctg aag ctg agc tct gtg acc gcc gcg gac acg gcc gtg tat tac tgt       288
Leu Lys Leu Ser Ser Val Thr Ala Ala Asp Thr Ala Val Tyr Tyr Cys
                 85                  90                  95 gcg aga gat agc agc agc tgg tac tac ggt atg gac gtc tgg ggc caa       336
Ala Arg Asp Ser Ser Ser Trp Tyr Tyr Gly Met Asp Val Trp Gly Gln
            100                 105                 110 ggg acc acg gtc acc gtc tca agc                                       360
Gly Thr Thr Val Thr Val Ser Ser
        115                 120
```

<210> SEQ ID NO 178
<211> LENGTH: 120
<212> TYPE: PRT
<213> ORGANISM: Artificial
<220> FEATURE:
<223> OTHER INFORMATION: Synthetic Construct

<400> SEQUENCE: 178

```
Glu Val Gln Leu Val Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                20                  25                  30

Asn Trp Trp Ser Trp Ile Arg Gln Pro Pro Gly Lys Gly Leu Glu Trp
```

```
                35                  40                  45
Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Asp Ser Ser Ser Trp Tyr Tyr Gly Met Asp Val Trp Gly Gln
            100                 105                 110

Gly Thr Thr Val Thr Val Ser Ser
        115                 120

<210> SEQ ID NO 179
<211> LENGTH: 348
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(348)

<400> SEQUENCE: 179 gag gtc cag ctg gtg gag tcc ggc cca gga ctg gtg aag cct tcg gag      48
Glu Val Gln Leu Val Glu Ser Gly Pro Gly Leu Val Lys Pro Ser Glu
 1               5                  10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
                20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
 65                  70                  75                  80 ctg aag ctg agc tct gtg acc gct gcg gac acg gcc gta tat tat tgt     288
Leu Lys Leu Ser Ser Val Thr Ala Ala Asp Thr Ala Val Tyr Tyr Cys
                85                  90                  95 gcg aga tcg acg tgg tcc ctt gac tac tgg ggc cag ggc acc ctg gtc     336
Ala Arg Ser Thr Trp Ser Leu Asp Tyr Trp Gly Gln Gly Thr Leu Val
            100                 105                 110 acc gtc tca agc                                                     348
Thr Val Ser Ser
        115

<210> SEQ ID NO 180
<211> LENGTH: 116
<212> TYPE: PRT
<213> ORGANISM: Artificial
<220> FEATURE:
<223> OTHER INFORMATION: Synthetic Construct

<400> SEQUENCE: 180

Glu Val Gln Leu Val Glu Ser Gly Pro Gly Leu Val Lys Pro Ser Glu
 1               5                  10                  15

Thr Leu Ser Leu Thr Cys Ala Val Ser Gly Gly Ser Ile Ser Ser Ser
                20                  25                  30
```

```
Asn Trp Trp Ser Trp Val Arg Gln Pro Pro Gly Lys Gly Leu Glu Trp
             35                  40                  45

Ile Gly Glu Ile Tyr His Ser Gly Ser Thr Asn Tyr Asn Pro Ser Leu
 50                      55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Ser Thr Trp Ser Leu Asp Tyr Trp Gly Gln Gly Thr Leu Val
                100                 105                 110

Thr Val Ser Ser
        115
```

<210> SEQ ID NO 181
<211> LENGTH: 354
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(354)

<400> SEQUENCE: 181

```
gag gtc cag ctg gtg gag tct ggc cca gga ctg gtg aag cct tcg ggg      48
Glu Val Gln Leu Val Glu Ser Gly Pro Gly Leu Val Lys Pro Ser Gly
  1               5                  10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
             20                  25                  30 aac tgg tgg agt tgg gtc cgc cag ccc cca ggg aag ggg ctg gag tgg    144
Asn Trp Trp Ser Trp Val Arg Gln Pro Pro Gly Lys Gly Leu Glu Trp
         35                      40                  45 att ggg gaa atc tat cat agt ggg agc acc aac tac aac ccg tcc ctc    192
Ile Gly Glu Ile Tyr His Ser Gly Ser Thr Asn Tyr Asn Pro Ser Leu
 50                      55                  60 aag agt cga gtc acc ata tca gta gac aag tcc aag aac cag ttc tcc    240
Lys Ser Arg Val Thr Ile Ser Val Asp Lys Ser Lys Asn Gln Phe Ser
 65                  70                  75                  80 ctg aag ctg agc tct gtg acc gct gcg gac acg gcc gta tat tac tgt    288
Leu Lys Leu Ser Ser Val Thr Ala Ala Asp Thr Ala Val Tyr Tyr Cys
                 85                  90                  95 gcg aga ctc tcg ttt gcc gat cct ttt gat atc tgg ggc caa ggg aca    336
Ala Arg Leu Ser Phe Ala Asp Pro Phe Asp Ile Trp Gly Gln Gly Thr
                100                 105                 110 atg gtc acc gtc tca agc                                             354
Met Val Thr Val Ser Ser
        115
```

<210> SEQ ID NO 182
<211> LENGTH: 118
<212> TYPE: PRT
<213> ORGANISM: Artificial
<220> FEATURE:
<223> OTHER INFORMATION: Synthetic Construct

<400> SEQUENCE: 182

```
Glu Val Gln Leu Val Glu Ser Gly Pro Gly Leu Val Lys Pro Ser Gly
  1               5                  10                  15

Thr Leu Ser Leu Thr Cys Ala Val Ser Gly Gly Ser Ile Ser Ser Ser
             20                  25                  30
```

```
Asn Trp Trp Ser Trp Val Arg Gln Pro Pro Gly Lys Gly Leu Glu Trp
         35                  40                  45
Ile Gly Glu Ile Tyr His Ser Gly Ser Thr Asn Tyr Asn Pro Ser Leu
 50                  55                  60
Lys Ser Arg Val Thr Ile Ser Val Asp Lys Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Ala Arg Leu Ser Phe Ala Asp Pro Phe Asp Ile Trp Gly Gln Gly Thr
                100                 105                 110
Met Val Thr Val Ser Ser
        115

<210> SEQ ID NO 183
<211> LENGTH: 366
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(366)

<400> SEQUENCE: 183 cag gtc cag ctg gtg cag tct ggg gct gag gtg aag aag cct ggg tcc        48
Gln Val Gln Leu Val Gln Ser Gly Ala Glu Val Lys Lys Pro Gly Ser
1               5                  10                  15 tcg gtg aag gtc tcc tgc aag gct tct gga ggc acc ttc agc agc tat        96
Ser Val Lys Val Ser Cys Lys Ala Ser Gly Gly Thr Phe Ser Ser Tyr
             20                  25                  30 gct atc agc tgg gtg cga cag gcc cct gga caa ggg ctt gag tgg atg       144
Ala Ile Ser Trp Val Arg Gln Ala Pro Gly Gln Gly Leu Glu Trp Met
         35                  40                  45 gga agg atc atc ccc atc ctt ggt ata gca aac tac gca cag aag ttc       192
Gly Arg Ile Ile Pro Ile Leu Gly Ile Ala Asn Tyr Ala Gln Lys Phe
     50                  55                  60 cag ggc aga gtc acg att acc gcg gac aaa tcc acg agc aca gcc tac       240
Gln Gly Arg Val Thr Ile Thr Ala Asp Lys Ser Thr Ser Thr Ala Tyr
65                  70                  75                  80 atg gag ctg agc agc ctg aga tct gag gac acg gcc gtg tat tac tgt       288
Met Glu Leu Ser Ser Leu Arg Ser Glu Asp Thr Ala Val Tyr Tyr Cys
                 85                  90                  95 gca tat ggt tcg ggg agt tat tac gac tac tac tac atg gac gtc tgg       336
Ala Tyr Gly Ser Gly Ser Tyr Tyr Asp Tyr Tyr Tyr Met Asp Val Trp
                100                 105                 110 ggc aaa ggg acc acg gtc acc gtc tca agc                               366
Gly Lys Gly Thr Thr Val Thr Val Ser Ser
        115                 120

<210> SEQ ID NO 184
<211> LENGTH: 122
<212> TYPE: PRT
<213> ORGANISM: Artificial
<220> FEATURE:
<223> OTHER INFORMATION: Synthetic Construct

<400> SEQUENCE: 184

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
```

```
                   20                  25                  30
Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Gly Ser Gly Ser Tyr Tyr Asp Tyr Tyr Tyr Met Asp Val Trp
            100                 105                 110

Gly Lys Gly Thr Thr Val Thr Val Ser Ser
            115                 120

<210> SEQ ID NO 185
<211> LENGTH: 357
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(357)

<400> SEQUENCE: 185 gag gtc cag ctg gtg cag tct ggg gga ggc ttg gtc cag cct ggg ggg       48
Glu Val Gln Leu Val Gln Ser Gly Gly Gly Leu Val Gln Pro Gly Gly
1               5                   10                  15 tcc ctg aga ctc tcc tgt tca gcc tcc gga ttc acc ttc agt agc tat       96
Ser Leu Arg Leu Ser Cys Ser Ala Ser Gly Phe Thr Phe Ser Ser Tyr
            20                  25                  30 gct atg cac tgg gtc cgc cag gct cca ggg aag gga ctg gaa tat gtt      144
Ala Met His Trp Val Arg Gln Ala Pro Gly Lys Gly Leu Glu Tyr Val
        35                  40                  45 tca act att agt agt aat ggg gat agc aca tac tac gca gac tcc gtg      192
Ser Thr Ile Ser Ser Asn Gly Asp Ser Thr Tyr Tyr Ala Asp Ser Val
    50                  55                  60 aag ggc aga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt      288
Leu Gln Met Asn Ser Leu Arg Ala Glu Asp Thr Ala Val Tyr Tyr Cys
                85                  90                  95 gcg aaa gaa gaa gta tgg cta cag gct ttt gat atc tgg ggc caa ggg      336
Ala Lys Glu Glu Val Trp Leu Gln Ala Phe Asp Ile Trp Gly Gln Gly
            100                 105                 110 aca atg gtc acc gtc tca agc                                          357
Thr Met Val Thr Val Ser Ser
        115

<210> SEQ ID NO 186
<211> LENGTH: 119
<212> TYPE: PRT
<213> ORGANISM: Artificial
<220> FEATURE:
<223> OTHER INFORMATION: Synthetic Construct

<400> SEQUENCE: 186

Glu Val Gln Leu Val Gln Ser Gly Gly Gly Leu Val Gln Pro Gly Gly
1               5                   10                  15
```

```
Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
            35                  40                  45

Ser Thr Ile Ser Ser Asn Gly Asp Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Glu Glu Val Trp Leu Gly Ala Phe Asp Ile Trp Gly Gln Gly
            100                 105                 110

Thr Met Val Thr Val Ser Ser
            115

<210> SEQ ID NO 187
<211> LENGTH: 345
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(345)

<400> SEQUENCE: 187 cag ctg cag ctg cag gag tcg ggc cca gga ctg gtg aag cct tcg gag      48
Gln Leu Gln Leu Gln Glu Ser Gly Pro Gly Leu Val Lys Pro Ser Glu
 1               5                  10                  15 acc ctg tcc ctc acc tgc act gtc tct ggt ggc tcc atc agt agt aac      96
Thr Leu Ser Leu Thr Cys Thr Val Ser Gly Gly Ser Ile Ser Ser Asn
            20                  25                  30 tgg tgg agt tgg gtc cgc cag ccc cca ggg aag ggc ctg gag tgg att     144
Trp Trp Ser Trp Val Arg Gln Pro Pro Gly Lys Gly Leu Glu Trp Ile
        35                  40                  45 ggg gaa atc tat cat agt ggg agc acc aac tac aac ccc tcc ctc aag     192
Gly Glu Ile Tyr His Ser Gly Ser Thr Asn Tyr Asn Pro Ser Leu Lys
    50                  55                  60 agt cga gtc acc atc tca gta gac acg tcc aag aac cag ttc tcc ctg     240
Ser Arg Val Thr Ile Ser Val Asp Thr Ser Lys Asn Gln Phe Ser Leu
 65                  70                  75                  80 aag ctg agc tct gtg acc gct gcg gac acg gcc gtg tat tac tgt gcg     288
Lys Leu Ser Ser Val Thr Ala Ala Asp Thr Ala Val Tyr Tyr Cys Ala
                85                  90                  95 aga gat aag gga tac atg gac gtc tgg ggc aaa ggg acc acg gtc acc     336
Arg Asp Lys Gly Tyr Met Asp Val Trp Gly Lys Gly Thr Thr Val Thr
            100                 105                 110 gtc tca agc                                                         345
Val Ser Ser
        115

<210> SEQ ID NO 188
<211> LENGTH: 115
<212> TYPE: PRT
<213> ORGANISM: Artificial
<220> FEATURE:
<223> OTHER INFORMATION: Synthetic Construct

<400> SEQUENCE: 188

Gln Leu Gln Leu Gln Glu Ser Gly Pro Gly Leu Val Lys Pro Ser Glu
 1               5                  10                  15
```

```
Thr Leu Ser Leu Thr Cys Thr Val Ser Gly Gly Ser Ile Ser Ser Asn
            20                  25                  30

Trp Trp Ser Trp Val Arg Gln Pro Gly Lys Gly Leu Glu Trp Ile
        35                  40                  45

Gly Glu Ile Tyr His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Gly Tyr Met Asp Val Trp Gly Lys Gly Thr Thr Val Thr
            100                 105                 110

Val Ser Ser
        115
```

<210> SEQ ID NO 189
<211> LENGTH: 363
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(363)

<400> SEQUENCE: 189

```
cag gta cag ctg cag cag tca ggg gct gag gtg aag aag cct ggg tcc      48
Gln Val Gln Leu Gln Gln Ser Gly Ala Glu Val Lys Lys Pro Gly Ser
1               5                   10                  15 tcg gtg aag gtc tcc tgc aag gct tct gga ggc acc ttc agc agc tat      96
Ser Val Lys Val Ser Cys Lys Ala Ser Gly Gly Thr Phe Ser Ser Tyr
            20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
        35                  40                  45 gga agg atc atc cct atc ctt ggt ata gca aac tac gca cag aag ttc     192
Gly Arg Ile Ile Pro Ile Leu Gly Ile Ala Asn Tyr Ala Gln Lys Phe
    50                  55                  60 cag ggc aga gtc acg att acc gcg gac aaa tcc acg agc aca gcc tac     240
Gln Gly Arg Val Thr Ile Thr Ala Asp Lys Ser Thr Ser Thr Ala Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg aga gat cat agg ttc gac tac gcc tgg tac ttc gat ctc tgg ggc     336
Ala Arg Asp His Arg Phe Asp Tyr Ala Trp Tyr Phe Asp Leu Trp Gly
            100                 105                 110 cgt ggc acc ctg gtc acc gtc tca agc                                 363
Arg Gly Thr Leu Val Thr Val Ser Ser
        115                 120
```

<210> SEQ ID NO 190
<211> LENGTH: 121
<212> TYPE: PRT
<213> ORGANISM: Artificial
<220> FEATURE:
<223> OTHER INFORMATION: Synthetic Construct

<400> SEQUENCE: 190

Gln Val Gln Leu Gln Gln Ser Gly Ala Glu Val Lys Lys Pro Gly Ser

```
                1               5                  10                  15
              Ser Val Lys Val Ser Cys Lys Ala Ser Gly Gly Thr Phe Ser Ser Tyr
                              20                  25                  30

Ala Ile Ser Trp Val Arg Gln Ala Pro Gly Gln Gly Leu Glu Trp Met
                              35                  40                  45

Gly Arg Ile Ile Pro Ile Leu Gly Ile Ala Asn Tyr Ala Gln Lys Phe
                              50                  55                  60

Gln Gly Arg Val Thr Ile Thr Ala Asp Lys Ser Thr Ser Thr Ala Tyr
              65                  70                  75                  80

Met Glu Leu Ser Ser Leu Arg Ser Glu Asp Thr Ala Val Tyr Tyr Cys
                              85                  90                  95

Ala Arg Asp His Arg Phe Asp Tyr Ala Trp Tyr Phe Asp Leu Trp Gly
                              100                 105                 110

Arg Gly Thr Leu Val Thr Val Ser Ser
                              115                 120
```

<210> SEQ ID NO 191
<211> LENGTH: 351
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(351)

<400> SEQUENCE: 191

```
cag gtg cag ctg cag gag tcg ggc cca gga ctg ctg aag cct tcg ggg        48
Gln Val Gln Leu Gln Glu Ser Gly Pro Gly Leu Leu Lys Pro Ser Gly
1               5                   10                  15 acc ctg tcc ctc acc tgc gct gtc tct ggt ggc tcc atc agc agt agc        96
Thr Leu Ser Leu Thr Cys Ala Val Ser Gly Gly Ser Ile Ser Ser Ser
                20                  25                  30 aac tgg tgg agt tgg gtc cgc cag ccc cca ggg gag ggg ctg gag tgg       144
Asn Trp Trp Ser Trp Val Arg Gln Pro Pro Gly Glu Gly Leu Glu Trp
            35                  40                  45 att ggg gaa atc tat cat agt ggg agc acc aac tac aac ccg tcc ctc       192
Ile Gly Glu Ile Tyr His Ser Gly Ser Thr Asn Tyr Asn Pro Ser Leu
        50                  55                  60 aag agt cga gtc acc ata tca gta gac aag tcc aag aac cag ttc tcc       240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtc tat tac tgt       288
Leu Lys Leu Ser Ser Val Thr Ala Ala Asp Thr Ala Val Tyr Tyr Cys
                85                  90                  95 gcg aga gat cta acg ggg agt ctt gac tac tgg ggc cag gga acc ctg       336
Ala Arg Asp Leu Thr Gly Ser Leu Asp Tyr Trp Gly Gln Gly Thr Leu
            100                 105                 110 gtc acc gtc tca agc                                                    351
Val Thr Val Ser Ser
            115
```

<210> SEQ ID NO 192
<211> LENGTH: 117
<212> TYPE: PRT
<213> ORGANISM: Artificial
<220> FEATURE:
<223> OTHER INFORMATION: Synthetic Construct

<400> SEQUENCE: 192

```
Gln Val Gln Leu Gln Glu Ser Gly Pro Gly Leu Leu Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Glu Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Leu Thr Gly Ser Leu Asp Tyr Trp Gly Gln Gly Thr Leu
            100                 105                 110

Val Thr Val Ser Ser
            115

<210> SEQ ID NO 193
<211> LENGTH: 351
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(351)

<400> SEQUENCE: 193 cag gtg cag ctg cag gag tcc ggc cca gga ctg gtg aag cct tcg ggg      48
Gln Val Gln Leu Gln Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga ata cgc tat gat gct ttt gat atc tgg ggc caa ggg aca atg     336
Ala Arg Ile Arg Tyr Asp Ala Phe Asp Ile Trp Gly Gln Gly Thr Met
            100                 105                 110 gtc acc gtc tca agc                                                 351
Val Thr Val Ser Ser
            115

<210> SEQ ID NO 194
<211> LENGTH: 117
<212> TYPE: PRT
<213> ORGANISM: Artificial
<220> FEATURE:
<223> OTHER INFORMATION: Synthetic Construct

<400> SEQUENCE: 194
```

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Arg Tyr Asp Ala Phe Asp Ile Trp Gly Gln Gly Thr Met
            100                 105                 110

Val Thr Val Ser Ser
        115
```

<210> SEQ ID NO 195
<211> LENGTH: 354
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(354)

<400> SEQUENCE: 195

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gct gcg gac acg gcc gtg tat tac tgt     288
Leu Lys Leu Ser Ser Val Thr Ala Ala Asp Thr Ala Val Tyr Tyr Cys
                85                  90                  95 gcc gtg acg gca gcc cat gat gct ttt gat atc tgg ggc caa ggg aca     336
Ala Val Thr Ala Ala His Asp Ala Phe Asp Ile Trp Gly Gln Gly Thr
            100                 105                 110 atg gtc acc gtc tca agc                                             354
Met Val Thr Val Ser Ser
        115
```

<210> SEQ ID NO 196
<211> LENGTH: 118
<212> TYPE: PRT
<213> ORGANISM: Artificial
<220> FEATURE:
<223> OTHER INFORMATION: Synthetic Construct

<400> SEQUENCE: 196

```
Gln Val Gln Leu Gln Glu Ser Gly Pro Gly Leu Val Lys Pro Ser Glu
1               5                   10                  15
Thr Leu Ser Leu Thr Cys Ala Val Ser Gly Gly Ser Ile Ser Ser Ser
            20                  25                  30
Asn Trp Trp Ser Trp Val Arg Gln Pro Pro Gly Lys Gly Leu Glu Trp
        35                  40                  45
Ile Gly Glu Ile Tyr His Ser Gly Ser Thr Asn Tyr Asn Pro Ser Leu
50                  55                  60
Lys Ser Arg Val Thr Ile Ser Val Asp Lys Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Val Thr Ala Ala His Asp Ala Phe Asp Ile Trp Gly Gln Gly Thr
            100                 105                 110
Met Val Thr Val Ser Ser
        115
```

<210> SEQ ID NO 197
<211> LENGTH: 357
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(357)

<400> SEQUENCE: 197

```
cag gtg cag cta cag cag tgg ggc cca gga ctg gtg aag cct tcg ggg      48
Gln Val Gln Leu Gln Gln Trp Gly Pro Gly Leu Val Lys Pro Ser Gly
1               5                   10                  15
acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30
aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45
att ggg gaa atc tat cat agt ggg agc acc aac tac aac ccg tcc ctc     192
Ile Gly Glu Ile Tyr His Ser Gly Ser Thr Asn Tyr Asn Pro Ser Leu
50                  55                  60
aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80
ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95
gcg aga gac agc agt ggc caa ggg tac ttt gac tac tgg ggc cag ggc     336
Ala Arg Asp Ser Ser Gly Gln Gly Tyr Phe Asp Tyr Trp Gly Gln Gly
            100                 105                 110
acc ctg gtc acc gtc tca agc                                          357
Thr Leu Val Thr Val Ser Ser
        115
```

<210> SEQ ID NO 198
<211> LENGTH: 119
<212> TYPE: PRT
<213> ORGANISM: Artificial
<220> FEATURE:
<223> OTHER INFORMATION: Synthetic Construct

<400> SEQUENCE: 198

| Gln | Val | Gln | Leu | Gln | Gln | Trp | Gly | Pro | Gly | Leu | Val | Lys | Pro | Ser | Gly |
|---|---|---|---|---|---|---|---|---|---|---|---|---|---|---|---|
| 1 | | | | 5 | | | | | 10 | | | | | 15 | |

Thr Leu Ser Leu Thr Cys Ala Val Ser Gly Gly Ser Ile Ser Ser Ser
           20               25               30

Asn Trp Trp Ser Trp Val Arg Gln Pro Pro Gly Lys Gly Leu Glu Trp
      35                 40              45

Ile Gly Glu Ile Tyr His Ser Gly Ser Thr Asn Tyr Asn Pro Ser Leu
  50               55              60

Lys Ser Arg Val Thr Ile Ser Val Asp Lys Ser Lys Asn Gln Phe Ser
65               70              75            80

Leu Lys Leu Ser Ser Val Thr Ala Ala Asp Thr Ala Val Tyr Tyr Cys
           85               90              95

Ala Arg Asp Ser Ser Gly Gln Gly Tyr Phe Asp Tyr Trp Gly Gln Gly
          100             105           110

Thr Leu Val Thr Val Ser Ser
        115

<210> SEQ ID NO 199
<211> LENGTH: 354
<212> TYPE: DNA
<213> ORGANISM: Artificial
<220> FEATURE:
<223> OTHER INFORMATION: Anti-IGF1R antibody heavy chain variable domain
     sequence
<220> FEATURE:
<221> NAME/KEY: CDS
<222> LOCATION: (1)..(354)

<400> SEQUENCE: 199

```
gag gtg cag ctg gtg cag tct ggg gct gag gtg aag aag cct ggg gcc      48
Glu Val Gln Leu Val Gln Ser Gly Ala Glu Val Lys Lys Pro Gly Ala
1               5                   10                  15 tca gtg aag gtc tcc tgc aag gct tct gga tac acc ttc act agc tat      96
Ser Val Lys Val Ser Cys Lys Ala Ser Gly Tyr Thr Phe Thr Ser Tyr
            20                  25                  30 gct atg cat tgg gtg cgc cag gcc ccc gga caa agg ctt gag tgg atg     144
Ala Met His Trp Val Arg Gln Ala Pro Gly Gln Arg Leu Glu Trp Met
        35                  40                  45 gga tgg atc aac gct ggc aat ggt aac aca aaa tat tca cag aag ttc     192
Gly Trp Ile Asn Ala Gly Asn Gly Asn Thr Lys Tyr Ser Gln Lys Phe
    50                  55                  60 cag ggc aga gtc acc atg acc agg gac acg tcc acg agc aca gtc tac     240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gct aga cac tcg tac tac tac ggt atg gac gtc tgg ggc caa ggc acc     336
Ala Arg His Ser Tyr Tyr Tyr Gly Met Asp Val Trp Gly Gln Gly Thr
            100                 105                 110 ctg gtc acc gtc tca agc                                             354
Leu Val Thr Val Ser Ser
        115
```

<210> SEQ ID NO 200
<211> LENGTH: 118
<212> TYPE: PRT
<213> ORGANISM: Artificial
<220> FEATURE:

<223> OTHER INFORMATION: Synthetic Construct

<400> SEQUENCE: 200

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Ser Tyr Tyr Tyr Gly Met Asp Val Trp Gly Gln Gly Thr
            100                 105                 110

Leu Val Thr Val Ser Ser
        115

<210> SEQ ID NO 201
<211> LENGTH: 360
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(360)

<400> SEQUENCE: 201 cag gtg cag cta cag cag tgg ggc gca gga ctg ttg aag cct tcg gag        48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac        96
Thr Leu Ser Leu Thr Cys Ala Val Tyr Gly Gly Ser Phe Ser Gly Tyr
            20                  25                  30 tac tgg agc tgg atc cgc cag ccc cca ggg aag ggg ctg gag tgg att       144
Tyr Trp Ser Trp Ile Arg Gln Pro Pro Gly Lys Gly Leu Glu Trp Ile
        35                  40                  45 ggg gaa atc aat cat agt gga agc acc aac tac aac ccg tcc ctc aag       192
Gly Glu Ile Asn His Ser Gly Ser Thr Asn Tyr Asn Pro Ser Leu Lys
    50                  55                  60 agt cga gtc acc ata tcg gta gac acg tcc aag aac cag ttc tcc ctg       240
Ser Arg Val Thr Ile Ser Val Asp Thr Ser Lys Asn Gln Phe Ser Leu
65                  70                  75                  80 aag ctg agc tct gtg acc gcc gcg gac acg gct gtg tat tac tgt gcg       288
Lys Leu Ser Ser Val Thr Ala Ala Asp Thr Ala Val Tyr Tyr Cys Ala
                85                  90                  95 aga gtc ggg tat agc cac ggc gaa gaa gtc ctg gac gtc tgg ggc aaa       336
Arg Val Gly Tyr Ser His Gly Glu Glu Val Leu Asp Val Trp Gly Lys
            100                 105                 110 ggg acc acg gtc acc gtc tca agc                                       360
Gly Thr Thr Val Thr Val Ser Ser
        115                 120

<210> SEQ ID NO 202
<211> LENGTH: 120
<212> TYPE: PRT
<213> ORGANISM: Artificial
<220> FEATURE:
<223> OTHER INFORMATION: Synthetic Construct

<400> SEQUENCE: 202

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Tyr Ser His Gly Glu Glu Val Leu Asp Val Trp Gly Lys
            100                 105                 110

Gly Thr Thr Val Thr Val Ser Ser
        115                 120
```

<210> SEQ ID NO 203
<211> LENGTH: 354
<212> TYPE: DNA
<213> ORGANISM: Artificial
<220> FEATURE:
<223> OTHER INFORMATION: Anti-IGF1R antibody heavy chain variable domain
      sequence
<220> FEATURE:
<221> NAME/KEY: CDS
<222> LOCATION: (1)..(354)

<400> SEQUENCE: 203

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc ggc aat tat      96
Thr Leu Ser Leu Thr Cys Thr Val Ser Gly Gly Ser Ile Gly Asn Tyr
            20                  25                  30 gac tgg agt tgg atc cgg cag ccc cca ggg aag gga ctg gag tgg att     144
Asp Trp Ser Trp Ile Arg Gln Pro Pro Gly Lys Gly Leu Glu Trp Ile
        35                  40                  45 ggg act atc tac tct agt ggg agt acg tac tac agt ccg tcc ctc aag     192
Gly Thr Ile Tyr Ser Ser Gly Ser Thr Tyr Tyr Ser Pro Ser Leu Lys
    50                  55                  60 agt cga ctc acc ata tca gta gac aag tcc aag aac cgg ttc tcc ctg     240
Ser Arg Leu Thr Ile Ser Val Asp Lys Ser Lys Asn Arg Phe Ser Leu
65                  70                  75                  80 aag ctg agc tct gtg acc gcc gcg gac acg gcc gtg tat tac tgt gcg     288
Lys Leu Ser Ser Val Thr Ala Ala Asp Thr Ala Val Tyr Tyr Cys Ala
                85                  90                  95 aga gca cga ggg tat agc agc ccc ttc gac ccc tgg ggc cag ggc acc     336
Arg Ala Arg Gly Tyr Ser Ser Pro Phe Asp Pro Trp Gly Gln Gly Thr
            100                 105                 110 ctg gtc acc gtc tca agc                                             354
Leu Val Thr Val Ser Ser
        115
```

<210> SEQ ID NO 204
<211> LENGTH: 118
<212> TYPE: PRT

<213> ORGANISM: Artificial
<220> FEATURE:
<223> OTHER INFORMATION: Synthetic Construct

<400> SEQUENCE: 204

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Asn Tyr
            20                  25                  30

Asp Trp Ser Trp Ile Arg Gln Pro Pro Gly Lys Gly Leu Glu Trp Ile
        35                  40                  45

Gly Thr Ile Tyr Ser Ser Gly Ser Thr Tyr Tyr Ser Pro Ser Leu Lys
    50                  55                  60

Ser Arg Leu Thr Ile Ser Val Asp Lys Ser Lys Asn Arg Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Tyr Ser Pro Phe Asp Pro Trp Gly Gln Gly Thr
            100                 105                 110

Leu Val Thr Val Ser Ser
            115
```

<210> SEQ ID NO 205
<211> LENGTH: 357
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(357)

<400> SEQUENCE: 205

```
cag gtc cag ctg gta cag tct ggg gct gag gtg aag aag cct ggg tcc      48
Gln Val Gln Leu Val Gln Ser Gly Ala Glu Val Lys Lys Pro Gly Ser
1               5                   10                  15 tcg gtg aag gtc tcc tgc aag gct tct gga ggc acc ttc agc agc tat      96
Ser Val Lys Val Ser Cys Lys Ala Ser Gly Gly Thr Phe Ser Ser Tyr
            20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
        35                  40                  45 gga ata atc aac cct agt ggt ggt agc aca agc tac gca cag aag ttc     192
Gly Ile Ile Asn Pro Ser Gly Gly Ser Thr Ser Tyr Ala Gln Lys Phe
    50                  55                  60 cag ggc aga gtc acc att acc agg gac aca tcc gcg agc aca gcc tac     240
Gln Gly Arg Val Thr Ile Thr Arg Asp Thr Ser Ala Ser Thr Ala Tyr
65                  70                  75                  80 atg gag ctg agc agc ctg aga tct gaa gac acg gct gtg tat tac tgt     288
Met Glu Leu Ser Ser Leu Arg Ser Glu Asp Thr Ala Val Tyr Tyr Cys
                85                  90                  95 gcg aga gat cgg tgg agg tac gat gct ttt gat atc tgg ggc caa ggg     336
Ala Arg Asp Arg Trp Arg Tyr Asp Ala Phe Asp Ile Trp Gly Gln Gly
            100                 105                 110 aca atg gtc acc gtc tca agc                                          357
Thr Met Val Thr Val Ser Ser
            115
```

<210> SEQ ID NO 206
<211> LENGTH: 119

<212> TYPE: PRT
<213> ORGANISM: Artificial
<220> FEATURE:
<223> OTHER INFORMATION: Synthetic Construct

<400> SEQUENCE: 206

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Arg Trp Arg Tyr Asp Ala Phe Asp Ile Trp Gly Gln Gly
            100                 105                 110
Thr Met Val Thr Val Ser Ser
        115
```

<210> SEQ ID NO 207
<211> LENGTH: 348
<212> TYPE: DNA
<213> ORGANISM: Artificial
<220> FEATURE:
<223> OTHER INFORMATION: Anti-IGF1R antibody heavy chain variable domain sequence
<220> FEATURE:
<221> NAME/KEY: CDS
<222> LOCATION: (1)..(348)

<400> SEQUENCE: 207

```
gag gtg cag ctg gtg gag tct ggc cca gga ctg gtg aag cct tcg ggg      48
Glu Val Gln Leu Val Glu Ser Gly Pro Gly Leu Val Lys Pro Ser Gly
1               5                   10                  15 acc ctg tcc ctc acc tgc gct gtc tct ggt ggc tcc atc agc agt agt      96
Thr Leu Ser Leu Thr Cys Ala Val Ser Gly Gly Ser Ile Ser Ser Ser
            20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
        35                  40                  45 att ggg gaa atc tat cat agt ggg agc acc aac tac aac ccg tcc ctc     192
Ile Gly Glu Ile Tyr His Ser Gly Ser Thr Asn Tyr Asn Pro Ser Leu
    50                  55                  60 aag agt cga gtc acc ata tca gta gac aag tcc aag aac cag ttc tcc     240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tac tgt     288
Leu Lys Leu Ser Ser Val Thr Ala Ala Asp Thr Ala Val Tyr Tyr Cys
                85                  90                  95 gcg aga gaa aaa tcg ggt atg gac gtc tgg ggc caa ggg acc acg gtc     336
Ala Arg Glu Lys Ser Gly Met Asp Val Trp Gly Gln Gly Thr Thr Val
            100                 105                 110 acc gtc tca agc                                                      348
Thr Val Ser Ser
        115
```

<210> SEQ ID NO 208

<211> LENGTH: 116
<212> TYPE: PRT
<213> ORGANISM: Artificial
<220> FEATURE:
<223> OTHER INFORMATION: Synthetic Construct

<400> SEQUENCE: 208

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Lys Ser Gly Met Asp Val Trp Gly Gln Gly Thr Thr Val
            100                 105                 110

Thr Val Ser Ser
        115

<210> SEQ ID NO 209
<211> LENGTH: 16
<212> TYPE: PRT
<213> ORGANISM: Artificial
<220> FEATURE:
<223> OTHER INFORMATION: Anti-IGF1R antibody light chain variable domain
      sequence and light chain variable domain consensus sequence

<400> SEQUENCE: 209

Arg Ser Ser Gln Ser Leu Leu His Ser Asn Gly Tyr Asn Tyr Leu Asp
1               5                   10                  15

<210> SEQ ID NO 210
<211> LENGTH: 16
<212> TYPE: PRT
<213> ORGANISM: Artificial
<220> FEATURE:
<223> OTHER INFORMATION: Anti-IGF1R antibody light chain variable domain
      sequence

<400> SEQUENCE: 210

Arg Ser Ser Gln Ser Leu Leu His Ser Ser Gly Tyr Asn Tyr Leu Asp
1               5                   10                  15

<210> SEQ ID NO 211
<211> LENGTH: 16
<212> TYPE: PRT
<213> ORGANISM: Artificial
<220> FEATURE:
<223> OTHER INFORMATION: Anti-IGF1R antibody light chain variable domain
      sequence

<400> SEQUENCE: 211

Arg Ser Ser Gln Ser Leu Leu His Ser Asn Gly Tyr Asn Tyr Leu Asn
1               5                   10                  15

<210> SEQ ID NO 212
<211> LENGTH: 16
<212> TYPE: PRT
<213> ORGANISM: Artificial

```
<220> FEATURE:
<223> OTHER INFORMATION: Anti-IGF1R antibody light chain variable domain
      sequence

<400> SEQUENCE: 212

Arg Ser Ser Gln Ser Leu Leu His Ser His Gly Tyr Asn Tyr Leu Asp
1               5                   10                  15

<210> SEQ ID NO 213
<211> LENGTH: 16
<212> TYPE: PRT
<213> ORGANISM: Artificial
<220> FEATURE:
<223> OTHER INFORMATION: Anti-IGF1R antibody light chain variable domain
      sequence

<400> SEQUENCE: 213

Arg Ser Ser Gln Ser Leu Leu His Ser Asn Gly Tyr Thr Tyr Leu Asp
1               5                   10                  15

<210> SEQ ID NO 214
<211> LENGTH: 16
<212> TYPE: PRT
<213> ORGANISM: Artificial
<220> FEATURE:
<223> OTHER INFORMATION: Anti-IGF1R antibody light chain variable domain
      sequence

<400> SEQUENCE: 214

Arg Ser Ser Gln Ser Leu Leu His Ser Asn Gly Tyr Asn Phe Leu Asp
1               5                   10                  15

<210> SEQ ID NO 215
<211> LENGTH: 16
<212> TYPE: PRT
<213> ORGANISM: Artificial
<220> FEATURE:
<223> OTHER INFORMATION: Anti-IGF1R antibody light chain variable domain
      sequence

<400> SEQUENCE: 215

Arg Ser Ser Gln Ser Leu Leu His Thr Asn Gly Tyr Asn Tyr Leu Asp
1               5                   10                  15

<210> SEQ ID NO 216
<211> LENGTH: 16
<212> TYPE: PRT
<213> ORGANISM: Artificial
<220> FEATURE:
<223> OTHER INFORMATION: Anti-IGF1R antibody light chain variable domain
      sequence

<400> SEQUENCE: 216

Arg Ser Ser Gln Ser Leu Leu His Thr Asn Gly Tyr Asp Tyr Leu Asp
1               5                   10                  15

<210> SEQ ID NO 217
<211> LENGTH: 13
<212> TYPE: PRT
<213> ORGANISM: Artificial
<220> FEATURE:
<223> OTHER INFORMATION: Anti-IGF1R antibody light chain variable domain
      sequence

<400> SEQUENCE: 217

Thr Gly Ser Gly Gly Asn Ile Ala Ser Asn Tyr Val Gln
1               5                   10
```

<210> SEQ ID NO 218
<211> LENGTH: 13
<212> TYPE: PRT
<213> ORGANISM: Artificial
<220> FEATURE:
<223> OTHER INFORMATION: Anti-IGF1R antibody light chain variable domain
      sequence

<400> SEQUENCE: 218

Thr Arg Ser Ser Gly Ser Ile Ala Ser Asn Tyr Val Gln
1               5                   10

<210> SEQ ID NO 219
<211> LENGTH: 13
<212> TYPE: PRT
<213> ORGANISM: Artificial
<220> FEATURE:
<223> OTHER INFORMATION: Anti-IGF1R antibody light chain variable domain
      sequence

<400> SEQUENCE: 219

Thr Arg Ser Ser Gly Asp Ile Asp Asn Asn Tyr Val Gln
1               5                   10

<210> SEQ ID NO 220
<211> LENGTH: 16
<212> TYPE: PRT
<213> ORGANISM: Artificial
<220> FEATURE:
<223> OTHER INFORMATION: Anti-IGF1R antibody light chain variable domain
      sequence

<400> SEQUENCE: 220

Thr Arg Asn Ser Gly Ser Ile Ala Ser Asn Phe Val Gln Trp Tyr Gln
1               5                   10                  15

<210> SEQ ID NO 221
<211> LENGTH: 12
<212> TYPE: PRT
<213> ORGANISM: Artificial
<220> FEATURE:
<223> OTHER INFORMATION: Anti-IGF1R antibody light chain variable domain
      sequence

<400> SEQUENCE: 221

Arg Ala Ser Gln Thr Ile Ser Ser Ser His Leu Ala
1               5                   10

<210> SEQ ID NO 222
<211> LENGTH: 11
<212> TYPE: PRT
<213> ORGANISM: Artificial
<220> FEATURE:
<223> OTHER INFORMATION: Anti-IGF1R antibody light chain variable domain
      sequence

<400> SEQUENCE: 222

Arg Ala Ser Gln Gly Ile Ser Arg Trp Leu Ala
1               5                   10

<210> SEQ ID NO 223
<211> LENGTH: 11
<212> TYPE: PRT
<213> ORGANISM: Artificial
<220> FEATURE:
<223> OTHER INFORMATION: Anti-IGF1R antibody light chain variable domain
      sequence

```
<400> SEQUENCE: 223

Arg Ala Ser Gln Gly Ile Ser Ser Tyr Leu Ala
1               5                   10

<210> SEQ ID NO 224
<211> LENGTH: 11
<212> TYPE: PRT
<213> ORGANISM: Artificial
<220> FEATURE:
<223> OTHER INFORMATION: Anti-IGF1R antibody light chain variable domain
      sequence

<400> SEQUENCE: 224

Arg Ala Ser Gln Ser Val Tyr Asn Tyr Leu Ala
1               5                   10

<210> SEQ ID NO 225
<211> LENGTH: 11
<212> TYPE: PRT
<213> ORGANISM: Artificial
<220> FEATURE:
<223> OTHER INFORMATION: Anti-IGF1R antibody light chain variable domain
      sequence

<400> SEQUENCE: 225

Arg Ala Ser Gln Ser Val Gly Ser Asn Leu Ala
1               5                   10

<210> SEQ ID NO 226
<211> LENGTH: 11
<212> TYPE: PRT
<213> ORGANISM: Artificial
<220> FEATURE:
<223> OTHER INFORMATION: Anti-IGF1R antibody light chain variable domain
      sequence

<400> SEQUENCE: 226

Arg Ser Ser Gln Gly Ile Gly Tyr Phe Leu Asn
1               5                   10

<210> SEQ ID NO 227
<211> LENGTH: 11
<212> TYPE: PRT
<213> ORGANISM: Artificial
<220> FEATURE:
<223> OTHER INFORMATION: Anti-IGF1R antibody light chain variable domain
      sequence

<400> SEQUENCE: 227

Arg Ala Ser Gln Ser Pro Gly Ile Phe Leu Asn
1               5                   10

<210> SEQ ID NO 228
<211> LENGTH: 11
<212> TYPE: PRT
<213> ORGANISM: Artificial
<220> FEATURE:
<223> OTHER INFORMATION: Anti-IGF1R antibody light chain variable domain
      consensus sequence
<220> FEATURE:
<221> NAME/KEY: MISC_FEATURE
<222> LOCATION: (5)..(5)
<223> OTHER INFORMATION: Xaa can be G or S
<220> FEATURE:
<221> NAME/KEY: MISC_FEATURE
<222> LOCATION: (6)..(6)
<223> OTHER INFORMATION: Xaa can be I or V
<220> FEATURE:
<221> NAME/KEY: MISC_FEATURE
```

```
<222> LOCATION: (7)..(7)
<223> OTHER INFORMATION: Xaa can be G or S
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be Y or F
<220> FEATURE:
<221> NAME/KEY: MISC_FEATURE
<222> LOCATION: (10)..(10)
<223> OTHER INFORMATION: Xaa can be L or N

<400> SEQUENCE: 228

Arg Ala Ser Gln Xaa Xaa Xaa Xaa Xaa Xaa Ala
1               5                   10

<210> SEQ ID NO 229
<211> LENGTH: 11
<212> TYPE: PRT
<213> ORGANISM: Artificial
<220> FEATURE:
<223> OTHER INFORMATION: Anti-IGF1R antibody light chain variable domain
      sequence

<400> SEQUENCE: 229

Ser Gly Asp Lys Leu Gly Asp Lys Tyr Val Gly
1               5                   10

<210> SEQ ID NO 230
<211> LENGTH: 11
<212> TYPE: PRT
<213> ORGANISM: Artificial
<220> FEATURE:
<223> OTHER INFORMATION: Anti-IGF1R antibody light chain variable domain
      sequence

<400> SEQUENCE: 230

Gln Gly Asp Ser Leu Arg Ile Tyr Tyr Thr Gly
1               5                   10

<210> SEQ ID NO 231
<211> LENGTH: 16
<212> TYPE: PRT
<213> ORGANISM: Artificial
<220> FEATURE:
<223> OTHER INFORMATION: Anti-IGF1R antibody light chain variable domain
      overall consensus sequence
<220> FEATURE:
<221> NAME/KEY: MISC_FEATURE
<222> LOCATION: (6)..(6)
<223> OTHER INFORMATION: Xaa can be L or I
<220> FEATURE:
<221> NAME/KEY: misc_feature
<222> LOCATION: (7)..(16)
<223> OTHER INFORMATION: Xaa can be any naturally occurring amino acid

<400> SEQUENCE: 231

Arg Ser Ser Gln Ser Xaa Xaa Xaa Xaa Xaa Xaa Xaa Xaa Xaa Xaa Xaa
1               5                   10                  15

<210> SEQ ID NO 232
<211> LENGTH: 7
<212> TYPE: PRT
<213> ORGANISM: Artificial
<220> FEATURE:
<223> OTHER INFORMATION: Anti-IGF1R antibody light chain variable domain
      sequence
```

```
<400> SEQUENCE: 232

Leu Gly Ser Asn Arg Ala Ser
1               5

<210> SEQ ID NO 233
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 233

Leu Gly Ser Tyr Arg Ala Ser
1               5

<210> SEQ ID NO 234
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 234

Leu Val Ser Asn Arg Ala Ser
1               5

<210> SEQ ID NO 235
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 235

Leu Gly Ser Asn Arg Asp Ser
1               5

<210> SEQ ID NO 236
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 236

Leu Gly Ser Thr Arg Ala Ser
1               5

<210> SEQ ID NO 237
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 237

Leu Gly Phe Asn Arg Ala Ser
1               5

<210> SEQ ID NO 238
<211> LENGTH: 7
<212> TYPE: PRT
```

```
<213> ORGANISM: Artificial
<220> FEATURE:
<223> OTHER INFORMATION: Anti-IGF1R antibody light chain variable domain
      consensus
      sequence

<400> SEQUENCE: 238

Leu Gly Ser Asn Arg Ala Ser
1               5

<210> SEQ ID NO 239
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 239

Ala Ala Ser Thr Leu Gln Ser
1               5

<210> SEQ ID NO 240
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 240

Ala Ala Ser Gly Leu Gln Ser
1               5

<210> SEQ ID NO 241
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 241

Ala Thr Ser Thr Leu Glu Ser
1               5

<210> SEQ ID NO 242
<211> LENGTH: 7
<212> TYPE: PRT
<213> ORGANISM: Artificial
<220> FEATURE:
<223> OTHER INFORMATION: Anti-IGF1R antibody light chain variable domain
      consensus sequence

<400> SEQUENCE: 242

Ala Ala Ser Thr Leu Gln Ser
1               5

<210> SEQ ID NO 243
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 243

Glu Asp Asn Gln Arg Pro Ser
```

```
<210> SEQ ID NO 244
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 244

Glu Asp Asn Arg Arg Pro Ser
1               5

<210> SEQ ID NO 245
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 245

Gln Asp Asn Lys Arg Pro Ser
1               5

<210> SEQ ID NO 246
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 246

Gly Lys Asn Asn Arg Pro Ser
1               5

<210> SEQ ID NO 247
<211> LENGTH: 7
<212> TYPE: PRT
<213> ORGANISM: Artificial
<220> FEATURE:
<223> OTHER INFORMATION: Anti-IGF1R antibody light chain variable domain
      consensus sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 247

Glu Asp Asn Xaa Arg Pro Ser
1               5

<210> SEQ ID NO 248
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 248

Asp Ala Ser Arg Arg Ala Thr
1               5

<210> SEQ ID NO 249
<211> LENGTH: 7
```

```
<212> TYPE: PRT
<213> ORGANISM: Artificial
<220> FEATURE:
<223> OTHER INFORMATION: Anti-IGF1R antibody light chain variable domain
      sequence

<400> SEQUENCE: 249

Asp Ala Ser Asn Arg Ala Thr
1               5

<210> SEQ ID NO 250
<211> LENGTH: 7
<212> TYPE: PRT
<213> ORGANISM: Artificial
<220> FEATURE:
<223> OTHER INFORMATION: Anti-IGF1R antibody light chain variable domain
      sequence

<400> SEQUENCE: 250

Gly Ala Gly Tyr Arg Ala Thr
1               5

<210> SEQ ID NO 251
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 251

Met Gln Ala Leu Gln Thr Pro Leu Thr
1               5

<210> SEQ ID NO 252
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 252

Met Gln Ala Phe Gln Thr Pro Leu Thr
1               5

<210> SEQ ID NO 253
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 253

Met Gln Ala Leu Gln Thr Pro Ile Thr
1               5

<210> SEQ ID NO 254
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 254

Met Gln Ala Leu Gln Thr Pro Tyr Thr
```

-continued

<210> SEQ ID NO 255
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 255

Met Gln Ala Leu Gln Thr Pro Phe Thr
1               5

<210> SEQ ID NO 256
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 256

Met Gln Ala Leu Gln Thr Pro His Thr
1               5

<210> SEQ ID NO 257
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 257

Met Gln Ala Leu Gln Thr Pro Asn Thr
1               5

<210> SEQ ID NO 258
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 258

Met Gln Ala Leu Gln Thr Pro Leu Ala
1               5

<210> SEQ ID NO 259
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 259

Met Gln Gly Leu Gln Thr Pro Leu Thr
1               5

<210> SEQ ID NO 260
<211> LENGTH: 9
<212> TYPE: PRT
<213> ORGANISM: Artificial
<220> FEATURE:
<223> OTHER INFORMATION: Anti-IGF1R antibody light chain variable domain sequence

<400> SEQUENCE: 260

Met Gln Ala Leu Glu Met Pro Leu Thr
1               5

<210> SEQ ID NO 261
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 261

Met Glu Ala Leu Gln Thr Pro Phe Thr
1               5

<210> SEQ ID NO 262
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 262

Met Gln Thr Leu Gln Thr Pro Leu Ser
1               5

<210> SEQ ID NO 263
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 263

Met Gln Gly Thr His Trp Pro Leu Thr
1               5

<210> SEQ ID NO 264
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 264

Met Gln Ser Leu Glu Val Pro Phe Thr
1               5

<210> SEQ ID NO 265
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 265

Met Gln Ala Thr His Trp Pro Tyr Thr
1               5

<210> SEQ ID NO 266

```
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 266

Met Gln Gly Thr His Trp Pro Tyr Thr
1               5

<210> SEQ ID NO 267
<211> LENGTH: 9
<212> TYPE: PRT
<213> ORGANISM: Artificial
<220> FEATURE:
<223> OTHER INFORMATION: Anti-IGF1R antibody light chain variable domain
      consensus sequence
<220> FEATURE:
<221> NAME/KEY: MISC_FEATURE
<222> LOCATION: (8)..(8)
<223> OTHER INFORMATION: Xaa may be any nonpolar amino acid

<400> SEQUENCE: 267

Met Gln Ala Leu Gln Thr Pro Xaa Thr
1               5

<210> SEQ ID NO 268
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 268

Gln Gln Arg Asn Asn Trp Pro Leu Thr
1               5

<210> SEQ ID NO 269
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 269

Gln Gln Arg Ser Asn Trp Pro Leu Thr
1               5

<210> SEQ ID NO 270
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 270

Gln Gln Ser Asn Ser Val Pro Leu Thr
1               5

<210> SEQ ID NO 271
<211> LENGTH: 9
<212> TYPE: PRT
<213> ORGANISM: Artificial
<220> FEATURE:
<223> OTHER INFORMATION: Anti-IGF1R antibody light chain variable domain
```

-continued sequence

<400> SEQUENCE: 271

Gln Gln Leu Asn Ser Tyr Pro Leu Thr
1               5

<210> SEQ ID NO 272
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 272

Gln Gln Ser His Ser Pro Pro Tyr Thr
1               5

<210> SEQ ID NO 273
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 273

Gln Gln Ala Ser Ser Phe Pro Ile Thr
1               5

<210> SEQ ID NO 274
<211> LENGTH: 9
<212> TYPE: PRT
<213> ORGANISM: Artificial
<220> FEATURE:
<223> OTHER INFORMATION: Anti-IGF1R antibody light chain variable domain
      consensus sequence
<220> FEATURE:
<221> NAME/KEY: MISC_FEATURE
<222> LOCATION: (3)..(3)
<223> OTHER INFORMATION: Xaa may be R or S
<220> FEATURE:
<221> NAME/KEY: MISC_FEATURE
<222> LOCATION: (4)..(4)
<223> OTHER INFORMATION: Xaa may be N or S
<220> FEATURE:
<221> NAME/KEY: MISC_FEATURE
<222> LOCATION: (5)..(5)
<223> OTHER INFORMATION: Xaa may be S or N
<220> FEATURE:
<221> NAME/KEY: MISC_FEATURE
<222> LOCATION: (6)..(6)
<223> OTHER INFORMATION: Xaa may be any nonpolar amino acid

<400> SEQUENCE: 274

Gln Gln Xaa Xaa Xaa Xaa Pro Leu Thr
1               5

<210> SEQ ID NO 275
<211> LENGTH: 10
<212> TYPE: PRT
<213> ORGANISM: Artificial
<220> FEATURE:
<223> OTHER INFORMATION: Anti-IGF1R antibody light chain variable domain
      sequence

<400> SEQUENCE: 275

Gln Ser Tyr Asp Ser Ser Asn Gln Arg Val
1               5                   10

<210> SEQ ID NO 276
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 276

Gln Ser Tyr Asp Pro Tyr Asn Arg Val
1               5

<210> SEQ ID NO 277
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 277

Gln Ser Tyr Asp Ser Ser Asn Val Val
1               5

<210> SEQ ID NO 278
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 278

Gln Ser Tyr Gln Ser Asp Asn Trp Val
1               5

<210> SEQ ID NO 279
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 279

Gln Ser Tyr Asp Ser Ala Asn Val Ile
1               5

<210> SEQ ID NO 280
<211> LENGTH: 9
<212> TYPE: PRT
<213> ORGANISM: Artificial
<220> FEATURE:
<223> OTHER INFORMATION: Anti-IGF1R antibody light chain variable domain
      consensus sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 280

Gln Ser Tyr Asp Ser Ser Asn Xaa Val
1               5

<210> SEQ ID NO 281
<211> LENGTH: 8
<212> TYPE: PRT
<213> ORGANISM: Artificial

<220> FEATURE:
<223> OTHER INFORMATION: Anti-IGF1R antibody light chain variable domain
      sequence

<400> SEQUENCE: 281

Gln Ala Trp Asp Ser Gly Thr Val
1               5

<210> SEQ ID NO 282
<211> LENGTH: 9
<212> TYPE: PRT
<213> ORGANISM: Artificial
<220> FEATURE:
<223> OTHER INFORMATION: Anti-IGF1R antibody light chain variable domain
      sequence

<400> SEQUENCE: 282

Gln His Tyr Gly Ser Ser Leu Arg Thr
1               5

<210> SEQ ID NO 283
<211> LENGTH: 10
<212> TYPE: PRT
<213> ORGANISM: Artificial
<220> FEATURE:
<223> OTHER INFORMATION: Anti-IGF1R antibody light chain variable domain
      sequence

<400> SEQUENCE: 283

Asn Ser Arg Asp Ile Thr Gly Val His Arg
1               5                   10

<210> SEQ ID NO 284
<211> LENGTH: 6
<212> TYPE: PRT
<213> ORGANISM: Artificial
<220> FEATURE:
<223> OTHER INFORMATION: Anti-IGF1R antibody heavy chain variable domain
      sequence and heavy chain variable domain consensus sequence

<400> SEQUENCE: 284

Ser Ser Asn Trp Trp Ser
1               5

<210> SEQ ID NO 285
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 285

Ser Asn Trp Trp Ser
1               5

<210> SEQ ID NO 286
<211> LENGTH: 6
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 286

Ser Asn Ile Trp Trp Ser
1               5

```
<210> SEQ ID NO 287
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 287

Gly Tyr Tyr Trp Ser
1               5

<210> SEQ ID NO 288
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 288

Asn Tyr Asp Trp Ser
1               5

<210> SEQ ID NO 289
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 289

Asn Tyr Tyr Trp Ser
1               5

<210> SEQ ID NO 290
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 290

Asp Phe Tyr Trp Ser
1               5

<210> SEQ ID NO 291
<211> LENGTH: 5
<212> TYPE: PRT
<213> ORGANISM: Artificial
<220> FEATURE:
<223> OTHER INFORMATION: Anti-IGF1R antibody heavy chain variable domain
      consensus sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 291

Xaa Tyr Tyr Trp Ser
1               5

<210> SEQ ID NO 292
<211> LENGTH: 5
<212> TYPE: PRT
<213> ORGANISM: Artificial
```

```
<220> FEATURE:
<223> OTHER INFORMATION: Anti-IGF1R antibody heavy chain variable domain
      sequence

<400> SEQUENCE: 292

Ser Tyr Ala Met Ser
1               5

<210> SEQ ID NO 293
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 293

Ser Tyr Ala Ile Ser
1               5

<210> SEQ ID NO 294
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 294

Ser Tyr Gly Met His
1               5

<210> SEQ ID NO 295
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 295

Ser Tyr Ala Met His
1               5

<210> SEQ ID NO 296
<211> LENGTH: 5
<212> TYPE: PRT
<213> ORGANISM: Artificial
<220> FEATURE:
<223> OTHER INFORMATION: Anti-IGF1R antibody heavy chain variable domain
      consensus
      sequence
<220> FEATURE:
<221> NAME/KEY: MISC_FEATURE
<222> LOCATION: (5)..(5)
<223> OTHER INFORMATION: Xaa may be S or H

<400> SEQUENCE: 296

Ser Tyr Ala Met Xaa
1               5

<210> SEQ ID NO 297
<211> LENGTH: 5
<212> TYPE: PRT
<213> ORGANISM: Artificial
<220> FEATURE:
<223> OTHER INFORMATION: Anti-IGF1R antibody heavy chain variable domain
      sequence
```

-continued

```
<400> SEQUENCE: 297

Ser His Gly Met His
1               5

<210> SEQ ID NO 298
<211> LENGTH: 7
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 298

Ser Ser Ser Tyr Tyr Trp Gly
1               5

<210> SEQ ID NO 299
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 299

Glu Ile Tyr His Ser Gly Ser Thr Asn Tyr Asn Pro Ser Leu Lys Ser
1               5                   10                  15

<210> SEQ ID NO 300
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 300

Glu Ile Tyr His Ser Gly Ser Thr Asn Tyr Asn Pro Ser Leu Glu Ser
1               5                   10                  15

<210> SEQ ID NO 301
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 301

Glu Ile Asn His Ser Gly Ser Thr Asn Tyr Asn Pro Ser Leu Lys Ser
1               5                   10                  15

<210> SEQ ID NO 302
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 302

Glu Val Tyr His Ser Gly Ser Thr Asn Tyr Asn Pro Ser Leu Lys Ser
1               5                   10                  15

<210> SEQ ID NO 303
<211> LENGTH: 16
<212> TYPE: PRT
```

<213> ORGANISM: Artificial
<220> FEATURE:
<223> OTHER INFORMATION: Anti-IGF1R antibody heavy chain variable domain
      sequence

<400> SEQUENCE: 303

Glu Ile Asn His Ser Gly Ser Thr Asn Tyr Asn Arg Ser Leu Lys Ser
1               5                   10                  15

<210> SEQ ID NO 304
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 304

Tyr Ile Tyr Tyr Ser Gly Ser Thr Tyr Tyr Asn Pro Ser Leu Lys Ser
1               5                   10                  15

<210> SEQ ID NO 305
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 305

Thr Ile Tyr Ser Ser Gly Ser Thr Tyr Tyr Ser Pro Ser Leu Lys Ser
1               5                   10                  15

<210> SEQ ID NO 306
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 306

Ser Ile Tyr Tyr Ser Gly Ser Thr Tyr Tyr Asn Pro Ser Leu Lys Ser
1               5                   10                  15

<210> SEQ ID NO 307
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 307

Tyr Ile Ser Asp Ser Gly Asn Thr Asn Tyr Asn Pro Ser Leu Lys Ser
1               5                   10                  15

<210> SEQ ID NO 308
<211> LENGTH: 16
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 308

Glu Val Asn Pro Arg Gly Ser Thr Asn Tyr Asn Pro Ser Leu Lys Ser
1               5                   10                  15

<210> SEQ ID NO 309
<211> LENGTH: 16
<212> TYPE: PRT
<213> ORGANISM: Artificial
<220> FEATURE:
<223> OTHER INFORMATION: Anti-IGF1R antibody heavy chain variable domain
      consensus sequence
<220> FEATURE:
<221> NAME/KEY: MISC_FEATURE
<222> LOCATION: (1)..(1)
<223> OTHER INFORMATION: Xaa may be E or Y
<220> FEATURE:
<221> NAME/KEY: MISC_FEATURE
<222> LOCATION: (2)..(2)
<223> OTHER INFORMATION: Xaa may be I or V
<220> FEATURE:
<221> NAME/KEY: MISC_FEATURE
<222> LOCATION: (3)..(3)
<223> OTHER INFORMATION: Xaa may be Y or N
<220> FEATURE:
<221> NAME/KEY: MISC_FEATURE
<222> LOCATION: (4)..(4)
<223> OTHER INFORMATION: Xaa may be H or Y
<220> FEATURE:
<221> NAME/KEY: MISC_FEATURE
<222> LOCATION: (9)..(9)
<223> OTHER INFORMATION: Xaa may be N or Y

<400> SEQUENCE: 309

Xaa Xaa Xaa Xaa Ser Gly Ser Thr Xaa Tyr Asn Pro Ser Leu Lys Ser
1               5                   10                  15

<210> SEQ ID NO 310
<211> LENGTH: 17
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 310

Thr Ile Ser Gly Ser Gly Gly Ser Thr Tyr Tyr Ala Asp Ser Val Lys
1               5                   10                  15

Gly

<210> SEQ ID NO 311
<211> LENGTH: 17
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 311

Ala Ile Ser Gly Ser Gly Gly Ser Thr Tyr Tyr Ala Asp Ser Val Lys
1               5                   10                  15

Gly

<210> SEQ ID NO 312
<211> LENGTH: 17
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 312

Thr Ile Ser Ser Asn Gly Asp Ser Thr Tyr Tyr Ala Asp Ser Val Lys

```
1               5                   10                  15
Gly

<210> SEQ ID NO 313
<211> LENGTH: 17
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 313

Val Ile Ser Tyr Asp Gly Ser Asn Lys Tyr Tyr Ala Asp Ser Val Lys
1               5                   10                  15

Gly

<210> SEQ ID NO 314
<211> LENGTH: 17
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 314

Tyr Ile Ser Ser Ser Ser Ser Thr Ile Tyr Tyr Ala Asp Ser Val Lys
1               5                   10                  15

Gly

<210> SEQ ID NO 315
<211> LENGTH: 24
<212> TYPE: PRT
<213> ORGANISM: Artificial
<220> FEATURE:
<223> OTHER INFORMATION: Anti-IGF1R antibody heavy chain variable domain
      consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa may be G or S
<220> FEATURE:
<221> NAME/KEY: MISC_FEATURE
<222> LOCATION: (7)..(7)
<223> OTHER INFORMATION: Xaa may be G or S

<400> SEQUENCE: 315

Xaa Ile Ser Xaa Ser Gly Xaa Ser Thr Tyr Tyr Ala Asp Ser Val Lys
1               5                   10                  15

Gly Cys Asn Ser Glu Asn Ser Ser
            20

<210> SEQ ID NO 316
<211> LENGTH: 17
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 316

Arg Ile Ile Pro Ile Leu Gly Ile Ala Asn Tyr Ala Gln Lys Phe Gln
1               5                   10                  15
```

Gly

<210> SEQ ID NO 317
<211> LENGTH: 17
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 317

Trp Ile Asn Ala Gly Asn Gly Asn Thr Lys Tyr Ser Gln Lys Phe Gln
1               5                   10                  15
Gly

<210> SEQ ID NO 318
<211> LENGTH: 17
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 318

Ile Ile Asn Pro Ser Gly Gly Ser Thr Ser Tyr Ala Gln Lys Phe Gln
1               5                   10                  15
Gly

<210> SEQ ID NO 319
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 319

Tyr Ser Ser Ser Arg Asn Asp Ala Phe Asp Ile
1               5                   10

<210> SEQ ID NO 320
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 320

Asp Gly Gln Leu Asp Ala Phe Asp Ile
1               5

<210> SEQ ID NO 321
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 321

Trp Ser Tyr Leu Asp Ala Phe Asp Ile
1               5

<210> SEQ ID NO 322
<211> LENGTH: 9

```
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 322

Ala Asn Arg Asp Asp Ala Phe Asp Ile
1               5

<210> SEQ ID NO 323
<211> LENGTH: 12
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 323

Glu Gly Asn Arg Thr Val Thr Ser Ala Phe Asp Ile
1               5                   10

<210> SEQ ID NO 324
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 324

Trp Thr Gly Arg Thr Asp Ala Phe Asp Ile
1               5                   10

<210> SEQ ID NO 325
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 325

Gln Gly Ala Leu Asp Ala Phe Asp Ile
1               5

<210> SEQ ID NO 326
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 326

Ser Ser Ser Trp Tyr Trp Asn Ala Phe Asp Ile
1               5                   10

<210> SEQ ID NO 327
<211> LENGTH: 8
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 327

Ser Gly Tyr Asp Ala Phe Asp Ile
```

```
<210> SEQ ID NO 328
<211> LENGTH: 8
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 328

Ala Ser Val Asp Ala Phe Asp Ile
1               5

<210> SEQ ID NO 329
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 329

Leu Ser Phe Ala Asp Pro Phe Asp Ile
1               5

<210> SEQ ID NO 330
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 330

Glu Glu Val Trp Leu Gln Ala Phe Asp Ile
1               5                   10

<210> SEQ ID NO 331
<211> LENGTH: 8
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 331

Ile Arg Tyr Asp Ala Phe Asp Ile
1               5

<210> SEQ ID NO 332
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 332

Thr Ala Ala His Asp Ala Phe Asp Ile
1               5

<210> SEQ ID NO 333
<211> LENGTH: 10
<212> TYPE: PRT
<213> ORGANISM: Artificial
<220> FEATURE:
<223> OTHER INFORMATION: Anti-IGF1R antibody heavy chain variable domain
``` sequence

<400> SEQUENCE: 333

Asp Arg Trp Arg Tyr Asp Ala Phe Asp Ile
1               5                   10

<210> SEQ ID NO 334
<211> LENGTH: 9
<212> TYPE: PRT
<213> ORGANISM: Artificial
<220> FEATURE:
<223> OTHER INFORMATION: Anti-IGF1R antibody heavy chain variable domain
      consensus sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 334

Xaa Ser Arg Leu Asp Ala Phe Asp Ile
1               5

<210> SEQ ID NO 335
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 335

Phe Trp Asp Tyr Tyr Gly Met Asp Val
1               5

<210> SEQ ID NO 336
<211> LENGTH: 7
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 336

Glu Lys Ser Gly Met Asp Val
1               5

<210> SEQ ID NO 337
<211> LENGTH: 8
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 337

Asp Arg Tyr Tyr Gly Met Asp Val
1               5

<210> SEQ ID NO 338
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 338

Asp Tyr Asp Ile Phe Gly Met Asp Val

```
<210> SEQ ID NO 339
<211> LENGTH: 13
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 339

Glu Arg Gly Ser Gly Trp Ser Leu Asp Asn Met Asp Val
1               5                   10

<210> SEQ ID NO 340
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 340

Asp Ser Ser Gly Phe Tyr Gly Met Asp Val
1               5                   10

<210> SEQ ID NO 341
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 341

Asp Gly Gly Tyr Tyr Tyr Tyr Gly Met Asp Val
1               5                   10

<210> SEQ ID NO 342
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 342

His Ser Tyr Tyr Tyr Gly Met Asp Val
1               5

<210> SEQ ID NO 343
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 343

Val Ser Gly Tyr Tyr Tyr Tyr Gly Met Asp Val
1               5                   10

<210> SEQ ID NO 344
<211> LENGTH: 14
<212> TYPE: PRT
<213> ORGANISM: Artificial
<220> FEATURE:
<223> OTHER INFORMATION: Anti-IGF1R antibody heavy chain variable domain
``` sequence

<400> SEQUENCE: 344

Ala Tyr Ser Ser Gly Trp Tyr Asp Tyr Tyr Gly Met Asp Val
1               5                   10

<210> SEQ ID NO 345
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 345

Asp Ser Ser Ser Trp Tyr Tyr Gly Met Asp Val
1               5                   10

<210> SEQ ID NO 346
<211> LENGTH: 13
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 346

Gly Ser Gly Ser Tyr Tyr Asp Tyr Tyr Tyr Met Asp Val
1               5                   10

<210> SEQ ID NO 347
<211> LENGTH: 7
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 347

Asp Lys Gly Tyr Met Asp Val
1               5

<210> SEQ ID NO 348
<211> LENGTH: 10
<212> TYPE: PRT
<213> ORGANISM: Artificial
<220> FEATURE:
<223> OTHER INFORMATION: Anti-IGF1R antibody heavy chain variable domain
      consensus sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 348

Ser Xaa Tyr Asp Tyr Tyr Gly Met Asp Val
1               5                   10

<210> SEQ ID NO 349
<211> LENGTH: 7
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 349

Gly Val Glu Gln Ile Asp Tyr

```
1               5
```

<210> SEQ ID NO 350
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 350

```
Asn Leu Ala Ala Gly Ala Val Ala Tyr
1               5
```

<210> SEQ ID NO 351
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 351

```
Leu Ser Tyr Gly Ser Gly Val Asp Tyr
1               5
```

<210> SEQ ID NO 352
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 352

```
Gly Gly Trp Tyr Gly Asp Tyr Phe Asp Tyr
1               5                   10
```

<210> SEQ ID NO 353
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 353

```
Gly Ile Ala Ala Ala Gly Gln Gly Asp Tyr
1               5                   10
```

<210> SEQ ID NO 354
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 354

```
Tyr Ser Tyr Gly Thr Val Gly Ile Asp Tyr
1               5                   10
```

<210> SEQ ID NO 355
<211> LENGTH: 8
<212> TYPE: PRT
<213> ORGANISM: Artificial
<220> FEATURE:
<223> OTHER INFORMATION: Anti-IGF1R antibody heavy chain variable domain -continued

```
                sequence

<400> SEQUENCE: 355

Ile Gly Pro Gly Gly Phe Asp Tyr
1               5

<210> SEQ ID NO 356
<211> LENGTH: 9
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 356

Val Gly Ser Gly Trp Tyr Val Asp Tyr
1               5

<210> SEQ ID NO 357
<211> LENGTH: 7
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 357

Asp His Gly Pro Phe Asp Tyr
1               5

<210> SEQ ID NO 358
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 358

Asp Arg Phe Gly Ser Gly His Leu Pro Asp Tyr
1               5                   10

<210> SEQ ID NO 359
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 359

Val Gly Tyr Ser Ser Gly Arg Asp Val Asp Tyr
1               5                   10

<210> SEQ ID NO 360
<211> LENGTH: 7
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 360

Ser Thr Trp Ser Leu Asp Tyr
1               5

<210> SEQ ID NO 361
```

```
<211> LENGTH: 8
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 361

Asp Leu Thr Gly Ser Leu Asp Tyr
1               5

<210> SEQ ID NO 362
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 362

Asp Ser Ser Gly Gln Gly Tyr Phe Asp Tyr
1               5                   10

<210> SEQ ID NO 363
<211> LENGTH: 9
<212> TYPE: PRT
<213> ORGANISM: Artificial
<220> FEATURE:
<223> OTHER INFORMATION: Anti-IGF1R antibody heavy chain variable domain
      consensus sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa may be any nonpolar amino acid

<400> SEQUENCE: 363

Xaa Xaa Gly Gly Gly Xaa Xaa Asp Tyr
1               5

<210> SEQ ID NO 364
<211> LENGTH: 14
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 364

Gly Pro Arg Pro Gly Arg Asp Gly Tyr Asn Tyr Phe Asp Asn
1               5                   10

<210> SEQ ID NO 365
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 365

His Arg Ser Ser Trp Ala Trp Tyr Phe Asp Leu
1               5                   10
```

<210> SEQ ID NO 366
<211> LENGTH: 12
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 366

Asp His Arg Phe Asp Tyr Ala Trp Tyr Phe Asp Leu
1               5                   10

<210> SEQ ID NO 367
<211> LENGTH: 12
<212> TYPE: PRT
<213> ORGANISM: Artificial
<220> FEATURE:
<223> OTHER INFORMATION: Anti-IGF1R antibody heavy chain variable domain
      consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 367

Xaa His Arg Xaa Asp Xaa Ala Trp Tyr Phe Asp Leu
1               5                   10

<210> SEQ ID NO 368
<211> LENGTH: 8
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 368

Phe Asn Tyr Tyr Asp Ser Ser Val
1               5

<210> SEQ ID NO 369
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 369

Gly Leu Gly Asp Ser Ser Gly Tyr Ile Leu
1               5                   10

<210> SEQ ID NO 370
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 370

Asp Ser Ser Gly Phe Tyr Gly Met Asp Val
1               5                   10

<210> SEQ ID NO 371
<211> LENGTH: 11
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 371

Asp Ser Ser Ser Trp Tyr Tyr Gly Met Asp Val
1               5                   10

<210> SEQ ID NO 372
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 372

Asp Ser Ser Gly Gln Gly Tyr Phe Asp Tyr
1               5                   10

<210> SEQ ID NO 373
<211> LENGTH: 7
<212> TYPE: PRT
<213> ORGANISM: Artificial
<220> FEATURE:
<223> OTHER INFORMATION: Anti-IGF1R antibody heavy chain variable domain
      consensus sequence
<220> FEATURE:
<221> NAME/KEY: misc_feature
<222> LOCATION: (5)..(7)
<223> OTHER INFORMATION: Xaa can be any naturally occurring amino acid

<400> SEQUENCE: 373

Asp Ser Ser Gly Xaa Xaa Xaa
1               5

<210> SEQ ID NO 374
<211> LENGTH: 8
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 374

Tyr Arg Ser Phe Gly Glu Ser Tyr
1               5

<210> SEQ ID NO 375
<211> LENGTH: 12
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 375

Val Gly Tyr Ser His Gly Glu Glu Val Leu Asp Val
1               5                   10

```
<210> SEQ ID NO 376
<211> LENGTH: 10
<212> TYPE: PRT
<213> ORGANISM: Artificial
<220> FEATURE:
<223> OTHER INFORMATION: Anti-IGF1R antibody heavy chain variable domain
      sequence

<400> SEQUENCE: 376

Ala Arg Gly Tyr Ser Ser Pro Phe Asp Pro
1               5                   10

<210> SEQ ID NO 377
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 377 cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt                         321
Pro Val Thr Lys Ser Phe Asn Arg Gly Glu Cys
            100                 105

<210> SEQ ID NO 378
<211> LENGTH: 107
<212> TYPE: PRT
<213> ORGANISM: Homo sapiens

<400> SEQUENCE: 378

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 379
<211> LENGTH: 990
<212> TYPE: DNA
<213> ORGANISM: Homo sapiens
<220> FEATURE:
<221> NAME/KEY: CDS
<222> LOCATION: (1)..(990)

<400> SEQUENCE: 379

| gcc | tcc | acc | aag | ggc | cca | tcg | gtc | ttc | ccc | ctg | gca | ccc | tcc | tcc | aag | 48 |
| Ala | Ser | Thr | Lys | Gly | Pro | Ser | Val | Phe | Pro | Leu | Ala | Pro | Ser | Ser | Lys | |
| 1 | | | | 5 | | | | | 10 | | | | | 15 | | |

| agc | acc | tct | ggg | ggc | aca | gcg | gcc | ctg | ggc | tgc | ctg | gtc | aag | gac | tac | 96 |
| Ser | Thr | Ser | Gly | Gly | Thr | Ala | Ala | Leu | Gly | Cys | Leu | Val | Lys | Asp | Tyr | |
| | | | 20 | | | | | 25 | | | | | 30 | | | |

| ttc | ccc | gaa | ccg | gtg | acg | gtg | tcg | tgg | aac | tca | ggc | gcc | ctg | acc | agc | 144 |
| Phe | Pro | Glu | Pro | Val | Thr | Val | Ser | Trp | Asn | Ser | Gly | Ala | Leu | Thr | Ser | |
| | | | | 35 | | | | | 40 | | | | | 45 | | |

| ggc | gtg | cac | acc | ttc | ccg | gct | gtc | cta | cag | tcc | tca | gga | ctc | tac | tcc | 192 |
| Gly | Val | His | Thr | Phe | Pro | Ala | Val | Leu | Gln | Ser | Ser | Gly | Leu | Tyr | Ser | |
| | 50 | | | | | 55 | | | | | 60 | | | | | |

| ctc | agc | agc | gtg | gtg | acc | gtg | ccc | tcc | agc | agc | ttg | ggc | acc | cag | acc | 240 |
| Leu | Ser | Ser | Val | Val | Thr | Val | Pro | Ser | Ser | Ser | Leu | Gly | Thr | Gln | Thr | |
| 65 | | | | | 70 | | | | | 75 | | | | | 80 | |

| tac | atc | tgc | aac | gtg | aat | cac | aag | ccc | agc | aac | acc | aag | gtg | gac | aag | 288 |
| Tyr | Ile | Cys | Asn | Val | Asn | His | Lys | Pro | Ser | Asn | Thr | Lys | Val | Asp | Lys | |
| | | | | 85 | | | | | 90 | | | | | 95 | | |

| aaa | gtt | gag | ccc | aaa | tct | tgt | gac | aaa | act | cac | aca | tgc | cca | ccg | tgc | 336 |
| Lys | Val | Glu | Pro | Lys | Ser | Cys | Asp | Lys | Thr | His | Thr | Cys | Pro | Pro | Cys | |
| | | | | 100 | | | | | 105 | | | | | 110 | | |

| cca | gca | cct | gaa | ctc | ctg | ggg | gga | ccg | tca | gtc | ttc | ctc | ttc | ccc | cca | 384 |
| Pro | Ala | Pro | Glu | Leu | Leu | Gly | Gly | Pro | Ser | Val | Phe | Leu | Phe | Pro | Pro | |
| | | | 115 | | | | | 120 | | | | | 125 | | | |

| aaa | ccc | aag | gac | acc | ctc | atg | atc | tcc | cgg | acc | cct | gag | gtc | aca | tgc | 432 |
| Lys | Pro | Lys | Asp | Thr | Leu | Met | Ile | Ser | Arg | Thr | Pro | Glu | Val | Thr | Cys | |
| 130 | | | | | 135 | | | | | 140 | | | | | | |

| gtg | gtg | gtg | gac | gtg | agc | cac | gaa | gac | cct | gag | gtc | aag | ttc | aac | tgg | 480 |
| Val | Val | Val | Asp | Val | Ser | His | Glu | Asp | Pro | Glu | Val | Lys | Phe | Asn | Trp | |
| 145 | | | | | 150 | | | | | 155 | | | | | 160 | |

| tac | gtg | gac | ggc | gtg | gag | gtg | cat | aat | gcc | aag | aca | aag | ccg | cgg | gag | 528 |
| Tyr | Val | Asp | Gly | Val | Glu | Val | His | Asn | Ala | Lys | Thr | Lys | Pro | Arg | Glu | |
| | | | | 165 | | | | | 170 | | | | | 175 | | |

| gag | cag | tac | aac | agc | acg | tac | cgt | gtg | gtc | agc | gtc | ctc | acc | gtc | ctg | 576 |
| Glu | Gln | Tyr | Asn | Ser | Thr | Tyr | Arg | Val | Val | Ser | Val | Leu | Thr | Val | Leu | |
| | | | 180 | | | | | 185 | | | | | 190 | | | |

| cac | cag | gac | tgg | ctg | aat | ggc | aag | gag | tac | aag | tgc | aag | gtc | tcc | aac | 624 |
| His | Gln | Asp | Trp | Leu | Asn | Gly | Lys | Glu | Tyr | Lys | Cys | Lys | Val | Ser | Asn | |
| | | | 195 | | | | | 200 | | | | | 205 | | | |

| aaa | gcc | ctc | cca | gcc | ccc | atc | gag | aaa | acc | atc | tcc | aaa | gcc | aaa | ggg | 672 |
| Lys | Ala | Leu | Pro | Ala | Pro | Ile | Glu | Lys | Thr | Ile | Ser | Lys | Ala | Lys | Gly | |
| | 210 | | | | | 215 | | | | | 220 | | | | | |

| cag | ccc | cga | gaa | cca | cag | gtg | tac | acc | ctg | ccc | cca | tcc | cgg | gat | gag | 720 |
| Gln | Pro | Arg | Glu | Pro | Gln | Val | Tyr | Thr | Leu | Pro | Pro | Ser | Arg | Asp | Glu | |
| 225 | | | | | 230 | | | | | 235 | | | | | 240 | |

| ctg | acc | aag | aac | cag | gtc | agc | ctg | acc | tgc | ctg | gtc | aaa | ggc | ttc | tat | 768 |
| Leu | Thr | Lys | Asn | Gln | Val | Ser | Leu | Thr | Cys | Leu | Val | Lys | Gly | Phe | Tyr | |
| | | | | 245 | | | | | 250 | | | | | 255 | | |

| ccc | agc | gac | atc | gcc | gtg | gag | tgg | gag | agc | aat | ggg | cag | ccg | gag | aac | 816 |
| Pro | Ser | Asp | Ile | Ala | Val | Glu | Trp | Glu | Ser | Asn | Gly | Gln | Pro | Glu | Asn | |

-continued

```
                260                 265                 270
aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac      912
Leu Tyr Ser Lys Leu Thr Val Asp Lys Ser Arg Trp Gln Gln Gly Asn
290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tct ccg ggt aaa                              990
Gln Lys Ser Leu Ser Leu Ser Pro Gly Lys
                325                 330
```

<210> SEQ ID NO 380
<211> LENGTH: 330
<212> TYPE: PRT
<213> ORGANISM: Homo sapiens

<400> SEQUENCE: 380

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
-continued

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

COMPOSITIONS FOR THE TREATMENT OF SOLID TUMORS

CROSS-REFERENCE TO RELATED APPLICATIONS

This application is a divisional application of U.S. patent application Ser. No. 14/357,039, filed on May 8, 2014, which is a 35 U.S.C. § 371 national phase entry of PCT Application PCT/US2012/064376, filed Nov. 9, 2012, published in English on May 16, 2013, as International Publication No. WO 2013/071056, and which claims priority to U.S. Provisional Patent Application No. 61/558,732, filed Nov. 11, 2011, the disclosure of each of which is hereby incorporated by reference herein in its entirety.

BACKGROUND OF THE INVENTION

IGF1R is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation and phosphorylation of cellular substrates (major substrates are IRS1 and Shc). The ligand-activated IGF1R induces mitogenic activity in normal cells and plays an important role in abnormal growth. A major physiological role of the IGF-1 system is the promotion of normal growth and regeneration. Overexpressed IGF1R (type 1 insulin-like growth factor receptor) can initiate mitogenesis and promote ligand-dependent neoplastic transformation. Furthermore, IGF1R plays an important role in the establishment and maintenance of the malignant phenotype. Unlike the epidermal growth factor (EGF) receptor, no mutant oncogenic forms of the IGF have been identified. However, several oncogenes have been demonstrated to affect IGF-1 and IGF1R expression. The correlation between a reduction of IGF1R expression and resistance to transformation has been seen. Exposure of cells to the mRNA antisense to IGF1R RNA prevents soft agar growth of several human tumor cell lines. IGF1R abrogates progression into apoptosis, both in vivo and in vitro, it has also been shown that a decrease in the level of IGF1R below wild-type levels causes apoptosis of tumor cells in vivo. The ability of IGF1R disruption to cause apoptosis appears to be diminished in normal, non-tumorigenic cells.

The IGF-1 pathway in human tumor development has an important role. IGF1R overexpression is frequently found in various tumors (breast, colon, lung, sarcoma) and is often associated with an aggressive phenotype. High circulating IGF1 concentrations are strongly correlated with prostate, lung and breast cancer risk. Furthermore, IGF is required for establishment and maintenance of the transformed phenotype in vitro and in vivo (Baserga R. Exp. Cell. Res., 1999, 253, 1-6). The kinase activity of IGF1R is essential for the transforming activity of several oncogenes: EGFR, PDGFR, SV40 T antigen, activated Ras, Raf; and v-Src. The expression of IGF1R in normal fibroblasts induces neoplastic phenotypes, which can then form tumors in vivo. IGF1R expression plays an important role in anchorage-independent growth. IGF1R has also been shown to protect cells from chemotherapy-, radiation-, and cytokine-induced apoptosis. Conversely, inhibition of endogenous IGF1R by dominant negative IGF1R, triple helix formation or antisense expression vector has been shown to repress transforming activity in vitro and tumor growth in animal models.

It has been shown that mammalian target of rapamycin (mTOR) inhibition can induce upstream insulin-like growth factor 1 receptor (IGF1R) signaling resulting in AKT activation in cancer cells. This phenomenon has been suggested to play a role in the attenuation of cellular responses to mTOR inhibition and may attenuate the clinical activity of mTOR inhibitors. Increase in pAKT has for instance been found in approximately 50% in the tumours of all patients in a Phase I study in patients with advanced solid tumours (Taberno et al., Journal of Clinical Oncology, 26 (2008), pp 1603-1610).

SUMMARY OF THE DISCLOSURE

The present invention provides a method for treating cancer in a subject, comprising, consisting of, or consisting essentially of administering to the subject in combination (e.g., simultaneously, sequentially, or alternately) therapeutically effective amounts of an IGF inhibitor and an mTOR inhibitor.

Another aspect of the present invention provides a method of treating cancer in a subject refractory to standard therapy, comprising, consisting of, or consisting essentially of administering to the subject a therapeutically effective amount of an IGF1R inhibitor in combination with a therapeutically effective amount of an mTOR inhibitor.

In certain embodiments, the IGF1R inhibitor comprises, consists of, or consists essentially of an antibody. In other embodiments, the antibody is a monoclonal antibody. In certain embodiments, the antibody comprises ganitumab (also known as AMG 479).

In another embodiment, the mTOR inhibitor is selected from the group consisting of rapamycin (sirolimus) and derivatives and/or analogs thereof, such as everolimus or RAD001; CCI-779, ABT578, SAR543, ascomycin (an ethyl analog of FK506), AP23573, AP23841, KU-0063794, INK-128, EX2044, EX3855, EX7518, or compounds that bind to the ATP-binding cleft of mTOR, such as AZD08055 and OS1027, and combinations thereof. In preferred embodiments, the mTOR inhibitor comprises everolimus.

In yet another embodiment, the IGF1R inhibitor and mTOR inhibitor are co-administered to the subject in the same formulation. In other embodiments, the IGF1R inhibitor and mTOR inhibitor are co-administered to the subject in different formulations (e.g., an intravenous formulation and an oral formulation).

In other embodiments, the IGF1R inhibitor and mTOR inhibitor are co-administered to the subject by the same route. Alternatively, in other embodiments the IGF1R inhibitor and mTOR inhibitor are co-administered to the subject by different routes.

In yet another embodiment, the administering to the subject is simultaneous in other embodiments, the administering to the subject is sequential.

In other embodiments, the IGF1R inhibitor is administered in an amount of about 0.1 mg/kg to about 50 mg/kg. In certain embodiments, the IGF1R inhibitor is administered in an amount of about 5 mg/kg to about 25 mg/kg, about 10 mg/kg to about 22 mg/kg, or about 12 mg/kg to 20 mg/kg. In specific embodiments, the IGF1R inhibitor is administered in an amount of about 12 mg/kg or an amount of about 20 mg/kg.

In yet other embodiments, the mTOR inhibitor is administered in an amount of about 0.1 mg to about 10 mg. In certain embodiments, the mTOR inhibitor is administered in an amount of about 2 mg to about 8 mg.

In other embodiments, the IGF1R inhibitor is administered in a manner selected from the group consisting of once every day, three times every week, two times every week, once every week, once every two weeks, once every three weeks, once every four weeks, or combinations thereof, with or without breaks, changes, or alterations, according to medical need.

In yet other embodiments, the mTOR inhibitor is administered in a manner selected from the group consisting of daily, six days a week, five days a week, four days a week, three days a week, two days a week, one day a week, or combinations thereof.

In certain embodiments, the methods comprise administering to the subject ganitumab at 12 mg/kg every two weeks and everolimus at 5 mg five times weekly.

Another aspect of the present invention provides a method of treating a solid tumor disease in a subject, comprising, consisting of, or consisting essentially of administering to the subject 12 mg/kg ganitumab every two weeks and 5 mg everolimus daily.

Another aspect of the present invention provides a method of treating a solid tumor disease in a subject comprising, consisting of, or consisting essentially of administering to the subject 12 mg/kg ganitumab every two weeks and 5 mg everolimus five days per week.

Another aspect of the present invention provides a method of treating a solid tumor disease in a subject comprising, consisting of, or consisting essentially of administering to the subject 12 mg/kg ganitumab every two weeks and 5 mg everolimus three days per week.

In some embodiments, the cancer is a non-small cell lung cancer, such as an adenocarcinoma, squamous cell carcinoma, large cell carcinoma, and the like.

In yet other embodiments, the subject is treated for at least two weeks, four weeks, eight weeks, at least three months, at least four months, at least six months, at least nine months, or at least for one year.

In certain embodiments, the solid tumor disease is a neuroendocrine tumor, a thyoma, a fibrous tumor or a metastatic colorectal cancer (mCRC.).

In certain embodiments, the methods further comprise, consist of, or consist essentially of administering to the subject a therapeutically effective amount of at least one of the following additional treatments selected from the group consisting of radiation, cytotoxic agents, chemotherapeutic agents, anti-cancer agents, and combinations thereof.

Another aspect of the present invention provides a pharmaceutical composition comprising, consisting of, or consisting essentially of an IGF1R inhibitor and an mTOR inhibitor in a pharmaceutically acceptable carrier.

In yet another aspect, the present invention provides a kit comprising, consisting of, or consisting essentially of a container, the container comprising an IGF1R inhibitor and an mTOR inhibitor, and printed instructions directing the use of a combined treatment of an IGF1R inhibitor and an mTOR inhibitor to a subject as a method for treating cancer in a subject. In certain embodiments, the kit further comprises a sterile diluent. In some embodiments, the IGF1R inhibitor and the mTOR inhibitor are in separate sub-containers.

BRIEF DESCRIPTION OF THE DRAWINGS

FIG. 1 provides nucleotide sequences encoding light chain variable domains L1 through L52 and heavy chain variable domains H1 through H52.

FIG. 2 provides amino acid sequences of light chain variable domains L1 through L52. CDR and FR regions are indicated.

FIG. 3 provides amino acid sequences of heavy chain variable domains through H52. CDR and FR regions are indicated.

FIG. 4 provides amino acid sequences of the light chain CDR1 regions of light chain variable domains L1 through L52. Consensus sequences for groups of related CDR sequences are also provided.

FIG. 5 provides amino acid sequences of the light chain CDR2 regions of light chain variable domains L1 through L52. Consensus sequences for groups of related CDR sequences are also provided.

FIG. 6 provides amino acid sequences of the light chain CDR3 regions of light chain variable domains L1 through L52. Consensus sequences for groups of related CDR, sequences are also provided.

FIG. 7 provides amino acid sequences of the heavy chain CDR1 regions of heavy chain variable domains H1 through H52. Consensus sequences for groups of related CDR sequences are also provided.

FIG. 8 provides amino acid sequences of the heavy chain CDR2 regions of heavy chain variable domains H1 through H52. Consensus sequences for groups of related CDR sequences are also provided.

FIG. 9 provides amino acid sequences of the heavy chain CDR3 regions of heavy chain variable domains H1 through H52. Consensus sequences for groups of related CDR sequences are also provided.

FIG. 10 provides the polypeptide sequence of a human kappa light chain antibody constant region and a human IgG1 heavy chain antibody constant region.

DESCRIPTION OF EMBODIMENTS

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Definitions

The following terms are believed to have well-recognized meanings in the art. However, the following definitions are set forth to facilitate explanation of the invention.

Articles "a" and "an" are used herein to refer to one or to more than one (i.e., at least on of the grammatical object of the article. By way of example, "an element" means at least one element, and thus can include more than one element.

The term "about" as used herein when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

As used herein, the tem "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like, for medical and/or laboratory research purposes. Preferably, the subject is a human patient. More preferably, the subject is a human patient that has cancer.

As used herein, the term "cancer" in a subject refers to the presence of cells possessing characteristics typical of cancer-causing cells, such as uncontrolled proliferation, immortality, metastatic potential, rapid growth and proliferation rate, and certain morphological features. Often, cancer cells will be in the form of a tumor or mass, but such cells may exist alone within a subject, or may circulate in the blood stream as independent cells, such as leukemic or lymphoma cells. Suitable examples for cancer as used herein include, but are not limited to, non-small cell lung (NSCL), pancreatic, head and neck, colon, ovarian or breast cancers, or Ewing's sarcoma. However, cancers that may be treated by the methods described herein include lung cancer, bronchioloalveolar cell lung cancer, bone cancer, skin cancer, cancer of the head or neck, cutaneous or intraocular melanoma, uterine cancer, ovarian cancer, rectal cancer, cancer of the anal region, stomach cancer, gastric cancer, uterine cancer, carcinoma of the fallopian tubes, carcinoma of the endometrium, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, Ewing's sarcoma, cancer of the urethra, cancer of the penis, prostate cancer, cancer of the bladder, cancer of the ureter, carcinoma of the renal pelvis, mesothelioma, hepatocellular cancer, biliary cancer, cancer of the kidney, renal cell carcinoma, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions. Also included within this definition is the term "solid tumor disease." As used herein, the term "solid tumor disease" refers to those conditions, such as cancer, that form an abnormal tumor mass, such as sarcomas, carcinomas, and lymphomas. Suitable examples of solid tumor diseases include, but are not limited to, non-small cell lung cancer (NSCLC), neuroendocrine tumors, thyomas, fibrous tumors, metastatic colorectal cancer (mCRC), and the like. In certain embodiments, the solid tumor disease is an adenocarcinoma, squamous cell carcinoma, large cell carcinoma, and the like.

As used herein, the term "IGF1R inhibitor" refers to any IGF1R inhibitor that is currently known in the art or that will be identified in the future, and includes any chemical entity that, upon administration to a subject, results in inhibition of a biological activity associated with activation of the IGF-1 receptor in the subject, including any of the downstream biological effects otherwise resulting from the binding to IGF1R of any of its natural ligands. Such IGF1R inhibitors include any agent that can block IGF1R activation or any of the downstream biological effects of IGF1R activation that are relevant to treating cancer in a subject.

An IGF1R inhibitor can act by any mechanism. Non-limiting examples of such mechanisms include binding directly to the intracellular domain of the receptor and inhibiting its kinase activity. Alternatively, such an inhibitor can act by occupying the ligand binding site or a portion thereof of the IGF-1 receptor, thereby making the receptor inaccessible to its natural ligand so that its normal biological activity is prevented or reduced. Alternatively, such an inhibitor can act by modulating the dimerization of IGF1R polypeptides, or interaction of IGF1R polypeptide with other proteins, reduce the amount of active IGF1R present on the cell surface (e.g., by reducing the amount of IGF1R that is transcribed, translated, post-translationally modified, or transported to the surface of the cell, or by increasing the rate at which IGF1R is removed from the cell surface) or enhance ubiquitination and endocytotic degradation of IGF1R. An IGF1R inhibitor can also act by reducing the amount of IGF-1 available to activate IGF1R, by for example antagonizing the binding of IGF-1 to its receptor, by reducing the level of IGF-1, or by promoting the association of IGF-1 with proteins other than IGF1R such as IGF binding proteins (e.g., IGFBP2 or IGFBP3). IGF1R inhibitors include, but are not limited to, low molecular weight inhibitors, antibodies or antibody fragments, antisense constructs, small inhibitory RNAs (e.g., RNA interference by dsRNA; RNAi), soluble receptor fragments, peptibodies, avimers, and ribozymes.

In some embodiments, IGF1R inhibitors may include, for example, imidazopyrazine IGF1R inhibitors, quinazoline IGF1R inhibitors, pyrido-pyrimidine IGF1R inhibitors, pyrimido-pyrimidine IGF1R inhibitors, pyrrolo-pyrimidine IGF1R inhibitors, pyrazolo-pyrimidine IGF1R inhibitors, phenylamino-pyrimidine IGF1R inhibitors, oxindole IGF1R inhibitors, indolocarbazole IGF1R inhibitors, phthalazine IGF1R inhibitors, isoflavone IGF1R inhibitors, quinalone IGF1R inhibitors, and tyrphostin IGF1R inhibitors, and all pharmaceutically acceptable salts and solvates of such IGF1R inhibitors, imidazopyrazine IGF1R inhibitors, pyrimidine-based IGF-1R inhibitors, cyclolignans, cyclolignans, pyrrolopyrimidines, pyrrolotriazine, pyrrolo[2,3-d], heteroaryl-aryl ureas, and the like.

Additional, specific examples of suitable IGF1R inhibitors include h7C10 (Centre de Recherche Pierre Fabre), an IGF-1 antagonist; EM-164 (ImmunoGen Inc.), an IGF1R modulator; CP-751871 (Pfizer Inc.), an IGF-1 antagonist; lanreotide (Ipsen), an IGF-1 antagonist; IGF1R oligonucleotides (Lynx Therapeutics Inc.); IGF-1 oligonucleotides (National Cancer Institute); IGF1R protein-tyrosine kinase inhibitors in development by Novartis (e.g., NVP-AEW541, Garcia-Echeverria, C. et al. (2004) Cancer Cell 5:231-239; or NVP-ADW742, Mitsiades, C. S. et al. (2004) Cancer Cell 5:221-230); IGF1R protein-tyrosine kinase inhibitors (Ontogen Corp); AG-1024 (Camirand, A. et al. (2005) Breast Cancer Research 7:R570-R579 (DOI 10.1186/bcr1028); Camirand, A. and Pollak, M. (2004) Brit. J. Cancer 90:1825-1829; Pfizer Inc.), an IGF-1 antagonist; the tyrphostins-AG-538 and I-OMe-AG 538; BMS-536924, a small molecule inhibitor of IGF1R; PNU-145156E (Pharmacia Upjohn SpA), an IGF-1 antagonist; BMS 536924, a dual IGF1R and IR kinase inhibitor (Bristol-Myers Squibb); AEW541 (Novartis); GSK621659A and GSK1838705 (Glaxo SmithKline); INSM-18 (Insured); linsitinib (OSI); BMS 754807 (Bristol-Myers Squibb); AXL-1717 (Axelar); NVP-ADW742 (Novartis); ANT-429 (Antyra); A-928605 (Abbott); AZD4253 (AstraZeneca); TAE226 (Novartis); AG1024 (Merck); KW-2450 (Kyowa); and XL-228 (Exelixis).

In yet other embodiments, the IGF1R inhibitor may include an antibody or antibody fragment that can partially or completely block IGF1R activation by its natural ligand. Antibody-based IGF1R inhibitors also include any anti-IGF-1 antibody or antibody fragment that can partially or completely block IGF1R activation. Non-limiting examples of antibody-based IGF1R inhibitors include those described in Larsson, O. et al (2005) Brit. J. Cancer 92:2097-2101 and Ibrahim, Y. H. and Yee, D. (2005) Clin. Cancer Res. 11:944s-950s; or being developed by Imclone (e.g., IMC-A12), or ganitumab, an anti-IGF1R antibody (Amgen), as described in "RECOMMENDED International Nonproprietary: Names: List 65," published by the World Health Organization, Avenue Appia 2, 1211 Geneva 27, Switzerland; R1507, an anti-IGF1R antibody (Genmab/Roche); AVE-1642, an anti-IGF1R antibody (Immunogen/Sanofi-Aventis); MK 0646 or h7C10, an anti-IGF1R antibody (Merck); or antibodies being develop by Schering-Plough Research Institute (e.g., SCH 717454 or 19D12; or as described in US Patent Application Publication Nos. US 2005/0136063 A1 and US 2004/0018191 A1). The IGF1R inhibitor can be a monoclonal antibody, or an antibody or antibody fragment having the binding specificity thereof. In a preferred embodiment, the IGF1R inhibitor is an antibody that binds specifically to the human IGF1R. More preferably, the antibody is ganitumab.

Any treatment that results in a reduction of an activity or signal mediated by IGF1R can be used in the methods of the present invention. Examples of such treatments are provided in Sachdev et al., 2007, Mol Cancer Ther. 6:1-12. In one embodiment, the treatment comprises administering to the subject a substance that reduces an activity mediated by IGF1R. Examples of such substances include, but are not limited to, antibodies (including fragments and derivatives thereof), peptibodies, and AVIMERS™ (Amgen, Inc., Thousand Oaks, Calif.) that bind to IGF1R, IGF-1, or IGF-2, soluble, IGF-1- and/or IGF-2-binding derivatives of IGF1R, small molecules that bind to R&M, IGF-2, IRS1, SHC, GRB2, SOS1, PI3K, SHP2, or any other molecule that acts in the IGF1R signaling cascade, IGF-1 or IGF-2 binding proteins (and derivatives thereof), inhibitory nucleic acids (such as siRNA) and derivatives thereof (including peptide nucleic acids). Non-limiting examples of such molecules can be found in, for example, U.S. Pat. No. 7,329,734 (issued Feb. 12, 2008) U.S. Pat. No. 7,173,005 (issued Feb. 6, 2007), U.S. Pat. No. 7,071,300 (issued Jul. 4, 2006), U.S. Pat. No. 7,020,563 (issued Mar. 28, 2006), U.S. Pat. No. 6,875,741 (issued Apr. 5, 2005); US Pat. App. Pub. No. 07/0299010 (published Dec. 27, 2007), 07/0265189 (published Nov. 15, 2007), 07/0135340 (published Jun. 14, 2007), 07/0129399 (published Jun. 7, 2007), 07/0004634 A1 (published Jan. 4, 2007), 05/0282761 A1 (published Dec. 22, 2005), 05/0054638 A1 (published Mar. 10, 2005), 04/0023887 A1 (published Feb. 5, 2004), 03/0236190 A1 (published Dec. 25, 2003), 03/0195147 A1 (published Oct. 16, 2003); PCT Pub. No. WO 07/099171 (published Sep. 7, 2007), WO 07/099166 (published Sep. 7, 2007), 07/031745 (published Mar. 22, 2007), WO 07/029106 (published Mar. 15, 2007), WO 07/029107 (published Mar. 15, 2007), WO 07/004060 (published Jan. 11, 2007), WO 06/074057 A2 (published Jul. 13, 2006), WO 06/069202 A2 (published Jun. 29, 2006), WO 06/017443 A2 (published Feb. 16, 2006), WO 06/012422 A1 (published Feb. 2, 2006), WO 06/009962 A2 (published Jan. 26, 2006), WO 06/009950 A2 (published Jan. 26, 2006), WO 06/009947 A2 (published Jan. 26, 2006), WO 06/009933 A2 (published Jan. 26, 2006), WO 05/097800 A1 (Oct. 20, 2005), WO 05/082415 A2 (published Sep. 9, 2005), WO 05/037836 A2 (published Apr. 28, 2005), WO 03/070911 A2 (published Aug. 28, 2003), WO 99/28347 A2 (published Jun. 10, 1999); European Pat. No. EP 1 732 898 31 (published Jan. 23, 2008), EP 0 737 248 B1 (published Nov. 14, 2007), European Pat. App. No. EP 1 496 935 A2 (published Jan. 19, 2005) and EP 1 432 433 A2 (published Jun. 30, 2004), and D'ambrosio et al., 1996, Cancer Res. 56:4013-20, each of which is incorporated herein by reference in its entirety. Specific examples of such molecules include OSI-906 (OSI Pharmaceuticals, Melvilee, N.Y.), BMS 536924 (Wittman et al., 2005, J Med Chem. 48:5639-43; Bristol Myers Squibb, New York, N.Y.) XL228 (Exelexis, South San Francisco, Calif.), INSM-18, NDGA, and rhIGFBP-3 (Insured, Inc., Richmond, Va.; Breuhahn et al, 2002006, Curr Cancer Ther Rev. 2:157-67; Youngren et al., 2005, Breast Cancer Res Treatment 94:37-46; U.S. Pat. No. 6,608,108), each of which reference is incorporated herein by reference in its entirety.

In one aspect, any suitable anti-IGF1R antibody, antibody fragment, or antibody derivative can be used in the methods of the present invention. In one embodiment, the antibody, antibody fragment, or antibody derivative binds to the extracellular domain of IGF1R. In another embodiment, the antibody, antibody fragment, or antibody derivative competes for binding to IGFR with IGF-1 and/or IGF-2. In another embodiment, the antibody, antibody fragment, or antibody derivative, when bound to IGF1R, reduces the amount of IGF-1 and/or IGF-2 that binds to the IGF1R. In another embodiment, the antibody, antibody fragment, or antibody derivative binds to the L1 subdomain of the IGF1R extracellular domain. In another embodiment, the antibody, antibody fragment, or antibody derivative binds to the CR subdomain of the IGF1R extracellular domain. In another embodiment, the antibody, antibody fragment, or antibody derivative binds to the L2 subdomain of the IGF1R extracellular domain. In another embodiment, the antibody, antibody fragment, or antibody derivative binds to the FnIII1 subdomain of the R&M extracellular domain. In another embodiment, the antibody, antibody fragment, or antibody derivative binds to the FnIII2-ID subdomain of the IGF1R extracellular domain. In another embodiment, the antibody, antibody fragment, or antibody derivative binds to the FnIII subdomain of the IGF1R extracellular domain. In another embodiment, the antibody, antibody fragment, or antibody derivative binds to more than one IGF1R extracellular domain. Non-limiting examples of anti-IGF1R antibodies that can be used in the methods of the present invention include each of the antibodies identified herein as L1H1, L2H2, L3H3, L4H4, L5H5 L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52, and IGF1R-binding fragments and derivatives thereof. Such antibodies, and methods of making and using them, are described in U.S. Pat. No. 7,871,611 and PCT Pub. No WO 2008/108986, incorporated herein by reference in their entirety. In one particular embodiment, the antibody comprises the light chain variable domain sequence of L16, the heavy chain variable domain sequence of 1-116, the human kappa light chain antibody constant region as herein described, and the human IgG1 heavy chain antibody constant region as herein described. Other non-limiting examples of anti-IGF1R antibodies for use in the methods of the present invention include dalotuzumab (MK 0646; Merck/Pierre Fabre); cixutumumab (IMC-A12; Eli Lilly/ImClone); figitumumab (CP-751, 871; Pfizer); robatumumab (SCH 717454; Schering-Plough); AVE-1642a (Sanofi-Aventis/Immunogen); RG1507 (Roche); BIIB022 (Biogen-Idec); rhuMab IGFR (Genentech/Roche); MED1573 (MedImmune); IGF1R MoAb (GSK) as well as those described in US Pat. App. Pub. No. 06/0040358 (published Feb. 23, 2006), 05/0008642 (published Jan. 13, 2005), 04/0228859 (published Nov. 18, 2004), e.g., antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein; PCT Pub. No. WO 06/138729 (published Dec. 28, 2006), WO 05/016970 (published Feb. 24, 2005), and Lu et al., 2004, J Biol Chem. 279:2856-65, e.g., antibodies 2F8, A12, and IMC-A12 as described therein; PCT Pub. No. WO 07/012614 (published Feb. 1, 2007), WO 07/000328 (published Jan. 4, 2007), WO 06/013472 (published Feb. 9, 2006), 05/058967 (published Jun. 30, 2005), 03/059951 (published Jul. 24, 2003), US Pat. App. Pub. No. 05/0084906 (published Apr. 21, 2005), e.g., antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein; US Pat. App. Pub. No. 05/0249728 (published Nov. 10, 2005), 05/0186203 (published Aug. 25, 2005), 04/0265307 (published Dec. 30, 2004), 03/0235582 (published Dec. 25, 2003), Maloney et al., 2003, Cancer Res. 63:5073-83, e.g., antibody EM164, resurfaced EM164, humanized EM164, huEM164 v1.0, huEM164 v1.1, huEM164 v1.2, and huEM164 v1.3, as described therein; U.S. Pat. No. 7,037,498 (issued May 2, 2006), US Pat. App. No. 05/0244408 (published Nov. 30, 2005), 04/0086503 (published May 6, 2004), Cohen, et al., 2005, Clinical Cancer Res. 11:2063-73, e.g., antibody CP-751,871, each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1; 4.9.2, and 4.17.3, as described therein; US Pat. App. No. 05/0136063 (published Jun. 23, 2005), 04/0018191 (published Jan. 29, 2004), e.g. antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; US Pat. App. No. 04/0202655 (published Oct. 14, 2004), e.g., antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; US Pat. App. No. 07/0243194 (published Oct. 18, 2007), e.g., antibodies M13-C06, M14-G11, M14-C03, M14-B01, M12-E01, and M12-G04, and antibodies produced by hybridomas P2A7.3E11, 20C8.3B8, P1A2.2B11, 20D8.24B11, P1E2.3B12, and P1G10.2B8. Each of the foregoing references is incorporated herein by reference in its entirety. Also suitable for use are antibodies, antibody fragments, or antibody derivatives that compete for binding to IGF1 receptor with one of the aforementioned antibodies. In one embodiment, the antibody, antibody fragment, or antibody derivative binds to the same epitope as one of the aforementioned antibodies, or to an epitope that overlaps with the epitope of one of the aforementioned antibodies.

As used herein, the term "mTOR inhibitor that binds to and directly inhibits both mTORC1 and mTORC2 kinases" refers to any mTOR inhibitor that binds to and directly inhibits both mTORC1 and mTORC2 kinases that is currently known in the art, or will be identified in the future, and includes any chemical entity that, upon administration to a patient, binds to and results in direct inhibition of both mTORC1 and mTORC2 kinases in the patient. Examples of mTOR inhibitors useful in the invention described herein include, but are not limited to, RAD rapamycin (sirolimus) and derivatives/analogs thereof such as everolimus or RAD001; CCI-779, ABT578, SAR543, ascomycin (an ethyl analog of FK506), AP23573, AP23841. KU-0063794, INK-128, EX2044, EX3855, EX7518, AZD08055 and OSI027. Particularly preferred mTOR inhibitors in accordance with the present invention are sirolimus and/or everolimus.

"Cell growth", as used herein, for example in the context of "tumor cell growth", unless otherwise indicated, is used as commonly used in oncology, where the term is principally associated with growth in cell numbers, which occurs by means of cell reproduction (i.e., proliferation) when the rate of the latter is greater than the rate of cell death (e.g., by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

"Tumor growth" or "tumor metastases growth", as used herein, unless otherwise indicated, is used as commonly used in oncology, where the term is principally associated with an increased mass or volume of the tumor or tumor metastases, primarily as a result of tumor cell growth.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer, refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means an agent or composition comprising the same that will elicit the biological or medical response of a tissue, system, animal or human that is being sought by the researcher, veterinarian, medical doctor or other clinician.

The term "therapeutically effective amount" or "effective amount" means the amount of the subject compound or agent or combination that will elicit the biological or medical response of a tissue, system, animal or human that is being sought by the researcher, veterinarian, medical doctor or other clinician.

The term "method for manufacturing a medicament" or "use of for manufacturing a medicament" relates to the manufacturing of a medicament for use in the indication as specified herein, and in particular for use in tumors, tumor metastases, or cancer in general. The term relates to the so-called "Swiss-type" claim format in the indication specified.

Unless otherwise defined, all technical terms used herein have the same meaning as commonly understood by one of ordinary skill in the art to which this disclosure belongs.

The present invention provides methods for treating cancer in a subject comprising, consisting of, or consisting essentially of administering to the subject a therapeutically effective amount of an IGF1R inhibitor, or pharmaceutical compositions thereof, in combination with an mTOR inhibitor, or pharmaceutical compositions thereof.

The present invention further provides methods for the treatment of cancer in a subject comprising administering to the subject in need of such treatment an amount of an IGF1R inhibitor and an amount of an mTOR inhibitor; wherein at least one of the amounts is administered as a sub-therapeutic amount.

The present invention also provides methods of treating cancer in a subject refractory to standard therapy, comprising administering to the subject a therapeutically effective amount of an IGF1R inhibitor in combination with an mTOR inhibitor.

In the preceding methods the order of administration of the first and second amounts can be simultaneous or sequential, i.e., the IGF1R inhibitor can be administered before the mTOR inhibitor, after the mTOR inhibitor, or at the same time as the mTOR inhibitor.

In the context of this invention, an "effective amount" of an IGF1R or mTOR inhibitor is as defined above. A "sub-therapeutic amount" of such inhibitors is an amount less than the effective amount for that inhibitor when used alone, but when combined with an effective or sub-therapeutic amount of another inhibitor can produce a result desired by the physician, due to, for example, synergy in the resulting efficacious effects, and may also result in reduced side effects.

The term "refractory" as used herein is used to define a cancer for which treatment (e.g., chemotherapy drugs, biological agents, and/or radiation therapy) has proven to be ineffective or insufficient. A refractory cancer tumor may shrink, but not to the point where the treatment is determined to be effective or sufficient. Typically however, the tumor stays the same size as it was before treatment (stable disease), or it grows (progressive disease).

For purposes of the present invention, administration "in combination", "co-administration of" and "co-administering" an IGF1R inhibitor and an mTOR inhibitor refer to any administration of the two inhibitors, either separately or together, where the two inhibitors are administered as part of an appropriate dose regimen designed to obtain the benefit of the combination therapy. Thus, the two inhibitors can be administered either as part of the same pharmaceutical composition or in separate pharmaceutical compositions. The IGF1R inhibitor can be administered prior to, at the same time as, or subsequent to administration of the mTOR inhibitor, or in some combination thereof. Where the mTOR inhibitor is administered to the patient at repeated intervals, e.g., during a standard course of treatment, the IGF1R inhibitor can be administered prior to, at the same time as, or subsequent to, each administration of the mTOR inhibitor, or some combination thereof, or at different intervals in relation to therapy with the mTOR inhibitor, or in a single dose prior to, at any time during, or subsequent to the course of treatment with the mTOR inhibitor.

The IGFR1 and mTOR inhibitors will typically be administered to the patient in a dose regimen that provides for the most effective treatment of the cancer (from both efficacy and safety perspectives) for which the subject is being treated, as known in the art. In conducting the treatment methods of the present invention, the inhibitors can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, and the medical judgment of the prescribing physician as based, e.g., on the results of published clinical studies. For those embodiments further requiring the administration of radiation or a radiochemical, the agent or treatment can be administered in any effective manner known in the art, as described briefly herein, above.

The amount of the IGF1R and mTOR inhibitors administered and the timing of administration will depend on the type (species, gender, age, weight, etc.) and condition of the subject being treated, the severity of the disease or condition being treated, and on the route of administration. In some instances, dosage levels below the lower limit of the aforesaid range may be more than adequate. While in other cases still larger doses may be employed without causing any harmful side effect, provided that such larger doses are first divided into several small doses for administration throughout the day. For example, the dose of IGF1R inhibitor may be in, but not limited to, the range of about 0.1 mg/kg to about 20 mg/kg, 1 mg/kg to about 19 mg/kg, 2 mg/kg to about 18 mg/kg, 3 mg/kg to about 17 mg/kg, 4 mg/kg to about 16 mg/kg, 5 mg/kg to about 15 mg/kg, 6 mg/kg to about 14 mg/kg, 7 mg/kg to about 13 mg/kg, 8 mg/kg to about 12 mg/kg. In certain embodiments, the dose is 12 mg/kg. Similarly, the dose of mTOR inhibitor may be in, but not limited to, the range of about 0.1 mg to about 10 mg, 1 mg to about 9 mg, 2 mg to about 8 mg, 3 mg to about 7 mg, 4 mg to about 6 mg. In certain embodiments, the dose is 5 mg.

The mTOR inhibitor and the IGF1R inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The mTOR inhibitor and the IGF1R inhibitor can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

Methods of preparing pharmaceutical compositions comprising mTOR inhibitors are known in the art. Methods of preparing pharmaceutical compositions comprising IGF1R inhibitors are also known in the art. In view of the teaching of the present invention, methods of preparing pharmaceutical compositions comprising both an mTOR inhibitor and an IGF1R inhibitor will be apparent from the art, from other known standard references, such as Remington's Pharmaceutical Sciences, Mack Publishing Company, Easton, Pa., 18th edition (1990).

For oral administration of the mTOR inhibitor or the IGF1R inhibitor, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, active agents may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the inhibitors, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is possible to topically administer either or both of the inhibitors, by way of, for example, creams, lotions, jellies, gels, pastes, ointments, salves and the like, in accordance with standard pharmaceutical practice. For example, a topical formulation comprising either the mTOR inhibitor and/or an IGF1R inhibitor in about 0.1% (w/v) to about 5% (w/v) concentration can be prepared.

In certain embodiments, the inhibitors are used for veterinary purposes. In such cases, the inhibitors can be administered separately or together to animals using any of the forms and by any of the routes described above. In a preferred embodiment, the mTOR inhibitor and/or an IGF1R inhibitor are administered in the form of a capsule, bolus, tablet, liquid drench, by injection or as an implant. As an alternative, the inhibitors can be administered with the animal feedstuff, and for this purpose a concentrated feed additive or premix may be prepared for a normal animal feed. Such formulations are prepared in a conventional manner in accordance with standard veterinary practice.

The present invention also encompasses the use of a therapeutically effective amount of a combination of an mTOR inhibitor and an IGF1R inhibitor for use in treating cancer or for the manufacture of a medicament for the treatment of cancer (e.g., tumors or tumor metastases) in a subject in need thereof, wherein each inhibitor in the combination can be administered to the patient either simultaneously or sequentially. The present invention also encompasses the use of a synergistically effective combination of mTOR inhibitor and an IGF1R inhibitor for use in treating cancer or for use in the manufacture of a medicament for the treatment of cancer in a subject in need thereof, wherein each inhibitor in the combination can be administered to the subject either simultaneously or sequentially. The present invention also encompasses the use of a combination of an mTOR inhibitor and an IGF1R inhibitor for use in treating abnormal cell growth or for the manufacture of a medicament for the treatment of abnormal cell growth in a subject in need thereof, wherein each inhibitor in the combination can be administered to the patient either simultaneously or sequentially. In some embodiments, the IGF1R inhibitor is administered in a manner selected from the group consisting of once a week, once every two weeks, once every three weeks, once every four weeks, or combinations thereof. In other embodiments, the mTOR inhibitor is administered in a manner selected from the group consisting of daily, six days a week, five days a week, three days a week, two days a week, one day a week, or combinations thereof.

In an alternative embodiment of any of the above uses the present invention also encompasses the use of a combination of an mTOR inhibitor and an IGF1R inhibitor in combination with another cytotoxic, chemotherapeutic or anti-cancer agents, or compounds that enhance the effects of such agents, for use in treating cancer or for the manufacture of a medicament for the treatment of cancer in a subject in need thereof, wherein each inhibitor or agent in the combination can be administered to the subject either simultaneously or sequentially. In this context, the "other anti-cancer agent or agent that enhances the effect of such an agent" can be any of the agents listed herein above that can be added to the anti-cancer agent/treatment and IGF1R inhibitor combination when treating subjects.

In the context of this invention, other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN™, chlorambucil (CHL; e.g. LEUKERAN™), cisplatin (C is P; e.g. PLATINOL™) busulfan (e.g. MYLERAN™), melphalan, carmustine (BCNU), streptozotocin, triethylenemelamine (TEM), mitomycin C, and the like; anti-metabolites, such as methotrexate (MIX), etoposide (VP16; VEPESID™), 6-mercaptopurine (6 MP), 6-thioguanine (6TG), cytarabine (Ara-C), 5-fluorouracil capecitabine (e.g. XELODA™), dacarbazine (DTIC), and the like; antibiotics, such as actinomycin D, doxorubicin (DXR; e.g. ADRIAMYCIN™), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL™) and pactitaxel derivatives, the cytostatic agents, glucocorticoids such as dexamethasone (DEX; e.g. DECADRON™) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: amifostine (e.g. ETHYOL™), dactinomycin, mechlorethamine (nitrogen mustard), streptozocin, cyclophosphamide, lomustine (CCNU), doxorubicin lipo (e.g., DOXIL™), gemcitabine (e.g. GEMZAR™), daunorubicin lipo (e.g. DAUNOXOME™), procarbazine, mitomycin, docetaxel (e.g. TAXOTERE™, aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

With regards to radiation or a radiopharmaceutical, the source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. Parameters of adjuvant radiation therapies are, for example, contained in International Patent Publication WO 99/60023.

The present invention further provides for any of the "methods of treatment" (or methods for reducing the side effects caused by treatment) described herein, a corresponding "use for treating" and/or "method for manufacturing a medicament" for administration with an mTOR inhibitor and use with the same indications and under identical conditions or modalities described for the method of treatment, characterized in that an IGF1R inhibitor is used, and such that where any additional agents, inhibitors or conditions are specified in alternative embodiments of the method of treatment they are also included in the corresponding alternative embodiment for the use for treating and/or method for manufacturing a medicament, in an alternative embodiment, the present invention further provides for any of the "methods of treatment" (or methods for reducing the side effects caused by treatment) described herein, a corresponding "method for medical treatment" or "method for manufacturing a medicament" for use with the same indications and under identical conditions or modalities described for the method of treatment, characterized in that a combination of an mTOR inhibitor and an IGF1R inhibitor is used, such that where any additional agents, inhibitors or conditions are specified in alternative embodiments of the method of treatment they are also included in the corresponding alternative embodiment for the method for medical use or for manufacturing a medicament.

The present invention further provides, for any of the methods, compositions or kits of the invention described herein in which a step or ingredient includes the phrase "comprising . . . a combination of an mTOR inhibitor and an IGF1R inhibitor", a corresponding method, composition or kit in which that phrase is substituted with the phrase "consisting essentially of . . . a combination of an mTOR inhibitor and an IGF1R inhibitor".

The present invention further provides, for any of the methods, compositions or kits of the invention described herein in which a step or ingredient includes the phrase "comprising . . . a combination of an mTOR inhibitor and an IGF1R inhibitor", a corresponding method, composition or kit in which that phrase is substituted with the phrase "consisting of a combination of an mTOR inhibitor and an IGF1R inhibitor".

The invention also encompasses a pharmaceutical composition that is comprised of a combination of an mTOR inhibitor and an IGF inhibitor in combination with a pharmaceutically acceptable carrier.

Preferably the composition is comprised of a pharmaceutically acceptable carrier and a non-toxic therapeutically effective amount of a combination of an mTOR inhibitor and an IGF1R inhibitor (including pharmaceutically acceptable salts of each component thereof).

Moreover, within this preferred embodiment, the invention encompasses a pharmaceutical composition for the treatment of cancer, the use of which results in the inhibition of growth of neoplastic cells, benign or malignant tumors, or metastases, comprising a pharmaceutically acceptable carrier and a non-toxic therapeutically effective amount of a combination of an mTOR inhibitor and an IGF1R inhibitor (including pharmaceutically acceptable salts of each component thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise a combination of an mTOR inhibitor and an IGF1R inhibitor (including pharmaceutically acceptable salts of each component thereof) as active ingredients, a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by the combination of an mTOR inhibitor and an IGF1R inhibitor (including pharmaceutically acceptable salts of each component thereof) of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, a combination of an mTOR inhibitor and an IGF1R inhibitor (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a combination of an mTOR inhibitor and an IGF1R inhibitor (including pharmaceutically acceptable salts of each component thereof). A combination of an mTOR inhibitor and an IGF1R inhibitor (including pharmaceutically acceptable salts of each component thereof), can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, a pharmaceutical composition can comprise a combination of an mTOR inhibitor and an IGF1R inhibitor in combination with another anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like. Further, the compositions can be in a form suitable for use in transdermal devices. These formulations may be prepared, utilizing a combination of a combination of an mTOR inhibitor and an IGF1R inhibitor (including pharmaceutically acceptable salts of each component thereof) of this invention, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a combination of an mTOR inhibitor and an IGF1R inhibitor (including pharmaceutically acceptable salts of each component thereof) may also be prepared in powder or liquid concentrate form.

Dosage levels for the compounds of the combination of this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

The disclosure may be better understood by reference to the following non-limiting Examples, which are provided as exemplary of the disclosure. The following examples are presented in order to more fully illustrate the preferred embodiments of the disclosure and should in no way be construed, however, as limiting the broad scope of the disclosure.

EXAMPLES

Example 1

Phase I Study of the IGF1R Antibody Ganitumab in Combination with Everolimus in Patients with Advanced Solid Tumors The maximum tolerated doses/recommended phase II dose for the doublet combination, ganitumab (G) plus everolimus (E) followed by an expanded cohort was evaluated to better understand the safety and tolerability profile of this drug combination.

The primary objective of this study was to determine the maximum tolerated dose (MTD) and Recommended Phase II Dose (RPTD) of G+E in patients with advanced solid tumors. Secondary objectives were to describe any toxicities associated with this regimen and to preliminarily describe clinical activity (progression-free survival (PFS)), overall survival (OS), partial response (PR), complete response (CR) or stable disease (SD)>6 months.

Materials and Methods:

For dose escalation, eligible patients had advanced solid tumors with adequate organ function and no increased risk for class-related toxicities. G was given intravenously, and E was orally administered; cycle length was 28 days. Stage I was a dose escalation; cohort size: 3-6 patients; Stage II was an expansion at MTD with a cohort size of 20 patients.

As shown in Table I below, G was dosed at 12 mg/kg every 14 days: E was dosed at 5 mg daily in cohort 1 and 5 mg three times weekly in cohort −1. An intermediate dose of E at 5 mg five times weekly was added to better maximize dose intensity. Dose limiting toxicity (DLT) was assessed in cycle 1.

TABLE 1

Dosing Scheme

| Dose Level | Ganitumab (mg/kg) every two weeks | Everolimus (mg) |
|---|---|---|
| 1 | 12 | 5, daily |
| −1 | 12 | 5, 3 days weekly |
| 1-b | 12 | 5, 5 days weekly |

Assessments:

AEs were graded according to the NCI Common Toxicity Criteria version 4.0. Efficacy was assessed every 2 cycles with computed tomography (CT) using Response Evaluation Criteria in Solid Tumors (RECIST 1.1) guidelines.

Eligibility:

(1) Key inclusion criteria included: histologically confirmed solid tumor malignancy for which standard therapy or palliative measures do not exist or are no longer effective; disease measurable by RECIST; age ≥18 years; Kamofsky performance status >70%; life expectancy of at least 3 months; and adequate organ and marrow function. (2) Key exclusion criteria included: inadequately controlled hypertension (>150/100 mmHg); significant or poorly controlled cardiovascular or vascular disease events within previous 6 months; history of significant bleeding episode within the 6 months prior to day 1 of the study; history of insterstitial lung disease, e.g., pneumonitis or pulmonary fibrosis, or any evidence of interstitial ling disease on baseline chest CT scan; proteinuria at screening as demonstrated by either urine protein: creatine (UPC ratio >1.0 or 24 hr collection >1 g/24 hr at screening; and required therapy with inhibitors or inducers of CYP3A4.

Results: Dose escalation was complete with 17 subjects evaluable for DLT toxicity and 16 evaluable for efficacy (see Table 2). Two out of 5 subjects experienced DLTs in cohort 1 due to dose holdings related to grade 3 hematologic toxicities: thrombocytopenia and neutropenia plus thrombocytopenia. No DLTs were observed out of 6 subjects in cohort −1; one DLT was observed out of 6 subjects in the intermediate cohort due to dose holding related to grade 2 intolerable skin rash and oral mucositis. Possible grade 3 treatment-related adverse events included neutropenia, thrombocytopenia, elevated AST/ALT, hypertriglyceridemia, vomiting and erythema multiforme minor. There were no grade ≥4 treatment-related toxicities. One non-treatment-related death was due to disease progression. Two subjects had clinically significant skin rashes which resulted in protocol discontinuation. Twelve subjects have available efficacy data; 4 subjects have not yet been restaged. Two subjects with refractory NSCLC, achieved a complete response. Six additional subjects had stable disease as best response. In 2 out of 3 cutaneous biopsies, dermapathology evaluation revealed hypersensitivity reaction in the form of superficial perivascular dermatitis to G (mild perivascular lymphocytic infiltrate with eosinophils). The third biopsy revealed spongiotic dermatitis with mixed inflammatory infiltrate with abundant eosinophils and is interpreted as part of the skin toxicity to G.

TABLE 2

Patient Information
Twenty-six subjects treated: 19 in dose escalation; 7 in expanded cohort

| Characteristic | Patients (n = 26) |
| --- | --- |
| Median age, years (range) | 56, (33-72) |
| Female:male, no. (%) | 11(42):15(58) |
| Type of primary tumor; no. (%) | |
| NSCLC | 10 (38) |
| Colorectal | 8 (31) |
| Neuroendocrine | 2 (8) |
| Other* | 6 (23) |

*Other includes: gastroesophageal, GIST, appendiceal, thymoma, solitary fibrous tumor, cholanglocarcinoma

TABLE 3

Determination of MTD/RPTD
Nineteen subjects treated; 17 subjects evaluable for DLT

| Cohort | Subjects | DLT Toxicity |
| --- | --- | --- |
| 1 | 5 | Grade 3 thrombocytopenia and neutropenia |
| | | Grade 3 thrombocytopenia |
| −1 | 8* | None |
| 1-b | 6 | Grade 2 intolerable skin rash and oral mucositis† |

*2 subjects were inevaluable for DLT
†Unable to receive 85% or scheduled doses G and/or E

TABLE 4

Treatment-Related Grade ≥3 Adverse Events

| Toxicity | Grade 3 | Grade 4 |
| --- | --- | --- |
| Hematologic | | |
| Neutropenia | 1 | 0 |
| Thrombocytopenia | 3 | 0 |
| Nonhematologic | | |
| Vomiting | 1 | 0 |
| Hypertriglyceridemia | 1 | 0 |

Efficacy:

25 out of 26 subjects are evaluable for efficacy. To date, and as shown in Table 3, 23 subjects have been restaged, two subjects have not yet been restaged. Two subjects with refractory NSCLC achieved CR after 4 months on the protocol. One of these subjects had sustained CR for over one year, the other subject has sustained CR for 5 months. Eight subjects achieved SD as best response. Of the subjects who achieved SD as a best response, one had a neuroendocrine tumor (unknown primary), one had a thymoma, one had a solitary fibrous tumor, one had mCRC, and four had NSCLC. In each of these cases, SD status was maintained for four months. Median PFS is 4 months, with a range of 4-13 months.

Conclusion:

The results of the trial demonstrate that G E at MTD is well-tolerated. The recommended phase II dose for this doublet combination is G at 12 mg/kg every two weeks and E at 5 mg five times weekly. At this dose, this novel regimen is well-tolerated with potential activity in NSCLC. DLTs were grade 3 thrombocytopenia and neutropenia, grade 3 thrombocytopenia, grade 2 intolerable skin rash and oral mucosilis. Potential clinical activity was observed in subjects with refractory NSCLC. Skin toxicities consistent with hypersensitivity to Ganitumab have been observed.

REFERENCES

1. King, E. R. et al. (2011) Recent Pat Anticancer Drug Discov.
2. Tolcher A. W. et al. (2009) *J. Clin. Oncol.* 27:5800-5807.
3. Schmelzle, T. et al. (2000) *Cell* 103:253-262.
4. O'Reilly, K. E. et al. (2006) *Cancer Res.* 66:1500-1508.
5. Wan, X. et al. (2007) *Oncogene* 26:1932-1940.

Variations and modifications of the herein described systems, apparatuses, methods and other applications will undoubtedly suggest themselves to those skilled in the art. Accordingly, the foregoing description should be taken as illustrative and not in a limiting sense.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

We claim:

1. A pharmaceutical composition comprising an IGF1R inhibitor and an mTOR inhibitor in a pharmaceutically acceptable carrier, wherein the IGF1R inhibitor is ganitumab and the mTOR inhibitor is everolimus.

2. The composition of claim 1, wherein the composition comprises ganitumab is in an amount of about 0.05 mg to about 5 g.

3. The composition of claim 1, wherein the composition comprises ganitumab is in an amount of about 0.5 mg to about 5 g.

4. The composition of claim 1, wherein the composition comprises ganitumab is in an amount of about 1 mg to about 2 g.

5. The composition of claim 1, wherein the composition comprises everolimus in an amount of about 0.1 mg to about 10 mg.

6. The composition of claim 1, wherein the composition comprises everolimus in an amount of about 2 mg to about 8 mg.

7. The composition of claim 1, wherein the composition comprises everolimus in an amount of about 5 mg.

8. A kit comprising an IGF1R inhibitor and an mTOR inhibitor, wherein the IGF1R inhibitor is ganitumab and the mTOR inhibitor is everolimus, and printed instructions directing the use of a combined treatment of ganitumab and everolimus for treating cancer in a subject.

9. The kit of claim 8, wherein the ganitumab and the everolimus are in separate containers.

10. The kit of claim 9, wherein the ganitumab and the everolimus are in separate containers.

11. The kit of claim 8, wherein the ganitumab and the everolimus are in a unit dosage form.

12. The kit of claim 11, herein the ganitumab and the everolimus are in the same containers.

13. The kit of claim 8, further comprising a sterile diluent.

* * * * *

UNITED STATES PATENT AND TRADEMARK OFFICE
CERTIFICATE OF CORRECTION

PATENT NO. : 9,931,402 B2  
APPLICATION NO. : 15/586727  
DATED : April 3, 2018  
INVENTOR(S) : Hurwitz et al.

Page 1 of 1

It is certified that error appears in the above-identified patent and that said Letters Patent is hereby corrected as shown below:

In the Specification

Column 2, Line 37: Please correct "OS1027" to read -- OSI027 --

Column 7, Line 31: Please correct "bind to R&M," to read -- bind to IGF1R, IGF-1, --

Column 8, Line 31: Please correct "R&M" to read -- IGF1R, --

Column 8, Line 56: Please correct "1-116" to read -- H16 --

Column 22, Line 29: Please correct "G E at MTD" to read -- G + E at MTD --

Signed and Sealed this  
Thirty-first Day of July, 2018

Andrei Iancu  
*Director of the United States Patent and Trademark Office*